(12) United States Patent
Finnis et al.

(10) Patent No.: US 9,057,061 B2
(45) Date of Patent: Jun. 16, 2015

(54) GENE EXPRESSION TECHNIQUE

(75) Inventors: Christopher John Arthur Finnis, Lenton (GB); Darrell Sleep, West Bridgford (GB); Gillian Shuttleworth, West Bridgford (GB)

(73) Assignee: NOVOZYMES BIOPHARMA DK A/S, Bagsvaerd (DK)

( * ) Notice: Subject to any disclaimer, the term of this patent is extended or adjusted under 35 U.S.C. 154(b) by 1815 days.

(21) Appl. No.: 11/722,539

(22) PCT Filed: Dec. 23, 2005

(86) PCT No.: PCT/GB2005/005085
§ 371 (c)(1),
(2), (4) Date: Jun. 22, 2007

(87) PCT Pub. No.: WO2006/067511
PCT Pub. Date: Jun. 29, 2006

(65) Prior Publication Data
US 2008/0193977 A1    Aug. 14, 2008

Related U.S. Application Data

(63) Continuation-in-part of application No. PCT/GB2004/005462, filed on Dec. 23, 2004, and a continuation-in-part of application No. PCT/GB2004/005435, filed on Dec. 23, 2004.

(30) Foreign Application Priority Data

Dec. 23, 2003  (GB) .................................. 0329681.1
Dec. 23, 2003  (GB) .................................. 0329722.3

(51) Int. Cl.
*C12N 15/63* (2006.01)
*C12N 15/67* (2006.01)
*C12N 15/81* (2006.01)
*C12P 21/00* (2006.01)
*C12N 9/90* (2006.01)
*C07K 14/395* (2006.01)
*C07K 14/79* (2006.01)

(52) U.S. Cl.
CPC ............... *C12N 9/90* (2013.01); *C07K 14/395* (2013.01); *C07K 14/79* (2013.01); *C07K 2319/35* (2013.01); *C12N 15/81* (2013.01); *C12N 2510/02* (2013.01)

(58) Field of Classification Search
None
See application file for complete search history.

(56) References Cited

U.S. PATENT DOCUMENTS

| | | |
|---|---|---|
| 4,302,386 A | 11/1981 | Stevens |
| 4,931,373 A | 6/1990 | Kawasaki et al. |
| 4,937,193 A | 6/1990 | Hinchliffe |
| 5,637,504 A | 6/1997 | Hinchliffe |
| 5,728,553 A | 3/1998 | Goodey |
| 5,773,245 A | 6/1998 | Wittrup |
| 5,783,385 A * | 7/1998 | Treco et al. ................ 506/7 |
| 6,291,205 B1 | 9/2001 | Tuite |
| 6,451,559 B1 | 9/2002 | Schreier |
| 6,455,279 B1 | 9/2002 | Ambrosius |
| 6,924,125 B2 | 8/2005 | Motwani |
| 6,929,929 B2 | 8/2005 | Buchner |
| 6,939,676 B2 * | 9/2005 | Burke et al. ............. 435/6.13 |
| 7,226,781 B1 | 6/2007 | Belyaev |
| 7,244,616 B2 | 7/2007 | Chan |
| 7,244,819 B2 | 7/2007 | Scholz |
| 2001/0034045 A1 | 10/2001 | Penttila |
| 2002/0192743 A1 | 12/2002 | Buchner |
| 2003/0100112 A1 | 5/2003 | Motwani |
| 2003/0125247 A1 | 7/2003 | Rosen |
| 2003/0221201 A1 | 11/2003 | Prior |
| 2003/0226155 A1 | 12/2003 | Sadeghi |
| 2004/0115790 A1 | 6/2004 | Pakula |
| 2004/0186070 A1 | 9/2004 | Penttila |
| 2004/0248238 A1 | 12/2004 | Watzele |
| 2005/0064545 A1 | 3/2005 | DeMarco |
| 2005/0191726 A1 | 9/2005 | Motwani |
| 2006/0110747 A1 | 5/2006 | Ramseier |
| 2007/0275889 A1 | 11/2007 | Sleep |
| 2008/0261861 A1 | 10/2008 | Sleep |

FOREIGN PATENT DOCUMENTS

| | | |
|---|---|---|
| EP | 0060057 A1 | 9/1982 |
| EP | 0171142 A1 | 2/1986 |
| EP | 0251744 A2 | 1/1988 |
| EP | 0286424 A1 | 10/1988 |
| EP | 0293793 A2 | 12/1988 |
| EP | 0073646 B1 | 5/1989 |
| EP | 0319067 A1 | 7/1989 |
| EP | 0366400 A2 | 5/1990 |
| EP | 0464590 A2 | 1/1992 |
| EP | 509841 | 10/1992 |

(Continued)

OTHER PUBLICATIONS

Vob et al. (Production of supercoiled multimeric plasmid DNA for biopharmaceutical application, Journal of Biotechnology 105 (2003) 205-213).*

(Continued)

*Primary Examiner* — Suzanne M Noakes
*Assistant Examiner* — Jae W Lee
(74) *Attorney, Agent, or Firm* — Michael W. Krenicky

(57) ABSTRACT

The present invention provides a method for producing a desired protein (such as a desired heterologous protein) comprising: (a) providing a host cell comprising a first recombinant gene encoding a protein comprising the sequence of a first chaperone protein, a second recombinant gene encoding a protein comprising the sequence of a second chaperone protein and a third gene, such as a third recombinant gene, encoding a desired protein (such as a desired heterologous protein), wherein the first and second chaperones are different; and (b) culturing the host cell in a culture medium to obtain expression of the first, second and third genes.

22 Claims, 30 Drawing Sheets

(56) References Cited

FOREIGN PATENT DOCUMENTS

| | | |
|---|---|---|
| EP | 0509841 A2 | 10/1992 |
| EP | 0258067 B1 | 3/1993 |
| EP | 0431880 B1 | 2/1996 |
| EP | 0387319 B1 | 3/1996 |
| EP | 0828004 A2 | 3/1998 |
| EP | 1748071 A1 | 1/2007 |
| JP | 910114047 | 10/1990 |
| JP | 2-295017 A | 4/1991 |
| WO | WO 88-08027 A1 | 10/1988 |
| WO | WO 89-07140 A1 | 8/1989 |
| WO | WO 90-01063 A1 | 2/1990 |
| WO | WO 90-13653 A1 | 11/1990 |
| WO | WO 92-04367 A1 | 3/1992 |
| WO | WO 92-13550 A1 | 8/1992 |
| WO | WO 93-22348 A1 | 11/1993 |
| WO | WO 93/25676 | 12/1993 |
| WO | WO 93-25676 A1 | 12/1993 |
| WO | WO 94-03617 A1 | 2/1994 |
| WO | WO 94-04687 A1 | 3/1994 |
| WO | WO 94-08012 A1 | 4/1994 |
| WO | WO 95-23857 A1 | 9/1995 |
| WO | WO 95-33833 A1 | 12/1995 |
| WO | WO 96-37515 A1 | 11/1996 |
| WO | WO 98-37208 A1 | 8/1998 |
| WO | WO 98-56928 A1 | 12/1998 |
| WO | WO 00-44772 A2 | 8/2000 |
| WO | 01/79258 A1 | 10/2001 |
| WO | 01/79271 A1 | 10/2001 |
| WO | 01/79442 A2 | 10/2001 |
| WO | 01/79443 A2 | 10/2001 |
| WO | 01/79444 A2 | 10/2001 |
| WO | 01/79480 A1 | 10/2001 |
| WO | WO 01-72783 A2 | 10/2001 |
| WO | WO 03/057897 | 7/2003 |
| WO | WO 03-057897 A2 | 7/2003 |
| WO | WO 03-066085 A2 | 8/2003 |
| WO | WO 03-066824 A2 | 8/2003 |
| WO | WO 2004-009819 A2 | 1/2004 |
| WO | WO 2004-015113 A2 | 2/2004 |
| WO | WO 2004-042036 A2 | 5/2004 |
| WO | WO 2004-083245 A2 | 9/2004 |
| WO | WO 2005/061718 | 7/2005 |
| WO | WO 2005-061718 A1 | 7/2005 |
| WO | WO 2005-061719 A1 | 7/2005 |
| WO | WO 2005/078105 | 8/2005 |
| WO | WO 2005-078105 A2 | 8/2005 |

OTHER PUBLICATIONS

Hartl, "Molecular chaperones in cellular protein folding", Nature, vol. 381, pp. 571-580 (1996).
Robinson et al., "Constitutive overexpression of secreted heterologous proteins decreases extractable BiP and protein disulfide isomerase levels in *Saccharomyces cerevisiae*", Biotechnology Progress, vol. 11, pp. 171-177 (1995).
Farquhar al., "Protein disulfide isomerase is essential for viability in *Saccharomyces cerevisiae*" Gene, vol. 108, pp. 81-89 (1991).
Robinson et al., "Protein disulfide isomerase overexpression increases secretion of foreign proteins in *Saccharomyces cerevisiae*"Biotechnology, vol. 12, pp. 381-384 (1994).
Hayano et al., "Protein disulfide isomerase mutant lacking its isomerase activity accelerates protein folding in the cell" FEBS Letters, vol. 377, pp. 505-511 (1995).
Shusta et al., "Increasing the secretory capacity of *Saccharomyces cerevisiae* for production of single chain antibody fragments", Nature Biotechnology, vol. 16, pp. 773-777 (1998).
Bao et al., "Secretion of human proteins from yeast: stimulation by duplication of polyubiquitin and protein disulfide isomerase genes in *Kluyveroymyces lactis*", Gene, vol. 272, pp. 103-110 (2001).
Botstein et al., "Sterile Host Yeasts (SHY): a eukaryotic system of biological containment for recombinant DNA experiments", Gene, vol. 8, pp. 17-24 (1979).
Rosenberg et al., "Synthesis in Yeast of a functional oxidation-resistant mutant of human $\alpha_1$-antitrypsin", Nature, vol. 312, pp. 77-80 (1984).
Parekh et al., "Expression level tuning for optimal heterologous protein secretion in *Saccharomyces cerevisiae*", Biotechnology Progress, vol. 13, pp. 117-122 (1997).
Bao et al., "Protein disulfide isomerase genes of *Kluyveroymyces lactis*", Yeast, vol. 16, pp. 329-341 (2000).
Gunther, R. et al., "Functional replacement of the *Saccharomyces cerevisiae* Trg1/Pdi proteins by members of the mammalian protein disulfide isomerase family", Journal of Biological Chemistry, vol. 268, pp. 7728-7732 (1993).
Hjelmqvist, L. et al., "ORMDL proteins are a conserved new family of endoplasmic reticulum membrane proteins", Genome Biology, vol. 3, No. 6, pp. 1-16 (2002).
Anonymous, Profold Vector Technology Internet Article, http://web.archive.org/web/20040816225908/http://www.abvector.com/technology.htm (2004).
Ali et al 1999, J Biol Chem 274, 24066-24073.
Bachmair & Ruis 1984, Monatsh Chem 115, 1229-1235.
BD pBridge three-Hybrid Vector 2003 Clontech Cat XP002325598.
Becker and Craig 1994, Eur J Biochem 219, 11-23.
Becker and Guarente 1990, Methods Enzymol 194, 182-187.
Beggs 1978, Nature 275, 104-109.
Berent et al 1985 Biotechniques 208.
Bijvoet et al 1991, Yeast 7, 347-356.
Broach & Hicks 1980, Cell 21, 501-508.
Broach et al 1982, Cell 29, 227-234.
Broach et al 1982, Cold Spring Harbor Symp Quant Biol 47, 1165-1174.
Broach et al 1985, Cell 16, 827-839.
Bulleid and Freedman 1988, Nature 335 (13), 649-651.
Cameron et al 1977, Nucleic Acids Res 4 (5) 1429-1448.
Cashmore et al 1986, Mol Gen Genet 203, 154-162.
Chen et al 1992, Cell 69, 647-658.
Cheng et al 1987, J Biol Chem 262 (23), 11221-11227.
Chinery & Hinchliffe 1989, Curr Genet 16, 21-25.
Chow et al 1992, J Cell Sci 101 (3), 709-719.
Christis et al 2008, FEBS 275, 4700-4727.
Clements et al 1991, Gene 106 (2), 267-271.
Cohen et al 1972, Proc Nat Acad Sci U S A 69 (8), 2110-2114.
Creasey et al 2003, Mol Biol 47 (1), 209-221.
Creighton et al 1980, J Mol Biol 142, 43-62.
Crouzet & Tuite 1987, Mol Gen Genet 210, 581-583.
Database NCBI—Access No. J01347 (Oct. 2007).
Database NCBI—Access No. M18274 (Apr. 1993).
Database NCBI—Access No. NC001398 (Dec. 2008).
Database NCBI—Access No. NC002054 (Jun. 2009).
Database NCBI—Access No. NC002055 (Jun. 2009).
Database NCBI—Access No. X02398 (Oct. 2008).
Database NCBI—Access No. X02608 (Oct. 2008).
Database NCBI—Access No. X03961 (Oct. 2008).
Database NCBI—Access No. NC001135 (Jun. 2009).
Database NCBI Access No. BAA00723 (Jun. 2009).
Database NCBI Access No. CAA38402 (Apr. 2005).
Database NCBI Access No. CAA42373 (Oct. 2008).
Database Swissprot—Access No. P02769 (Jun. 2009).
Database Swissprot—Access No. P08835 (May 2009).
Database Swissprot—Access No. P49822 (Jun. 2009).
Database Swissprot—Access No. O73860 (Jun. 2009).
Database Swissprot—Access No. O89020 (Jun. 2009).
Database Swissprot—Access No. P01012 (Jun. 2009).
Database Swissprot—Access No. P14639 (May 2009).
Database Swissprot—Access No. P19121 (Jun. 2009).
Database Swissprot—Access No. P35747 (May 2011).
Database Swissprot—Access No. P36953 (Jun. 2009).
Database Swissprot—Access No. P39090 (Jun. 2009).
Database Swissprot—Access No. P49064 (May 2009).
Database Swissprot—Access No. P49065 (May 2009).
Database Swissprot—Access No. Q28522 (May 2009).
Demolder et al 1994, J Biotechnol 32, 179-189.
Dockal et al 1999, J Biol Chem 274, 29303-29310.
Dong-Hee Lee et al 2001, J Biochem Mol Biol 34 (2), 102-108.

(56) References Cited

OTHER PUBLICATIONS

Edman et al 1985, Nature 317, 267-270.
Elble 1992, Biotechniques 13, 18-20.
Finnis et al 1993, Eur J Biochem 212, 201-210.
Fischer & Schmid 1990, Biochemistry 29, 2205-2212.
Frand & Kaiser 1998, Mol Cell 1, 161-170.
Freedman 1984, Trends Biochem Sci 9 (10), 438-441.
Freedman 1987, Nature 329, 196-197.
Freedman et al 1988, Biochem Soc Transactions 16, 96-99.
Freedman et al 1989, Biochem Soc Symp 55, 167-192.
Futcher 1988, Yeast 4, 27-40.
Futcher & Cox 1984, J Bacteriol 157 (1), 283-290.
Geetha-Habib et al 1988, Cell 54, 1053-1060.
Gietz & Sugino 1988, Gene 74, 527-534.
Gilbert 1989, Biochemistry 28, 7298-7305.
Glover & Lindquist 1998, Cell 94, 73-82.
Grainge et al 2001, J Mol Biol 314, 717-733.
Guenther et al 1993, J Bio Chem 268, (11), 7728-7732.
Harris and Aisen 1991 Iron carriers and iron proteins, 5.
Hartl 1996, Nature 381, 571-580.
Hartley & Donelson 1980, Nature 286, 860-865.
Hawkins and Freedman 1990, J Biochem 275, 335-339.
Hayano et al 1995, FEBS Lett 377, 505-511.
Hillson et al 1984, Methods Enzymol 107, 281-294.
Hjelmqvist et al 2002, Gen Biol 3 (6) research 0027.1.
Ho et al 2002, Nature 415, 180-183.
Hochstrasser 1996, Ann Rev Genet 30, 405-39.
Hoheisel 1994, Biotechniques 17, 456-460.
Hohenblum 2003, J Biotechnol 102, 281-290.
Hollenberg 1982, Curr Top Microbiol Immunobiol 96, 119-114.
Huh et al 2003, Nature 425, 686-691.
Inan et al 2006, Biotechnol Bioeng 93, 771-778.
Irie et al 1991, Gene 108 (1), 139-144.
Irie et al 1991, Mol Gen Genet 225 (2), 257-265.
Isoyama et al 2001, J Biol Chem 276 (24), 21863-21869.
Ito et al 1983, J Bacteriol 153 (1), 163-168.
Jayaram 1985, Proc Natl Acad Sci U S A 82, 5875-5879.
Kaska et al 1990, J Biochem 268, 63-68.
Kauffman et al 2002, Biotechnol Prog 18, 942-950.
Kerry-Williams et al 1998, Yeast 14, 161-169.
Khan et al 2002, Int J Biol Macromol 30, 171-178.
Kikuchi 1983, Cell 35, 487-493.
Kim et al 1998, Proc Natl Acad Sci U S A 95, 12860-12865.
Kim et al 2003, J Biotechnol 101, 81-87.
Kramer et al 2001, J Biochem 357, 83-95.
Kunkel et al 1987 Methods Enzymol 154, 367-382.
Laboissiere et al 1995, J Biol Chem 270, 28006-28009.
Lambert et al 2001, Proc Natl Acad Sci U S A 98, 4652-4657.
Lee 1992, Biotechniques 12, 677.
Lewis & Pelham 1990, Nature 348, 162-163.
Livingston & Hahne 1979, Proc Natl Acad Sci U S A 76 (8), 3727-3731.
Lodi et al 2005, Appl Env Microbiol 71, 4359-4363.
Ludwig & Bruschi 1991, Plasmid 25, 81-95.
Lund et al 1985, J Biol Chem 260, 7609-7613.
Lundstrom and Holmgren 1990, J Biol Chem 265 (16), 9114-9120.
Martzen et al 1999, Science 286, 1153-1155.
Mason et al 1991, Prot Expres Purif, 2, 214-220.
Mason et al 1993, Biochemistry 32, 5472-5479.
Mason et al 1996, Prot Expres Purif 8, 119-125.
Mason et al 1998, J Biochem 330, 35-40.
Mason et al 2002, Biochemistry 41, 9448-9454.
Mattanovich et al 2004, J Biotechnol 113, 121-135.
Mead et al 1986, Mol Gen Genet 205, 417-421.
Meyer-Leon 1984, Cold Spring Harbor Sym Quant Bio 49, 797.
Moralejo et al 2001, Mol Gen Genet 266, 246-253.
Mosammaparast et al 2002, J Biol Chem 277 (1), 862-868.
Murray J et al 1988, J Mol Biol 200 (3) 601-607.
Ngosuwan et al 2003, J Biol Chem 278 (9), 7034-7042.
Norgaard et al 2001, J Cell Biol 152, 553-562.
Norgaard et al 2003, Yeast 20, 645-652.
Nutt et al 1988, J Biol Chem 262, 10162-10167.
Ozkaynak et al 1984, Nature 312, 663-666.
Ozkaynak et al 1987, EMBO J 6, 1429-1439.
Painting et al 1984, J Appl Bacteriol 56, 331-335.
Parekh & Wittrup 1997, Biotechnol Progr 13, 117-122.
Parkkonen et al 1998, J Biochem 256, 1005-1011.
Pelham 1990, Trends Biotechnol 15, 483-486 (rel 11069 Spec).
Pemberton et al 1998, Curr Op Biotechnol 10, 392-399.
Peters 1996, All About Albumin Biochem Gen Med applns, Acad Press 170-181.
Pihlajaniemi et al 1987, EMBO J 6 (3), 643-649.
Piper and Curran 1990, Curr Genet 17, 119-123.
Prasad et al 1987, Proc Natl Acad Sci U S A 84, 2189-2193.
pYEX4T-1 Vector Info 1998 Clontech Cat #6169-1.
Qianwa Liang et al 1993, J Agric Food Chem 41, 1800-1807.
Qui et al 2006, Cell Mol Life Sci 63, 2560-2570.
Reynolds et al 1987, Mol Cell Biol 7 (10) 3566-3573.
Robinson et al 1996, J Biol Chem 271, 10017-10022.
Rose & Broach 1990, Methods Enzymol 185, 234-279.
Roth & Pierce 1987, Biochemistry 26 (14), 4179-4182.
Rothman 1989, Cell 59, 591-601.
Ryan and Wente 2000, Curr Op Cell Biol 12, 361-371.
Sambrook et al 2001, Laboratory Manual, 3rd ed Cold Spring Harbor.
Schein 1989, Nature Biotechnol 7, 1141-1149.
Scherens et al 1991, Yeast 7, 185-193.
Seedorf & Silver 1997, Proc Natl Acad Sci U S A 94, 8590-8595.
Semenza et al 1990, Cell 61, 1349-1357.
Senecoff et al 1985, Proc Natl Acad Sci U S A 82, 7270-7274.
Sengupta et al 2001, J Bacteriol 183 (7), 2306-2315.
Sherman et al 1986 Cold Spring Harbor Lab Methods Yeast Genetics, Lab Manual.
Shin et al 1995, Proc Natl Acad Sci U S A 92, 2820-2824.
Shusta et al 1998, Nature Biotechnol 16, 773-777.
Sleep 1990, Biotechnology 8, 42-46.
Sleep et al 1991, Nature Biotechnol 9 (2), 183-187.
Sleep et al 2001, Yeast, 18 (5), 403-421.
Smith et al 1985, Science 229, 1219-1224.
Solovyov et al 2004, J Biol Chem 297 (33), 34095-34100.
Southern 1975, J Mol Biol 98, 503-517.
Sutton & Broach 1985, Mol Cell Biol 5 (10), 2770-2780.
Testa 2002, Proteins of Iron Metabolism, CRC Press.
Thompson et al 1994, Nucleic Acids Res 22 (22), 4673-4680.
Toh-e et al 1986, Basic Life Sci 40, 425.
Tong et al 2004, Science 303, 808-813.
Toyn et al 2000, Yeast 16, 553-560.
Ueta et al 2003, J Biol Chem 278 (50), 50120-50127.
Valkonen et al 2003, Appl Environ Microbiol 69, 2065-2072.
Vaux et al 1990, Nature 345, 495-502.
Volkert & Broach 1986, Cell 46, 541-550.
Volkert et al 1989, Microbiol Rev 53, 299-317.
Weeke B 1976 Rocket Immunoelectrophoresis, Scan J Immunology 2 (1).
Williamson 1985, Yeast 1, 1-14.
Yamauchi et al 1987, Biochem Biophys Res Com 146, 1485-1492.
Zealey et al 1988, Mol Gen Genet 211, 155-159 11079.
Breslow et al 2008, Nat Methods 5 (8), 711-718.
Dolinski 1997, Proc Natl Aad Sci USA 94, 13093-13098.
Jin et al 2008, Mol Biol Cell 19, 284-296.
Kurihara et al 1994, J Cell Biol 126 (4), 911-23.
Lawrence et al 2004, Mol Cel Biol 24 (8), 3307-3323.
Liang et al 2007, Mol Biol Cell 18, 4741-4749.
Palmer et al 2003, J Cell Sci 116, 2361-2373.
Yoshikawa et al 2008, FEMS Yeast Res 9 (1), 32-44.
Chen et al, 1994,Genbank Acces No. U16761.
Giaever et al 2002, Nature 418 (6896), 387-391.
Nishizawa et al 1989, Appl Microbiol Biotech 32, 317-322.
Panaretou et al 2002, Mol Cell 10, 1307-1318.
Sahasrabudhe et al 1998, Prot Exp Purif 14, 425-433.
Schreuder et al 1996, Vaccine 14(5), 383-388.
Tonkool P 2001, Acta Biotechnol 21(2), 189-193.
Wood et al, 2005, Genbank Acces No. NM-001018416.
AB Vector—ProFold—ERI 2004, Internet Article.

(56) References Cited

OTHER PUBLICATIONS

AB Vector Technol 2011, Internet Article.
Vob et al, 2003, J Biotechnol 105, 205-213.
Boeke et al, 1987, Methods Enzymol 154, 164-175.
Brachmann et al, 1998, Yeast 30(14), 115-132.
Chen et al, 1994, Genbank Acces No. U16761.
Fassler, 2004, EMBO Rep 5(1), 28-29.
Jones et al, 2003, Physiol Genomics 16, 107-118.
Rose et al, 1987, Gene 60, 237-243.
Shevchuk et al, 2004, Nucl Acids Res 32(2), e19.
Wolkowicz et al, 2004, Methods Mol Biol 246, 391-411.
Cell Sciences Catalogue (2000).
Concise Medical Dictionary—Antibiotic (2002).
Concise Medical Dictionary—Coagulation Factors (2002).
Concise Medical Dictionary—Metabolite (2002).
Cyanovirin N database extract (2011).
Esmon et al 1974, J Biol Chem, 7789-7807.
Hoffbrand et al 2005, Postgraduate Haematology 887-888.
Joerger, 2003 Poultry Science 82:640-647.
Lewin 1997 Genes VI, 1223.
Molecular Biology of the Cell 1994.
Ghaemmaghami et al 2003, Nature 425, 737-741.
Han et al, 2010, PNAS 107(13), 5851-5856.
Kimura et al, 2004, Biochem Biophys Res Commun 320, 359-365.
Nishikawa et al, 1997, J Biol Chem 272 (20), 12889-12892.
Schroder et al, 2005, Mutation Res 569(1), 39-63.
Stoldt et al, 1996, Yeast 12, 523-529.
Walsh et al, 2004, EMBO Reports 5, 567-571.
Alberts et al, 1994, Molecular Biology of the Cell, Garland Publishing—Ab.
Freedman, 1989, Cell 57, 1069-1072.
Harmsen et al, 1996, Appl Micro Biotechnol 46, 365-370.
Ludwig et al, 1993, Gene 132, 33-40.
Single-domain antibody (dAb)—Glossary of Biochem Mol Bio webpage May 2014.
Tanha et al, 2002, J Immun Metho 263, 97-109.
Saccharomyces Genome Database, 2009, webpage download Jul. 17, 2009.
Stanford Genome Database, 2009, webpage download Jul. 7, 2009.
VAD 2005 J Biotech 116, 251-260.

\* cited by examiner

Figure 20A

```
              CTAGTCTCTTTTTCCAATTTCCACGGTTGCATTTGTTGTGCTTGTTGTTACAACACAACTAAACGAAAAACCGTATGGACATATATATATATCATTATATATATATATATATATATA
              |....|....|....|....|....|....|....|....|....|....|....|....|....|....|....|....|....|....|....|....|....|
              10        20        30        40        50        60        70        80        90       100       110
S288c long    CTAGTCTCTTTTTCCAATTTCCACGGTTGCATTTGTTGTGCTTGTTGTTACAACACAACTAAACGAAAAACGAAAAACCGTATGGACATACATATATATATATCATTATATATATATATATATATA 110
SKQ2n long    CTAGTCTCTTTTTCCAATTTCCACGGTAGCATTTGTTGTGCTTGTTGTTACAACACAACACAACAAACGAAAAACCGTATGGACATACATATATATATATCATTATATATATATATATATATA 110

TATATTTGTTACGGTGCATTTCTTGTTGTCAAGCAGCATGTCTAATTGTAATTTTAAAGCTGCCAAGCTCTACATTAAGAAAAAACATACATCTATCCGTTATGAAG
              |....|....|....|....|....|....|....|....|....|....|....|....|....|....|....|....|....|....|....|....|....|
              120       130       140       150       160       170       180       190       200       210       220
S288c long    ----TTTGTTACGGTGCATTTCTTGTTGTCAAGCAGCATGTCTAATTGTAATTTTAAAGCTGCCAAGCTCTACATTAAAGAAAAAACATACATCTATCCGTTATGAAG 216
SKQ2n long    TATATTTGTTACGGTGCATTTCTTGTTGTCAAGCAGCATGTCTAATTGTAATTTTAAAGCTGCCAAGCTCTACATTAAAGAAAAAACATACATCTATCCGTTATGAAG 220

TTTTTCTGCTGGTGCGTCCTGTCATGGTCCTCCGTCGTCGCCCTCCGTTGCTGCCAACAAGAGGTCTGTGCCCCTGAAGACTCCGTGTGTTAAGTTGGCCAC
              |....|....|....|....|....|....|....|....|....|....|....|....|....|....|....|....|....|....|....|....|....|
              230       240       250       260       270       280       290       300       310       320       330
S288c long    TTTTTCTGCTGGTGCGTCCTGTCATGGTCCTCCGTCGTCGCCCTCCGTTGCTGCCAACAAGAGGTCTGTGCCCCTGAAGACTCCGTGTGTTAAGTTGGCCAC 326
SKQ2n long    TTTTTCTGCTGGTGCGTCCTGTCATGGTCCTCCGTCGTCGCCCTCCGTTGCTGCCAACAAGAGGTCTGTGCCCCTGAAGACTCCGTGTGTTAAGTTGGCCAC 330

CGACTCTTCAATGAGTACATTCAGTGCACGACTTGGCTTGGCTTGCATGGTCCTCCATGGTGGCCACTGTAAGAACATTGCAGGTTCCAAGCTTGAAGATTTTCAAA
              |....|....|....|....|....|....|....|....|....|....|....|....|....|....|....|....|....|....|....|....|....|
              340       350       360       370       380       390       400       410       420       430       440
S288c long    CGACTCCTCAATGAGTACATTCAGTGCCACGACTTGGCTTGGCTTGCATGGTCCTCCATGGTGGCCACTGTAAGAACATGGCTCTCTGAATACGTTAAACGCCGG 436
SKQ2n long    CGACTCTTTCAATGAATACATTCAGTGCCACGACTTGGCTTGGCTTGCATGGTCCTCCATGGTGGCCACTGTAAGAACATGGCTCTCTGAATACGTTAAACGCCGG 440

AGACTTTAGTTGAGAAAAACATTGATGCTTGGCCCAGATCGAACTGACTGTACTGAAAACCAGGATCTGTATGGAACACCAGGATCTGTATGATGAAACCAGGATCTGTATGATG
              |....|....|....|....|....|....|....|....|....|....|....|....|....|....|....|....|....|....|....|....|....|
              450       460       470       480       490       500       510       520       530       540       550
S288c long    AGACTTTAGTTGAGAAAAACATTGATGCTTGGCCCAGATCGACTGACTGTACTGAAAACCAGGATCTGTATGGAACACCAGGATCTGTATGATGAAACCAGGTTCCAAGCTTGAAGATTTTCAAA 546
SKQ2n long    AGACTTTAGTTGAGAAAAACATTGATGCTTGGCCCAGATCGACTGACTGTACTGAAAACCAGGATCTGTATGGAACACCAGGATCTGTATGATGAAACCAGGTTCCAAGCTTGAAGATTTTCAAA 550

AACAGGATGTTAACAACTGATCGATCGATTACGAGGGACCTAGAACTGCCGAGGGACCTAGAACTGCCGAGGGACCTATTGTCCAATTCATGATCAAGCAAAGCAACGGCCAACGGCGTTGCTTGCCTGATCT
              |....|....|....|....|....|....|....|....|....|....|....|....|....|....|....|....|....|....|....|....|....|
              560       570       580       590       600       610       620       630       640       650       660
S288c long    AACAGGATGTTAACAACTGATCGATCGATTACGAGGGACCTAGAACTGCCGAGGGACCTAGAACTGCCGAGGGACCATTGTCCAATTCATGATCAAGCAAAGCAACGGCCAACGGCGTTGCCGTTGCTTGCTGATCT 656
SKQ2n long    AACAGGATGTTAACAACTGATCGATCGATTACGAGGGACCTAGAACTGCCGAGGGACCTAGAACTGCCGAGGGACCATTGTCCAATTCATGATCAAGCAAAGCAACGGCCAACGGCGTTGCCGTTGCTTGCTGATCT 660
```

```
              GATCTTGAGAACCAAGATTCCTCTGTCTTCCAATTGGTCGGTAAGAACCATGACGAAATGTCAAGAAGAAGAGTTCAAGACCCAAAGAAGGAGGTTCTTGTTTTGTACTATGCCCATGGT 1420
              GATCTTGAGAACCAAGATTCCTCTGTCTTCCAATTGGTCGGTAAGAACCATGACGAAATGTCAAGAAGAAGAGTTCAAGACCCAAAGAAGGAGGTTCTTGTTTTGTACTATGCCCATGGT 1430
S288c long         1330      1340      1350      1360      1370      1380      1390      1400      1410      1420      1430
SKQ2n long
```

```
              GTGGTCACTGTAAGAGATTGGCCCCAACTTACCAAGAGACTAGCTAGTGATCCAACGCCACATCCGACGTTTTGATTGCTAAACTAGACCACACTGAAAACGATGTC 1540
              GTGGTCACTGTAAGAGATTGGCCCCAACTTACCAAGAGACTAGCTAGTGATCCAACGCCACATCCGACGTTTTGATTGCTAAACTAGACCACACTGAAAACGATGTC 1540
S288c long         1440      1450      1460      1470      1480      1490      1500      1510      1520      1530      1540
SKQ2n long
```

```
              AGAGCGCTCGTAATTGAAGGTTACCAACAATGCCTTATACCAGGTGGTAAGAGTTCCGAATCTGTTGTGTACCAAGGTTCCAAGATCCTTGGACTCTTTATTCGACTT 1650
              AGAGCGCTCGTAATTGAAGGTTACCAACAATGCCTTATACCAGGTGGTAAGAGTTCCGAATCTGTTGTGTACCAAGGTTCCAAGATCCTTGGACTCTTTATTCGACTT 1650
S288c long         1550      1560      1570      1580      1590      1600      1610      1620      1630      1640      1650
SKQ2n long
```

```
              CATCAAGAAAACGTCACTTGGACGTTGACGGTAAGGCCTTGAGCGGTAAGGCCTTGAGCGGTAAGGCCTTGACCGAGAAGCTGGTAGGGAGGAG------------TGCTG 1730
              CATCAAGAAAACGTCACTTGGACGTTGACGGTAAGGCCTTGAGCGGTAAGGCCTTGAGCGGTAAGGCCTTGACCGAGAAGCTGGTAGGGAGGAGTGACCGCTGACCGCTG 1760
S288c long         1660      1670      1680      1690      1700      1710      1720      1730      1740      1750      1760
SKQ2n long
```

```
              ACGCTGAATTGGCTGACGAAGAAGATGCCATTCACGATGAATTGTAATTCAGATTCGATCACTTTGGTTTCATTCAATGATTATATAAAATTTCTAGGAAGTTTTTT 1860
              ACGCTGAATTGGCTGACGAAGAAGATGCCATTCACGATGAATTGTAATTCAGATTCGATCACTTTGGTTTCATTCAATGATTATATAAAATTTCTAGGAAGTTTTTT 1870
S288c long         1770      1780      1790      1800      1810      1820      1830      1840      1850      1860      1870
SKQ2n long
```

```
              AAAAAAATCATAAAAAGATAAACGTTAAAATTCAAACACAATAGTTGTTCGCTATATTCGTCACACTGCACGAACGCCTTA 1950
              AAAAAAATCATAAAAAGATAAACGTTAAAATTCAAACACAATAGTTGTTCGCTATATTCGTCACACTGCACGAACGCCTTA 1950
S288c long         1880      1890      1900      1910      1920      1930      1940      1950
SKQ2n long
```

GENE EXPRESSION TECHNIQUE

CROSS-REFERENCE TO RELATED APPLICATIONS

This application is a 35 U.S.C. 371 national application of PCT/GB2005/005085 filed Dec. 23, 2005. which is a continuation-in-part of PCT/GB2004/005435 and PCT/GB2004/005462 both filed Dec. 23, 2004, which respectively claim priority to UK application nos. 0329722.3 and 0329681.1 both filed on Dec. 23, 2003, the contents of which are fully incorporated herein by reference.

FIELD OF THE INVENTION

The present application relates to gene expression techniques.

BACKGROUND OF THE INVENTION

The listing or discussion of a prior-published document in this specification should not necessarily be taken as an acknowledgement that the document is part of the state of the art or is common general knowledge.

The class of proteins known as chaperones has been defined by Hartl (1996, Nature, 381, 571-580) as a protein that binds to and stabilises an otherwise unstable conformer of another protein and, by controlled binding and release, facilitates its correct fate in vivo, be it folding, oligomeric assembly, transport to a particular subcellular compartment, or disposal by degradation.

BiP (also known as GRP78, Ig heavy chain binding protein and Kar2p in yeast) is an abundant ~70 kDa chaperone of the hsp 70 family, resident in the endoplasmic reticulum (ER), which amongst other functions, serves to assist in transport in the secretory system and fold proteins.

Protein disulphide isomerase (PDI) is a chaperone protein, resident in the ER that is involved in the catalysis of disulphide bond formation during the post-translational processing of proteins.

Studies of the secretion of both native and foreign proteins have shown that transit from the ER to the Golgi is the rate-limiting step. Evidence points to a transient association of the BiP with normal proteins and a more stable interaction with mutant or misfolded forms of a protein. As a result, BiP may play a dual role in solubilising folding precursors and preventing the transport of unfolded and unassembled proteins. Robinson and Wittrup, 1995, Biotechnol. Prog. 11. 171-177, have examined the effect of foreign protein secretion on BiP (Kar2p) and PDI protein levels in Saccharomyces cerevisiae and found that prolonged constitutive expression of foreign secreted proteins reduces soluble BiP and PDI to levels undetectable by Western analysis. The lowering of ER chaperone and foldase levels as a consequence of heterologous protein secretion has important implications for attempts to improve yeast expression/secretion systems.

Expression of chaperones is regulated by a number of mechanisms, including the unfolded protein response (UPR).

Using recombinant techniques, multiple PDI gene copies have been shown to increase PDI protein levels in a host cell (Farquhar et al, 1991, Gene, 108, 81-89).

Co-expression of the gene encoding PDT and a gene encoding a heterologous disulphide-bonded protein was first suggested in WO 93/25676, published on 23 Dec. 1993, as a means of increasing the production of the heterologous protein. WO 93/25676 reports that the recombinant expression of antistasin and tick anticoagulant protein can be increased by co-expression with PDI.

This strategy has been exploited to increase the recombinant expression of other types of protein.

Robinson et al, 1994, Bio/Technology, 12, 381-384 reported that a recombinant additional PDI gene copy in Saccharomyces cerevisiae could be used to increase the recombinant expression of human platelet derived growth factor (PDGF) B homodimer by ten-fold and Schizosacharomyces pombe acid phosphatase by four-fold.

Hayano et al, 1995, FEBS Letters, 377, 505-511 described the co-expression of human lysozyme and PDI in yeast. Increases of around 30-60% in functional lysozyme production and secretion were observed.

Shusta et al, 1998, Nature Biotechnology, 16, 773-777 reported that the recombinant expression of single-chain antibody fragments (scFv) in Saccharomyces cerevisiae could be increased by between 2-8 fold by, over-expressing PDI in the host cell.

Bao & Fukuhara, 2001, Gene, 272, 103-110 reported that the expression and secretion of recombinant human serum albumin (rHSA) in the yeast Kluyveromyces lactis could be increased by 15-fold or more by co-expression with an additional recombinant copy of the yeast PDI gene (KlPDI1).

In order to produce co-transformed yeast comprising both a PDI gene and a gene for a heterologous protein, WO 93/25676 taught that the two genes could be chromosomally integrated; one could be chromosomally integrated and one present on a plasmid; each gene could be introduced on a different plasmid; or both genes could be introduced on the same plasmid. WO 93/25676 exemplified expression of antistasin from the plasmid pKH4α2 in yeast strains having a chromosomally integrated additional copy of a PDI gene (Examples 16 and 17); expression of antistasin from the vector K911 with an additional PDI gene copy being present on a multicopy yeast shuttle vector named YEp24 (Botstein et al, 1979, Gene, 8, 17-24) (Example 20); and expression of both the antistasin and the PDI genes from the yeast shuttle vector pC1/1 (Rosenberg et al, 1984,. Nature, 312, 77-80) under control of the GAL10 and GAL1 promoters, respectively. Indeed, Robinson and Wittrup, 1995, op. cit., also used the GAL1-GAL10 intergenic region to express erythropoietin and concluded that production yeast strains for the secretion of heterologous proteins should be constructed using tightly repressible, inducible promoters, otherwise the negative effects of sustained secretion (i.e. lowered detectable BiP and PDI) would be dominant after the many generations of cell growth required to fill a large-scale fermenter.

Subsequent work in the field has identified chromosomal integration of transgenes as the key to maximising recombinant protein production.

Robinson et al, 1994, op. cit., obtained the observed increases in expression of PDGF and S. pombe acid phosphatase using an additional chromosomally integrated PDI gene copy. Robinson et al reported that attempts to use the multi-copy 2 μm expression vector to increase PDI protein levels had had a detrimental effect on heterologous protein secretion.

Hayano et al, 1995, op. cit. described the introduction of genes for human lysozyme and PDI into a yeast host each on a separate linearised integration vector, thereby to bring about chromosomal integration.

Shusta et al, 1998, op. cit., reported that in yeast systems, the choice between integration of a transgene into the host chromosome versus the use of episomal expression vectors can greatly affect secretion and, with reference to Parekh &

Wittrup, 1997, *Biotechnol. Prog.*, 13, 117-122, that stable integration of the scFv gene into the host chromosome using a δ integration vector was superior to the use of a 2 μm-based expression plasmid. Parekh & Wittrup, op. cit., had previously taught that the expression of bovine pancreatic trypsin inhibitor (BPTI) was increased by an order of magnitude using a δ integration vector rather than a 2 μm-based expression plasmid. The 2 μm-based expression plasmid was said to be counter-productive for the production of heterologous secreted protein.

Bao & Fukuhara, 2001, op. cit., reported that "It was first thought that the KlPDI1 gene might be directly introduced into the multi-copy vector that carried the rHSA expression cassette. However, such constructs were found to severely affect yeast growth and plasmid stability. This confirmed our previous finding that the KlPDI1 gene on a multi-copy vector was detrimental to growth of *K. lactis* cells (Bao et al, 2000)". Bao et al, 2000, *Yeast*, 16, 329-341, as referred to in the above-quoted passage of Bao & Fukuhara, reported that the KlPDI1 gene had been introduced into *K. lactis* on a multi-copy plasmid, pKan707, and that the presence of the plasmid caused the strain to grow poorly. Bao et al concluded that over-expression of the KlPDI1 gene was toxic to *K. lactis* cells. In the light of the earlier findings in Bao et al, Bao & Fukuhara chose to introduce a single duplication of KlPDI1 on the host chromosome.

Against this background, we had previously surprisingly demonstrated that, contrary to the suggestions in the prior art, when the genes for a chaperone protein and a heterologous protein are co-expressed on a 2 μm-family multi-copy plasmid in yeast, the production of the heterologous protein is substantially increased.

Our earlier application, which has been published as WO 2005/061718, from which this application claims priority, disclosed a method for producing heterologous protein comprising:
(a) providing a host cell comprising a 2 μm-family plasmid, the plasmid comprising a gene encoding a protein comprising the sequence of a chaperone protein and a gene encoding a heterologous protein;
(b) culturing the host cell in a culture medium under conditions that allow the expression of the gene encoding the chaperone protein and the gene encoding a heterologous protein;
(c) purifying the thus expressed heterologous protein from the culture medium; and
(d) optionally, lyophilising the thus purified protein.

As discussed above, Bao et al, 2000, *Yeast*, 16, 329-341 reported that over-expression of the *K. lactis* PDI gene KlPDI1 was toxic to *K. lactis* cells. Against this background we have surprisingly found that, not only is it possible to over-express PDI and other chaperones without the detrimental effects reported in Bao et al, but that two different chaperones can be recombinantly over-expressed in the same cell and, rather than being toxic, can increase the expression of proteins, including heterologous proteins, to levels higher than the levels obtained by individual expression of either of the chaperones. This was not expected. On the contrary, in light of the teaching of Bao et al, one would think that over-expression of two chaperones would be even more toxic than the over-expression of one. Moreover, in light of some initial findings which are also reported below in the present application, it was expected that the increases in heterologous protein expression obtained by co-expression with a single chaperone would be at the maximum level possible for the cell system used. Therefore, it was particularly surprising to find that yet further increases in protein expression could be obtained by co-expression of two different chaperones with the protein.

SUMMARY OF THE INVENTION

Accordingly, as a first aspect of the present invention there is provided a method for producing a desired protein, such as a heterologous protein, comprising providing a host cell comprising a first recombinant gene encoding a protein comprising the sequence of a first chaperone protein, a second recombinant gene encoding a protein comprising the sequence of a second chaperone protein and a third gene (optionally the third gene being recombinant) encoding the desired protein (optionally a heterologous protein), wherein the first and second chaperones are different; and culturing the host cell in a culture medium under conditions that allow the expression of the first, second and third genes.

Optionally the thus expressed desired protein may, or may not, be purified from the cultured host cell or the culture medium.

Optionally, the thus purified desired protein may, or may not, be lyophilised.

The method may, or may not, further comprise the step of formulating the purified desired protein with a carrier or diluent and optionally presenting the thus formulated protein in a unit dosage form, in the manner discussed above.

The term "recombinant gene" includes nucleic acid sequences that operate independently as "stand alone" expressible sequences to produce an encoded protein or, in the alternative, nucleic acid sequences introduced that operate in combination with endogenous sequences (such as by integration into an endogenous sequence so as to produce a nucleic acid sequence that is different to the endogenous sequence) within the host to cause increased expression of a target protein.

A "recombinant gene" is typically a gene that is not naturally found in the context used. For example, a gene that is integrated, at an integration site, into the chromosome of a host organism can be said to be a "recombinant gene" if it comprises a sequence that does not naturally occur at the integration site. Thus, the "recombinant gene" may, or may not, comprise a non-natural sequence in the coding, regulatory or any other region of the gene, or may, or may not, comprise the sequence of a naturally occurring gene but be introduced into the chromosome of a host organism at an integration site at which that sequence does not naturally occur. The same issues apply, *mutatis mutandis*, to the insertion of a "recombinant gene" into a plasmid.

The terms "chromosomally integrated" and "integrated into the chromosome of the host cell" are well recognised terms of the art. For avoidance of doubt, these terms include the integration of polynucleotide sequences in any inheritable nuclear material that naturally occurs in a host cell, other than for naturally occurring plasmids. Thus, a poly,nucleotide sequence that is "integrated into the chromosome of the host cell" may, or may not, be integrated into the chromosome of a procaryotic (such as a bacterial) cell, or into any part of the genome of a eucaryotic cell, such as into nuclear genetic material including the chromosome (or, one of the chromosomes), the mitochondrial genome or the chloroplast genome.

The first and second chaperones may, or may not, each individually, be one of the specifically listed chaperones as discussed below, and are a combination of chaperones that, when co-expressed in the same host cell, provide at least an additive effect to the increase in expression of the desired protein. By "additive effect" we mean that the level of expression of the desired protein in the host cell is higher when the first and second recombinant genes are simultaneously co-expressed with the third gene as compared to the same system wherein (i) the first recombinant gene is co-expressed with the third gene in the absence of the expression of the second recombinant gene and (ii) the second recombinant gene is co-expressed with the third gene in the absence of the expression of the first recombinant gene.

The term "chaperone" as used herein refers to a protein that binds to and stabilises an otherwise unstable conformer of another protein, and by controlled binding and release, facilitates its correct fate in vivo, be it folding, oligomeric assembly, transport to a particular subcellular compartment, or disposal by degradation. Accordingly a chaperone is also a protein that is involved in protein folding, or which has chaperone activity or is involved in the unfolded protein response. Chaperone proteins of this type are known in the art, see for example the Stanford Genome Database (SGD), which can be found on the world wide web at www.yeastgenome.org. Preferred chaperones are eucaryotic chaperones, especially preferred chaperones are yeast chaperones, including AHA1, CCT2, CCT3, CCT4, CCT5, CCT6, CCT7, CCT8, CNS1, CPR3, CPR6, ERO1, EUG1, FMO1, HCH1, HSP10, HSP12, HSP104, HSP26, HSP30, HSP42, HSP60, HSP78, HSP82, JEM1, MDJ1, MDJ2, MPD1, MPD2, PDI1, PFD1, ABC1, APJ1, ATP11, ATP12, BTT1, CDC37, CPR7, HSC82, KAR2, LHS1, MGE1, MRS11, NOB1, ECM10, SSA1, SSA2, SSA3, SSA4, SSC1, SSE2, SIL1, SLS1, ORM1, ORM2, PER1, PTC2, PSE1, UBI4 and HAC1 or a truncated intronless HAC1 (Valkonen et al. 2003, Applied Environ. Micro., 69, 2065), as well as TIM9, PAM18 (also known as TIM14) and TCP1 (also known as CCT1).

A chaperone useful in the practice of the present invention may, or may not, be:
- a heat shock protein, such as a protein that is a member of the hsp70 family of proteins (including Kar2p, SSA and SSB proteins, for example proteins encoded by SSA1, SSA2, SSA3, SSA4, SSB1 and SSB2), a protein that is a member of the HSP90-family, or a protein that is a member of the HSP40-family or proteins involved in their modulation (e.g. Sil1p), including DNA-J and DNA-J-like proteins (e.g. Jem1p, Mdj2p);
- a protein that is a member of the karyopherin/importin family of proteins, such as the alpha or beta families of karyopherin/importin proteins, for example the karyopherin beta protein PSE1;
- a protein that is a member of the ORMDL family described by Hjelmqvist et al, 2002, Genome Biology, 3(6), research0027.1-0027.16, such as Orm2p.
- a protein that is naturally located in the endoplasmic reticulum or elsewhere in the secretory pathway, such as the golgi. For example, a protein that naturally acts in the lumen of the endoplasmic reticulum (ER), particularly in secretory cells such as PDI
- a protein that is transmembrane protein anchored in the ER, such as a member of the ORMDL family described by Hjelmqvist et al, 2002, supra, (for example, Orm2p);
- a protein that acts in the cytosol, such as the hsp70 proteins, including SSA and SSB proteins, for example protein production SSA1, SSA2, SSA3, SSA4, SSB1 and SSB2;
- a protein that acts in the nucleus, the nuclear envelope and/or the cytoplasm, such as Pse1p;
- a protein that is "essential" to the viability of the cell, such as PDI, or a protein encoded by one of the following genes: CCT2, CCT3, CCT4, CCT5, CCT6, CCT7, CCT8, CNS1, ERO1, HSP10, HSP60, PDI1, CDC37, KAR2, MGE1, MRS11, NOB1, SSC1, TIM9, PAM18 and TCP1, or a protein that is an essential karyopherin protein, such as Pse1p;
- a protein that is involved in sulphydryl oxidation or disulphide bond formation, breakage or isomerization, or a protein that catalyses thiol:disulphide interchange reactions in proteins, particularly during the biosynthesis of secretory and cell surface proteins, such as protein disulphide isomerases (e.g. Pdi1p, Mpd1p), homologues (e.g. Eug1p) and/or related proteins (e.g. Mpd2p, Fmo1p, Ero1p):
- a protein that is involved in protein synthesis, assembly or folding, such as PDI and Ssa1p;
- a protein that binds preferentially or exclusively to unfolded, rather than mature protein, such as the hsp70 proteins, including SSA and SSB proteins, for example proteins encoded by SSA1, SSA2, SSA3, SSA4, SSB1 and SSB2;
- a protein that prevents aggregation of precursor proteins in the cytosol, such as the hsp70 proteins, including SSA and SSB proteins, for example proteins encoded by SSA1, SSA2, SSA3, SSA4, SSB1 and SSB2;
- a protein that binds to and stabilises damaged proteins, for example Ssa1p;
- a protein that is involved in the unfolded protein response or provides for increased resistance to agents (such as tunicamycin and dithiothreitol) that induce the unfolded protein response, such as a member of the ORMDL family described by Hjelmqvist et al, 2002, supra (for example, Orm2p) or proteins involved in the response to stress (e.g. Ubi4p);
- a protein that is a co-chaperone and/or a protein indirectly involved in protein folding and/or the unfolded protein response (e.g. hsp104p, Mdj1p);
- a protein that is involved in the nucleocytoplasmic transport of macromolecules, such as Pse1p;
- a protein that mediates the transport of macromolecules across the nuclear membrane by recognising nuclear location sequences and nuclear export sequences and interacting with the nuclear pore complex, such as PSE1;
- a protein that is able to reactivate ribonuclease activity against RNA of scrambled ribonuclease as described in as described in EP 0 746 611 and Hillson et al, 1984, Methods Enzymol., 107, 281-292, such as PDI;
- a protein that has an acidic pI (for example, 4.0-4.5), such as PDI;
- a protein that is a member of the Hsp70 family, and optionally possesses an N-terminal ATP-binding domain and a C-terminal peptide-binding domain, such as Ssa1p.
- a protein that is a peptidyl-prolyl cis-trans isomerases (e.g. Cpr3p, Cpr6p);
- a protein that is a homologue of known chaperones (e.g. Hsp10p);
- a protein that is a mitochondrial chaperone (e.g. Cpr3p);
- a protein that is a cytoplasmic or nuclear chaperone (e.g. Cns1p);
- a protein that is a membrane-bound chaperone (e.g. Orm2p, Fmo1p);
- a protein that has chaperone activator activity or chaperone regulatory activity (e.g. Aha1p, Hac1p, Hch1p);
- a protein that transiently binds to polypeptides in their immature form to cause proper folding transportation and/or secretion, including proteins required for efficient translocation into the endoplasmic reticulum (e.g. Lhs1p) or their site of action within the cell (e.g. Pse1p);

a protein that is a involved in protein complex assembly and/or ribosome assembly (e.g. Atp11p, Pse1p, Nob1p);
a protein of the chaperonin T-complex (e.g. Cct2p);
a protein of the prefoldin complex (e.g. Pfd1p);
a mitochondrial intermembrane space protein such as Tim9p;
a protein that can form a complex, in vivo, with Mrs11p/Tim10p, such as Tim9p;
a protein that is involved in the mediation of import and insertion of polytopic inner membrane proteins, such as Tim9p;
a protein that can prevent the aggregation of incoming proteins, such as Tim9p;
a protein that can be a functional constituent of the mitochondrial import motor associated with presequence translocase (along with Ssc1p, Tim44p, Mge1p and Pam16p) such as Pam18p;
a protein that can stimulate the ATPase activity of Ssc1p, such as to drive mitochondrial import, such as Pam18p;
a protein that contains a J domain, such as Pam18p;
a protein that can act as an alpha subunit of chaperonin-containing T-complex, which mediates protein folding in the cytosol, such as Tcp1p;
a protein that can play a role in the in maintenance of an actin cytoskeleton, such as Tcp1p; or
a protein that is, or is a homolog to, a *Drosophila melanogaster* or mouse tailless complex polypeptide, such as Tcp1p.

A preferred chaperone is protein disulphide isomerase (PDI) or a fragment or variant thereof having an equivalent ability to catalyse the formation of disulphide bonds within the lumen of the endoplasmic reticulum (ER). By "PDI" we include any protein having the ability to reactivate the ribonuclease activity against RNA of scrambled ribonuclease as described in EP 0 746 611 and Hillson et al, 1984, *Methods Enzymol.,* 107, 281-292.

PDI is an enzyme which typically catalyzes thiol:disulphide interchange reactions, and is a major resident protein component of the ER lumen in secretory cells. A body of evidence suggests that it plays a role in secretory protein biosynthesis (Freedman, 1984, *Trends Biochem. Sci.,* 9, 438-41) and this is supported by direct cross-linking studies in situ (Roth and Pierce, 1987, *Biochemistry,* 26, 4179-82). The finding that microsomal membranes deficient in PDI show a specific defect in cotranslational protein disulphide (Bulleid and Freedman, 1988, *Nature,* 335, 649-51) implies that the enzyme functions as a catalyst of native disulphide bond formation during the biosynthesis of secretory and cell surface proteins. This role is consistent with what is known of the enzyme's catalytic properties in vitro; it catalyzes thiol: disulphide interchange reactions leading to net protein disulphide formation, breakage or isomerization, and can typically catalyze protein folding and the formation of native disulphide bonds in a wide variety of reduced, unfolded protein substrates (Freedman et al., 1989, *Biochem. Soc. Symp.,* 55, 167-192). PDI also functions as a chaperone since mutant PDI lacking isomerase activity accelerates protein folding (Hayano et al, 1995, *FEBS Letters,* 377, 505-511). Recently, sulphydryl oxidation, not disulphide isomerisation was reported to be the principal function of Protein Disulphide Isomerase in *S. cerevisiae* (Solovyov et al., 2004, *J. Biol. Chem.,* 279 (33) 34095-34100). The DNA and amino acid sequence of the enzyme is known for several species (Scherens et al, 1991, *Yeast,* 7, 185-193; Farquhar et al, 1991, *Gene,* 108, 81-89; EP074661; EP0293793; EP0509841) and there is increasing information on the mechanism of action of the enzyme purified to homogeneity from mammalian liver (Creighton et al, 1980, *J. Mol. Biol.,* 142, 43-62; Freedman et al, 1988, *Biochem. Soc. Trans.,* 16, 96-9; Gilbert, 1989, *Biochemistry,* 28, 7298-7305; Lundstrom and Holmgren, 1990, *J. Biol. Chem.,* 265, 9114-9120; Hawkins and Freedman, 1990, *Biochem. J.,* 275, 335-339). Of the many protein factors currently implicated as mediators of protein folding, assembly and translocation in the cell (Rothman, 1989, *Cell,* 59, 591-601), PDI has a well-defined catalytic activity.

The deletion or inactivation of the endogenous PDI gene in a host results in the production of an inviable host. In other words, the endogenous PDI gene is an "essential" gene.

PDI is readily isolated from mammalian tissues and the homogeneous enzyme is a homodimer (2×57 kD) with characteristically acidic pI (4.0-4.5) (Hillson et al, 1984, op. cit.). The enzyme has also been purified from wheat and from the alga *Chlamydomonas reinhardii* (Kaska et al, 1990, *Biochem. J.,* 268, 63-68), rat (Edman et al, 1985, *Nature,* 317, 267-270), bovine (Yamauchi et al, 1987, *Biochem. Biophys. Res. Comm.,* 146, 1485-1492), human (Pihlajaniemi et al, 1987, *EMBO J.,* 6, 643-9), yeast (Scherens et al, supra; Farquhar et al, op. cit.) and chick (Parkkonen et al, 1988, *Biochem. J.,* 256, 1005-1011). The proteins from these vertebrate species show a high degree of sequence conservation throughout and all show several overall features first noted in the rat PDI sequence (Edman et al., 1985, op. cit.).

Preferred PDI sequences include those from humans and those from yeast species, such as *S. cerevisiae*.

A yeast protein disulphide isomerase precursor, PDI1, can be found as Genbank accession no. CAA42373 or BAA00723 and has a sequence of 522 amino acids as described in WO 2005/061718, the contents of which are incorporated herein by reference.

An alternative yeast protein disulphide isomerase sequence can be found as Genbank accession no. CAA38402, which has a sequence of 530 amino acids as described in WO 2005/061718, the contents of which are incorporated herein by reference.

The alignment of these sequences (the sequence of Genbank accession no. CAA42373 or BAA00723 first, the sequence of Genbank accession no. CAA38402 second) in WO 2005/061718, the contents of which are incorporated herein by reference, shows that the differences between these two sequences are a single amino acid difference at position 114 (highlighted in bold) and that the sequence defined by Genbank accession no. CAA38402 contains the additional amino acids EADAEAEA at positions 506-513.

Variants and fragments of the above PDI sequences, and variants of other naturally occurring PDI sequences are also included in the present invention. A "variant", in the context of PDI, refers to a protein wherein at one or more positions there have been amino acid insertions, deletions, or substitutions, either conservative or non-conservative, provided that such changes result in a protein whose basic properties, for example enzymatic activity (type of and specific activity), thermostability, activity in a certain pH-range (pH-stability) have not significantly been changed. "Significantly" in this context means that one skilled in the art would say that the properties of the variant may, or may not, still be different but would not be unobvious over the ones of the original protein.

By "conservative substitutions" is intended combinations such as Val, Ile, Leu, Ala, Met; Asp, Glu; Asn, Gln; Ser, Thr, Gly, Ala; Lys, Arg, His; and Phe, Tyr, Trp. Preferred conservative substitutions include Gly, Ala; Val, Ile, Leu; Asp, Glu; Asn, Gln; Ser, Thr; Lys, Arg; and Phe, Tyr.

A "variant" typically has at least 25%, at least 50%, at least 60% or at least 70%, preferably at least 80%, more preferably at least 90%, even more preferably at least 95%, yet more preferably at least 99%, most preferably at least 99.5% sequence identity to the polypeptide from which it is derived.

The percent sequence identity between two polypeptides may be determined using suitable computer programs, as discussed below. Such variants may, or may not, be natural or made using the methods of protein engineering and site-directed mutagenesis as are well known in the art.

A "fragment", in the context of PDI, refers to a protein wherein at one or more positions there have been deletions. Thus the fragment may, or may not, comprise at most 5, 10, 20, 30, 40 or 50%, typically up to 60%, more typically up to 70%, preferably up to 80%, more preferably up to 90%, even more preferably up to 95%, yet more preferably up to 99% of the complete sequence of the full mature PDI protein. Particularly preferred fragments of PDI protein comprise one or more whole domains of the desired protein.

A fragment or variant of PDI may, or may not, be a protein that, when expressed recombinantly in a host cell, can complement the deletion of the endogenously encoded PDI gene in the host cell, such as *S. cerevisiae*, and may, or may not, for example, be a naturally occurring homolog of PDI, such as a homolog encoded by another organism, such as another yeast or other fungi, or another eucaryote such as a human or other vertebrate, or animal or by a plant.

Where the first chaperone is PDI, particularly mammalian or yeast PDI, then in one embodiment the second chaperone is not an hsp70 chaperone protein (such as yeast KAR2, HSP70, BiP, SSA1-4, SSB1, SSC1, SSD1 or a eucaryotic hsp70 protein such as HSP68, HSP72, HSP73, HSC70, clathrin uncoating ATPase, IgG heavy chain binding protein (BiP), glucose-regulated proteins 75, 78 and 80 (GPR75, GRP78 and GRP80) and the like). Specifically in one embodiment the first chaperone is not yeast PDI when the second chaperone is yeast KAR2.

Specifically in another embodiment the first chaperone is not mammalian PDI when the second chaperone is mammalian BiP.

Alternatively, where the first and second chaperones are, for example, PDI, particularly mammalian or yeast PDI, and an hsp70 chaperone protein as described above, respectively, then the desired protein may be a heterologous protein that may or may not be a protein selected from— mammalian gene products such as enzymes, cytokines, growth factors, hormones, vaccines, antibodies and the like; erythropoietin, insulin, somatotropin, growth hormone releasing factor, platelet derived growth factor, epidermal growth factor, transforming growth factor α, transforming growth factor β, epidermal growth factor, fibroblast growth factor, nerve growth factor, insulin-like growth factor I, insulin-like growth factor II, clotting Factor VIII, superoxide dismutase, α-interferon, γ-interferon, interleukin-1, interleukin-2, interleukin-3, interleukin-4, interleukin-5, interleukin-6, granulocyte colony stimulating factor, multi-lineage colony stimulating activity, granulocyte-macrophage stimulating factor, macrophage colony stimulating factor, T cell growth factor, lymphotoxin and the like; or human gene products;

any gene product which can be used as a vaccine, including any structural, membrane-associated, membrane-bound or secreted gene product of a mammalian pathogen, including viruses, bacteria, single-celled or multi-celled parasites which can infect or attack a mammal, in particular viruses such as human immunodeficiency virus (HIV), *R. rickettsii*, vaccinia, Shigella, poliovirus, adenovirus, influenza, hepatitis A, hepatitis B, dengue virus, Japanese B encephalitis, *Varicella zoster*, cytomegalovirus, hepatitis A, rotavirus, as well as vaccines against viral diseases like Lyme disease, measles, yellow fever, mumps, rabies, herpes, influenza, parainfluenza and the like; or bacteria such as *Vibrio cholerae, Salmonella typhi, Bordetella pertussis, Streptococcus pneumoniae, Hemophilus influenza, Clostridium tetani, Corynebacterium diphtheriae, Mycobactrium leprae, Neisseriaqonorrhoeae, Neisseriameningitidis, Coccidioides immitis* and the like.

Another preferred chaperone is a protein comprising the sequence of a protein encoded by the gene SSA1, or a fragment or variant thereof having an equivalent chaperone-like activity. SSA1, also known as YG100, is located on chromosome I of the *S. cerevisiae* genome and is 1.93-kbp in size.

One published protein sequence of the protein encoded by the gene SSA1 is as described in WO 2005/061718, the contents of which are incorporated herein by reference.

A published coding sequence for SSA1 is also described in WO 2005/061718, the contents of which are incorporated herein by reference, although it will be appreciated that the sequence can be modified by degenerate substitutions to obtain alternative nucleotide sequences which encode an identical protein product.

The protein Ssa1p belongs to the Hsp70 family of proteins and is resident in the cytosol. Hsp70s possess the ability to perform a number of chaperone activities; aiding protein synthesis, assembly and folding; mediating translocation of polypeptides to various intracellular locations, and resolution of protein aggregates (Becker & Craig, 1994, *Eur. J. Biochem.* 219, 11-23). Hsp70 genes are highly conserved, possessing an N-terminal ATP-binding domain and a C-terminal peptide-binding domain. Hsp70 proteins interact with the peptide backbone of, mainly unfolded, proteins. The binding and release of peptides by hsp70 proteins is an ATP-dependent process and accompanied by a conformational change in the hsp70 (Becker & Craig, 1994, supra).

Cytosolic hsp70 proteins are particularly involved in the synthesis, folding and secretion of proteins (Becker & Craig, 1994, supra). In *S. cerevisiae* cytosolic hsp70 proteins have been divided into two groups; SSA (SSA 1-4) and SSB (SSB 1 and 2) proteins, which are functionally distinct from each other. The SSA family is "essential" in that at least one protein from the group must be active to maintain cell viability (Becker & Craig, 1994, supra). Cytosolic hsp70 proteins bind preferentially to unfolded and not mature proteins. This suggests that they prevent the aggregation of precursor proteins, by maintaining them in an unfolded state prior to being assembled into multimolecular complexes in the cytosol and/or facilitating their translocation to various organelles (Becker & Craig, 1994, supra). SSA proteins are particularly involved in posttranslational biogenesis and maintenance of precursors for translocation into the endoplasmic reticulum and mitochondria (Kim et al., 1998, *Proc. Natl. Acad. Sci. USA.* 95, 12860-12865; Ngosuwan et al., 2003, *J. Biol. Chem.* 278 (9), 7034-7042). Ssa1p has been shown to bind damaged proteins, stabilising them in a partially unfolded form and allowing refolding or degradation to occur (Becker & Craig, 1994, supra; Glover & Lindquist, 1998, *Cell.* 94, 73-82).

Demolder et al, 1994, *J. Biotechnol.*, 32, 179-189 reported that over-expression of SSA1 in yeast provided for increases in the expression of a recombinant chromosomally integrated gene encoding human interferon-δ. There is no suggestion that increases in heterologous gene expression could be achieved if SSA1 and human interferon-β were to be encoded by recombinant genes on the same plasmid. In fact, in light of more recent developments in the field of over-expression of chaperones in yeast (e.g. Robinson et al, 1994, op. cit.; Hayano et al, 1995, op. cit.; Shusta et al, 1998, op. cit; Parekh & Wittrup, 1997, op. cit.; Bao & Fukuhara, 2001, op. cit.; and Bao et al, 2000, op. cit) the skilled person would have been disinclined to express SSA1 from a 2 μm-family plasmid at all, much less to express both SSA1 and a heterologous protein from a 2 μm-family plasmid in order to increase the expression levels of a heterologous protein.

Variants and fragments of is a protein comprising the sequence of a protein encoded by the gene SSA1 are also included in the present invention. A "variant", in the context of a protein encoded by the gene SSA1, refers to a protein having the sequence of native Ssa1p other than at one or more positions where there have been amino acid insertions, deletions, or substitutions, either conservative or non-conservative, provided that such changes result in a protein whose basic properties, for example enzymatic activity (type of and specific activity), thermostability, activity in a certain pH-range (pH-stability) have not significantly been changed. "Significantly" in this context means that one skilled in the art would say that the properties of the variant may still be different but would not be unobvious over the ones of the original protein.

By "conservative substitutions" is intended combinations such as Val, Ile, Leu, Ala, Met; Asp, Glu; Asn, Gln; Ser, Thr; Gly, Ala; Lys, Arg, His; and Phe, Tyr, Trp. Preferred conservative substitutions include Gly, Ala; Val, Ile, Leu; Asp, Glu; Asn, Gln; Ser, Thr; Lys, Arg; and Phe, Tyr.

A "variant" of Ssa1p typically has at least 25%, at least 50%, at least 60% or at least 70%, preferably at least 80%, more preferably at least 90%, even more preferably at least 95%, yet more preferably at least 99%, most preferably at least 99.5% sequence identity to the sequence of native Ssa1p.

The percent sequence identity between two polypeptides may be determined using suitable computer programs, as discussed below. Such variants may, or may not, be natural or made using the methods of protein engineering and site-directed mutagenesis as are well known in the art.

A "fragment", in the context of Ssa1p, refers to a protein having the sequence of native Ssa1p other than for at one or more positions where there have been deletions. Thus the fragment may, or may not, comprise at most 5, 10, 20, 30, 40 or 50%, typically up to 60%, more typically up to 70%, preferably up to 80%, more preferably up to 90%, even more preferably up to 95%, yet more preferably up to 99% of the complete sequence of the full mature Ssa1p protein. Particularly preferred fragments of SSA1 protein comprise one or more whole domains of the desired protein.

A fragment or variant of Ssa1p may, or may not, be a protein that, when expressed recombinantly in a host cell, such as S. cerevisiae, can complement the deletion of the endogenously encoded SSA1 gene (or homolog thereof) in the host cell and may, or may not, for example, be a naturally occurring homolog of Ssa1p, such as a homolog encoded by another organism, such as another yeast or other fungi, or another eucaryote such as a human or other vertebrate, or animal or by a plant.

Another preferred chaperone is protein comprising the sequence of a protein encoded by the PSE1 gene, or a fragment or variant thereof having equivalent chaperone-like activity.

PSE1, also known as KAP121, is an essential gene, located on chromosome XIII.

A published protein sequence for the protein Pse1p is as described in WO 2005/061718, the contents of which are incorporated herein by reference.

A published nucleotide coding sequence of PSE1 is also described in WO 2005/061718, the contents of which are incorporated herein by reference, although it will be appreciated that the sequence can be modified by degenerate substitutions to obtain alternative nucleotide sequences which encode an identical protein product.

The PSE1 gene is 3.25-kbp in size. Pse1p is involved in the nucleocytoplasmic transport of macromolecules (Seedorf & Silver, 1997, Proc. Natl. Acad. Sci. USA. 94, 8590-8595). This process occurs via the nuclear pore complex (NPC) embedded in the nuclear envelope and made up of nucleoporins (Ryan & Wente, 2000. Curr. Opin. Cell Biol. 12, 361-371). Proteins possess specific sequences that contain the information required for nuclear import, nuclear localisation sequence (NLS) and export, nuclear export sequence (NES) (Pemberton et al., 1998, Curr. Opin. Cell Biol. 10, 392-399). Pse1p is a karyopherin/importin, a group of proteins, which have been divided up into α and β families. Karyopherins are soluble transport factors that mediate the transport of macromolecules across the nuclear membrane by recognising NLS and NES, and interact with and the NPC (Seedorf & Silver 1997, supra; Pemberton et al;, 1998, supra; Ryan & Wente, 2000, supra). Translocation through the nuclear pore is driven by GTP hydrolysis, catalysed by the small GTP-binding protein, Ran (Seedorf & Silver, 1997, supra). Pse1p has been identified as a karyopherin β. 14 karyopherin β proteins have been identified in S. cerevisiae, of which only 4 are "essential". This is perhaps because multiple karyopherins may mediate the transport of a single macromolecule (Isoyama et al., 2001, J. Biol. Chem. 276 (24), 21863-21869). Pse1p is localised to the nucleus, at the nuclear envelope, and to a certain extent to the cytoplasm. This suggests the protein moves in and out of the nucleus as part of its transport function (Seedorf & Silver, 1997, supra). Pse1p is involved in the nuclear import of transcription factors (Isoyama et al., 2001, supra; Ueta et al., 2003, J. Biol. Chem. 278 (50), 50120-50127), histones (Mosammaparast et al., 2002, J. Biol. Chem. 277 (1), 862-868), and ribosomal proteins prior to their assembly into ribosomes (Pemberton et al., 1998, supra). It also mediates the export of mRNA from the nucleus. Karyopherins recognise and bind distinct NES found on RNA-binding proteins, which coat the RNA before it is exported from the nucleus (Seedorf & Silver, 1997, Pemberton et al., 1998, supra).

As nucleocytoplasmic transport of macromolecules is essential for proper progression through the cell cycle, nuclear transport factors, such as Pse1p are novel candidate targets for growth control (Seedorf & Silver, 1997, supra).

Overexpression of Pse1p (protein secretion enhancer) in S. cerevisiae has also been shown to increase endogenous protein secretion levels of a repertoire of biologically active proteins (Chow et al., 1992; J. Cell. Sci. 101 (3), 709-719). There is no suggestion that increases in heterologous gene expression could be achieved if Pse1p and a heterologous protein were both to be encoded by recombinant genes on the same plasmid. In fact, in light of more recent developments in the over-expression of chaperones in yeast (e.g. Robinson et al, 1994, op. cit.; Hayano et al, 1995, op. cit. Shusta et al, 1998, op. cit; Parekh & Wittrup, 1997, op. cit.; Bao & Fukuhara, 2001, op. cit.; and Bao et al, 2000, op. cit) the skilled person would not have attempted to over-express a PSE1 gene from a 2 μm-family plasmid at all, much less to express both Pse1p and a heterologous protein from a 2 μm-family plasmid in order to increase the expression levels of a heterologous protein.

Variants and fragments of Pse1p are also included in the present invention. A "variant", in the context of Pse1p, refers to a protein having the sequence of native Pse1p other than for at one or more positions where there have been amino acid insertions, deletions, or substitutions, either conservative or non-conservative, provided that such changes result in a protein whose basic properties, for example: enzymatic activity (type of and specific activity), thermostability, activity in a certain pH-range (pH-stability) have not significantly been changed. "Significantly" in this context means that one skilled in the art would say that the properties of the variant may still be different but would not be unobvious over the ones of the original protein.

By "conservative substitutions" is intended combinations such as Val, Ile, Leu, Ala, Met; Asp, Glu; Asn, Gln; Ser, Thr, Gly, Ala; Lys, Arg, His; and Phe, Tyr, Trp. Preferred conservative substitutions include Gly, Ala; Val, Ile, Leu; Asp, Glu; Asn, Gln; Ser, Thr; Lys, Arg; and Phe, Tyr.

A "variant" of Pse1p typically has at least 25%. at least 50%, at least 60% or at least 70%, preferably at least 80%, more preferably at least 90%, even more preferably at least 95%, yet more preferably at least 99%, most preferably at least 99.5% sequence identity, to the sequence of native Pse1p.

The percent sequence identity between two polypeptides may be determined using suitable computer programs, as discussed below. Such variants may, or may not, be natural or made using the methods of protein engineering and site-directed mutagenesis as are well known in the art.

A "fragment", in the context of Pse1p, refers to a protein having the sequence of native Pse1p other than for at one or more positions where there have been deletions. Thus the fragment may, or may not, comprise at most 5, 10, 20, 30, 40 or 50%, typically up to 60%, more typically up to 70%, preferably up to 80%, more preferably up to 90%, even more preferably up to 95%, yet more preferably up to 99% of the complete sequence of the full mature Pse1p protein. Particularly preferred fragments of Pse1p protein comprise one or more whole domains of the desired protein.

A fragment or variant of Pse1p may, or may not, be a protein that, when expressed recombinantly in a host cell, such as S. cerevisiae, can complement the deletion of the endogenous PSE1 gene in the host cell and may, or may not, for example, be a naturally occurring homolog of Pse1p, such as a homolog encoded by another organism, such as another yeast or other fungi, or another eucaryote such as a human or other vertebrate, or animal or by a plant.

Another preferred chaperone is a protein comprising the sequence of a protein encoded by the ORM2 gene, or a fragment or variant thereof having equivalent chaperone-like activity.

ORM2, also known as YLR350W, is located on chromosome XII (positions 828729 to 829379) of the S. cerevisiae genome and encodes an evolutionary conserved protein with similarity to the yeast protein Orm1p. Hjelmqvist et al, 2002, *Genome Biology*, 3(6), research 0027.1-0027.16 reports that ORM2 belongs to gene family comprising three human genes (ORMDL1, ORMDL2 and ORMDL3) as well as homologs in microsporidia, plants, *Drosophila*, urochordates and vertebrates. The ORMDL genes are reported to encode transmembrane proteins anchored in the proteins endoplasmic reticulum (ER).

The protein Orm2p is required for resistance to agents that induce the unfolded protein response. Hjelmqvist et al, 2002 (supra) reported that a double knockout of the two S. cerevisiae ORMDL homologs (ORM1 and ORM2) leads to a decreased growth rate and greater sensitivity to tunicamycin and dithiothreitol.

One published sequence of Orm2p is as described in WO 2005/061718, the contents of which are incorporated herein by reference.

The above protein is encoded in S. cerevisiae by the coding nucleotide sequence also as described in WO 2005/061718, the contents of which are incorporated herein by reference, although it will be appreciated that the sequence can be modified by degenerate substitutions to obtain alternative nucleotide sequences which encode an identical protein product.

Variants and fragments of Orm2p are also included in the present invention. A "variant", in the context of Orm2p, refers to a protein having the sequence of native Orm2p other than for at one or more positions where there have been amino acid insertions, deletions, or substitutions, either conservative or non-conservative, provided that such changes result in a protein whose basic properties, for example enzymatic activity (type of and specific activity), thermostability, activity in a certain pH-range (pH-stability) have not significantly been changed. "Significantly" in this context means that one skilled in the art would say that the properties of the variant may still be different but would not be unobvious over the ones of the original protein.

By "conservative substitutions" is intended combinations such as Val, Ile, Leu, Ala, Met; Asp, Glu; Asn, Gln; Ser, Thr, Gly, Ala; Lys, Arg, His; and Phe, Tyr, Trp. Preferred conservative substitutions include Gly, Ala; Val, Ile, Leu; Asp, Glu; Asn, Gln; Ser, Thr; Lys, Arg; and Phe, Tyr.

A "variant" of Orm2p typically has at least 25%, at least 50%, at least 60% or at least 70%, preferably at least 80%, more preferably at least 90%, even more preferably at least 95%, yet more preferably at least 99%, most preferably at least 99.5% sequence identity to the sequence of native Orm2p.

The percent sequence identity between two polypeptides may be determined using suitable computer programs, as discussed below. Such variants may, or may not, be natural or made using the methods of protein engineering and site-directed mutagenesis as are well known in the art.

A "fragment", in the context of Orm2p, refers to a protein having the sequence of native Orm2p other than for at one or more positions where there have been deletions. Thus the fragment may, or may not, comprise at most 5, 10, 20, 30, 40 or 50%, typically up to 60%, more typically up to 70%, preferably up to 80%, more preferably up to 90%, even more preferably up to 95%, yet more preferably up to 99% of the complete sequence of the full mature Orm2p protein. Particularly preferred fragments of Orm2p protein comprise one or more whole domains of the desired protein.

A fragment or variant of Orm2p may, or may not, be a protein that, when expressed recombinantly in a host cell, such as S. cerevisiae, can complement the deletion of the endogenous ORM2 gene in the host cell and may, or may not, for example, be a naturally occurring homolog of Orm2p, such as a homolog encoded by another organism, such as another yeast or other fungi, or another eucaryote such as a human or other vertebrate, or animal or by a plant.

A gene encoding a protein comprising the sequence of a chaperone may, or may not, be formed in a like manner to that discussed below for genes encoding heterologous proteins, with particular emphasis on combinations of ORFs and regulatory regions.

Thus, one preferred chaperone is protein disulphide isomerase; another preferred chaperone is Orm2p or a fragment or variant thereof. In a particularly preferred embodiment, the first and second chaperones are protein disulphide isomerase and Orm2p or a fragment or variant thereof.

Further preferred combinations for the first and second chaperones, respectively, may, or may not, be encoded by the genes AHA1 and CCT2; AHA1 and CCT3; AHA1 and CCT4; AHA1 and CCT5; AHA1 and CCT6; AHA1 and CCT7; AHS1 and CCT8; AHA1 and CNS1; AHA1 and CPR3; AHA1 and CPR6; AHA1 and ERO1; AHA1 and EUG1; AHA1 and FMO1; AHA1 and HCH1; AHA1 and HSP10; AHA1 and HSP12; AHA1 and HSP104; AHA1 and HSP26; AHA1 and HSP30; AHA1 and HSP42; AHA1 and HSP60; AHA1 and HSP78; AHA1 and HSP82; AHA1 and JEM1; AHA1 and MDJ1; AHA1 and MDJ2; AHA1 and MPD1; AHA1 and MPD2; AHA1 and PDI1; AHA1 and PFD1; AHA1 and ABC1; AHA1 and APJ1; AHA1 and ATP11; AHA1 and ATP12; AHA1 and BTT1; AHA1 and CDC37; AHA1 and CPR7; AHA1 and HSC82; AHA1 and KAR2; AHA1 and LHS1; AHA1 and MGE1; AHA1 and MRS11; AHA1 and NOB1; AHA1 and ECM10; AHA1 and SSA1; AHA1 and SSA2; AHA1 and SSA3; AHA1 and SSA4; AHA1 and SSC1; AHA1 and SSE2; AHA1 and SIL1; AHA1 and SLS1; AHA1 and ORM1; AHA1 and ORM2; AHS1 and PER1; AHA1 and PTC2; AHA1 and PSE1; AHA1 and UBI4; AHA1 and HAC1 or a truncated intronless HAC1; CCT2 and CCT3; CCT2 and CCT4; CCT2 and CCT5; CCT2 and CCT6; CCT2 and CCT7; CCT2 and CCT8; CCT2 and CNS1; CCT2 and CPR3; CCT2 and CPR6; CCT2 and ERO1; CCT2 and EUG1; CCT2 and FMO1; CCT2 and HCH1; CCT2 and HSP10; CCT2 and HSP12; CCT2 and HSP104; CCT2 and HSP26; CCT2 and HSP30; CCT2 and HSP42; CCT2 and HSP60; CCT2 and HSP78; CCT2 and HSP82; CCT2 and JEM1; CCT2 and MDJ1; CCT2 and MDJ2; CCT2 and MPD1; CCT2 and MPD2; CCT2 and PDI1; CCT2 and PFD1; CCT2 and ABC1; CCT2 and APJ1; CCT2 and ATP11; CCT2 and ATP12; CCT2 and BTT1; CCT2 and CDC37; CCT2 and CPR7; CCT2 and HSC82; CCT2 and KAR2; CCT2 and LHS1; CCT2 and MGE1; CCT2 and MRS11; CCT2 and NOB1; CCT2 and ECM10; CCT2 and SSA1; CCT2 and SSA2; CCT2 and SSA3; CCT2 and SSA4; CCT2 and SSC1; CCT2 and SSE2; CCT2 and SIL1; CCT2 and SLS1; CCT2 and ORM1; CCT2 and ORM2; CCT2 and PER1; CCT2 and PTC2; CCT2 and PSE1; CCT2 and UBI4; CCT2 and HAC1 or a truncated intronless HAC1; CCT3 and CCT4; CCT3 and CCT5; CCT3 and CCT6; CCT3 and CCT7; CCT3 and CCT8; CCT3 and CNS1; CCT3 and CPR3; CCT3 and CPR6; CCT3 and ERO1; CCT3 and EUG1; CCT3 and FMO1; CCT3 and HCH1; CCT3 and HSP10; CCT3 and HSP12; CCT3 and HSP104; CCT3 and HSP26; CCT3 and HSP30; CCT3 and HSP42; CCT3 and HSP60; CCT3 and HSP78; CCT3 and HSP82; CCT3 and JEM1; CCT3 and MDJ1; CCT3 and MDJ2; CCT3 and MPD1; CCT3 and MPD2; CCT3 and PDI1; CCT3 and PFD1; CCT3 and ABC1; CCT3 and APJ1; CCT3 and ATP11; CCT3 and ATP12; CCT3 and BTT1; CCT3 and CDC37; CCT3 and CPR7; CCT3 and HSC82; CCT3 and KAR2; CCT3 and LHS1; CCT3 and MGE1; CCT3 and MRS11; CCT3 and NOB1; CCT3 and ECM10; CCT3 and SSA1; CCT3 and SSA2; CCT3 and SSA3; CCT3 and SSA4; CCT3 and SSC1; CCT3 and SSE2; CCT3 and SIL1; CCT3 and SLS1; CCT3 and ORM1; CCT3 and ORM2; CCT3 and PER1; CCT3 and PTC2; CCT3 and PSE1; CCT3 and UBI4; CCT3 and HAC1 or a truncated intronless HAC1; CCT4 and CCT5; CCT4 and CCT6; CCT4 and CCT7; CCT4 and CCT8; CCT4 and CNS1; CCT4 and CPR3; CCT4 and CPR6; CCT4 and ERO1; CCT4 and EUG1; CCT4 and FMO1; CCT4 and HCH1; CCT4 and HSP10; CCT4 and HSP12; CCT4 and HSP104; CCT4 and HSP26; CCT4 and HSP30; CCT4 and HSP42; CCT4 and HSP60; CCT4 and HSP78; CCT4 and HSP82; CCT4 and JEM1; CCT4 and MDJ1; CCT4 and MDJ2; CCT4 and MPD1; CCT4 and MPD2; CCT4 and PDI1; CCT4 and PFD1; CCT4 and ABC1; CCT4 and APJ1; CCT4 and ATP11; CCT4 and ATP12; CCT4 and BTT1; CCT4 and CDC37; CCT4 and CPR7; CCT4 and HSC82; CCT4 and KAR2; CCT4 and LHS1; CCT4 and MGE1; CCT4 and MRS11; CCT4 and NOB1; CCT4 and ECM10; CCT4 and SSA1; CCT4 and SSA2; CCT4 and SSA3; CCT4 and SSA4; CCT4 and SSC1; CCT4 and SSE2; CCT4 and SIL1; CCT4 and SLS1; CCT4 and ORM1; CCT4 and ORM2; CCT4 and PER1; CCT4 and PTC2; CCT4 and PSE1; CCT4 and UBI4; CCT4 and HAC1 or a truncated intronless HAC1; CCT5 and CCT6; CCT5 and CCT7; CCT5 and CCT8; CCT5 and CNS1; CCT5 and CPR3; CCT5 and CPR6; CCT5 and ERO1; CCT5 and EUG1; CCT5 and FMO1; CCT5 and HCH1; CCT5 and HSP10; CCT5 and HSP12; CCT5 and HSP104; CCT5 and HSP26; CCT5 and HSP30; CCT5 and HSP42; CCT5 and HSP60; CCT5 and HSP78; CCT5 and HSP82; CCT5 and JEM1; CCT5 and MDJ1; CCT5 and MDJ2; CCT5 and MPD1; CCT5 and MPD2; CCT5 and PDI1; CCT5 and PFD1; CCT5 and ABC1; CCT5 and APJ1; CCT5 and ATP11; CCT5 and ATP12; CCT5 and BTT1; CCT5 and CDC37; CCT5 and CPR7; CCT5 and HSC82; CCT5 and KAR2; CCT5 and LHS1; CCT5 and MGE1; CCT5 and MRS11; CCT5 and NOB1; CCT5 and ECM10; CCT5 and SSA1; CCT5 and SSA2; CCT5 and SSA3; CCT5 and SSA4; CCT5 and SSC1; CCT5 and SSE2; CCT5 and SIL1; CCT5 and SLS1; CCT5 and ORM1; CCT5 and ORM2; CCT5 and PER1; CCT5 and PTC2; CCT5 and PSE1; CCT5 and UBI4; CCT5 and HAC1 or a truncated intronless HAC1; CCT6 and CCT7; CCT6 and CCT8; CCT6 and CNS1; CCT6 and CPR3; CCT6 and CPR6; CCT6 and ERO1; CCT6 and EUG1; CCT6 and FMO1; CCT6 and HCH1; CCT6 and HSP10; CCT6 and HSP12; CCT6 and HSP104; CCT6 and HSP26; CCT6 and HSP30; CCT6 and HSP42; CCT6 and HSP60; CCT6 and HSP78; CCT6 and HSP82; CCT6 and JEM1; CCT6 and MDJ1; CCT6 and MDJ2; CCT6 and MPD1; CCT6 and MPD2; CCT6 and PDI1; CCT6 and PFD1; CCT6 and ABC1; CCT6 and APJ1; CCT6 and ATP11; CCT6 and ATP12; CCT6 and BTT1; CCT6 and CDC37; CCT6 and CPR7; CCT6 and HSC82; CCT6 and KAR2; CCT6 and LHS1; CCT6 and MGE1; CCT6 and MRS11; CCT6 and NOB1; CCT6 and ECM10; CCT6 and SSA1; CCT6 and SSA2; CCT6 and SSA3; CCT6 and SSA4; CCT6 and SSC1; CCT6 and SSE2; CCT6 and SIL1; CCT6 and SLS1; CCT6 and ORM1; CCT6 and ORM2; CCT6 and PER1; CCT6 and PTC2; CCT6 and PSE1; CCT6 and UBI4; CCT6 and HAC1 or a truncated intronless HAC1; CCT7 and CCT8; CCT7 and CNS1; CCT7 and CPR3; CCT7 and CPR6; CCT7 and ERO1; CCT7 and EUG1; CCT7 and FMO1; CCT7 and HCH1; CCT7 and HSP10; CCT7 and HSP12; CCT7 and HSP104; CCT7 and HSP26; CCT7 and HSP30; CCT7 and HSP42; CCT7 and HSP60; CCT7 and HSP78; CCT7 and HSP82; CCT7 and JEM1; CCT7 and MDJ1; CCT7 and MDJ2; CCT7 and MPD1; CCT7 and MPD2; CCT7 and PDI1; CCT7 and PFD1; CCT7 and ABC1; CCT7 and APJ1; CCT7 and ATP11; CCT7 and ATP12; CCT7 and BTT1; CCT7 and CDC37; CCT7 and CPR7; CCT7 and HSC82; CCT7 and KAR2; CCT7 and LHS1; CCT7 and MGE1; CCT7 and MRS11; CCT7 and NOB1; CCT7 and ECM10; CCT7 and SSA1; CCT7 and SSA2; CCT7 and SSA3; CCT7 and SSA4; CCT7 and SSC1; CCT7 and SSE2; CCT7 and SIL1; CCT7 and SLS1; CCT7 and ORM1; CCT7 and ORM2; CCT7 and PER1; CCT7 and PTC2; CCT7 and PSE1; CCT7 and UBI4; CCT7 and HAC1 or a truncated intronless HAC1; CCT8 and CNS1; CCT8 and CPR3; CCT8 and CPR6; CCT8 and ERO1; CCT8 and EUG1; CCT8 and FMO1; CCT8 and HCH1; CCT8 and HSP10; CCT8 and HSP12; CCT8 and HSP104; CCT8 and HSP26; CCT8 and HSP30; CCT8 and HSP42; CCT8 and HSP60; CCT8 and HSP78; CCT8 and HSP82; CCT8 and JEM1; CCT8 and MDJ1; CCT8 and MDJ2; CCT8 and MPD1; CCT8 and MPD2; CCT8 and PDI1; CCT8 and PFD1; CCT8 and ABC1; CCT8 and APJ1; CCT8 and ATP11; CCT8 and ATP12; CCT8 and BTT1; CCT8 and CDC37; CCT8 and CPR7; CCT8 and HSC82; CCT8 and KAR2; CCT8 and LHS1; CCT8 and MGE1; CCT8 and MRS11; CCT8 and NOB1; CCT8 and ECM10; CCT8 and SSA1; CCT8 and SSA2; CCT8 and SSA3; CCT8 and SSA4; CCT8 and SSC1; CCT8 and SSE2; CCT8 and SIL1; CCT8 and SLS1; CCT8 and ORM1; CCT8 and ORM2; CCT8 and PLR1; CCT8 and PTC2; CCT8 and PSE1; CCT8 and UBI4; CCT8 and HAC1 or a truncated intronless HAC1; CNS1 and CPR3; CNS1 and CPR6; CNS1 and ERO1; CNS1 and EUG1; CNS1 and FMO1; CNS1 and HCH1; CNS1 and HSP10; CNS1 and HSP12; CNS1 and HSP104; CNS1 and HSP26; CNS1 and HSP30; CNS1 and HSP42; CNS1 and HSP60; CNS1 and HSP78; CNS1 and HSP82; CNS1 and JEM1, CNS1 and MDJ1; CNS1 and MDJ2; CNS1 and MPD1; CNS1 and MPD2; CNS1 and PDI1; CNS1 and PFD1; CNS1 and ABC1; CNS1 and APJ1; CNS1 and ATP11; CNS1 and ATP12; CNS1 and BTT1; CNS1 and CDC37; CNS1 and CPR 7; CNS1 and HSC82; CNS1 and KAR2; CNS1 and LHS1; CNS1 and MGE1; CNS1 and MRS11; CNS1 and NOB1; CNS1 and ECM10; CNS1 and SSA1; CNS1 and SSA2; CNS1 and SSA3; CNS1 and SSA4; CNS1 and SSC1; CNS1 and SSE2; CNS1 and SIL1; CNS1 and SLS1; CNS1 and ORM1; CNS1 and ORM2; CNS1 and PER1; CNS1 and PTC2; CNS1 and PSE1; CNS1 and UBI4; CNS1 and HAC1 or a truncated intronless HAC1; CPR3 and CPR6; CPR3 and ERO1; CPR3 and EUG1; CPR3 and FMO1; CPR3 and HCH1; CPR3 and HSP10; CPR3 and HSP12; CPR3 and HSP104; CPR3 and HSP26; CPR3 and HSP30; CPR3 and HSP42; CPR3 and HSP60; CPR3 and HSP78; CPR3 and HSP82; CPR3 and JEM1; CPR3 and MDJ1; CPR3 and MDJ2; CPR3 and MPD1; CPR3 and MPD2; CPR3 and PDI1; CPR3 and PFD1; CPR3 and ABC1; CPR3 and APJ1; CPR3 and ATP11; CPR3 and ATP12; CPR3 and BTT1; CPR3 and CDC37; CPR3 and CPR7; CPR3 and HSC82; CPR3 and KAR2; CPR3 and LHS1; CPR3 and MGE1; CPR3 and MRS11; CPR3 and NOB1; CPR3 and ECM10; CPR3 and SSA1; CPR3 and SSA2; CPR3 and SSA3; CPR3 and SSA4; CPR3 and SSC1; CPR3 and SSE2; CPR3 and SIL1; CPR3 and SLS1; CPR3 and ORM1; CPR3 and ORM2; CPR3 and PER1; CPR3 and PTC2; CPR3 and PSE1; CPR3 and UBI4; CPR3 and HAC1 or a truncated intronless HAC1; CPR6 and ERO1; CPR6 and EUG1; CPR6 and FMO1; CPR6 and HCH1; CPR6 and HSP10; CPR6 and HSP12; CPR6 and HSP104; CPR6 and HSP26; CPR6 and HSP30; CPR6 and HSP42; CPR6 and HSP60; CPR6 and HSP78; CPR6 and HSP82; CPR6 and JEM1; CPR6 and MDJ1; CPR6 and MDJ2; CPR6 and MPD1; CPR6 and MPD2; CPR6 and PDI1; CPR6 and PFD1; CPR6 and ABC1; CPR6 and APJ1; CPR6 and ATP11; CPR6 and ATP12; CPR6 and BTT1; CPR6 and CDC37; CPR6 and CPR7; CPR6 and HSC82; CPR6 and KAR2; CPR6 and LHS1; CPR6 and MGE1; CPR6 and MRS11; CPR6 and NOB1; CPR6 and ECM10; CPR6 and SSA1; CPR6 and SSA2; CPR6 and SSA3; CPR6 and SSA4; CPR6 and SSC1; CPR6 and SSE2; CPR6 and SIL1; CPR6 and SLS1; CPR6 and ORM1; CPR6 and ORM2; CPR6 and PFR1; CPR6 and PTC2; CPR6 and PSE1; CPR6 and UBI4; CPR6 and HAC1 or a truncated intronless HAC1; ERO1 and EUG1; ERO1 and FMO1; ERO1 and HCH1; ERO1 and HSP10; ERO1 and HSP12; ERO1 and HSP104; ERO1 and HSP26; ERO1 and HSP30; ERO1 and HSP42; ERO1 and HSP60; ERO1 and HSP78; ERO1 and HSP82: ERO1 and JEM1; ERO1 and MDJ1; ERO1 and MDJ2; ERO1 and MPD1; ERO1 and MPD2; ERO1 and PDI1; ERO1 and PFD1; ERO1 and ABC1; ERO1 and APJ1; ERO1 and ATP11; ERO1 and ATP12; ERO1 and BTT1; ERO1 and CDC37; ERO1 and CPR7; ERO1 and HSC82; ERO1 and KAR2; ERO1 and LHS1; ERO1 and MGE1; ERO1 and MRS11; ERO1 and NOB1; ERO1 and ECM10; ERO1 and SSA1; ERO1 and SSA2; ERO1 and SSA3; ERO1 and SSA4; ERO1 and SSC1; ERO1 and SSE2; ERO1 and SIL1; ERO1 and SLS1; ERO1 and ORM1; ERO1 and ORM2; ERO1 and PER1; ERO1 and PTC2; ERO1 and PSE1; ERO1 and UBI4; ERO1 and HAC1 or a truncated intronless HAC1; EUG1 and FMO1; EUG1 and HCH1; EUG1 and HSP10; EUG1 and HSP12; EUG1 and HSP104; EUG1 and HSP26; EUG1 and HSP30; EUG1 and HSP42; EUG1 and HSP60; EUG1 and HSP78; EUG1 and HSP82; EUG1 and JEM1; EUG1 and MDJ1; EUG1 and MDJ2; EUG1 and MPD1; EUG1 and MPD2; EUG1 and PDI1; EUG1 and PFD1; EUG1 and ABC1; EUG1 and APJ1; EUG1 and ATP11; EUG1 and ATP12; EUG1 and BTT1; EUG1 and CDC37; EUG1 and CPR7; EUG1 and HSC82; EUG1 and KAR2; EUG1 and LHS1; EUG1 and MGE1; EUG1 and MRS11; EUG1 and NOB1; EUG1 and ECM10; EUG1 and SSA1; EUG1 and SSA2; EUG1 and SSA3; EUG1 and SSA4; EUG1 and SSC1; EUG1 and SSE2; EUG1 and SIL1; EUG1 and SLS1; EUG1 and ORM1; EUG1 and ORM2; EUG1 and PER1; EUG1 and PTC2; EUG1 and PSE1; EUG1 and UBI4; EUG1 and HAC1 or a truncated intronless HAC1; FMO1 and HCH1; FMO1 and HSP10; FMO1 and HSP12; FMO1 and HSP104; FMO1 and HSP26; FMO1 and HSP30; FMO1 and HSP42; FMO1 and HSP60; FMO1 and HSP78; FMO1 and HSP82; FMO1 and JEM1; FMO1 and MDJ1; FMO1 and MDJ2; FMO1 and MPD1; FMO1 and MPD2; FMO1 and PDI1; FMO1 and PFD1; FMO1 and ABC1; FMO1 and APJ1; FMO1 and ATP11; FMO1 and ATP12; FMO1 and BTT1; FMO1 and CDC37: FMO1 and CPR7; FMO1 and HSC82; FMO1 and KAR2; FMO1 and LHS1; FMO1 and MGE1; FMO1 and MRS11; FMO1 and NOB1; FMO1 and EMO10; FMO1 and SSA1; FMO1 and SSA2; FAO1 and SSA3; FMO1 and SSA4; FMO1 and SSC1; FMO1 and SSE2; FMO1 and SIL1; FMO1 and SLS1; FMO1 and ORM1; FMO1 and ORM2; FMO1 and PER1; FMO1 and PTC2; FMO1 and PSE1; FMO1 and UBI4; FMO1 and HAC1 or a truncated intronless HAC1; HCH1 and HSP10; HCH1 and HSP12; HCH1 and HSP104; HCH1 and HSP26; HCH1 and HSP30; HCH1 and HSP42; HCH1 and HSP60; HCH1 and HSP78; HCH1 and HSP82; HCH1 and JEM1; HCH1 and MDJ1; HCH1 and MDJ2; HCH1 and MPD1; HCH1 and MPD2; HCH1 and PDI1; HCH1 and PFD1; HCH1 and ABC1; HCH1 and APJ1; HCH1 and ATP11; HCH1 and ATP12; HCH1 and BTT1; HCH1 and CDC37; HCH1 and CPR7; HCH1 and HSC82; HCH1 and KAR2; HCH1 and LHS1; HCH1 and MGE1; HCH1 and MRS11; HCH1 and NOB1; HCH1 and ECM10; HCH1 and SSA1; HCH1 and SSA2; HCH1 and SSA3; HCH1 and SSA4; HCH1 and SSC1; HCH1 and SSE2; HCH1 and SIL1; HCH1 and SLS1; HCH1 and ORM1; HCH1 and ORM2; HCH1 and PER1; HCH1 and PTC2; HCH1 and PSE1; HCH1 and UBI4; HCH1 and HAC1 or a truncated intronless HAC1; HSP10 and HSP12; HSP10 and HSP104; HSP10 and HSP26; HSP10 and HSP30; HSP10 and HSP42; HSP10 and HSP60; HSP10 and HSP78; HSP10 and HSP82; HSP10 and JEM1; HSP10 and MDJ1; HSP10 and MDJ2; HSP10 and MPD1; HSP10 and MPD2; HSP10 and PDI1; HSP10 and PFD1; HSP10 and ABC1; HSP10 and APJ1; HSP10 and ATP11; HSP10 and ATP12; HSP10 and BTT1; HSP10 and CDC37; HSP10 and CPR7; HSP10 and HSC82; HSP10 and KAR2; HSP10 and LHS1; HSP10 and MGE1; HSP10 and MRS11; HSP10 and NOB1; HSP10 and ECM10; HSP10 and SSA1; HSP10 and SSA2; HSP10 and SSA3; HSP10 and SSA4; HSP10 and SSC1; HSP10 and SSE2; HSP10 and SIL1; HSP10 and SLS1; HSP10 and ORM1; HSP10 and ORM2; HSP10 and PER1; HSP10 and PTC2; HSP10 and PSE1; HSP10 and UBI4; HSP10 and HAC1 or a truncated intronless HAC1; HSP12 and HSP104; HSP12 and HSP26; HSP12 and HSP30; HSP12 and HSP42; HSP12 and HSP104; HSP12 and HSP78; HSP12 and HSP82; HSP12 and JEM1; HSP12 and MDJ1; HSP12 and MDJ2; HSP12 and MPD1; HSP12 and MPD2; HSP12 and PDI1; HSP12 and PFD1; HSP12 and ABC1; HSP12 and APJ1; HSP12 and ATP11; HSP12 and ATP12; HSP12 and BTT1; HSP12 and CDC37; HSP12 and CPR7; HSP12 and HSC82; HSP12 and KAR2; HSP12 and LHS1; HSP12 and MGE1; HSP12 and MRS11; HSP12 and NOB1; HSP12 and EMC10; HSP12 and SSA1; HSP12 and SSA2; HSP12 and SSA3; HSP12 and SSA4; HSP12 and SSC1; HSP12 and SSE2; HSP12 and SIL1; HSP12 and SLS1; HSP12 and ORM1; HSP12 and ORM2; HSP12 and PER1; HSP12 and PTC2; HSP12 and PSE1; HSP12 and UBI4; HSP12 and HAC1 or a truncated intronless HAC1; HSP104 and HSP26; HSP104 and HSP30; HSP104 and HSP42; HSP104 and HSP60; HSP104 and HSP78; HSP104 and HSP82; HSP104 and JEM1; HSP104 and MDJ1; HSP104 and MDJ2; HSP104 and MPD1; HSP104 and MPD2; HSP104 and PDI1; HSP104 and PFD1; HSP104 and ABC1; HSP104 and APJ1; HSP104 and ATP11; HSP104 and ATP12; HSP104 and BTT1; HSP104 and CDC37; HSP104 and CPR7; HSP104 and HSC82; HSP104 and KAR2; HSP104 and LHS1; HSP104 and MGE1; HSP104 and MRS11; HSP104 and NOB1; HSP104 and EMC10; HSP104 and SSA1; HSP104 and SSA2; HSP104 and SSA3; HSP104 and SSA4; HSP104 and SSC1; HSP104 and SSE2; HSP104 and SIL1; HSP104 and SLS1; HSP104 and ORM1; HSP104 and ORM2; HSP104 and PER1; HSP104 and PTC2; HSP104 and PSE1; HSP104 and UBI4; HSP104 and HAC1 or a truncated intronless HAC1; HSP26 and HSP30; HSP26 and HSP42; HSP26 and HSP60; HSP26 and HSP78; HSP26 and HSP82; HSP26 and JEM1; HSP26 and MDJ1; HSP26 and MDJ2; HSP26 and MPD1; HSP26 and MPD2; HSP26 and PDI1; HSP26 and PFD1; HSP26 and ABC1; HSP26 and APJ1; HSP26 and ATP11; HSP26 and ATP12; HSP26 and BTT1; HSP26 and CDC37; HSP26 and CPR7; HSP26 and HSC82; HSP26 and KAR2; HSP26 and LHS1; HSP26 and MGE1; HSP26 and MRS11; HSP26 and NOB1; HSP26 and ECM10; HSP26 and SSA1; HSP26 and SSA2; HSP26 and SSA3; HSP26 and SSA4; HSP26 and SSC1; HSP26 and SSE2; HSP26 and SIL1; HSP26 and SLS1; HSP26 and ORM1; HSP26 and ORM2; HSP26 and PER1; HSP26 and PTC2; HSP26 and PSE1; HSP26 and UBI4; HSP26 and HAC1 or a truncated intronless HAC1; HSP30 and HSP42; HSP30 and HSP60; HSP30 and HSP78; HSP30 and HSP82; HSP30 and JEM1; HSP30 and MDJ1; HSP30 and MDJ2; HSP30 and MPD1; HSP30 and MPD2; HSP30 and PDI1; HSP30 and PFD1; HSP30 and ABC1; HSP30 and APJ1; HSP30 and ATP11; HSP30 and ATP12; HSP30 and BTT1; HSP30 and CDC37; HSP30 and CPR7; HSP30 and HSC82; HSP30 and KAR2; HSP30 and LHS1; HSP30 and MGE1; HSP30 and MRS11; HSP30 and NOB1; HSP30 and ECM10; HSP30 and SSA1; HSP30 and SSA2; HSP30 and SSA3; HSP30 and SSA4; HSP30 and SSC1; HSP30 and SSE2; HSP30 and SIL1; HSP30 and SLS1; HSP30 and ORM1; HSP30 and ORM2; HSP30 and PER1; HSP30 and PTC2; HSP30 and PSE1; HSP30 and UBI4; HSP30 and HAC1 or a truncated intronless HAC1; HSP42 and HSP60; HSP42 and HSP78; HSP42 and HSP82; HSP42 and JEM1; HSP42 and MDJ1; HSP42 and MDJ2; HSP42 and MPD1; HSP42 and MPD2; HSP42 and PDI1; HSP42 and PFD1; HSP42 and ABC1; HSP42 and APJ1; HSP42 and ATP11; HSP42 and ATP12; HSP42 and BTT1; HSP42 and CDC37; HSP42 and CPR7; HSP42 and HSC82; HSP42 and KAR2; HSP42 and LHS1; HSP42 and MGE1; HSP42 and MRS11; HSP42 and NOB1; HSP42 and ECM10; HSP42 and SSA1; HSP42 and SSA2; HSP42 and SSA3; HSP42 and SSA4; HSP42 and SSC1; HSP42 and SSE2; HSP42 and SIL1; HSP42 and SLS1; HSP42 and ORM1; HSP42 and ORM2; HSP42 and PER1; HSP42 and PTC2; HSP42 and PSE1; HSP42 and UBI4; HSP42 and HAC1 or a truncated intronless HAC1; HSP60 and HSP78; HSP60 and HSP82; HSP60 and JEM1; HSP60 and MDJ1; HSP60 and MDJ2; HSP60 and MPD1; HSP60 and MPD2; HSP60 and PDI1; HSP60 and PFD1; HSP60 and ABC1; HSP60 and APJ1; HSP60 and ATP11; HSP60 and ATP12; HSP60 and BTT1; HSP60 and CDC37; HSP60 and CPR7; HSP60 and HSC82; HSP60 and KAR2; HSP60 and LHS1; HSP60 and MGE1; HSP60 and MRS11; HSP60 and NOB1; HSP60 and ECM10; HSP60 and SSA1; HSP60 and SSA2; HSP60 and SSA3; HSP60 and SSA4; HSP60 and SSC1; HSP60 and SSE2; HSP60 and SIL1; HSP60 and SLS1; HSP60 and ORM1; HSP60 and ORM2; HSP60 and PER1; HSP60 and PTC2; HSP60 and PSE1; HSP60 and UBI4; HSP60 and HAC1 or a truncated intronless HAC1; HSP78 and HSP82; HSP78 and JEM1; HSP78 and MDJ1; HSP78 and MDJ2; HSP78 and MPD1; HSP78 and MPD2; HSP78 and PDI1; HSP78 and PFD1; HSP78 and ABC1; HSP78 and APJ1; HSP78 and ATP11; HSP78 and ATP12; HSP78 and BTT1; HSP78 and CDC37; HSP78 and CPR7; HSP78 and HSC82; HSP78 and KAR2; HSP78 and LHS1; HSP78 and MGE1; HSP78 and MRS11; HSP78 and NOB1; HSP78 and ECM10; HSP78 and SSA1; HSP78 and SSA2; HSP78 and SSA3; HSP78 and SSA4; HSP78 and SSC1; HSP78 and SSE9; HSP78 and SIL1; HSP78 and SLS1; HSP78 and ORM1; HSP78 and ORM2; HSP78 and PER1; HSP78 and PTC2; HSP78 and PSE1; HSP78 and UBI4; HSP78 and HAC1 or a truncated intronless HAC1; HSP82 and JEM1; HSP82 and MDJ1; HSP82 and MDJ2; HSP82 and MPD1; HSP82 and MPD2; HSP82 and PDI1; HSP82 and PFD1; HSP82 and ABC1; HSP82 and ATP1; HSP82 and ATP11; HSP82 and ATP12; HSP82 and BTT1; HSP82 and CDC37; HSP82 and CPR7; HSP82 and HSC82; HSP82 and KAR2; HSP82 and LHS1; HSP82 and MGE1; HSP82 and MRS11; HSP82 and NOB1; HSP82 and ECM10; HSP82 and SSA1; HSP82 and SSA2; HSP82 and SSA3; HSP82 and SSA4; HSP82 and SSC1; HSP82 and SSE2; HSP82 and SIL1; HSP82 and SLS1; HSP82 and ORM1; HSP82 and ORM2; HSP82 and PER1; HSP82 and PTC2; HSP82 and PSE1; HSP82 and UBI4; HSP82 and HAC1 or a truncated intronless HAC1; JEM1 and MDJ1; JEM1 and MDJ2; JEM1 and MAD1; JEM1 and MPD2; JEM1 and PDI1; JEM1 and PFD1; JEM1 and ABC1; JEM1 and APJ1; JEM1 and ATP11; JEM1 and ATP12; JEM1 and BTT1; JEM1 and CDC37; JEM1 and CPR7; JEM1 and HSC82; JEM1 and KAR2; JEM1 and LHS1; JEM1 and MGE1; JEM1 and MRS11; JEM1 and NOB1; JEM1 and EMC10; JEM1 and SSA1; JEM1 and SSA2; JEM1 and SSA3; JEM1 and SSA4; JEM1 and SSC1; JEM1 and SSE2; JEM1 and SIL1; JEM1 and SLS1; JEM1 and ORM1; JEM1 and ORM2; JEM1 and PER1; JEM1 and PTC2; JEM1 and PSE1; JEM1 and UBI4; JEM1 and HAC1 or a truncated intronless HAC1; MDJ1 and MDJ2; MDJ1 and MPD1; MDJ1 and MPD2; MDJ1 and MDJ1; MDJ1 and PFD1; MDJ1 and ABC1; MDJ1 and APJ1; ADJ1 and ATP11; MDJ1 and ATP12; MDJ1 and BTT1; MDJ1 and CDC37; MDJ1 and CPR7; ADJ1 and HSC82; MDJ1 and KAR2; MDJ1 and LHS1; MDJ1 and MGE1; MDJ1 and MRS11; MDJ1 and NOB1; MDJ1 and ECM10; MDJ1 and SSA1; MDJ1 and SSA2; MDJ1 and SSA3; MDJ1 and SSA4; MDJ1 and SSC1; MDJ1 and SSE2; MDJ1 and SIL1; MDJ1 and SLS1; MDJ1 and ORM1; MDJ1 and ORM2; MDJ1 and PER1; MDJ11 and PTC2; MDJ1 and PSE1; MDJ1 and UBI4; MDJ1 and HAC1 or a truncated intronless HAC1; MDJ2 and MPD1; MDJ2 and MPD2; MDJ2 and MDJ2 and PFD1; MDJ2 and ABC1; MDJ2 and APJ1; MDJ2 and ATP11; MDJ2 and ATP12; MDJ2 and BTT1; MDJ2 and CDC37; MDJ2 and CPR7; MDJ2 and HSC82; MDJ2 and KAR2; MDJ2 and LHS1; MDJ2 and MGE1; MDJ2 and MRS11; MDJ2 and NOB1; MDJ2 and ECM10; MDJ2 and SSA1; MDJ2 and SSA2; MDJ2 and SSA3; MDJ2 and SSA4; MDJ2 and SSC1; MDJ2 and SSE2; MDJ2 and SIL1; MDJ2 and SLS1; MDJ2 and ORM1; MDJ2 and ORM2; MDJ2 and PER1; MDJ2 and PTC2; MDJ2 and PSE1; MDJ2 and UBI4; MDJ2 and HAC1 or a truncated intronless HAC1; MPD1 and MPD2; MPD1 and PDI1; MPD1 and PFD1; MPD1 and ABC1; MPD1 and APJ1; MPD1 and ATP11; MPD1 and ATP12; MPD1 and BTT1; APD1 and CDC37; MPD1 and CPR7; MPD1 and HSC82; MPD1 and KAR2; MPD1 and LHS1; MPD1 and MGE1; MPD1 and MRS11; MPD1 and NOB1; MPD1 and ECM10; MPD1 and SSA1; MPD1 and SSA2; MPD1 and SSA3; MPD1 and SSA4; MPD1 and SSC1; MPD1 and SSE2; MPD1 and SIL1; MPD1 and SLS1; MPD1 and ORM1; MPD1 and ORM2; MPD1 and PER1; MPD1 and PTC2; MPD1 and PSE1; MPD1 and UBI4; MPD1 and HAC1 or a truncated intronless HAC1; MPD2 and PDI1; MPD2 and PFD1; MPD2 and ABC1; MPD2 and APJ1; MPD2 and ATP11; MPD2 and ATP12; MPD2 and BTT1; MPD2 and CDC37; MPD2 and CPR7; MPD2 and HSC82; MPD2 and KAR2; MPD2 and LHS1; MPD2 and MGE1; MPD2 and MARS11; MPD2 and NOB1; MPD2 and ECM10; MPD2 and SSA1; MPD2 and SSA2; MPD2 and SSA3; MPD2 and SSA4; MPD2 and SSC1; MPD2 and SSE2; MPD2 and SIL1; MPD2 and SLS1; MPD2 and ORM1; MPD2 and ORM2; MPD2 and PER1; MPD2 and PTC2; MPD2 and PSE1; APD2 and UBI4; MPD2 and HAC1 or a truncated intronless HAC1; PDI1 and PFD1; PDI1 and ABC1; PDI1 and APJ1; PDI1 and ATP11; PDI1 and ATP12; PDI1 and BTT1; PDI1 and CDC37; PDI1 and CPR7; PDI1 and HSC82; PDI1 and KAR2; PDI1 and LHS1; PDI1 and MGE1; PDI1 and MRS11; PDI1 and NOB1; PDI1 and ECM10; PDI1 and SSA1; PDI1 and SSA2; PDI1 and SSA3; PDI1 and SSA4; PDI1 and SSC1; PDI1 and SSE2; PDI1 and SIL1; PDI1 and SLS1; PDI1 and ORM1; PDI1 and ORM2; PDI1 and PER1; PDI1 and PTC2; PDI1 and PSE1; PDI1 and UBI4; PDI1 and HAC1 or a truncated intronless HAC1; PFD1 and ABC1; PFD1 and APJ1; PED1 and ATP11; PFD1 and ATP12; PFD1 and BTT1; PFD1 and CDC37; PFD1 and CPR7; PFD1 and HSC82; PFD1 and KAR2; PFD1 and LHS1; PFD1 and MGE1; PFD1 and MRS1 I; PFD1 and NOB1; PFD1 and ECM10; PFD1 and SSA1; PFD1 and SSA2; PFD1 and SSA3; PFD1 and SSA4; PFD1 and SSC1; PFD1 and SSE2; PFD1 and SIL1; PFD1 and SLS1; PFD1 and ORM1; PFD1 and ORM2; PFD1 and PER1; PFD1 and PTC2; PFD1 and PSE1; PFD1 and UBI4; PFD1 and HAC1 or a truncated intronless HAC1; ABC1 and APJ1; ABC1 and ATP11; ABC1 and ATP12; ABC1 and BTT1; ABC1 and CDC37; ABC1 and CPR7; ABC1 and HSC82; ABC1 and KAR2; ABC1 and LHS1; ABC1 and MGE1; ABC1 and MRS11; ABC1 and NOB1; ABC1 and ECM10; ABC1 and SSA1; ABC1 and SSA2; ABC1 and SSA3; ABC1 and SSA4; ABC1 and SSC1; ABC1 and SSE2; ABC1 and SIL1; ABC1 and SLS1; ABC1 and ORM1; ABC1 and ORM2; ABC1 and PER1; ABC1 and PTC2; ABC1 and PSE1; ABC1 and UBI4; ABC1 and HAC1 or a truncated intronless HAC1; APJ1 and ATP11; APJ1 and ATP12; APJ1 and BTT1; APJ1 and CDC37; APJ1 and CPR7; APJ1 and HSC82; APJ1 and KAR2; APJ1 and LHS1; APJ1 and MGE1; APJ1 and MRS11; APJ1 and NOB1; APJ1 and ECM10; APJ1 and SSA1; APJ1 and SSA2; APJ1 and SSA3; APJ1 and SSA4; APJ1 and SSC1; APJ1 and SSE2; APJ1 and SIL1; APJ1 and SLS1; APJ1 and ORM1; APJ1 and ORM2; APJ1 and PER1; APJ1 and PTC2; APJ1 and PSE1; APJ1 and UBI4; APJ1 and HAC1 or a truncated intronless HAC1; ATP11 and ATP12; ATP11 and BTT1; ATP11 and CDC37; ATP11 and CPR7; ATP11 and HSC82; ATP11 and KAR2; ATP11 and LHS1; ATP11 and MGE1; ATP11 and MRS11; ATP11 and NOB1; ATP11 and ECM10; ATP11 and SSA1; ATP11 and SSA2; ATP11 and SSA3; ATP11 and SSA4; ATP11 and SSC1; ATP11 and SSE2; ATP11 and SIL1; ATP11 and SLS1; ATP11 and ORM1; ATP11 and ORM2; ATP11 and PER1; ATP11 and PTC2; ATP11 and PSE1; ATP11 and UBI4; ATP11 and HAC1 or a truncated intronless HAC1; ATP12 and BTT1; ATP12 and CDC37. ATP12 and CPR7; ATP12 and HSC82; ATP12 and KAR2; ATP12 and LHS1; ATP12 and MGE1; ATP12 and MRS11; ATP12 and NOB1; ATP12 and ECM10; ATP12 and SSA1; ATP12 and SSA2; ATP12 and SSA3; ATP12 and SSA4; ATP12 and SSC1; ATP12 and SSE2; ATP12 and SIL1; ATP12 and SLS1; ATP12 and ORM1; ATP12 and ORM2; ATP12 and PER1; ATP12 and PTC2; ATP12 and PSE1; ATP12 and UBI4; ATP12 and HAC1 or a truncated intronless HAC1; BTT1 and CDC37; BTT1 and CPR7; BTT1 and HSC82; BTT1 and KAR2; BTT1 and LHS1; BTT1 and MGE1; BTT1 and MRS11; BTT1 and NOB1; BTT1 and ECM10; BTT1 and SSA1; BTT1 and SSA2; BTT1 and SSA3; BTT1 and SSA4; BTT1 and SSC1; BTT1 and SSE2; BTT1 and SIL1; BTT1 and SLS1; BTT1 and ORM1; BTT1 and ORM2: BTT1 and PER1; BTT1 and PTC2; BTT1 and PSE1; BTT1 and UBI4; BTT1 and HAC1 or a truncated intronless HAC1; CDC37 and CPR7; CDC37 and HSC82; CDC37 and KAR2; CDC37 and LHS1; CDC37 and MGE1; CDC37 and MRS11; CDC37 and NOB1; CDC37 and ECM10; CDC37 and SSA1; CDC37 and SSA2; CDC37 and SSA3; CDC37 and SSA4; CDC37 and SSC1; CDC37 and SSE2; CDC37 and SIL1; CDC37 and SLS1; CDC37 and ORM1; CDC37 and ORM2; CDC37 and PER1; CDC37 and PTC2; CDC37 and PSE1; CDC37 and UBI4; CDC37 and HAC1 or a truncated intronless HAC1; CPR7 and HSC82; CPR7 and KAR2; CPR7 and LHS1; CPR7 and MGE1; CPR7 and MRS11; CPR7 and NOB1; CPR7 and ECM10; CPR7 and SSA1; CPR7 and SSA2; CPR7 and SSA3; CPR7 and SSA4; CPR7 and SSC1; CPR7 and SSE2; CPR7 and SIL1; CPR7 and SLS1; CPR7 and ORM1; CPR7 and ORM2; CPR7 and PER1; CPR7 and PTC2; CPR7 and PSE1; CPR7 and UBI4; CPR7 and HAC1 or a truncated intronless HAC1; HSC82 and KAR2; HSC82 and LHS1; HSC82 and MGE1; HSC82 and MRS11; HSC82 and NOB1; HSC82 and ECM10; HSC82 and SSA1; HSC82 and SSA2; HSC82 and SSA3; HSC82 and SSA4; HSC82 and SSC1; HSC82 and SSE2; HSC82 and SIL1; HSC82 and SLS1; HSC82 and ORM1; HSC82 and ORM2; HSC82 and PER1; HSC82 and PTC2; HSC82 and PSE1; HSC82 and UBI4; HSC82 and HAC1 or a truncated intronless HAC1; KAR2 and LHS1; KAR2 and MGE1; KAR2 and MRS11; KAR2 and NOB1; KAR2 and ECM10; KAR2 and SSA1; KAR2 and SSA2; KAR2 and SSA3; KAR2 and SSA4; KAR2 and SSC1; KAR2 and SSE2; KAR2 and SIL1; KAR2 and SLS1; KAR2 and ORM1; KAR2 and ORM2; KAR2 and PER1; KAR2 and PTC2; KAR2 and PSE1; KAR2 and UBI4; KAR2 and HAC1 or a truncated intronless HAC1; LHS1 and MGE1; LHS1 and MARS11; LHS1 and NOB1; LHS1 and ECM10; LHS1 and SSA1; LHS1 and SSA2; LHS1 and SSA3; LHS1 and SSA4; LHS1 and SSC1; LHS1 and SSE2; LHS1 and SIL1; LHS1 and SLS1; LHS1 and ORM1; LHS1 and ORM2; LHS1 and PER1; LHS1 and PTC2; LHS1 and PSE1; LHS1 and UBI4; LHS1 and HAC1 or a truncated intronless HAC1; MGE1 and MRS11; MGE1 and NOB1; MGE1 and ECM10; MGE1 and SSA1; MGE1 and SSA2; MGE1 and SSA3; MGE1 and SSA4; MGE1 and SSC1; MGE1 and SSE2; MGE1 and SIL1; MGE1 and SLS1; MGE1 and ORM1; MGE1 and ORM2; MGE1 and PER1; MGE1 and PTC2; MGE1 and PSE1; MGE1 and UBI4; MGE1 and HAC1 or a truncated intronless HAC1; MRS11 and NOB1; MRS11 and ECM10; MRS11 and SSA1; MRS11 and SSA2; MRS11 and SSA3; MRS11 and SSA4; MRS11 and SSC1; MRS11 and SSE2; MRS11 and SIL1; MRS11 and SLS1; MRS11 and ORM1; MRS11 and ORM2; MRS11 and PER1; MRS11 and PTC2; MRS11 and PSE1; MRS11 and UBI4; MRS11 and HAC1 or a truncated intronless HAC1; NOB1 and EMC10; NOB1 and SSA1; NOB1 and SSA2; NOB1 and SSA3; NOB1 and SSA4; NOB1 and SSC1; NOB1 and SSE2; NOB1 and SIL1; NOB1 and SLS1 NOB1 and ORM1; NOB1 and ORM2; NOB1 and PER1; NOB1 and PTC2; NOB1 and PSE1; NOB1 and UBI4; NOB1 and HAC1 or a truncated intronless HAC1; ECM10 and SSA1; ECM10 and SSA2; ECM10 and SSA3; ECM10 and SSA4; ECM10 and SSC1; ECM10 and SSE2; ECM10 and SIL1; ECM10 and SLS1; ECM10 and ORM1; ECM10 and ORM2; ECM10 and PER1; ECM10 and PTC2; ECM10 and PSE1; ECM10 and UBI4; ECM10 and HAC1 or a truncated intronless HAC1; SSA1 and SSA2; SSA1 and SSA3; SSA1 and SSA4; SSA1 and SSC1; SSA1 and SSE2; SSA1 and SIL1; SSA1 and SLS1; SSA1 and ORM1; SSA1 and ORM2; SSA1 and PER1; SSA1 and PTC2; SSA1 and PSE1; SSA1 and UBI4; SSA1 and HAC1 or a truncated intronless HAC1; SSA2 and SSA3; SSA2 and SSA4; SSA2 and SSC1; SSA2 and SSE2; SSA2 and SIL1; SSA2 and SLS1; SSA2 and ORM1; SSA2 and ORM2; SSA2 and PER1; SSA2 and PTC2; SSA2 and PSE1; SSA2 and UBI4; SSA2 and HAC1 or a truncated intronless HAC1; SSA3 and SSA4; SSA3 and SSC1; SSA3 and SSE2; SSA3 and SIL1; SSA3 and SLS1; SSA3 and ORM1; SSA3 and ORM2; SSA3 and PTC1; SSA3 and PTC2; SSA3 and PSE1; SSA3 and UBI4; SSA3 and HAC1 or a truncated intronless HAC1; SSA4 and SSC1; SSA4 and SSE2; SSA4 and SIL1; SSA4 and SLS1; SSA4 and ORM1; SSA4 and ORM2; SSA4 and PER1; SSA4 and PTC2; SSA4 and PSE1; SSA4 and UBI4; SSA4 and HAC1 or a truncated intronless HAC1; SSC1 and SSE2; SSC1 and SIL1; SSC1 and SLS1; SSC1 and ORM1; SSC1 and ORA42; SSC1 and PER1; SSC1 and PTC2; SSC1 and PSE1; SSC1 and UBI4; SSC1 and HAC1 or a truncated intronless HAC1; SSE2 and SIL1; SSE2 and SLS1; SSE2 and ORM1; SSE2 and ORM2; SSE2 and PER1; SSE2 and PTC2; SSE2 and PSE1; SSE2 and UBI4; SSE2 and HAC1 or a truncated intronless HAC1; SIL1 and SLS1; SIL1 and ORM1; SIL1 and ORM2; SIL1 and PER1; SIL1 and PTC2; SIL1 and PSE1; SIL1 and UBI4; SIL1 and HAC1 or a truncated intronless HAC1; SLS1 and ORM1; SLS1 and ORM2; SLS1 and PER1; SLS1 and PTC2; SLS1 and PSE1; SLS1 and UBI4; SLS1 and HAC1 or a truncated intronless HAC1; ORM1 and ORM2; ORM1 and PER1; ORM1 and PTC2; ORM1 and PSE1; ORM1 and UBI4; ORM1 and HAC1 or a truncated intronless HAC1; ORM2 and PER1; ORM2 and PTC2; ORM2 and PSE1; ORM2 and UBI4; ORM2 and HAC1 or a truncated intronless HAC1; PER1 and PTC2; PER1 and PSE1; PER1 and UBI4; PER1 and HAC1 or a truncated intronless HAC1; PTC2 and PSE1; PTC2 and UBI4; PTC2 and HAC1 or a truncated intronless HAC1; PSE1 and UBI4; PSE1 and HAC1 or a truncated intronless HAC1; UBI4 and HAC1 or a truncated intronless HAC1, TIM9 and AHA1; TIM9 and CCT2; TIM9 and CCT3; TIM9 and CCT4; TIM9 and CCT5; TIM9 and CCT6; TIM9 and CCT7; TIM9 and CCT8; TIM9 and CNS1; TIM9 and CPR3; TIM9 and CPR6; TIM9 and ERO1; TIM9 and EUG1; TIM9 and FMO1; TIM9 and HCH1; TIM9 and HSP10; TIM9 and HSP12; TIM9 and HSP104; TIM9 and HSP26; TIM9 and HSP30; TIM9 and HSP42; TIM9 and HSP60; TIM9 and HSP78; TIM9 and HSP82; TIM9 and JEM1; TIM9 and MDJ1; TIM9 and MDJ2; TIM9 and MPD1; TIM9 and MPD2; TIM9 and PDI1; TIM9 and PFD1; TIM9 and ABC1; TIM9 and APJ1; TIM9 and ATP11; TIM9 and ATP12; TIM9 and BTT1; TIM9 and CDC37; TIM9 and CPR7; TIM9 and HSC82; TIM9 and KAR2; TIM9 and LHS1; TIM9 and MGE1; TIM9 and AIRS11; TIM9 and NOB1; TIM9 and ECM10; TIM9 and SSA1; TIM9 and SSA2; TIM9 and SSA3; TIM9 and SSA4; TIM9 and SSC1; TIM9 and SSE2; TIM9 and SIL1; TIM9 and SLS1; TIM9 and ORM1; TIM9 and ORM2; TIM9 and PER1; TIM9 and PTC2; TIM9 and PSE1; TIM9 and UBI4; TIM9 and HAC1 or a truncated intronless HAC1; PAM18 and AHA1, PAM18 and CCT2; PAM18 and CCT3; PAM18 and CCT4; PAM18 and CCT5; PAM18 and CCT6; PAM18 and CCT7; PAM18 and CCT8; PAM18 and CNS1; PAM18 and CPR3; PAM18 and CPR6; PAM18 and ERO1; PAM18 and EUG1; PAM18 and FMO1; PAM18 and HCH1; PAM18 and HSP10; PAM18 and HSP12; PAM18 and HSP104; PAM18 and HSP26; PAM18 and HSP30; PAM18 and HSP42; PAM18 and HSP60; PAM18 and HSP78; PAM18 and HSP82; PAM18 and JEM1; PAM18 and MDJ1; PAM18 and MDJ2; PAM18 and MPD1; PAM18 and MPD2; PAM18 and PDI1; PAM18 and PFD1; PAM18 and ABC1; PAM18 and APJ1; PAM18 and ATP11; PAM18 and ATP12; PAM18 and BTT1; PAM18 and CDC37; PAM18 and CPR7; PAM18 and HSC82; PAM18 and KAR2; PAM18 and LHS1; PAM18 and MGE1; PAM18 and MRS11; PAM18 and NOB1; PAM18 and ECM10; PAM18 and SSA1; PAM18 and SSA2; PAM18 and SSA3; PAM18 and SSA4; PAM18 and SSC1; PAM18 and SSE2; PAM18 and SIL1; PAM18 and SLS1; PAM18 and ORM1; PAM18 and ORM2; PAM18 and PER1; PAM18 and PTC2; PAM18 and PSE1; PAM18 and UBI4; PAM18 and HAC1 or a truncated intronless HAC1; TCP1 and AHA1, TCP1 and CCT2; TCP1 and CCT3; TCP1 and CCT4; TCP1 and CCT5; TCP1 and CCT6; TCP1 and CCT7; TCP1 and CCT8; TCP1 and CNS1; TCP1 and CPR3; TCP1 and CPR6; TCP1 and ERO1; TCP1 and EUG1; TCP1 and FMO1; TCP1 and HCH1; TCP1 and HSP10; TCP1 and HSP12; TCP1 and HSP104; TCP1 and HSP26; TCP1 and HSP30; TCP1 and HSP42; TCP1 and HSP60; TCP1 and HSP78; TCP1 and HSP82; TCP1 and JEM1; TCP1 and MDJ1; TCP1 and MDJ2; TCP1 and MPD1; TCP1 and MPD2; TCP1 and PDI1; TCP1 and PFD1; TCP1 and ABC1; TCP1 and APJ1; TCP1 and ATP11; TCP1 and ATP12; TCP1 and BTT1; TCP1 and CDC37; TCP1 and CPR7; TCP1 and HSC82; TCP1 and KAR2; TCP1 and LHS1; TCP1 and MGE1; TCP1 and MRS11; TCP1 and NOB1; TCP1 and ECM10; TCP1 and SSA1; TCP1 and SSA2; TCP1 and SSA3; TCP1 and SSA4; TCP1 and SSC1; TCP1 and SSE2; TCP1 and SIL1; TCP1 and SLS1; TCP1 and ORM1; TCP1 and ORM2; TCP1 and PER1; TCP1 and PTC2; TCP1 and PSE1; TCP1 and UBI4; TCP1 and HAC1 or a truncated intronless HAC1; TIM9 and PAM18, TIM9 and TCP1, or PAM1 8 and TCP1.

The first, second and third recombinant genes may, or may not, each individually be present on a plasmid within the host cell (which may, or may not, be a 2 µm-family plasmid, as discussed above) or be chromosomally integrated within the genome of the host cell. It will be appreciated that any combination of plasmid and chromosomally integrated first, second and third recombinant genes may be used. For example, the first, second and third recombinant genes may, or may not, each individually be present on a plasmid, and this may, or may not, be either the same plasmid or different plasmids. Alternatively, the first recombinant gene may, or may not, be present on a plasmid, and second and third recombinant genes may, or may not, be chromosomally integrated within the genome of the host cell. Alternatively, the first and second recombinant genes may, or may not, be present on a plasmid and the third recombinant gene may, or may not, be chromosomally integrated within the genome of the host cell. Alternatively, the first and third recombinant genes may, or may not, be present on a plasmid and the second recombinant gene may, or may not, be chromosomally integrated within the genome of the host cell. Alternatively, the first and second recombinant gene may, or may not, be chromosomally integrated within the genome of the host cell and the third recombinant gene may, or may not, be present on a plasmid. Alternatively, the first, second and third recombinant genes may, or may not, each individually be chromosomally integrated within the genome of the host cell.

Plasmids used for this purpose may, or may not, be plasmids, such as 2 µm-family plasmids, as defined below. Thus, in one embodiment, a method according to the first aspect of the invention does not involve a host cell in which the first, second and third recombinant genes are all present on the 2 µm-family plasmid.

Accordingly, as a second aspect, the present invention also provides a plasmid wherein the plasmid comprises two different genes (the first and second recombinant genes) encoding different chaperones. In one preferred embodiment, the plasmid may, or may not, further comprise a gene encoding a heterologous protein (the third recombinant gene), such as a heterologous protein as described above. A plasmid according to the second aspect of the invention may, or may not, be a 2 µm-family plasmid.

A third aspect of the present invention provides for the use of the plasmid of the second aspect of the invention as an expression vector to increase the production of a desired protein, including as heterologous protein, such as a fungal (optionally yeast) or vertebrate protein. The desired protein may, or may not, be encoded by a recombinant gene that is present as part of the plasmid, or present in the host cell on a different plasmid, or present in the host cell as a transgene that is integrated in the host cell's chromosome.

A fourth aspect of the invention provides a host cell comprising a plasmid as defined above. The host cell may, or may not, further comprise a recombinant gene encoding a desired heterologous protein. Sphere the recombinant gene that encodes the desired heterologous protein (the "third recombinant gene") is not present as part of the same plasmid that encodes the first and second chaperones, then the host cell may, or may not, comprise the third recombinant gene on a different plasmid, or as a transgene that is integrated in the host cell's chromosome.

As a fifth aspect, the present invention provides a host cell which comprises the first, second and third recombinant genes. The first, second and third recombinant genes may, or may not, each individually be present on a plasmid within the host cell (which may, or may not, be a 2 µm-family plasmid, as discussed above) or be chromosomally integrated within the genome of the host cell. It will be appreciated that any combination of plasmid and chromosomally integrated first, second and third recombinant genes may be used, as discussed above. Thus, the host cell may, or may not, comprise the first, second and third recombinant genes each individually present on a plasmid, and this may, or may not, be either the same plasmid or different plasmids. Alternatively, the host cell may, or may not, comprise the first recombinant gene on a plasmid, and second and third recombinant genes chromosomally integrated within the genome of the host cell. Alternatively, the host cell may., or may not, comprise the first and second recombinant genes on a plasmid and the third recombinant gene chromosomally integrated within the genome of the host cell. Alternatively, the host cell may, or may not, comprise the first and third recombinant genes on a plasmid and the second recombinant gene chromosomally integrated within the genome of the host cell. Alternatively, the host cell may, or may not, comprise the first and second recombinant genes chromosomally integrated within the genome of the host cell and the third recombinant gene present on a plasmid. Alternatively, the host cell may, or may not, comprise the first, second and third recombinant genes each individually chromosomally integrated within the genome of the host cell.

The 2 µm-Family Plasmids:

For the purposes of the present invention, a plasmid may, or may not, be a 2 µm-family plasmid. Certain closely related species of budding yeast have been shown to contain naturally occurring circular double stranded DNA plasmids. These plasmids, collectively termed 2 µm-family plasmids, include pSR1, pSB3 and pSB4 from *Zygosaccharomyces rouxii* (formerly classified as *Zygosaccharomyces bisporus*), plasmids pSB1 and pSB2 from *Zygosaccharomyces bailii*, plasmid pSM1 from *Zygosaccharomyces fermentati*, plasmid pKD1 from *Kluyveromyces drosphilarum*, an un-named plasmid from *Pichia membranaefaciens* (hereinafter "pPM1") and the 2 µm plasmid (such as shown in FIG. 1) and variants (such as Scp1, Scp2 and Scp3) from *Saccharomyces cerevisiae* (Volkert, et al., 1989, *Microbiological Reviews*, 53, 299; Murray et al., 1988, *J. Mol. Biol.* 200, 601, Painting, et al., 1984, *J. Applied Bacteriology*, 56, 331).

As a family of plasmids these molecules share a series of common features in that they typically possess two inverted repeats on opposite sides of the plasmid, have a similar size around 6-kbp (range 4757 to 6615-bp), three open reading frames, one of which encodes for a site specific recombinase (FLP) and an autonomously replicating sequence (ARS), also known as an origin of replication (ori), located close to the end of one of the inverted repeats. (Futcher, 1988, *Yeast*, 4, 27; Murray et al., op. cit., and Toh-e et al., 1986, *Basic Life Sci.* 40, 425). Despite their lack of discernible DNA sequence homology, their shared molecular architecture and the conservation of function of the three open reading frames have demonstrated a common ancestral link between the family members.

The above naturally occurring 2 µm-family plasmids may, or may not, be used in the present invention, but this invention is not limited to the use of naturally occurring 2 µm-family plasmids. For the purposes of this invention, a 2 µm-family plasmid may, or ma)y not, be as described below.

A 2 µm-family plasmid is a circular, double stranded, DNA plasmid. It is typically small, such as between 3,000 to 10,000 bp, optionally between 4,500 to 7000 bp, excluding recombinantly inserted sequences.

A 2 µm-family plasmid typically comprises at least three open reading frames ("ORFs") that each encodes a protein that functions in the stable maintenance of the 2 µm-family plasmid as a multicopy plasmid. The proteins encoded by the three ORFs can be designated FLP, REP1 and REP2. Where a 2 µm-family plasmid comprises not all three of the ORFs encoding FLP, REP1 and REP2 then ORFs encoding the missing protein(s) should be supplied in trans, either on another plasmid or by chromosomal integration.

A "FLP" protein is a protein capable of catalysing the site-specific recombination between inverted repeat sequences recognised by. FLP. The inverted repeat sequences are termed FLP recombination target (FRT) sites and each is typically present as part of a larger inverted repeat (see below,). Preferred FLP proteins comprise the sequence of the FLP proteins encoded by one of plasmids pSR1, pSB1, pSB2, pSB3, pSB4, pSM1, pKD1, pPM1 and the 2 μm plasmid, for example as described in Volkert et al, op. cit., Murray et al, op. cit., and Painting et al., op. cit. Variants and fragments of these FLP proteins are also included in the present invention. "Fragments" and "variants" are those which retain the ability of the native protein to catalyse the site-specific recombination between the same FRT sequences. Such variants and fragments will usually have at least 50%, 60%, 70%, 80%, 90%, 95%, 98%, 99%, or more, homology with an FLP protein encoded by one of plasmids pSR1, pSB1, pSB2, pSB3, pSB4, pSM1, pKD1, pPM1 and the 2 μm plasmid. Different FLP proteins can have different FRT sequence specificities. A typical FRT site may, or may not, comprise a core nucleotide sequence flanked by inverted repeat sequences. In the 2 μm plasmid, the FRT core sequence is 8 nucleotides in length and the flanking inverted repeat sequences are 13 nucleotides in length (Volkert et al, op. cit.). However the FRT site recognised by any given FLP protein may, or may not, be different to the 2 μm plasmid FRT site.

REP1 and REP2 are proteins involved in the partitioning of plasmid copies during cell division, and may, or may not, also have a role in the regulation of FLP expression. Considerable sequence divergence has been observed between REP1 proteins from different 2 μm-family plasmids, whereas no sequence alignment is possible between REP2 proteins derived from different 2 μm-family plasmids. Preferred REP1 and REP2 proteins comprise the sequence of the REP1 and REP2 proteins encoded by one of plasmids pSR1, pSB1, pSB2, pSB3, pSB4, pSM1, pKD1, pPM1-and the 2 μm plasmid, for example as described in Volkert et al, op. cit., Murray et al, op. cit., and Painting et al, op. cit. Variants and fragments of these REP1 and REP2 proteins are also included in the present invention. "Fragments" and "variants" of REP1 and REP2 are those which, when encoded by the plasmid in place of the native ORF, do not substantially disrupt the stable multicopy maintenance of the plasmid within a suitable yeast population. Such variants and fragments of REP1 and REP2 will usually have at least 5%, 10%, 20%, 30%, 40%, 50%, 60%, 70%, 80%, 90%, 95%, 98%, 99%, or more, homology with a REP1 and REP2 protein, respectively as encoded by one of plasmids pSR1, pSB1, pSB2, pSB3, pSB4, pSM1, pKD1, pPM1 and the 2 μm plasmid. The REP1 and REP2 proteins encoded by the ORFs on the plasmid must be compatible. It is preferred that the REP1 and REP2 proteins have the sequences of REP1 and REP2 proteins encoded by the same naturally occurring 2 μm-family plasmid, such as pSR1, pSB1, pSB2, pSB3, pSB4, pSM1, pKD1, pPM1 and the 2 μm plasmid, or variant or fragments thereof. A 2 μm-family plasmid typically comprises two inverted repeat sequences. The inverted repeats may be any size, so long as they each contain an FRT site (see above). The inverted repeats are typically highly homologous. They may, or may not, share greater than 50%, 60%, 70%, 80%, 90%, 95%, 96%, 97%, 98%, 99%, 99.5% or more sequence identity. In a preferred embodiment they are identical. Typically the inverted repeats are each between 200 to 1000 bp in length. Preferred inverted repeat sequences may, or may not, each have a length of from 200 to 300 bp, 300 to 400 bp, 400 to 500 bp, 500 to 600 bp, 600 to 700 bp, 700 to 800 bp, 800 to 900 bp, or 900 to 1000 bp. Particularly preferred inverted repeats are those of the plasmids pSR1 (959 bp), pSB1 (675 bp), pSB2 (477 bp), pSB3 (391 bp), pSM1 (352 bp), pKD1 (346 bp), the 2 μm plasmid (599 bp), pSB4 or pPM1.

The sequences of the inverted repeats may,. or may not, be varied. However, the sequences of the FRT site in each inverted repeat should be compatible with the specificity of the FLP protein encoded by the plasmid, thereby to enable the encoded FLP protein to act to catalyse the site-specific recombination between the inverted repeat sequences of the plasmid. Recombination between inverted repeat sequences (and thus the ability of the FLP protein to recognise the FRT sites with the plasmid) can be determined by methods known in the art. For example, a plasmid in a yeast cell under conditions that favour FLP expression can be assayed for changes in the restriction profile of the plasmid which would result from a change in the orientation of a region of the plasmid relative to another region of the plasmid. The detection of changes in restriction profile indicate that the FLP protein is able to recognise the FRT sites in the plasmid and therefore that the FRT site in each inverted repeat are compatible with the specificity of the FLP protein encoded by the plasmid.

In a particularly preferred embodiment, the sequences of inverted repeats, including the FRT sites, are derived from the same 2 μm-family plasmid as the ORF encoding the FLP protein, such as pSR1, pSB1, pSB2, pSB3, pSB4, pSM1, pKD1, pPM1 or the 2 μm plasmid.

The inverted repeats are typically positioned with the 2 μm-family plasmid such that the two regions defined between the inverted repeats (e.g. such as defined as UL and US in the 2 μm plasmid) are of approximately similar size, excluding exogenously introduced sequences such as transgenes. For example, one of the two regions may, or may not, have a length equivalent to at least 40%, 50%, 60%, 70%, 80%, 90%, 95% or more, up to 100%, of the length of the other region.

A 2 μm-family plasmid typically comprises the ORF that encodes FLP and one inverted repeat (arbitrarily termed "IR1" to distinguish it from the other inverted repeat mentioned in the next paragraph) juxtaposed in such a manner that IR1 occurs at the distal end of the FLP ORF, without any intervening coding sequence, for example as seen in the 2 μm plasmid. By "distal end" in this context we mean the end of the FLP ORF opposite to the end from which the promoter initiates its transcription. In a preferred embodiment, the distal end of the FLP ORF overlaps with IR1.

A 2 μm-family plasmid typically comprises the ORF that encodes REP2 and the other inverted repeat (arbitrarily termed "IR2" to distinguish it from IR1 mentioned in the previous paragraph) juxtaposed in such a manner that IR2 occurs at the distal end of the REP2 ORF, without any intervening coding sequence, for example as seen in the 2 μm plasmid. By "distal end" in this context we mean the end of the REP2 ORF opposite to the end from which the promoter initiates its transcription.

In one embodiment, the ORFs encoding REP2 and FLP may, or may not, be present on the same region of the-two regions defined between the inverted repeats of the 2 μm-family plasmid, which region may be the bigger or smaller of the regions (if there is any inequality in size between the two regions).

In one embodiment, the ORFs encoding REP2 and FLP may, or may not, be transcribed from divergent promoters.

Typically, the regions defined between the inverted repeats (e.g. such as defined as UL and US in the 2 μm plasmid) of a 2 μm-family plasmid may, or may not, comprise not more than two endogenous genes that encode a protein that functions in the stable maintenance of the 2 μm-family plasmid as a multicopy plasmid. Thus in a preferred embodiment, one region of the plasmid defined between the inverted repeats may, or may not, comprise not more than the ORFs encoding FLP and REP2; FLP and REP1; or REP1 and REP2, as endogenous coding sequence.

A 2 μm-family plasmid typically comprises an origin of replication (also known as an "autonomously replicating sequence—"ARS"), which is typically bidirectional. Any appropriate ARS sequence can be present. Consensus sequences typical of yeast chromosomal origins of replication may, or may not, be appropriate (Broach et al, 1982, *Cold Spring Harbor Symp. Quant. Biol.*, 47, 1165-1174; Williamson, *Yeast*, 1985, 1, 1-14). Preferred ARSs include those isolated from pSR1, pSB1, pSB2, pSB3, pSB4, pSM1, pKD1, pPM1 and the 2 μm plasmid.

Thus, a preferred 2 μm-family plasmid may, or may not, comprise ORFs encoding FLP, REP1 and REP2, two inverted repeat sequences each inverted repeat comprising an FRT site compatible with the encoded FLP protein, and an ARS sequence. Preferably the FRT sites are derived from the same 2 μm-family plasmid as the sequence of the encoded FLP protein. More preferably the sequences of the encoded REP1 and REP2 proteins are derived from the same 2 μm-family plasmid as each other. Even more preferably, the FRT sites are derived from the same 2 μm-family plasmid as the sequence of the encoded FLP, REP1 and REP2 proteins. Yet more preferably, the sequences of the ORFs encoding FLP, REP1 and REP2, and the sequence of the inverted repeats (including the FRT sites) are derived from the same 2 μm-family plasmid. Furthermore, the ARS site may, or may not, be derived from the same 2 μm-family plasmid as one or more of the ORFs of FLP, REP1 and REP2, and the sequence of the inverted repeats (including the FRT sites).

The term "derived from" includes sequences having an identical sequence to the sequence from which they are derived. However, variants and fragments thereof, as defined above, are also included. For example, an FLP gene having a sequence derived from the FLP gene of the 2 μm plasmid may, or may not, have a modified promoter or other regulatory sequence compared to that of the naturally occurring gene. Additionally or alternatively, an FLP gene having a sequence derived from the FLP gene of the 2 μm plasmid may, or may not, have a modified nucleotide sequence in the open reading frame which may, or may not, encode the same protein as the naturally occurring gene, or may, or may not, encode a modified FLP protein. The same considerations apply to other sequences on a 2 μm-family plasmid having a sequence derived from a particular source.

Optionally, a 2 μm-family plasmid may, or may not, comprise a region derived from the STB region (also known as REP3) of the 2 μm plasmid, as defined in Volkert et al, op. cit. The STB region in a 2 μm-family plasmid of the invention may, or may not, comprise two or more tandem repeat sequences, such as three, four, five or more. Alternatively, no tandem repeat sequences may be present. The tandem repeats may be any size, such as 10, 20, 30, 40, 50, 60 70, 80, 90, 100 bp or more in length. The tandem repeats in the STB region of the 2 μm plasmid are 62 bp in length. It is not essential for the sequences of the tandem repeats to be identical. Slight sequence variation can be tolerated. It may, or may not, be preferable to select an STB region from the same plasmid as either or both of the REP1 and REP2 ORFs. The STB region is thought to be a cis-acting element and preferably is not transcribed.

Optionally, a 2 μm-family plasmid may, or may not, comprise an additional ORF that encodes a protein that functions in the stable maintenance of the 2 μm-family plasmid as a multicopy plasmid. The additional protein can be designated RAF or D. ORFs encoding the RAF or D gene can be seen on, for example, the 2 μm plasmid and pSM1. Thus a RAF or D ORF can comprise a sequence suitable to encode the protein product of the RAF or D gene ORFs encoded by the 2 μm plasmid or pSM1, or variants and fragments thereof. Thus variants and fragments of the protein products of the RAF or D genes of the 2 μm plasmid or pSM1 are also included in the present invention. "Fragments" and "variants" of the protein products of the RAF or D genes of the 2 μm plasmid or pSM1 are those which, when encoded by the 2 μm plasmid or pSM1 in place of the native ORF, do not disrupt the stable multicopy maintenance of the plasmid within a suitable yeast population. Such variants and fragments will usually have at least 5%, 10%, 20%, 30%, 40%, 50%, 60%, 70%, 80%, 90%, 95%, 98%, 99%, or more, homology with the protein product of the RAF or D gene ORFs encoded by the 2 μm plasmid or pSM1.

A naturally occurring 2 μm-family plasmid may, or may not, be preferred. A naturally occurring 2 μm-family plasmid is any plasmid havinig the features defined above, which plasmid is found to naturally exist in yeast, i.e. has not been recombinantly modified to include heterologous sequence. Optionally the naturally occurring 2 μm-family plasmid is selected from pSR1 (Accession No. X02398), pSB3 (Accession No. X02608) or pSB4 as obtained from *Zygosacchatomyces rouxii*, pSB1 or pSB$^2$ (Accession No. NC_002055 or M18274) both as obtained from *Zygosaccharomyces bailli*, pSM1 (Accession No. NC_002054) as obtained from *Zygosaccharomyces fermentati*, pKD1 (Accession No. X03961) as obtained from *Kluyveromyces drosophilarum*, pPM1 from *Pichia membranaefaciens* or, preferably, the 2 μm plasmid (Accession No. NC_001398 or J01347) as obtained from *Saccharomyces cerevisiae*. Accession numbers in this paragraph refer to NCBI deposits.

The 2 μm plasmid (FIG. 1) is a 6,318-bp double-stranded DNA plasmid, endogenous in most *Saccharomyces cerevisiae* strains at 60-100 copies per haploid genome. The 2 μm plasmid comprises a small unique (US) region and a large unique (UL) region, separated by two 599-bp inverted repeat sequences. Site-specific recombination of the inverted repeat sequences results in inter-conversion between the A-form and B-form of the plasmid in vivo (Volkert & Broach, 1986, *Cell*, 46, 541). The two forms of 2 μm differ only in the relative orientation of their unique regions.

While DNA sequencing of a cloned 2 μm plasmid (also known as Scp1) from *Saccharonmyces cerevisiae* gave a size of 6,318-bp (Hartley and Donelson, 1980, *Nature*, 286, 860), other slightly smaller variants of 2 μm, Scp2 and Scp3, are known to exist as a result of small deletions of 125-bp and 220-bp, respectively, in a region known as STB (Cameron et al., 1977, *Nucl. Acids Res.*, 4, 1429: Kikuchi, 1983, *Cell*, 35, 487 and Livingston & Hahne, 1979, *Proc. Natl. Acad. Sci. USA*, 76, 3727). In one study about 80% of natural *Saccharomyces* strains from around the world contained DNA homologous to 2 μm (by Southern blot analysis) (Hollenberg, 1982, *Current Topics in Microbiology and Immunobiology*, 96, 119). Furthermore, variation (genetic polymorphism) occurs within the natural population of 2 μm plasmids found in *S. cerevisiae* and *S. carlsbergensis*, with the NCB1 sequence (accession number NC_001398) being one example.

The 2 μm plasmid has a nuclear localisation and displays a high level of mitotic stability (Mead et al, 1986, *Molecular & General Genetics*, 205, 417). The inherent stability of the 2 μm plasmid results from a plasmid-encoded copy number amplification and partitioning mechanism, which can be compromised during the development of chimeric vectors (Futcher & Cox, 1984, *J. Bacteriol.*, 157, 283; Bachmair & Ruis, 1984, *Monalshefte für Cheimie*, 115, 1229). A yeast strain, which contains a 2 µm plasmid is known as [cir⁺], while a yeast strain which does not contain a 2 µm plasmid is known as [cir⁰].

The US-region of the 2 µm plasmid contains the REP2 and FLP genes, and the UL-region contains the REP1 and D (also known as RAF) genes, the STB-locus and the origin of replication (Broach & Hicks, 1980, *Cell*, 21, 501; Sutton & Broach, 1985, *Mol. Cell. Biol.*, 5, 2770). The Flp recombinase binds to FRT-sites (Flp Recognition Target) within the inverted repeats to mediate site-specific recombination, which is essential for natural plasmid amplification and control of plasmid copy number in vivo (Senecoff et al, 1985, *Proc. Natl. Acad. Sci. U.S.A.*, 82, 7270; Jayaram, 1985, *Proc. Natl. Acad. Sci. U.S.A.*, 82, 5875). The copy number of 2 µm-family plasmids can be significantly affected by changes in Flp recombinase activity (Sleep et al, 2001, *Yeast*, 18, 403; Rose & Broach, 1990, *Methods Enzmol.*, 185, 234). The Rep1 and Rep2 proteins mediate plasmid segregation, although their mode of action is unclear (Sengupta et al, 2001, *J. Bacteriol.*, 183, 9306). They also repress transcription of the FLP gene (Reynolds et al, 1987, *Mol. Cell. Biol.*, 7, 3566).

The FLP and REP2 genes of the 2 µm plasmid are transcribed from divergent promoters, with apparently no intervening sequence defined between them. The FLP and REP2 transcripts both terminate at the same sequence motifs within the inverted repeat sequences, at 24-bp and 178-bp respectively after their translation termination codons (Sutton & Broach, 1985, *Mol. Cell. Biol.*, 5, 2770).

In the case of FLP, the C-terminal coding sequence also lies within the inverted repeat sequence. Furthermore, the two inverted repeat sequences are highly conserved over 599-bp, a feature considered advantageous to efficient plasmid replication and amplification in vivo, although only the FRT-sites (less than 65-bp) are essential for site-specific recombination in vitro (Senecoff et al, 1985, *Proc. Natl. Acad. Sci. U.S.A.*, 82, 7270; Jayaram, 1985, *Proc. Natl. Acad. Sci. U.S.A.*, 82, 5875; Meyer-Leon et al, 1984, *Cold Spring Harbor Symposia On Quantitative Biology*, 49, 797). The key catalytic residues of Flp are arginine-308 and tyrosine-343 (which is essential) with strand-cutting facilitated by histidine-309 and histidine 345 (Prasad et al, 1987, *Proc. Natl. Acad. Sci. U.S.A.*, 84, 2189; Chen et al, 1992, *Cell*, 69, 647; Grainge et al, 2001, *J. Mol. Biol.*, 314, 717).

Two functional domains are described in Rep2. Residues 15-58 form a Rep1-binding domain, and residues 59-296 contain a self-association and STB-binding region (Sengupta et al, 2001, *J. Bacteriol.*, 183, 2306).

Chimeric or large deletion mutant derivatives of 2 µm which lack many of the essential functional regions of the 2 µm plasmid but retain the functional cis element ARS and STB, cannot effectively partition between mother and daughter cells at cell division. Such plasmids can do so if these functions are supplied in trans, by for instance the provision of a functional 2 µm plasmid within the host, such as a [cir⁺] host.

Genes of interest have previously been inserted into the UL-region of the 2 µm plasmid. For example, see plasmid pSAC3U1 in EP 0 286 424 and the plasmid shown in FIG. 2 of WO 2005/061718, which includes a β-lactamase gene (for ampicillin resistance), a LEU2 selectable marker and an oligonucleotide linker, the latter two of which are inserted into a unique SnaBI-site within the UL-region of the 2 µm-like disintegration vector, pSAC3 (see EP 0 286 424). The *E. coli* DNA between the XbaI-sites that contains the ampicillin resistance gene is lost from the plasmid shown in FIG. 2 of WO 2005/061718 after transformation into yeast. This is described in Chinery & Hinchliffe, 1989, *Curr. Genet.*, 16, 21 and EP 0 286 424, where these types of vectors are designated "disintegration vectors". Further polynucleotide insertions can be made in a NotI-site within a linker (Sleep et al, 1991, *Biotechnology* (N Y), 9, 183).

Alternative insertion sites in 2 µm plasmid are known in the art, including those described in Rose & Broach (1990, *Methods Enzymol.*, 185, 234-279), such as plasmids pCV19, pCV20, CV$_{neo}$, which utilise an insertion at EcoRI in FLP, plasmids pCV21, pGT41 and pYE which utilise EcoRI in D as the insertion site, plasmid pHKB52 which utilises PstI in D as the insertion site, plasmid pJDB248 which utilises an insertion at PstI in D and EcoRI in D, plasmid pJDB219 in which PstI in D and EcoRI in FLP are used as insertion sites, plasmid G18, plasmid pAB18 which utilises an insertion at Cla1 in FLP, plasmids pGT39 and pA3, plasmids pYT11, pYT14 and pYT11-LEU which use PstI in D as the insertion site, and plasmid PTY39 which uses RcoRI in FLP as the insertion site. Other 2 µm plasmids include pSAC3, pSAC3U1, pSAC3U2, pSAC300, pSAC310, pSAC3C1, pSAC3PL1, pSAC3SL4, and pSAC3SC1 are described in EP 0 286 424 and Chinery & Hinchliffe (1989, *Curr. Genet.*, 16, 21-25) which also described PstI, EagI or SnaBI as appropriate 2 µm insertion sites. Further 2 µm plasmids include pAYE255, pAYE316, pAYE443, pAYE522 (Kerry-Williams et al, 1998, *Yeast*, 14, 161-169), pDB2244 (WO 00/44772), and pAYE329 (Sleep et al, 2001, *Yeast*, 18, 403-421).

In one preferred embodiment, one or more genes are inserted into a 2 µm-family plasmid within an untranscribed region around the ARS sequence. For example, in the 2 µm plasmid obtained from *S. cerevisiae*, the untranscribed region around the ARS sequence extends from the end of the D gene to the beginning of ARS sequence. Insertion into SnaBI (near the origin of replication sequence ARS) is described in Chinery & Hinchliffe, 1989, *Curr. Genet.*, 16, 21-25. The skilled person will appreciate that gene insertions can also be made in the untranscribed region at neighbouring positions to the SnaBI site described in Chinery & Hinchliffe.

In another preferred embodiment, REP2 and FLP genes in a 2 µm-family plasmid each have an inverted repeat adjacent to them, and one or more genes are inserted into a 2 µm-family plasmid within the region between the first base after the last functional codon of either the REP2 gene or the FLP gene and the last base before the FRT site in the inverted repeat adjacent to said gene. The last functional codon of either a REP2 gene or a FLP gene is the codon in the open reading frame of the gene that is furthest downstream from the promoter of the gene whose replacement by a stop codon will lead to an unacceptable loss of multicopy stability of the plasmid, as defined herein. Thus, disruption of the REP2 or FLP genes at any point downstream of the last functional codon in either gene, by insertion of a polynucleotide sequence insertion, deletion or substitution will not lead to an unacceptable loss of multicopy stability of the plasmid.

For example, the REP2 gene of the 2 µm plasmid can be disrupted after codon 59 and that the FLP gene of the 2 µm plasmid can be disrupted after codon 344, each without a loss of multicopy stability of the plasmid. The last functional codon in equivalent genes in other 2 µm-family plasmids can be determined routinely by making mutants of the plasmids in either the FLP or REP2 genes and following the tests set out herein to determine whether the plasmid retains multicopy stability. Thus, a plasmid insertion site as defined in WO 2005/061719 may, or may not, be used to carry one or more a recombinant genes according to any aspect of the present invention.

One can determine whether a plasmid retains multicopy stability using test such as defined in Chinery & Hinchliffe (1989, *Curr. Genet.*, 16, 21-25). For yeast that do not grow in the non-selective media (YPD, also designated YEPD) defined in Chinery & Hinchliffe (1989, *Curr. Genet,* 16, 21-25) other appropriate non-selective media might be used. Plasmid stability may be defined as the percentage cells remaining prototrophic for the selectable marker after a defined number of generations. The number of generations will preferably be sufficient to show a difference between a control plasmid, such as pSAC35 or pSAC310, or to shown comparable stability to such a control plasmid. The number of generations may be 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100 or more. Higher numbers are preferred. The acceptable plasmid stability might be 1%, 2%, 3%, 4%, 5%, 10%, 15%, 20%, 25%, 30%, 40%, 50%, 60%, 70%, 75%, 80%, 85%, 90%, 95%, 96%, 97%, 98%, 99%, 99.9% or substantially 100%. Higher percentages are preferred. The skilled person will appreciate that, even though a plasmid may have a stability less than 100% when grown on non-selective media, that plasmid can still be of use when cultured in selective media. For example plasmid pDB2711 as described in the examples is only 10% stable when the stability is determined accordingly to test of Example 2 of WO 2005/061719, but provides a 15-fold increase in recombinant transferrin productivity in shake flask culture under selective growth conditions.

Thus one or more gene insertions may, or may not, occur between the first base after the last functional codon of the REP2 gene and the last base before the FRT site in an inverted repeat adjacent to said gene, preferably between the first base of the inverted repeat and the last base before the FRT site, more preferably at a position after the translation termination codon of the REP2 gene and before the last base before the FRT site.

Additionally or alternatively one or more gene insertions may, or may not, occur between the first base after the last functional codon of the FLP gene and the last base before the FRT site in an inverted repeat adjacent to said gene, preferably between the first base of the inverted repeat and the last base before the FRT site, more preferably between the first base after the end of the FLP coding sequence and the last base before the FRT site, such as at the first base after the end of the FLP coding sequence.

In one preferred embodiment, where the 2 μm-family plasmid is based on the 2 μm plasmid of *S. cerevisiae*, it is a disintegration vector as known in the art (for example, see EP 286 424, the contents of which are incorporated herein by reference). A disintegration vector may, or may not, be a 2 μm plasmid vector comprising a DNA sequence which is intended to be lost by recombination, three 2 μm FRT sites, of which one pair of sites is in direct orientation and the other two pairs are in indirect orientation, and a DNA sequence of interest (such as an *E. coli* origin of replication and bacterial selectable marker), the said sequence to be lost being located between the said sites which are in direct orientation.

Thus, the sequence to be lost may, or may not, comprise a selectable marker DNA sequence.

A preferred disintegration vector may, or may not, comprise a complete 2 μm plasmid additionally carrying (i) a bacterial plasmid DNA sequence necessary for propagation of the vector in a bacterial host; (ii) an extra 2 μm FRT site; and a selectable marker DNA sequence for yeast transformation; the said bacterial plasmid DNA sequence being present and the extra FRT site being created at a restriction site, such as XbaI, in one of the two inverted repeat sequences of the 2 μm plasmid, the said extra FRT site being in direct orientation in relation to the endogenous FRT site of the said one repeat sequence, and the bacterial plasmid DNA sequence being sandwiched between the extra FRT site and the endogenous FRT site of the said one repeat sequence. In a preferred disintegration vector, all bacterial plasmid DNA sequences may, or may not, be sandwiched as said. A particularly preferred 2 μm plasmid vector has substantially the configuration of pSAC3 as shown in EP 286 424.

The term "disintegration vector" as used herein also includes plasmids as defined in U.S. Pat. No. 6,451,559, the contents of which are incorporated herein by reference. Thus a disintegration vector may, or may not, be a 2 μm vector that, other than DNA sequence encoding non-yeast polypeptides, contains no bacterial (particularly *E. coli*) origin of replication, or more preferably no bacterial (particularly *E. coli*) sequence and preferably all DNA in said vector, other than DNA sequence encoding non-yeast polypeptides, is yeast-derived DNA.

Desired Proteins and Other Proteins Defined by the Present Application:

The terms "protein" and "desired protein" as used herein includes all natural and non-natural proteins, polypeptides and peptides. For the purposes of the present invention, a "heterologous protein" is a protein that is encoded by a "recombinant gene" as described above. The "heterologous protein" may, or may not, be identical in sequence to a protein that is encoded by one of more other genes that naturally occur in the expression system that is used (by "expression system" we include the meaning of a host cell's genome (typically the chromosome) where the "recombinant gene" is chromosomally integrated, or a plasmid where the "recombinant gene" is encoded by a plasmid). For example, in the context of a "heterologous protein" that is encoded by a "recombinant gene" carried on a 2 μm-family plasmid, the "heterologous protein" may, or may not, be a protein that is not naturally encoded by a 2 μm-family plasmid and can also be described as a "non 2 μm-family plasmid protein". For convenience, the terms "heterologous protein" and "non 2 μm-family plasmid protein" are used synonymously in this application. Optionally therefore, when encoded by a 2 μm-family, the heterologous protein is not a FLP, REP1, REP2, or a RAF/D protein as encoded by any one of pSR1, pSB3 or pSB4 as obtained from *Z. rouxii*, pSB1 or pSB2 both as obtained from *Z. bailli*, pSM1 as obtained from *Z. fermentati*, pKD1 as obtained from *K. drosophilarum*, pPM1 as obtained from *P. membranaefaciens* or the 2 μm plasmid as obtained from *S. cerevisiae*.

A gene encoding a desired heterologous, or other, protein comprises a polynucleotide sequence encoding the heterologous protein (typically according to standard codon usage for any given organism), designated the open reading frame ("ORF"). The gene may, or may not, additionally comprise some polynucleotide sequence that does not encode an open reading frame (termed "non-coding region").

Non-coding region in the gene may, or may not, contain one or more regulatory sequences, operatively linked to the ORF, which allow for the transcription of the open reading frame and/or translation of the resultant transcript.

The term "regulatory sequence" refers to a sequence that modulates (i.e., promotes or reduces) the expression (i.e., the transcription and/or translation) of an ORF to which it is operably linked. Regulatory regions typically include promoters, terminators, ribosome binding sites and the like. The skilled person will appreciate that the choice of regulatory region will depend upon the intended expression system. For example, promoters may, or may not, be constitutive or inducible and may, or may not, be cell- or tissue-type specific or non-specific. Suitable regulatory regions, may, or may not, be 5 bp, 10 bp, 15 bp, 20 bp, 25 bp, 30 bp, 35 bp, 40 bp, 45 bp, 50 bp, 60 bp, 70 bp, 80 bp, 90 bp, 100 bp, 120 bp, 140 bp, 160 bp, 180 bp, 200 bp, 220 bp, 240 bp, 260 bp, 280 bp, 300 bp, 350 bp, 400 bp, 450 bp, 500 bp, 550 bp, 600 bp, 650 bp, 700 bp, 750 bp, 800 bp, 850 bp, 900 bp, 950 bp, 1000 bp, 1100 bp, 1200 bp, 1300 bp, 1400 bp, 1500 bp or greater, in length.

Those skilled in the art will recognise that the gene encoding a chaperone, for example PDI, may, or may not, additionally comprise non-coding regions and/or regulatory regions. Such non-coding regions and regulatory regions are not restricted to the native non-coding regions and/or regulatory regions normally associated with the chaperone ORF.

Where the expression system is yeast, such as *Saccharomyces cerevisiae*, suitable promoters for *S. cerevisiae* include those associated with the PGK1 gene, GAL1 or GAL10 genes, TEF1, TEF2, PYK1, PMA1, CYC1, PHO5, TRP1, ADH1, ADH2, the genes for glyceraldehyde-3-phosphate dehydrogenase, hexokinase, pyruvate decarboxylase, phosphofructokinase, triose phosphate isomerase, phosphoglucose isomerase, glucokinase, α-mating factor pheromone, a-mating factor pheromone, the PRB1 promoter, the PRA1 promoter, the GPD1 promoter, and hybrid promoters involving hybrids of parts of 5' regulatory regions with parts of 5' regulatory regions of other promoters or with upstream activation sites (e.g. the promoter of EP-A-258 067).

Suitable transcription termination signals are well known in the art. Where the host cell is eucaryotic, the transcription termination signal is optionally derived from the 3' flanking sequence of a eucaryotic gene, which contains proper signals for transcription termination and polyadenylation. Suitable 3' flanking sequences may, or may not, for example, be those of the gene naturally linked to the expression control sequence used, i.e. may, or may not, correspond to the promoter. Alternatively, they may be different. In that case, and where the host is a yeast, optionally *S. cerevisiae*, then the termination signal of the *S. cerevisiae* ADH1, ADH2, CYC1, or PGK1 genes are preferred.

It may, or may not, be beneficial for the promoter and open reading frame of the gene, such as a gene encoding the chaperone (e.g. PDI1) or a desired protein (such as a heterologous desired protein), to be flanked by transcription termination sequences so that the transcription termination sequences are located both upstream and downstream of the promoter and open reading frame, in order to prevent transcriptional read-through into neighbouring genes, such as 2 μm genes, and vice versa.

In one embodiment, the favoured regulatory sequences in yeast, such as *Saccharomyces cerevisiae*, include: a yeast promoter (e.g. the *Saccharomyces cerevisiae* PRB1 promoter), as taught in EP 431 880; and a transcription terminator, optionally the terminator from *Saccharomyces* ADH1, as taught in EP 60 057. Optionally, the vector incorporates at least two translation stop codons.

It may, or may not, be beneficial for the non-coding region to incorporate more than one DNA sequence encoding a translational stop codon, such as UAA, UAG or UGA, in order to minimise translational read-through and thus avoid the production of elongated, non-natural fusion proteins. The translation stop codon UAA is preferred.

The term "operably linked" includes within its meaning that a regulatory sequence is positioned within any non-coding region in a gene such that it forms a relationship with an ORF that permits the regulatory region to exert an effect on the ORF in its intended manner. Thus a regulatory region "operably linked" to an ORF is positioned in such a way that the regulatory region is able to influence transcription and/or translation of the ORF in the intended manner, under conditions compatible with the regulatory sequence.

In one preferred embodiment, the desired protein (such as the heterologous desired protein) is secreted. In that case, a sequence encoding a secretion leader sequence which, for example, comprises most of the natural HSA secretion leader, plus a small portion of the *S. cerevisiae* α-mating factor secretion leader as taught in WO 90/01063 may, or may not, be included in the open reading frame.

Alternatively, the desired protein (such as a heterologous desired protein) may, or may not, be intracellular.

The desired protein (such as a heterologous desired protein) may, or may not, comprise the sequence of a eucaryotic protein, or a fragment or variant thereof. Suitable eucaryotes include fungi, plants and animals. In one embodiment the heterologous protein may, or may not, be a fungal protein, such as a yeast protein. In another preferred embodiment the desired protein (such as a heterologous desired protein) may, or may not, be an animal protein. Exemplary animals include vertebrates and invertebrates. Exemplary, vertebrates include mammals, such as humans, and non-human mammals.

Thus the desired protein (such as a heterologous desired protein) may, or may not, comprise the sequence of a yeast protein. It may, or may not, for example, comprise the sequence of a yeast protein from the same host from which a 2 μm-family plasmid is derived, particularly if the gene encoding the heterologous protein is integrated into said 2 μm-family plasmid. Those skilled in the art will recognise that a method, use or plasmid of the invention may, or may not, comprise DNA sequences encoding more than one heterologous protein, more than one chaperone, or more than one heterologous protein and more than one chaperone.

In another embodiment, the desired protein (such as a desired heterologous protein) may, or may not, comprise the sequence of albumin, a monoclonal antibody, an etoposide, a serum protein (such as a blood clotting factor), antistasin, a tick anticoagulant peptide, transferrin, lactoferrin, endostatin. angiostatin, collagens, immunoglobulins or immunoglobulin-based molecules or fragment of either (e.g. a Small Modular ImmunoPharmaceutical™ ("SMIP") or dAb, Fab' fragments, F(ab')2, scAb, scFv or scFv fragment), a Kunitz domain protein (such as those described in WO 03/066824, with or without albumin fusions), interferons, interleukins, IL10, IL11, IL2, interferon α species and sub-species, interferon β species and sub-species, interferon γ species and sub-species, leptin, CNTF, $CNTF_{Ax15}$, IL1-receptor antagonist, erythropoietin (EPO) and EPO mimics, thrombopoietin (TPO) and TPO mimics, prosaptide, cyanovirin-N, 5-helix, T20 peptide, T1249 peptide, HIV gp41, HIV gp120 urokinase, prourokinase, tPA, hirudin, platelet derived growth factor, parathyroid hormone, proinsulin, insulin, glucagon, glucagon-like peptides, insulin-like growth factor, calcitonin, growth hormone, transforming growth factor β, tumour necrosis factor, G-CSF, GM-CSF, M-CSF, FGF, coagulation factors in both pre and active forms, including but not limited to plasminogen, fibrinogen, thrombin, pre-thrombin, pro-thrombin, von Willebrand's factor, $α_1$-antitrypsin, plasminogen activators, Factor VII, Factor VIII, Factor IX, Factor X and Factor XIII, nerve growth factor, LACI, platelet-derived endothelial cell growth factor (PD-ECGF), glucose oxidase, serum cholinesterase, aprotinin, amyloid precursor protein, inter-alpha trypsin inhibitor, antithrombin III, apo-lipoprotein species, Protein C, Protein S, a metabolite, an antibiotic, or a variant or fragment of any of the above.

A "variant", in the context of the above-listed proteins, refers to a protein wherein at one or more positions there have been amino acid insertions, deletions, or substitutions, either conservative or non-conservative, provided that such changes result in a protein whose basic properties, for example enzymatic activity or receptor binding (type of and specific activity), thermostability, activity in a certain pH-range (pH-stability) have not significantly been changed. "Significantly" in this context means that one skilled in the art would say that the properties of the variant may still be different but would not be unobvious over the ones of the original protein.

By "conservative substitutions" is intended combinations such as Val, Ile, Leu, Ala, Met; Asp, Glu; Asn, Gln; Ser, Thr; Gly, Ala; Lys, Arg, His; and Phe, Tyr, Trp. Preferred conservative substitutions include Gly, Ala; Val, Ile, Leu; Asp, Glu; Asn, Gln; Ser, Thr; Lys, Arg; and Phe, Tyr.

A "variant" typically has at least 25%, at least 50%, at least 60% or at least 70%, preferably at least 80%, more preferably at least 90%, even more preferably at least 95%, yet more preferably at least 99%, most preferably at least 99.5% sequence identity to the polpeptide from which it is derived.

The percent sequence identity between two polypeptides may be determined using suitable computer programs, for example the GAP program of the University of Wisconsin Genetic Computing Group and it will be appreciated that percent identity is calculated in relation to polypeptides whose sequence has been aligned optimally.

The alignment may alternatively be carried out using the Clustal W program (Thompson et al., (1994) *Nucleic Acids Res.*, 22(22), 4673-80). The parameters used may, or may not, be as follows:

Fast pairwise alignment parameters: K-tuple(word) size; 1, window size; 5, gap penalty; 3, number of top diagonals; 5. Scoring method: x percent.

Multiple alignment parameters: gap open penalty; 10, gap extension penalty; 0.05.

Scoring matrix: BLOSUM.

Such variants may, or may not, be natural or made using the methods of protein engineering and site-directed mutagenesis as are well known in the art.

A "fragment", in the context of the above-listed proteins, refers to a protein wherein at one or more positions there have been deletions. Thus the fragment may, or may not, comprise at most 5, 10, 20, 30, 40 or 50% of the complete sequence of the full mature polypeptide. Typically a fragment comprises up to 60%, more typically up to 70%, preferably up to 80%, more preferably up to 90%, even more preferably up to 95%, yet more preferably up to 99% of the complete sequence of the full desired protein. Particularly preferred fragments of a protein comprise one or more whole domains of the protein.

In one particularly preferred embodiment the desired protein (such as a desired heterologous protein) comprises the sequence of albumin or a variant or fragment thereof.

By "albumin" we include a protein comprising the sequence of an albumin protein obtained from any source. Typically the source is mammalian. In one preferred embodiment the serum albumin is human serum albumin ("HSA"). The term "human serum albumin" includes the meaning of a serum albumin having an amino acid sequence naturally occurring in humans, and variants thereof. Optionally the albumin has the amino acid sequence disclosed in WO 90/13653 or a variant thereof. The HSA coding sequence is obtainable by known methods for isolating cDNA corresponding to human genes, and is also disclosed in, for example, EP 73 646 and EP 286 424.

In another preferred embodiment the "albumin" comprises the sequence of bovine serum albumin. The term "bovine serum albumin" includes the meaning of a serum albumin having an amino acid sequence naturally occurring in cows, for example as taken from Swissprot accession number P02769, and variants thereof as defined below. The term "bovine serum albumin" also includes the meaning of fragments of full-length bovine serum albumin or variants thereof, as defined below.

In another preferred embodiment the albumin comprises the sequence of an albumin derived from one of serum albumin from dog (e.g. see Swissprot accession number P49822), pig (e.g. see Swissprot accession number P08835), goat (e.g. as available from Sigma as product no. A2514 or A4164), turkey (e.g. see Swissprot accession number O73860), baboon (e.g. as available from Sigma as product no. A1516), cat (e.g. see Swissprot accession number P49064), chicken (e.g. see Swissprot accession number P19121), ovalbumin (e.g. chicken ovalbumin) (e.g. see Swissprot accession number P01012), donkey (e.g. see Swissprot accession number P39090), guinea pig (e.g. as available from Sigma as product no. A3060, A2639, O5483 or A6539), hamster (e.g. as available from Sigma as product no. A5409), horse (e.g. see Swissprot accession number P35747), rhesus monkey (e.g. see Swissprot accession number Q28522), mouse (e.g. see Swissprot accession number O89020), pigeon (e.g. as defined by Khan et al, 2002, *Int. J. Biol. Macromol.*, 30(3-4),171-8), rabbit (e.g. see Swissprot accession number P49065), rat (e.g. see Swissprot accession number P36953) and sheep (e.g. see Swissprot accession number P14639) and includes variants and fragments thereof as defined below.

Many naturally occurring mutant forms of albumin are known. Many are described in Peters, (1996, *All About Albumin: Biochemistry, Genetics and Medical Applications*, Academic Press, Inc., San Diego, Calif., p. 170-181). A variant as defined above may, or may not, be one of these naturally occurring mutants.

A "variant albumin" refers to an albumin protein wherein at one or more positions there have been amino acid insertions, deletions, or substitutions, either conservative or non-conservative, provided that such changes result in an albumin protein for which at least one basic property, for example binding activity (tripe of and specific activity e.g. binding to bilirubin), osmolarity (oncotic pressure, colloid osmotic pressure), behaviour in a certain pH-range (pH-stability) has not significantly been changed. "Significantly" in this context means that one skilled in the art would say that the properties of the variant may still be different but would not be unobvious over the ones of the original protein.

By "conservative substitutions" is intended combinations such as Gly, Ala; Val, Ile, Leu; Asp, Glu; Asn, Gln; Ser, Thr; Lys, Arg; and Phe, Tyr. Such variants may, or may not, be made by techniques well known in the art, such as by site-directed mutagenesis as disclosed in U.S. Pat. No. 4,302,386 issued 24 Nov. 1981 to Stevens, incorporated herein by reference.

Typically an albumin variant will have more than 40%, usually at least 50%, more typically at least 60%, preferably at least 70%, more preferably at least 80%, yet more preferably at least 90%, even more preferably at least 95%, most preferably at least 98% or more sequence identity with naturally occurring albumin. The percent sequence identity between two polypeptides may be determined using suitable computer programs, for example the GAP program of the University of Wisconsin Genetic Computing Group and it will be appreciated that percent identity is calculated in relation to polypeptides whose sequence has been aligned optimally. The alignment may alternatively be carried out using the Clustal W program (Thompson et al., 1994). The parameters used may, or may not, be as follows:

Fast pairwise alignment parameters: K-tuple(word) size; 1, window size; 5, gap penalty; 3, number of top diagonals; 5.

Scoring method: x percent. Multiple alignment parameters: gap open penalty; 10, gap extension penalty; 0.05. Scoring matrix: BLOSUM.

The term "fragment" as used above includes any fragment of full-length albumin or a variant thereof, so long as at least one basic property, for example binding activity (type of and specific activity e.g. binding to bilirubin), osmolarity (oncotic pressure, colloid osmotic pressure), behaviour in a certain pH-range (pH-stability) has not significantly been changed. "Significantly" in this context means that one skilled in the art would say that the properties of the variant may still be different but would not be unobvious over the ones of the original protein. A fragment will typically be at least 50 amino acids long. A fragment may, or may not, comprise at least one whole sub-domain of albumin. Domains of HSA have been expressed as recombinant proteins (Dockal, M. et al., 1999, *J. Biol. Chem.*, 274, 29303-29310), where domain I was defined as consisting of amino acids 1-197, domain II was defined as consisting of amino acids 189-385 and domain III was defined as consisting of amino acids 381-585. Partial overlap of the domains occurs because of the extended α-helix structure (h10-h1) which exists between domains I and II, and between domains II and III (Peters, 1996, op. cit., Table 2-4). HSA comprises six sub-domains (sub-domains IA, IB, IIA, IIB, IIIA and IIIB). Sub-domain IA comprises amino acids 6-105, sub-domain IB comprises amino acids 120-177, sub-domain IIA comprises amino acids 200-291, sub-domain IIB comprises amino acids 316-369, sub-domain IIIA comprises amino acids 392-491 and sub-domain IIIB comprises amino acids 512-583. A fragment may, or may not, comprise a whole or part of one or more domains or sub-domains as defined above, or any combination of those domains and/or sub-domains.

In another particularly preferred embodiment the desired protein (such as a desired heterologous protein) comprises the sequence of transferrin or a variant or fragment thereof. The term "transferrin" as used herein includes all members of the transferrin family (Testa, *Proteins of iron metabolism*, CRC Press, 2002; Harris & Aisen, *Iron carriers and iron proteins*, Vol. 5, Physical Bioinorganic Chemistry, VCH, 1991) and their derivatives, such as transferrin, mutant transferrins (Mason et al, 1993, *Biochemistry*, 32, 5472; Mason et al, 1998, *Biochem. J.*, 330(1), 35), truncated transferring, transferrin lobes (Mason et al, 1996, *Protein Expr. Purif.*, 8, 119; Mason et al, 1991, *Protein Expr. Purif.*, 2, 214), lactoferrin, mutant lactoferrins, truncated lactoferrins, lactoferrin lobes or fusions of any of the above to other peptides, polypeptides or proteins (Shin et al, 1995, *Proc. Natl. Acad. Sci. USA*. 92, 2820; Ali et al, 1999, *J. Biol. Chem.*, 274, 24066; Mason et al, 2002, *Biochemistry*), 41, 9448).

The transferrin may, or may not, be human transferrin. The term "human transferrin" is used herein to denote material which is indistinguishable from transferrin derived from a human or which is a variant or fragment thereof. A "variant" includes insertions, deletions and substitutions, either conservative or non-conservative, where such changes do not substantially alter the useful ligand-binding or immunogenic properties of transferrin.

Mutants of transferrin are included in the invention. Such mutants may, or may not, have altered immunogenicity. For example, transferrin mutants may, or may not, displays modified (e.g. reduced) glycosylation. The N-linked glycosylation pattern of a transferrin molecule can be modified by adding/removing amino acid glycosylation consensus sequences such as N-X-S/T, at any or all of the N, X, or S/T position. Transferrin mutants may, or may not, be altered in their natural binding to metal ions and/or other proteins, such as transferrin receptor. An example of a transferrin mutant modified in this manner is exemplified below.

We also include naturally-occurring polymorphic variants of human transferrin or human transferrin analogues. Generally, variants or fragments of human transferrin will have at least 5%, 10%, 15%, 20%, 30%, 40% or 50% (preferably at least 80%, 90% or 95%) of human transferrin's ligand binding activity (for example iron-binding), weight for weight. The iron binding activity of transferrin or a test sample can be determined spectrophotometrically by 470 nm:280 nm absorbance ratios for the proteins in their iron-free and fully iron-loaded states. Reagents should be iron-free unless stated otherwise. Iron can be removed from transferrin or the test sample by dialysis against 0.1M citrate, 0.1M acetate, 10 mM EDTA pH4.5. Protein should be at approximately 20 mg/mL in 100 mM HEPES, 10 mM $NaHCO_3$ pH8.0. Measure the 470 nm:280 nm absorbance ratio of apo-transferrin (Calbiochem, CN Biosciences, Nottingham, UK) diluted in water so that absorbance at 280 nm can be accurately determined spectrophotometrically (0% iron binding). Prepare 20 mM iron-nitrilotriacetate (FeNTA) solution by dissolving 191 mg nitrotriacetic acid in 2 mL 1M NaOH, then add 2 mL 0.5M ferric chloride. Dilute to 50 mL with deionised water. Fully load apo-transferrin with iron (100% iron binding) by adding a sufficient excess of freshly prepared 20 mM FeNTA, then dialyse the holo-transferrin preparation completely against 100 mM HEPES, 10 mM $NaHCO_3$ pH8.0 to remove remaining FeNTA before measuring the absorbance ratio at 470 nm:280 nm. Repeat the procedure using test sample, which should initially be free from iron, and compare final ratios to the control.

Additionally, single or multiple heterologous fusions comprising any of the above; or single or multiple heterologous fusions to albumin, transferrin or immunoglobins or a variant or fragment of any of these may, or may not, be used. Such fusions include albumin N-terminal fusions, albumin C-terminal fusions and co-N-terminal and C-terminal albumin fusions as exemplified by WO 01/79271, and transferrin N-terminal fusions, transferrin C-terminal fusions, and co-N-terminal and C-terminal transferrin fusions.

Examples of transferrin fusions are given in US patent applications US2003/0221201 and US2003/0226155, Shin, et al., 1995, *Proc Natl Acad Sci USA* 92, 2820, Ali, et al., 1999, *J Biol Chem*, 274, 24066, Mason, et al., 2002, *Biochemistry*, 41, 9448, the contents of which are incorporated herein by reference.

The skilled person will also appreciate that the open reading frame of any other gene or variant, or part or either, can be utilised as an open reading frame for use with the present invention. For example, the open reading frame may, or may not, encode a protein comprising any sequence, be it a natural protein (including a zymogen), or a variant, or a fragment (which may, or may not, for example, be a domain) of a natural protein; or a totally synthetic protein; or a single or multiple fusion of different proteins (natural or synthetic). Such proteins can be taken, but not exclusively, from the lists provided in WO 01/79258. WO 01/79271, WO 01/79442, WO 01/79443, WO 01/79444 and WO 01/79480, or a variant or fragment thereof the disclosures of which are incorporated herein by reference. Although these patent applications present the list of proteins in the context of fusion partners for albumin, the present invention is not so limited and, for the purposes of the present invention, any of the proteins listed therein may, or may not, be presented alone or as fusion partners for albumin, the Fc region of immunoglobulin, transferrin, lactoferrin or any other protein or fragment or variant of any of the above, as a desired polypeptide.

The desired protein (such as a desired heterologous protein) may, or may not, be a therapeutically active protein. In other words, it may, or may not, have a recognised medical effect on individuals, such as humans. Many different types of therapeutically active protein are well known in the art.

The desired protein (such as a desired heterologous protein) may, or may not, be a protein that is useful in diagnostic techniques. Many different types of diagnostically useful protein are well known in the art.

The desired protein (such as a desired heterologous protein) may, or may not, be a protein that has no relationship to healthcare. It may, or may not, for example, be a protein that has a utility as an industrial, domestic or nutritional (e.g. as a foodstuff or additive) agent. Many different types of proteins having industrial, domestic and/or nutritional utilities are also well known in the art.

The desired protein (such as a desired heterologous protein) may, or may not, comprise a leader sequence effective to cause secretion in a host cell, such as in a yeast cell.

Numerous natural or artificial polypeptide signal sequences (also called secretion pre regions) have been used or developed for secreting proteins from host cells.

The signal sequence directs the nascent protein towards the machinery of the cell that exports proteins from the cell into the surrounding medium or, in some cases, into the periplasmic space. The signal sequence is usually, although not necessarily, located at the N-terminus of the primary translation product and is generally, although not necessarily, cleaved off the protein during the secretion process, to yield the "mature" protein.

In the case of some proteins the entity that is initially secreted, after the removal of the signal sequence, includes additional amino acids at its N-terminus called a "pro" sequence, the intermediate entity being called a "pro-protein". These pro sequences may, or may not, assist the final protein to fold and become functional, and are usually then cleaved off. In other instances, the pro region simply provides a cleavage site for an enzyme to cleave off the pre-pro region and is not known to have another function.

The pro sequence can be removed either during the secretion of the protein from the cell or after export from the cell into the surrounding medium or periplasmic space.

Polypeptide sequences which direct the secretion of proteins, whether they resemble signal (i.e. pre) sequences or pre-pro secretion sequences, are referred to as leader sequences. The secretion of proteins is a dynamic process involving translation, translocation and post-translational processing, and one or more of these steps may not necessarily be completed before another is either initiated or completed.

For production of proteins in eucaryotic species such as the yeasts *Saccharomyces cerevisiae, Zygosaccharomyces* species, *Klujveromyces lactis* and *Pichia pastoris*, known leader sequences include those from the *S. cerevisiae* acid phosphatase protein (Pho5p) (see EP 366 400), the invertase protein (Suc2p) (see Smith et al. (1985) *Science*, 229, 1219-1224) and heat-shock protein-150 (Hsp150p) (see WO 95/33833). Additionally, leader sequences from the *S. cerevisiae* mating factor alpha-1 protein (MFα-1) and from the human lysozyme and human serum albumin (HSA) protein have been used, the latter having been used especially, although not exclusively, for secreting human albumin. WO 90/01063 discloses a fusion of the MFα-1 and HSA leader sequences, which advantageously reduces the production of a contaminating fragment of human albumin relative to the use of the MFα-1 leader sequence. Modified leader sequences are also disclosed in WO 2004/009819 and in the examples of this application; the reader will appreciate that those leader sequences can be used with proteins other than transferrin. In addition, the natural transferrin leader sequence may, or may not, be used to direct secretion of transferrin and other heterologous proteins.

Where a chaperone that is recombinantly expressed according to the present invention is protein disulphide isomerase, then optionally the desired protein (such as a desired heterologous protein) may, or may not, comprise disulphide bonds in its mature form. Any disulphide bonds may, or may not, be intramolecular and/or intermolecular.

The desired protein (such as a desired heterologous protein) may, or may not, be a commercially useful protein, such as a therapeutically, diagnostically, industrially, domestically or nutritionally useful protein. Some proteins, such as heterologously expressed proteins, are intended to interact with the cell in which they are expressed in order to bring about a beneficial effect on the cell's activities. These proteins are not, in their own right, commercially useful. Commercially useful proteins are proteins that have a utility ex vivo of the cell in which they are expressed. Nevertheless, the skilled reader will appreciate that a commercially useful protein may, or may not, also have a biological effect on the host cell expressing it (such as a heterologous protein), but that that effect is not the main or sole reason for expressing the protein therein.

Commercially useful proteins may include proteins that are useful as metabolites or antibiotics, and the like.

In one embodiment it is preferred that the desired protein (such as a desired heterologous protein) is not β-lactamase. In another embodiment it is preferred that the desired protein (such as a desired heterologous protein) is not antistasin. However, the reader will appreciate that neither of these provisos exclude genes encoding either β-lactamase or antistasin from being present in a host cell or on a plasmid of the invention, merely that the gene encoding the desired protein (such as a desired heterologous protein) encodes a protein other than β-lactamase and/or antistasin.

Plasmids useful in the practice of the present invention can, unless specified otherwise, be any type of plasmid. For the purposes of the present invention, references to "plasmids" may, or may not, also include a reference to other types of vectors. It may be appropriate to choose a suitable plasmid based on the host cell system in which it will be used.

Many plasmids and other vectors are known for the transformation of various expression systems, including systems employing: bacteria (e.g. *Bacillus subtilis* or *Escherichia coli*) transformed with, for example, recombinant bacteriophage, plasmid or cosmid DNA expression vectors; yeasts (e.g. *Saccharomyces cerevisiae* or *Pichia pastoris*) transformed with, for example, yeast expression vectors; insect cell systems transformed with, for example, viral expression vectors (e.g. baculovirus); planit cell systems transfected with, for example viral or bacterial expression vectors; animal cell systems, either in cell culture, transgenic or as gene therapy, transfected with, for example, adenovirus expression vectors.

Typical procaryotic vector plasmids are: pUC18, pUC19, pBR322 and pBR329 available from Biorad Laboratories (Richmond, Calif., USA); pTrc99A, pKK223-3, pKK233-3, pDR540 and pRIT5 available from Pharmacia (Piscataway, N.J., USA); pBS vectors, Phagescript vectors, Bluescript vectors, pNH8A, pNH16A, pNH18A, pNH46A available from Stratagene Cloning Systems (La Jolla, Calif. 92037, USA).

A typical mammalian cell vector plasmid is pSVL available from Pharmacia (Piscataway, N.J., USA). This vector uses the SV40 late promoter to drive expression of cloned genes, the highest level of expression being found in T antigen-producing cells, such as COS-1 cells. An example of an inducible mammalian expression vector is pMSG, also available from Pharmacia (Piscataway, N.J., USA). This vector lo uses the glucocorticoid-inducible promoter of the mouse mammary tumour virus long terminal repeat to drive expression of the cloned gene.

Useful yeast plasmid vectors include the 2 μm-family plasmids (as described above), as well as pRS403-406 and pRS413-416 which are generally available from Stratagene Cloning Systems (La Jolla, Calif. 92037, USA). Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (YCps). Other YIps and YCps plasmids may also be used.

Plasmids for use in any aspect of the present invention can be prepared by modifying plasmids, such as 2 μm-family plasmids, known in the art by inserting the required sequences (for example, one or more genes encoding chaperones and/or one or more genes encoding a heterologous protein) using techniques well known in the art such as are described in by Sambrook et al., Molecular Cloning: A Laboratory Manual, 2001, 3rd edition, the contents of which are incorporated herein by reference. For example, one such method involves ligation via cohesive ends. Compatible cohesive ends can be generated on a DNA fragment for insertion and plasmid by the action of suitable restriction enzymes. These ends will rapidly anneal through complementary base pairing and remaining nicks can be closed by the action of DNA ligase.

A further method uses synthetic double stranded oligonucleotide linkers and adaptors. DNA fragments with blunt ends are generated by bacteriophage T4 DNA polymerase or E.coli DNA polymerase I which remove protruding 3' termini and fill in recessed 3' ends. Synthetic linkers and pieces of blunt-ended double-stranded DNA, which contain recognition sequences for defined restriction enzymes, can be ligated to blunt-ended DNA fragments by T4 DNA ligase. They are subsequently digested with appropriate restriction enzymes to create cohesive ends and ligated to an expression vector with compatible termini. Adaptors are also chemically synthesised DNA fragments which contain one blunt end used for ligation but which also possess one preformed cohesive end. Alternatively a DNA fragment or DNA fragments can be ligated together by the action of DNA ligase in the presence or absence of one or more synthetic double stranded oligonucleotides optionally containing cohesive ends.

Synthetic linkers containing a variety of restriction endonuclease sites are commercially available from a number of sources including Sigma-Genosys Ltd, London Road, Pampisford, Cambridge, United Kingdom.

Appropriate insertion sites in plasmids (such as 2 μm-family plasmids) include, but are not limited to, those discussed above.

Host Cells

The present invention also provides a host cell comprising recombinant genes and/or plasmid according to any aspect of the present invention. The host cell may be any type of cell. Many suitable host cell expression systems are known, including bacteria (for example *E. coli* and *Bacillus subtilis*), yeasts (for example *Succharomyces cerevisiae, Pichia pastoris* and *Kluyveromyces lactis*), filamentous fungi (for example *Aspergillus*), plant cells, whole plants, animal cells and insect cells. Bacterial and yeast host cells may, or may not, be preferred. Bacterial host cells may be useful for cloning purposes. Yeast host cells may be useful for expression of genes present in the plasmid.

In one embodiment the host cell may, or may not, be a yeast cell, such as a member of the *Saccharomyces, Kluyveromyces, Arxula, Yarrowia, Candida, Schizosaccharomyces, Debaryomyces, Xanthophyllomyces, Geotrichum, Ashbya, Hortaea, Schwanniomyces, Trichosporon, Xanthophyllomyces,* or *Pichia* genus. Yeast such *Saccharomyces cerevisiae, Kluyveromyces lactis, Pichia pastoris, Pichia membranaefaciens, Zygosaccharomyces rouxii, Zygosaccharomyces bailii, Zygosaccharomyces fermentati, Kluyveromyces drosphilarum, Pichia methanolica, Hansenula polymorpha* (also known as *Pichia augusta*), *Arxula adeninivorans, Yarrowia lipolytica, Candida boidinii Candida utilis, Schizosaccharomyces pombe* may, or may not, be preferred. Other suitable yeast may, or may not, include *Debaryomyces hansenii, Xanthophyllomyces dendrorhous, Geotrichum candidum, Ashbya gossypii, Hortaea werneckii, Schwanniomyces occidentalis, Trichosporon domesticum,* and/or *Xanthophyllomyces dendrorhous,*

It is may, or may not, be particularly advantageous to use a yeast deficient in one or more protein mannosyl transferases involved in O-glycosylation of proteins, for instance by disruption of the gene coding sequence, as discussed in WO 2004/083245, the contents of which are incorporated herein by reference.

In another embodiment the host cell may, or may not, be an animal cell. For example, the animal cell may, or may not, be a mammalian cell, such as a human cell type.

The host cell type may, or may not, be selected for compatibility with a plasmid type being used. Plasmids obtained from one yeast type can be maintained in other yeast types (Irie et al, 1991, *Gene,* 108(1), 139-144; Irie et al, 1991, *Mol. Gen. Genet.,* 225(2), 257-265). For example, pSR1 from *Zygosaccharomyces rouxaii* can be maintained in *Saccharomyces cerevisiae*. Optionally, the host cell is compatible with a 2 μm-family plasmid (see above for a full description of the following plasmids). For example, where the plasmid is based on pSR1, pSB3 or pSB4 then a suitable yeast cell is *Zygosaccharomyces rouxii;* where the plasmid is based on pSB1 or pSB2 then a suitable yeast cell is *Zygosaccharomyces bailli;* where the plasmid is based on pSM1 then a suitable yeast cell is *Zygosaccaromyces fermentati;* where the plasmid is based on pKD1 then a suitable yeast cell is *Kluyveromyces drosophilarum;* where the plasmid is based on pPM1 then a suitable yeast cell is *Pichia membranaefaciens;* where the plasmid is based on the 2 μm plasmid then a suitable yeast cell is *Saccharomyces cerevisiae* or *Saccharomyces carlsbergensis*. It is particularly preferred that the plasmid is based on the 2 μm plasmid and the yeast cell is *Saccharomyces cerevisiae.*

A 2 μm-family plasmid of the invention can be said to be "based on" a naturally occurring plasmid if it comprises one, two or preferably three of the genes FLP, REP1 and REP2 having sequences derived from that naturally occurring plasmid.

It may, or may not, be particularly advantageous to use a yeast deficient in one or more protein mannosyl transferases involved in O-glycosylation of proteins, for instance by disruption of the gene coding sequence.

Recombinantly expressed proteins can be subject to undesirable post-translational modifications by the producing host cell. For example, the albumin protein sequence does not contain any sites for N-linked glycosylation and has not been reported to be modified, in nature, by O-linked glycosylation. However, it has been found that recombinant human albumin ("rHA") produced in a number of yeast species can be modified by O-linked glycosylation, generally involving mannose. The mannosylated albumin is able to bind to the lectin Concanavalin A. The amount of mannosylated albumin produced by the yeast can be reduced by using a yeast strain deficient in one or more of the PMT genes (WO 94/04687). The most convenient way of achieving this is to create a yeast which has a defect in its genome such that a reduced level of one of the Pmt proteins is produced. For example, there may, or may not, be a deletion, insertion or transposition in the coding sequence or the regulatory regions (or in another gene regulating the expression of one of the PMT genes) such that little or no Pmt protein is produced. Alternatively, the yeast could be transformed to produce an anti-Pmt agent, such as an anti-Pmt antibody.

If a yeast other than *S. cerevisiae* is used, disruption of one or more of the genes equivalent to the PMT genes of *S. cerevisiae* is also beneficial, e.g. in *Pichia pastoris* or *Kluyveromyces lactis*. The sequence of PMT1 (or any other PA4T gene) isolated from *S. cerevisiae* may, or may not, be used for the identification or disruption of genes encoding similar enzymatic activities in other fungal species. The cloning of the PMT1 homologue of *Kluyveromyces lactis* is described in WO 94/04687.

The yeast may, or may not, have a deletion of the HSP150 and/or YAP3 genes as taught respectively in WO 95/33833 and WO 95/23857.

A plasmid as defined above, may, or may not, be introduced into a host through standard techniques. With regard to transformation of procaryotic host cells, see, for example, Cohen et al (1972) *Proc. Natl. Acad. Sci. USA* 69, 2110 and Sambrook et al (2001) *Molecular Cloning, A Laboratory Manual*, 3rd Ed. Cold Spring Harbor Laboratory, Cold Spring Harbor, N.Y. Transformation of yeast cells is described in Sherman et al (1986) *Methods In Yeast Genetics, A Laboratory Manual*, Cold Spring Harbor, N.Y. The method of Beggs (1978) *Nature* 275, 104-109 is also useful. Methods for the transformation of *S. cerevisiae* are taught generally in EP 251 744, EP 258 067 and WO 90/01063, all of which are incorporated herein by reference. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA.

Electroporation is also useful for transforming cells and is well known in the art for transforming yeast cell, bacterial cells and vertebrate cells. Methods for transformation of yeast by electroporation are disclosed in Becker & Guarente (1990) *Methods Enzymol.* 194, 182.

Generally, where a plasmid is used, it will transform not all of the hosts and it will therefore be necessary to select for transformed host cells. Thus, a plasmid may, or may not, comprise a selectable marker, including but not limited to bacterial selectable marker and/or a yeast selectable marker. A typical bacterial selectable marker is the β-lactamase gene although many others are known in the art. Yeast selectable marker include LEU2, TRP1, HIS3, HIS4, URA3, URA5, SFA1, ADE2, MET15, LYS5, LYS2, ILV2, FBA1, PSE1, PDI1 and PGK1. Those skilled in the art will appreciate that any gene whose chromosomal deletion or inactivation results in an inviable host, so called "essential" genes, can be used as a selective marker if a functional gene is provided on the plasmid, as demonstrated for PGK1 in a pgk1 yeast strain (Piper and Curran, 1990, *Curr. Genet.* 17, 119). Suitable "essential" genes can be found within the Stanford Genome Database (SGD), http:://db.yeastgenome.org). Any "essential" gene product (e.g. a product of one of the PDI1, PSE1, PGK1 or FBA1 genes, and others described elsewhere in this application) which, when deleted or inactivated, does not result in an auxotrophic (biosynthetic) requirement, can be used as a selectable marker on a plasmid in a host cell that, in the absence of the plasmid, is unable to produce that gene product, to achieve increased plasmid stability without the disadvantage of requiring the cell to be cultured under specific selective conditions. By "auxotrophic (biosynthetic) requirement" we include a deficiency which can be complemented by nutrient and other additions or modifications to the growth medium. Cells unable to express functional Pgk1p or Fba1p can, however, be complemented by certain additions to growth media and such gene products may not be preferred "essential proteins" according to the present invention. Therefore, preferred "essential marker genes" in the context of the present invention are those that, when deleted or inactivated in a host cell, result in a deficiency which cannot be complemented by any additions or modifications to the growth medium, expect where those additions or modifications are, for example, a polynucleotide, that can restore the ability of the host cell to express the product of the "essential" marker gene, or the product of the "essential" marker gene itself.

Accordingly, a plasmid as provided by, for use in a method of, or comprised in a host cell of the present invention may, or may not, comprise more than one selectable marker.

One selection technique involves incorporating into the expression vector a DNA sequence marker, with any necessary control elements, that codes for a selectable trait in the transformed cell. These markers include dihydrofolate reductase, G418 or neomycin resistance for eucaryotic cell culture, and tetracyclin, kanamycin or ampicillin (i.e. β-lactamase) resistance genes for culturing in *E. coli* and other bacteria. Alternatively, the gene for such selectable trait can be on another vector, which is used to co-transform the desired host cell.

Another method of identifying successfully transformed cells involves growing the cells resulting from the introduction of the plasmid, optionally to allow the expression of a recombinant polypeptide (i.e. where a polypeptide which is encoded by a polynucleotide sequence on the plasmid and is not naturally produced by the host). Cells can be harvested and lysed and their DNA or RNA content examined for the presence of the recombinant sequence using a method such as that described by Southern (1975) *J. Mol. Biol.* 98, 503 or Berent et al (1985) *Biotech.* 3, 208 or other methods of DNA and RNA analysis common in the art. Alternatively, the presence of a polypeptide in the supernatant of a culture of a transformed cell can be detected using antibodies.

In addition to directly assaying for the presence of recombinant DNA, successful transformation can be confirmed by well known immunological methods when the recombinant DNA is capable of directing the expression of the protein. For example, cells successfully transformed with an expression vector produce proteins displaying appropriate antigenicity. Samples of cells suspected of being transformed are harvested and assayed for the protein using suitable antibodies.

Thus, in addition to the transformed host cells themselves, the present invention also contemplates a culture of those cells, optionally a monoclonal (clonally homogeneous) culture, or a culture derived from a monoclonal culture, in a nutrient medium. Alternatively, transformed cells may, or may not, represent an industrially/commercially or pharmaceutically useful product and can be used without further purification or can be purified from a culture medium and optionally formulated with a carrier or diluent in a manner appropriate to their intended industrial/commercial or pharmaceutical use, and optionally packaged and presented in a manner suitable for that use. For example, whole cells could be immobilised; or used to spray a cell culture directly on to/into a process, crop or other desired target. Similarly, whole cell, such as yeast cells can be used as capsules for a huge variety of applications, such as fragrances, flavours and pharmaceuticals.

Transformed host cells may, or may not, be cultured for a sufficient time and under appropriate conditions known to those skilled in the art, and in view of the teachings disclosed herein, to permit the expression of one or more recombinant chaperones and a desired protein (such as a desired heterologous protein).

The culture medium may, or may not, be non-selective or may or may not place a selective pressure on the maintenance of the plasmid.

The thus produced desired protein (such as a desired heterologous protein) may, or may not, be present intracellularly or, if secreted, in the culture medium and/or periplasmic space of the host cell.

Protein Recovery and Formulation

The step of purifying the thus expressed desired protein (such as a desired heterologous protein) from the cultured host cell or the culture medium optionally comprises cell immobilization, cell separation and/or cell breakage, but always comprises at least one other purification step different from the step or steps of cell immobilization, separation and/or breakage.

Cell immobilization techniques, such as encasing the cells using calcium alginate bead, are well known in the art. Similarly, cell separation techniques, such as centrifugation, filtration (e.g. cross-flow filtration, expanded bed chromatography and the like are well known in the art. Likewise, methods of cell breakage, including beadmilling, sonication, enzymatic exposure and the like are well known in the art.

The at least one other purification step may be any other step suitable for protein purification known in the art. For example purification techniques for the recovery of recombinantly expressed albumin have been disclosed in: IAO 92/04367, removal of matrix-derived dye; EP 464 590, removal of yeast-derived colorants; EP 319 067, alkaline precipitation and subsequent application of the albumin to a lipophic phase; and WO 96/37515, U.S. Pat. No. 5,728,553 and WO 00/44772, which describe complete purification processes; all of which are incorporated herein by reference.

Proteins other than albumin may be purified from the culture medium by any technique that has been found to be useful for purifying such proteins.

Suitable methods include ammonium sulphate or ethanol precipitation, acid or solvent extraction, anion or cation exchange chromatography, phosphocellulose chromatography, hydrophobic interaction chromatography, affinity chromatography, hydroxylapatite chromatography, lectin chromatography, concentration, dilution, pH adjustment, diafiltration, ultrafiltration, high performance liquid chromatography ("HPLC"), reverse phase HPLC, conductivity adjustment and the like.

In one embodiment, any one or more of the above mentioned techniques may, or may not, be used to further purify the thus isolated protein to a commercially or industrially acceptable level of purity. By commercially or industrially acceptable level of purity, we include the provision of the protein at a concentration of at least $0.01$ $g.L^{-1}$, $0.02$ $g.L^{-1}$, $0.03$ $g.L^{-1}$, $0.04$ $g.L^{-1}$, $0.05$ $g.L^{-1}$, $0.06$ $g.L^{-1}$, $0.07$ $g.L^{-1}$, $0.08$ $g.L^{-1}$, $0.09$ $g.L^{-1}$, $0.1$ $g.L^{-}$, $0.2$ $g.L^{-1}$, $0.3$ $g.L^{-1}$, $0.4$ $g.L^{-1}$, $0.5$ $g.L^{-1}$, $0.6$ $g.L^{-1}$, $0.7$ $g.L^{-1}$, $0.8$ $g.L^{-1}$, $0.9$ $g.L^{-1}$, $1$ $g.L^{-1}$, $2$ $g.L^{-1}$, $3$ $g.L^{-1}$, $4$ $g.L^{-1}$, $5$ $g.L^{-1}$, $6$ $g.L^{-1}$, $7$ $g.L^{-1}$, $8$ $g.L^{-1}$, $9$ $g.L^{-1}$, $10$ $g.L^{-1}$, $15$ $g.L^{-1}$, $20$ $g.L^{-1}$, $25$ $g.L^{-1}$, $30$ $g.L^{-1}$, $40$ $g.L^{-1}$, $50$ $g.L^{-1}$, $60$ $g.L^{-1}$, $70$ $g.L^{-1}$, $70$ $g.L^{-1}$, $90$ $g.L^{-1}$, $100$ $g.L^{-1}$, $150$ $g.L^{-1}$, $200$ $g.L^{-1}$, $250$ $g.L^{-1}$, $300$ $g.L^{-1}$, $350$ $g.L^{-1}$, $400$ $g.L^{-1}$, $500$ $g.L^{-1}$, $600$ $g.L^{-1}$, $700$ $g.L^{-1}$, $800$ $g.L^{-1}$, $900$ $g.L^{-1}$, $1000$ $g.L^{-1}$, or more.

It is preferred that the desired protein (such as a desired heterologous protein) is purified to achieve a pharmaceutically acceptable level of purity. A protein has a pharmaceutically acceptable level of purity if it is essentially pyrogen free and can be administered in a pharmaceutically efficacious amount without causing medical effects not associated with the activity of the protein.

The resulting desired protein (such as a desired heterologous protein) may, or may not, be used for any of its known utilities, which, in the case of albumin, include i.v. administration to patients to treat severe burns, shock and blood loss, supplementing culture media, and as an excipient in formulations of other proteins.

Although it is possible for a therapeutically, diagnostically, industrially, domestically or nutritionally useful desired protein (such as a desired heterologous protein) obtained by a process of the of the invention to be presented or administered alone, it is preferable to present it as a formulation (such as a pharmaceutical formulation, particularly in the case of therapeutically and/or diagnostically useful proteins), together with one or more acceptable carriers or diluents. The carrier(s) or diluent(s) must be "acceptable" in the sense of being compatible with the desired protein and, where the formulation is intended for administration to a recipient, then not deleterious to the recipient thereof. Typically, the carriers or diluents will be water or saline which will be sterile and pyrogen free.

Optionally the thus formulated protein will be presented in a unit dosage form, such as in the form of a tablet, capsule, injectable solution or the like.

In a sixth aspect of the present invention there is provided a method for producing a desired protein (such as a desired heterologous protein), such as a desired protein as defined above for an earlier aspect of the present invention, comprising: providing a host cell comprising a first recombinant gene encoding the protein comprising the sequence of Orm2p or a variant thereof and a second gene, optionally a second recombinant gene, encoding a desired protein (such as a desired heterologous protein), optionally with the proviso that the first and second genes are not both present within the host cell on the same 2 μm-family plasmid; and culturing the host cell in a culture medium under conditions that allow the expression of the first and second genes. The method may, or may not, further comprise the step of purifying the thus expressed desired protein (such as a desired heterologous protein) from the cultured host cell or the culture medium; and optionally, lyophilising the thus purified protein; and optionally formulating the purified desired protein (such as a desired heterologous protein) with a carrier or diluent; and optionally presenting the thus formulated protein in a unit dosage form.

In the manner discussed above, the host cell may, or may not, further comprise a further recombinant gene encoding a protein comprising the sequence of an alternative chaperone to Orm2p or a variant thereof.

Either or both of the first and second genes in the sixth aspect of the invention may or may not be recombinant genes that are expressed from a plasmid, and optionally from the same plasmid, provided that where both genes are expressed from the same plasmid then that plasmid is not a 2 μm-family plasmid. A further recombinant gene encoding a protein comprising the sequence of an alternative chaperone to Orm2p or a variant thereof may, or may not, also be expressed from a plasmid, optionally from the same plasmid as either or both of the first and second recombinant genes. Except where both of the first and second genes are recombinant genes that are co-expressed from the same plasmid then either one may, or may not, be individually expressed from a 2 µm-family plasmid, such as the 2 µm plasmid. Alternatively, one or both of the first and second genes of the sixth aspect of the invention may, or may not, be integrated into the chromosome of the host cell. The further recombinant gene encoding a protein comprising the sequence of an alternative chaperone to Orm2p or a variant thereof may, or may not, be integrated into the chromosome of the host cell, irrespective of whether or not the first and second genes are expressed from a plasmid or are chromosomally integrated.

The present invention also provides, in a seventh aspect, a host cell as defined above in respect of the sixth aspect, which host cell comprises a first recombinant gene encoding a protein comprising the sequence of Orm2p or a variant or fragment thereof and a second gene, such as a recombinant gene, encoding a desired protein (such as a desired heterologous protein), optionally with the proviso that the first and second genes are not present within the host cell on the same 2 µm-family plasmid.

The present invention also provides, in an eighth aspect, for the use of a nucleic acid sequence encoding the protein Orm2p or a variant thereof to increase the production, in a host cell (such as a host cell as defined above), of a desired protein (such as a desired heterologous protein) encoded by a gene, such as a recombinant gene, in the host cell by co-expression of the nucleic acid sequence and the gene within the host cell (but optionally not including co-expression of these genes from the same 2 µm-family plasmid). Either or both of the nucleic acid sequence and the gene encoding the desired protein may, or may not, be expressed from a plasmid within the host cell, and optionally from the same plasmid. In the manner discussed above, the host cell may, or may not, further comprise a recombinant gene encoding an alternative chaperone to Orm2p or a variant thereof, which may, or may not, be located on a plasmid within the host cell, optionally on the same plasmid as either or both of the nucleic acid sequence and a gene encoding the desired protein. Suitable plasmids include a 2 µm-family plasmid, such as the 2 µm plasmid, as discussed above.

In a ninth aspect of the present invention there is also provided the use of a plasmid as an expression vector to increase the production of a heterologous protein by providing a recombinant gene encoding the heterologous protein and a gene encoding Orm2p or a variant thereof on the same plasmid, optionally with the proviso that the plasmid is not a 2 µm-family plasmid. The plasmid may, or may not, further comprise a gene encoding an alternative chaperone to Orm2p or a variant thereof in the manner discussed above.

Accordingly, in a tenth aspect, the present invention also provides a plasmid, optionally an expression plasmid, comprising a first gene encoding the protein Orm2p or a variant or fragment thereof and a second gene encoding a heterologous protein, as discussed above, optionally with the proviso that the plasmid is not a 2 µm-family plasmid. The plasmid may, or may not, further comprise a third gene encoding an alternative chaperone to Orm2p or a variant thereof. In a preferred embodiment, the third gene encodes a protein comprising the sequence of protein disulphide isomerase.

We have also demonstrated that a plasmid-borne gene encoding a protein comprising the sequence of an "essential" protein can be used to stably maintain the plasmid in a host cell that, in the absence of the plasmid does not produce the "essential" protein. This has the advantage of ensuring the genetic stability of the organism in the chosen culture conditions, and thereby improving the reproducibility and reliability of individual cultures and furthermore enables prolonged culture without reduced productivity due to plasmid loss.

A preferred "essential" protein is a chaperone which may or may not provide the further advantage that, as well as acting as a selectable marker to increase plasmid stability, its expression simultaneously increases the expression of one or more desired proteins, such as a heterologous protein encoded by a recombinant gene, within the host cell. This system is advantageous because it allows the user to minimise the number of recombinant genes that need to be carried by a plasmid. For example, typical prior art plasmids carry marker genes (such as those as described above) that enable the plasmid to be stably maintained during host cell culturing process. Such marker genes need to be retained on the plasmid in addition to any further genes that are required to achieve a desired effect. However, the ability of plasmids to incorporate exogenous DNA sequences is limited and it is therefore advantageous to minimise the number of sequence insertions required to achieve a desired effect. Moreover, some marker genes (such as auxotrophic marker genes) require the culturing process to be conducted under specific conditions in order to obtain the effect of the marker gene. Such specific conditions may not be optimal for cell growth or protein production, or may require inefficient or unduly expensive growth systems to be used.

Thus, it is possible to use a recombinant gene that encodes a protein comprising the sequence of an "essential" protein as a plasmid-borne gene to increase plasmid stability, where the plasmid is present within a cell that, in the absence of the plasmid, is unable to produce the "essential" protein. It will be appreciated that the question of whether or not a protein is "essential" will depend on the system in which it is use; it is possible that a protein that is not "essential" in one host organism might become "essential" when one or more other genes is deleted, disrupted, inactivated, modified or affected in that same host, and thereby be used as an "essential" plasmid-borne gene, as described above likewise whether or not a protein is "essential" may depend on certain physical conditions, such as pH, temperature and/or oxygen levels under which the host cell is cultured.

It is preferred that the "essential protein" is one that, when its encoding gene(s) in a host cell are deleted or inactivated, does not result in the host cell developing an auxotrophic (biosynthetic) requirement. By "auxotrophic (biosynthetic) requirement" we include a deficiency that can be complemented by additions or modifications to the growth medium, in particular additions of, or modifications to, the nutrient composition of the growth medium. Thus, the "essential protein" would be an auxotrophic marker protein if the inactivation of its encoding gene, in a host cell, resulted in the production of an auxotrophic mutant, i.e. a mutant organism that, in order to grow and survive, requires a particular additional nutrient that the normal (unmutated strain) does not—it is preferred that the "essential protein" is not an auxotrophic marker protein. Therefore, an "essential marker gene" which encodes an "essential protein", in the context of the present invention is one that, when deleted or inactivated in a host cell, results in a deficiency which cannot be complemented by additions or modifications, typically nutrient additions or modifications, to the growth medium, expect where those additions or modifications are, for example, a polynucleotide, that can restore the ability of the host cell to express the product of the "essential" marker gene, or the product of the "essential" marker gene itself. In other words, it may, or may not, be preferred if the "essential protein" is not a protein that, in nature, is involved in the metabolic conversion of nutrients by a host cell. The advantage of this system is that the "essential marker gene" can be used as a selectable marker on a plasmid in host cell that, in the absence of the plasmid, is unable to produce that gene product, to achieve increased plasmid stability without the disadvantage of requiring the cell to be cultured under specific selective (e.g. selective nutrient) conditions. Therefore, the host cell can be cultured under conditions that do not have to be adapted for any particular marker gene, without losing plasmid stability. For example, host cells produced using this system can be cultured in non-selective media such as complex or rich media, and under non-selective growth conditions (e.g. such as pH, temperature and/or oxygen levels), which may be more economical, and/or more supportive growth media/conditions, than the minimal media and/or specifically adapted growth conditions that are commonly used to give auxotrophic, and other, marker genes their effect.

The cell may, or may not, for example, have the endogenous copy (or copies) of the gene (or genes) encoding the "essential" protein deleted or otherwise inactivated.

It is particularly preferred if the "essential protein" is an "essential" chaperone, as this can provide the dual advantage of improving plasmid stability without the need for selective growth conditions and increasing the production of desired proteins, such as endogenously encoded or a heterologous proteins, in the host cell. This system also has the advantage that it minimises the number of recombinant genes that need to be carried by the plasmid if one chooses to use overexpression of an "essential" chaperone to increase protein production by the host cell.

Preferred "essential proteins" for use in this aspect of the invention include the "essential" chaperones encoded by the genes PDI1 and PSE1 which, when the endogenous gene(s) encoding these proteins are deleted or inactivated in a host cell, do not result in the host cell developing an auxotrophic (biosynthetic) requirement.

Preferred "essential" chaperones are eucaryotic chaperones, especially preferred "essential" chaperones are yeast chaperones, including chaperones comprising the sequence of proteins encoded by a gene selected from CCT2, CCT3, CCT4, CCT5, CCT6, CCT7, CCT8, CNS1, ERO1 (in the absence of diamide), HSP10, HSP60, PDI1, CDC37, KAR2, MGE1, MRS11, NOB1, SSC1, PSE1, TIM9, PAM18 and TCP1.

It is noted that a host cell that is mutated to inactive ERO1 can be complemented by growth in the presence of the oxidant diamide (Frand & Kaiser, 1998, *Molecular Cell*, 1, 161-170), but diamide is not a "nutrient" addition of the type discussed above in respect of auxotrophic mutations. Diamide is not a commonly used component of growth media and an ERO1 mutant that is transformed with a plasmid comprising the ERO1 gene can be grown in rich media without loss of plasmid stability.

Accordingly, in an eleventh aspect, the present invention also provides a host cell comprising a plasmid (such as a plasmid as defined above by any of the previous aspects of the invention), the plasmid comprising a gene that encodes an "essential" protein, such as a chaperone, wherein, in the absence of the plasmid, the host cell is unable to produce the "essential" protein. Preferably, in the absence of the plasmid, the host cell is inviable. Typically the host cell has been genetically modified to render it unable to produce a functional copy of the "essential" protein from a chromosomally-encoded (or otherwise endogenous) gene. The host cell may, or may not, further comprise a recombinant gene encoding a heterologous protein, such as those described above in respect of earlier aspects of the invention.

The present invention also provides, in a twelfth aspect, a plasmid comprising, as the sole yeast selectable marker, optionally as the sole selectable marker, a gene encoding an "essential" protein, such as an "essential" chaperone. The plasmid may, or may not, further comprise a gene encoding a heterologous protein. The plasmid may, or may not, be a 2 μm-family plasmid.

The present invention also provides, in a thirteenth aspect, a method for producing a desired protein (such as a desired heterologous protein) comprising the steps of: providing a host cell comprising a plasmid, the plasmid comprising a gene that encodes an "essential" protein, such as a chaperone, wherein, in the absence of the plasmid, the host cell is unable to produce the "essential" protein and wherein the host cell further comprises a gene, such as a recombinant gene, encoding a desired protein (such as a desired heterologous protein); culturing the host cell in a culture medium under conditions that allow the expression of the "essential" protein and the desired protein; and optionally purifying the thus expressed desired protein from the cultured host cell or the culture medium; and further optionally, lyophilising the thus purified protein. Thus, a host cell used in this method may, or may not, be a host cell according to the eleventh aspect of the invention and/or the host call may, or may not, be transformed with a plasmid according to the twelfth aspect of the invention.

The method may, or may not, further comprise the step of formulating the purified desired protein (such as a desired heterologous protein) with a carrier or diluent and optionally presenting the thus formulated protein in a unit dosage form, in the manner discussed above.

In one preferred embodiment, the step of "culturing the host cell in a culture medium under conditions that allow the expression of the "essential" protein and the desired protein" involves culturing the host cell in medium that is not specifically adapted to be selective for the presence of any genes on the plasmid, other than for the presence of the gene encoding the "essential" protein. Thus in one embodiment, the step of culturing the host cells may, or may not, be performed in non-selective media, such as complex or rich media and/or under conditions (such as pH, temperature and/or oxygen levels) that are not specifically adapted to select for the presence of the "essential" protein. A medium can be described as non-selective for the purposes of the present situation if it is not specifically adapted to deprive the host cell of a product, typically a nutrient product, that is ordinarily provided to maximise, or otherwise allow, the growth of host cells that have not been modified to prevent the expression of the "essential" protein. For example, a medium (the "test medium") may be a non-selective medium, for the purposes of the present invention if, when one compares plasmid stability in a first host cell type grown in the "test medium" to plasmid stability in a second cell type grown in the "test medium" when each cell type is grown for 5, 10, 15, 20, 25 or 30 generations in the "test medium", wherein—
  (i) the first host cell type is a host cell according to the eleventh aspect of the present invention;
  (ii) the second host cell type is a host cell according to the eleventh aspect of the present invention except that it has been modified to restore the ability of the host cell to produce the "essential" protein in the absence of the plasmid (which is not to say that the second host cell type does not contain a plasmid encoding the "essential" protein, just that it can produce the "essential" protein even when the plasmid is not present);
then the plasmid stability observed in the second cell type is less than 99%. 98%, 95%, 90%, 80%, 70%, 60%, 50%, 40%, 30%, 20%, 15%, 10%, 5%, 4%, 3%, 2%, 1% or less of the plasmid stability observed in the first cell type. Thus, in this embodiment, and despite being grown under non-selective conditions, it is preferable for method of the thirteenth aspect of the present invention to produce host cells which display substantially 100% plasmid stability after 5, 10, 15, 20, 25 or 30 generations.

A fourteenth aspect of the present invention also provides for the use of a polynucleotide that encodes an "essential" protein (as defined above) to increase the stability of a plasmid in a host cell, particularly under non-selective conditions, by integration of the polynucleotide into the plasmid to produce a modified plasmid, wherein the host cell is unable to produce the "essential" protein in the absence of the modified plasmid. The increase in stability may, or may not, be at least 1% (i.e. 1.01 times), 2%, 3%, 4%, 5%, 6%, 7%, 8%, 9%, 10%, 20%, 30%, 40%, 50%, 60%, 70%, 80%, 90%, 100% (i.e. 2-fold), 3-fold, 4-fold, 5-fold, 6-fold s, 7-fold, 8-fold, 9-fold, 10-fold or more greater than the level of stability of the lo unmodified plasmid in the same host cell that has been modified to produce the "essential" protein, when grown for at least five generations under non-selective conditions.

In one embodiment of the fourteenth aspect of the present invention, the plasmid may, or may not, additionally comprise a gene that encodes a further desired heterologous protein, such as defined above in respect of earlier aspects of the present invention. In that case, the use may, or may not, be to improve the productivity of the desired heterologous protein, such as when the host cell comprising the plasmid is grown under non-selective conditions.

In one preferred embodiment, the "essential" protein is a chaperone and may, or may not, be used to simultaneously increase the stability of a plasmid in the host cell and increase the ability of the host cell to produce a desired protein product. The desired protein product may, or may not, be an endogenously encoded protein or may, or may not, be a heterologous protein as defined by the earlier aspects of the invention. WTlere the protein product is a heterologous protein, it may, or may not, be encoded by a recombinant gene that has been integrated into the chromosome of the host cell, or by a gene that is present on a plasmid in the host cell, such as the modified plasmid comprising the polynucleotide that encodes the "essential" protein as defined above.

We have also found that the effects of recombinantly-provided chaperones according to the other embodiments of the present invention can be modulated by modifying the promoters that control the expression levels of the chaperone(s). Surprisingly we have found that, in some cases, shorter promoters result in increased expression of a desired protein. Without being bound by theory we believe that this is because the expression of a recombinant chaperone in host cells that already express desired proteins at high levels can cause the cells to overload themselves with desired protein (such as a desired heterologous protein), thereby achieving little or no overall increase in production of the desired protein. In those cases, it may, or may not, be beneficial to provide recombinant chaperone genes with truncated promoters.

Accordingly, in a fifteenth aspect of the present invention there is provided a polynucleotide (such as a plasmid as defined above) comprising the sequence of a promoter operably connected to a coding sequence encoding a chaperone (such as those described above), for use in increasing the expression of a desired protein (such as a desired heterologous protein), such as those described above, in a host cell (such as those described above) by expression of the polynucleotide sequence within the host cell, wherein the promoter is characterised in that it achieves a modified, such as a higher or lower, level of expression of the chaperone than would be achieved if the coding sequence were to be operably connected to its naturally occurring promoter.

The present invention also provides, in a sixteenth aspect, a method for producing a desired protein (such as a desired heterologous protein) comprising the steps of: providing a host cell comprising a recombinant gene that comprising the sequence of promoter operably connected to a coding sequence encoding a chaperone, the promoter being characterised in that it achieves a lower level of expression of the chaperone than would be achieved if the coding sequence were to be operably connected to its naturally occurring promoter, and the host cell further comprising a gene, such as a recombinant gene, encoding a desired protein (such as a desired heterologous protein); culturing the host cell under conditions that allow the expression of the chaperone and the desired protein; and optionally purifying the thus expressed desired protein from the cultured host cell or the culture medium; and further optionally, lyophilising the thus purified protein; and optionally further formulating the purified desired protein with a carrier or diluent; and optionally presenting the thus formulated protein in a unit dosage form, in the manner discussed above.

As is apparent from the examples of the present application, the combination of recombinantly expressed PDI and transferrin-based proteins provides a surprisingly high level of transferrin expression. For example, transferrin expression in a system that includes a chromosomally encoded recombinant PDI gene provided a 2-fold increase (compared to a control in which there is no chromosomally encoded recombinant PDI gene). This increase was 5-times greater than an equivalent system comprising a recombinant gene encoding human albumin in place of the recombinant transferrin gene.

The host may be any cell type, such as a procaryotic cell (e.g. bacterial cells such as *E. coli*) or a eucaryotic cell. Preferred eucaryotic cells include fungal cells, such as yeast cells, and mammalian cells. Exemplary yeast cells are discussed above. Exemplary mammalian cells include human cells.

Host cells as described above can be cultured to produce recombinant transferrin-based proteins. The thus produced transferrin-based proteins can be isolated from the culture and purified, optionally to a pharmaceutically acceptable level of purity, for example using techniques known in the art and/or as set out above. Purified transferrin-based proteins may, or may not, be formulated with a pharmaceutically acceptable carrier or diluent and may, or may not, be presented in unit dosage form.

The present invention will now be exemplified with reference to the following non-limiting examples and figures.

BRIEF DESCRIPTION OF THE FIGURES

Figure 20B:
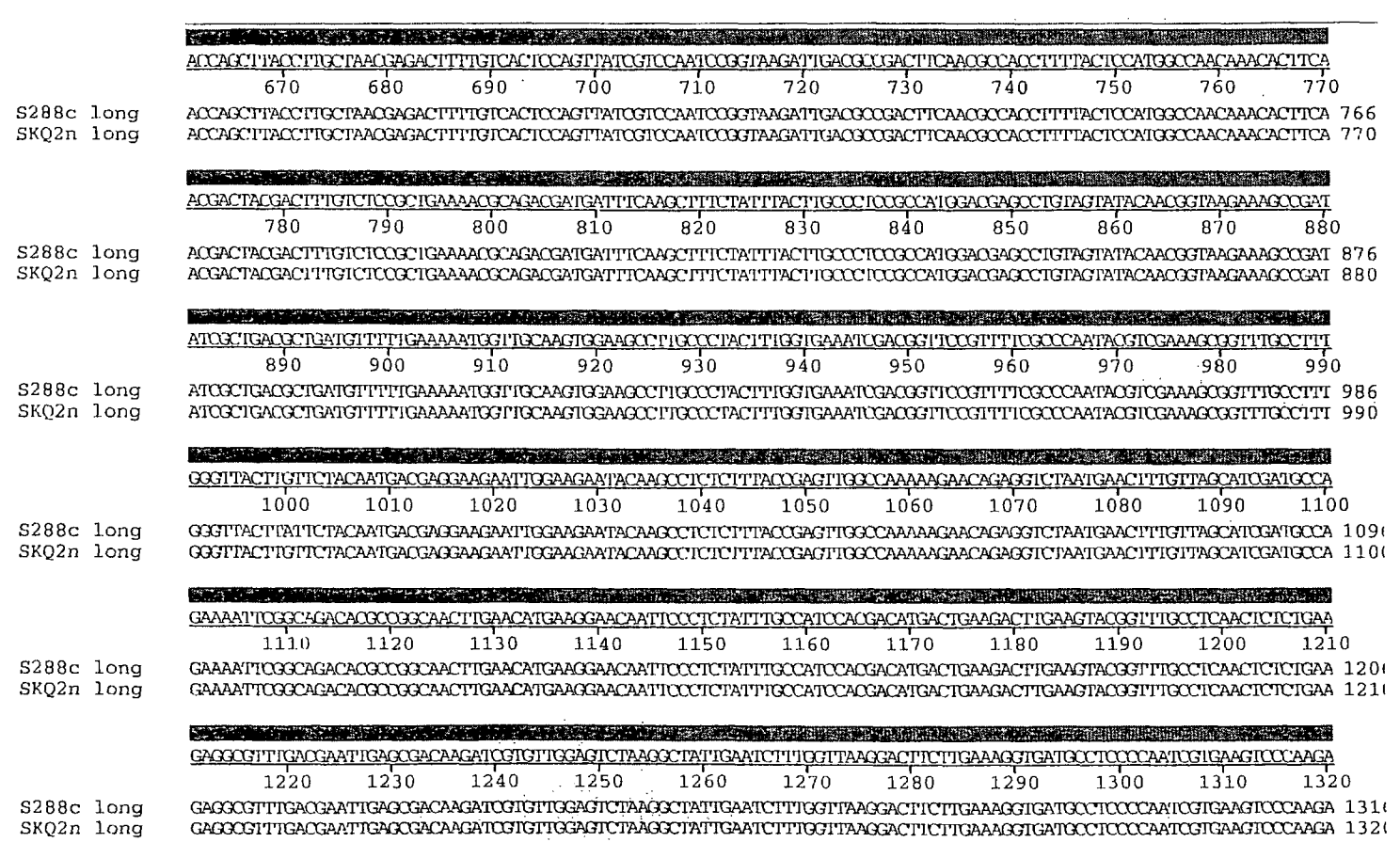

FIG. 20 shows a sequence alignment of the SKQ2n and S288c gene sequences with long promoters, as described in Example 6.

EXAMPLES

Two types of expression cassette have been used to exemplify secretion of a recombinant human transferrin mutant (N413Q, N611 Q) from S. cerevisiae. One type uses a modified HSA(pre)/MFα1(pro) leader sequence (named the "modified fusion leader" sequence). The second type of expression cassette uses only the modified HSA(pre) leader sequence.

The 24 amino acid sequence of the "modified fusion leader" is MKWVFIVSILFLFSSAYSRSLDKR.

The 18 amino acid sequence of the modified HSA(pre) leader sequence is MKWVFIVSILFLFSSAYS.

Transferrin (N413Q, N611Q) expression using these two cassettes has been studied in S. cerevisiae using the 2 µm expression vector with and without an additional copy of the S. cerevisiae PDI gene, PDI1.

Example 1

Construction of Expression Plasmids

Plasmids pDB2515, pDB2529, pDB2536, pDB2688, pDB2690, pDB2711, pDB2921, pDB2928, pDB2929, pDB2930, pDB2931, pDB2932 and pDB2690 were constructed as described in Example 1 of WO 2005/061718, the contents of which are incorporated herein by reference.

Example 2

Expression of Transferrin

A S. cerevisiae control strain was transformed to leucine prototrophy with all the transferrin (N413Q, N611Q) expression plasmids, and cryopreserved stocks were prepared.

Strains were grown for four days at 30° C. in 10 mL BMMD cultures in 50 mL conical flasks shaken at 200 rpm. The titres of recombinant transferrin secreted into the culture supernatants were compared by rocket immunoelectrophoresis (RIE as described in Weeke, B., 1976, "Rocket immunoelectrophoresis" In N. H. Azelsen, J. Kroll, and B. Weeke [eds.], A manual of quantitative immunoelectrophoresis. Methods and applications. Universitetsforlaget, Oslo, Norway), reverse phase high performance liquid chromatography (RP-HPLC) (Table 1), and non-reducing SDS polyacrylamide electrophoresis stained with colloidal Coomassie blue stain (SDS-PAGE). The increase in recombinant transferrin secreted when S. cerevisiae PDI1 was over-expressed was estimated to be greater than 10-fold.

By, RP-HPLC analysis (using the method described in Example 2 of WO 2005/061718, the contents of which are incorporated herein by reference) the increase in transferrin secretion was determined to be 18-fold for the modified fusion leader sequence and 15-fold for the modified HSA-pre leader sequence (Table 1).

Figure 4:
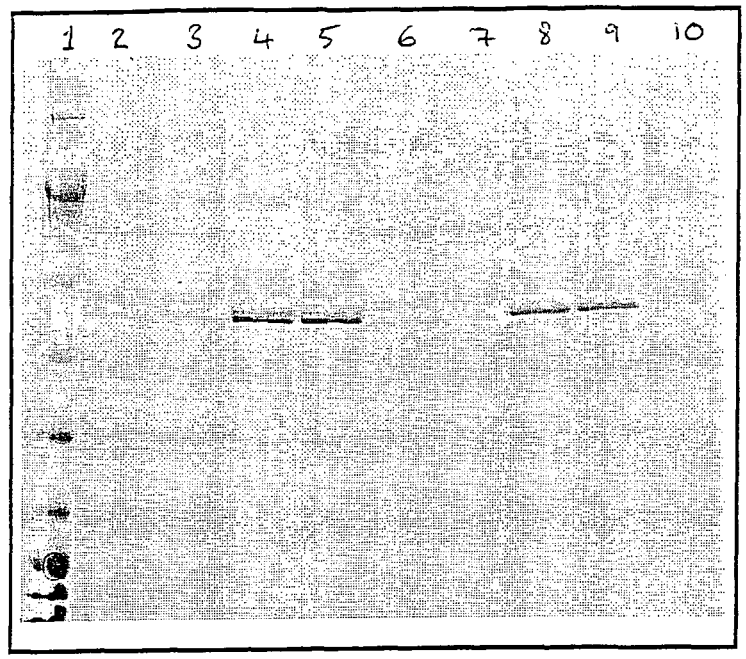
FIG. 4 shows the results of SDS-PAGE analysis of recombinant transferrin secretion with and without PDI1 over-expression. BMMD shake flask cultures were grown for 4-days and 10 µL supernatant analysed on non-reducing SDS-PAGE (4-12% NuPAGE®, MOPS buffer. InVitrogen) with GelCode® Blue reagent (Pierce). 1=SeeBlue Plus2 Markers (InVitrogen). 2=pDB2536; 3=pDB2536; 4=pDB2711; 5=pDB2711; 6=pDB2931; 7=pDB2931; 8=pDB2929; 9=pDB2929; 10=pSAC35 control.

FIG. 4 shows an SD S-PAGE comparison of the recombinant transferrin secreted by S. cerevisiae strains with and without additional PDI1 expression.

TABLE 1

| Plasmid | Secretory Leader | Additional PDI1 | Average Transferrin Titre (µg · mL⁻¹) (n = 2) | Estimated Increase due to Additional PDI1 |
|---------|------------------|-----------------|-----------------------------------------------|-------------------------------------------|
| pSAC35  | None             | No              | 0.4                                           | —                                         |
| pDB2536 | Fusion Leader    | No              | 6.2                                           | —                                         |
| pDB2711 | Fusion Leader    | Yes             | 112.8                                         | 18-fold                                   |
| pDB2931 | Modified HSA-pre Leader | No       | 5.1                                           | —                                         |
| pDB2929 | Modified HSA-pre Leader | Yes      | 76.1                                          | 15-fold                                   |

Figure 1:
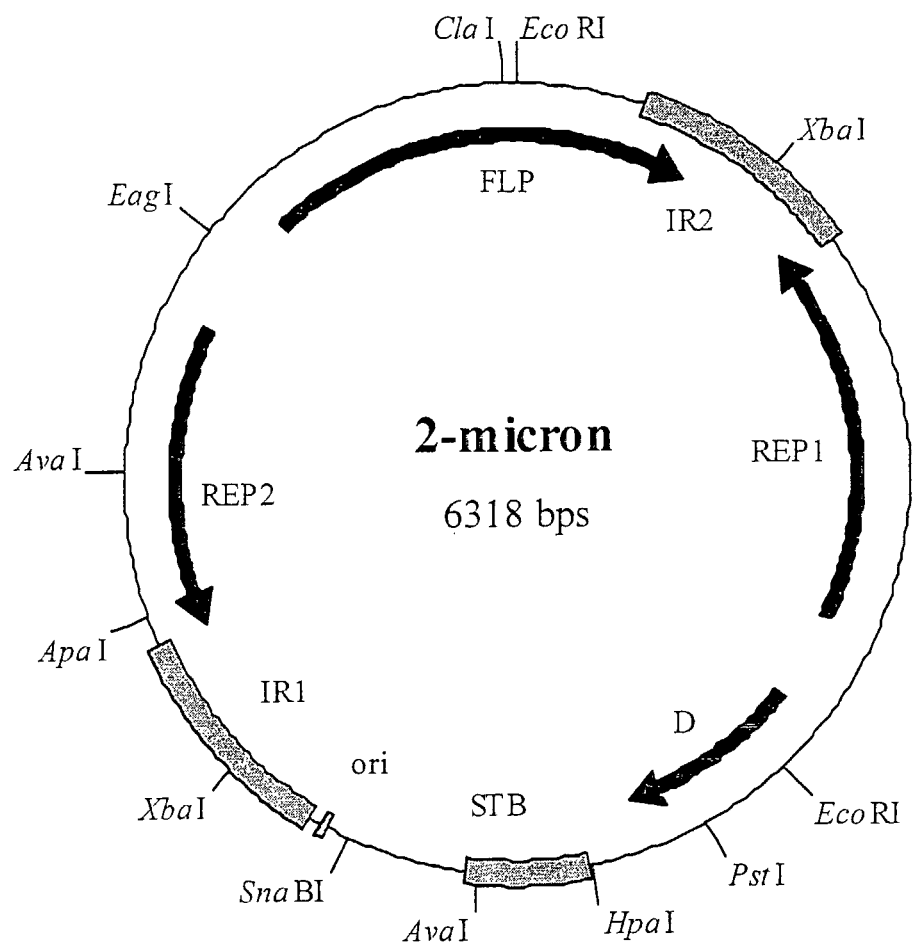
FIG. 1 shows a map of a typical 2 µm plasmid.
Figure 2:
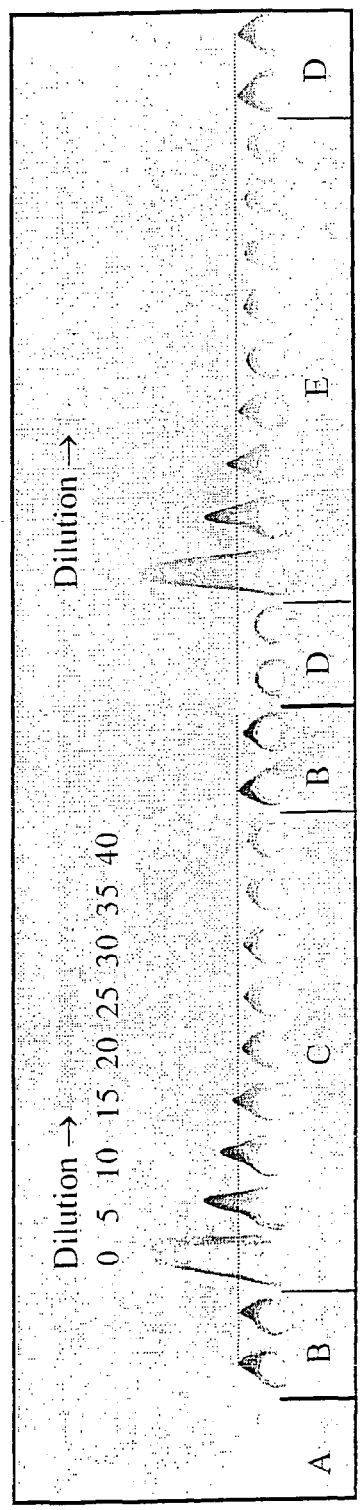
FIG. 2 shows the results of rocket immunoelectrophoresis (RIE) determination of increased recombinant transferrin (N413Q, N611Q) secretion with PDI1 over-expression. Cryopreserved yeast stocks were grown for 4-days in 10 mL BMMD shake flask cultures and supernatants were loaded at 5 µL per well. Goat polyclonal anti-transferrin (human) antiserum (Calbiochem) was used at 40 µL per rocket immunoelectrophoresis gel (50 mL). A=Control strain [pSAC35], duplicate flasks: B=Control strain [pDB2536], duplicate flasks; C=Control strain [pDB2711], neat to 40-fold aqueous dilutions; D=Control strain [pDB2931], duplicate flasks; E=Control strain [pDB2929], neat to 40-fold aqueous dilutions.
Figure 3:
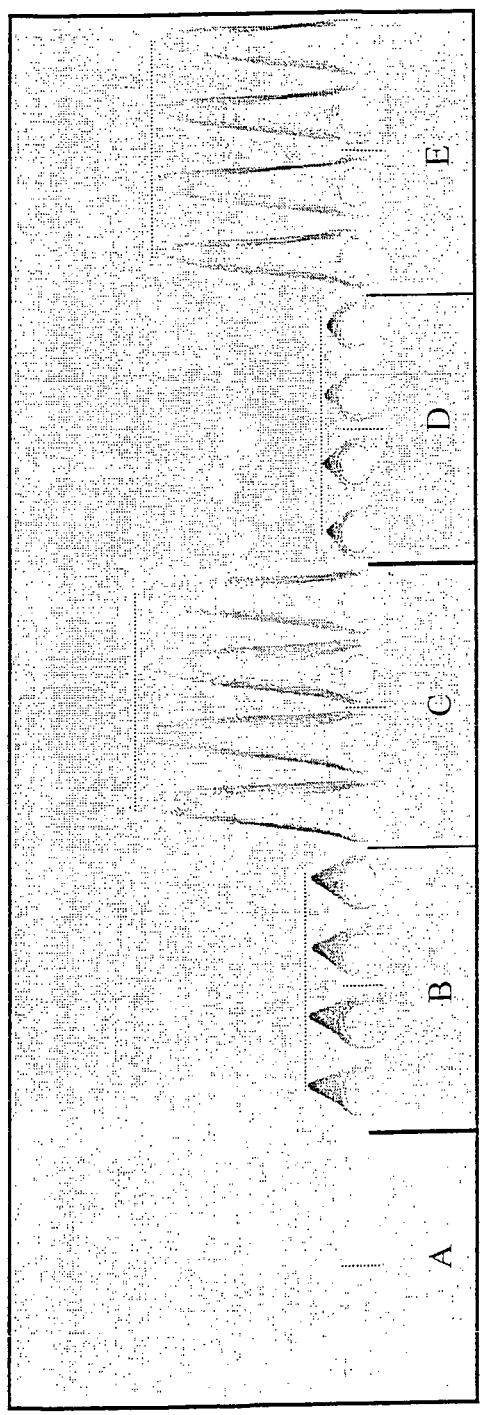
FIG. 3 shows the results of RIE analysis of recombinant transferrin (N413Q, N611Q) secretion with and without PDI1 over-expression. Cryopreserved yeast stocks were grown for 4-days in 10 mL BMMD shake flask cultures and supernatants were loaded at 5 µL per well. Duplicate loadings were made of supernatants from two individual cultures of each strain. Goat polyclonal anti-transferrin (human) antiserum (Calbiochem) was used at 40 µL per rocket immunoelectrophoresis gel (50 mL). A=Control strain [pSAC35]; B=Control strain [pDB2536]; C=Control strain [pDB2711]; D=Control strain [pDB2931]; E=Control strain [pDB2929].

RIE analysis indicated that the increased transferrin secretion in the presence of additional copies of PDI1 was approximately 15-fold (FIG. 2). By RIE analysis the increase appeared slightly larger for the modified HSA-pre leader sequence than for the modified fusion leader sequence (FIG. 3).

Example 3

Chromosomal Over-Expression of PDI

S. cerevisiae Strain A was selected to investigate the secretion of recombinant glycosylated transferrin expression from plasmid pDB2506 and recombinant non-glycosylated transferrin (N413Q, N611Q) from plasmid pDB2536. Strain A has the following characteristics—
  additional chromosomally integrated PDI1 gene integrated at the host PDI1 chromosomal location.
  the URA3 gene and bacterial DNA sequences containing the ampicillin resistance gene were also integrated into the S. cerevisiae genome at the insertion sites for the above genes.
A control strain had none of the above insertions.

Control strain [cir⁰] and Strain A [cir⁰] were transformed to leucine prototrophy with pDB2506 (recombinant transferrin), pDB2536 (recombinant non-glycosylated transferrin (N413Q, N611Q)) or pSAC35 (control). Transformants were selected on BMMD-agar.

Figure 5:
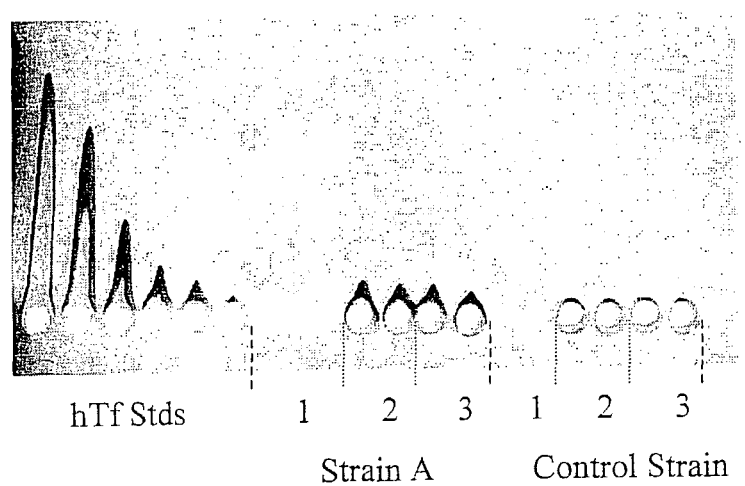
FIG. 5 shows RIE analysis of recombinant transferrin secretion from S. cerevisiae strains with an additional integrated copy of PDI1. 5-day BMMD shake flask culture supernatants were loaded at 5 mL per well. Strains contained: 1) pSAC35 (negative control); 2) pDB2536 (recombinant non-glycosylated transferrin (N413Q, N611Q)) or 3) pDB2506 (same as plasmid pDB2536 but the transferrin ORF encodes transferrin without the N→Q mutations at positions 413 and 611, i.e. recombinant glycosylated transferrin). Each well contained a sample derived from an individual transformant. Standards were human plasma holo-transferrin (Calbiochem) at 100, 50, 20, 10, 5 and 2 mg.L$^{-1}$.

The relative level of transferrin secretion in BMMD shake flask culture was determined for each strain/plasmid combination by rocket immunoelectrophoresis (RIE). FIG. 5 shows that both strains secreted both the glycosylated and non-glycosylated recombinant transferrins into the culture supernatant.

The levels of both the glycosylated and non-glycosylated transferrins secreted from Strain A [pDB2506] and Strain A [pDB2536] respectively, appeared higher than the levels secreted from the control strain. Hence, at least in shake flask culture, PDI1 integrated into the host genome at the PDI1 locus in Strain A has enhanced transferrin secretion.

Furthermore, the increase in transferrin secretion observed between control strain [pDB2536] and Strain A [pDB2536] appeared to be at least a 100% increase by RIE. In contrast, the increase in rflk monomer secretion between control strain [pDB2305] and Strain A [pDB2305] was approximately 20% (data not shown). Therefore, the increase in transferrin secretion due to the additional copy of PDI1 in Strain A was surprising large considering that transferrin has 19 disulphide bonds, compared to rHA with 17 disulphide bonds. Additional copies of the PDI1 gene may be particularly beneficial for the secretion from S. cerevisiae of proteins from the transferrin family, and their derivatives.

Figure 6:
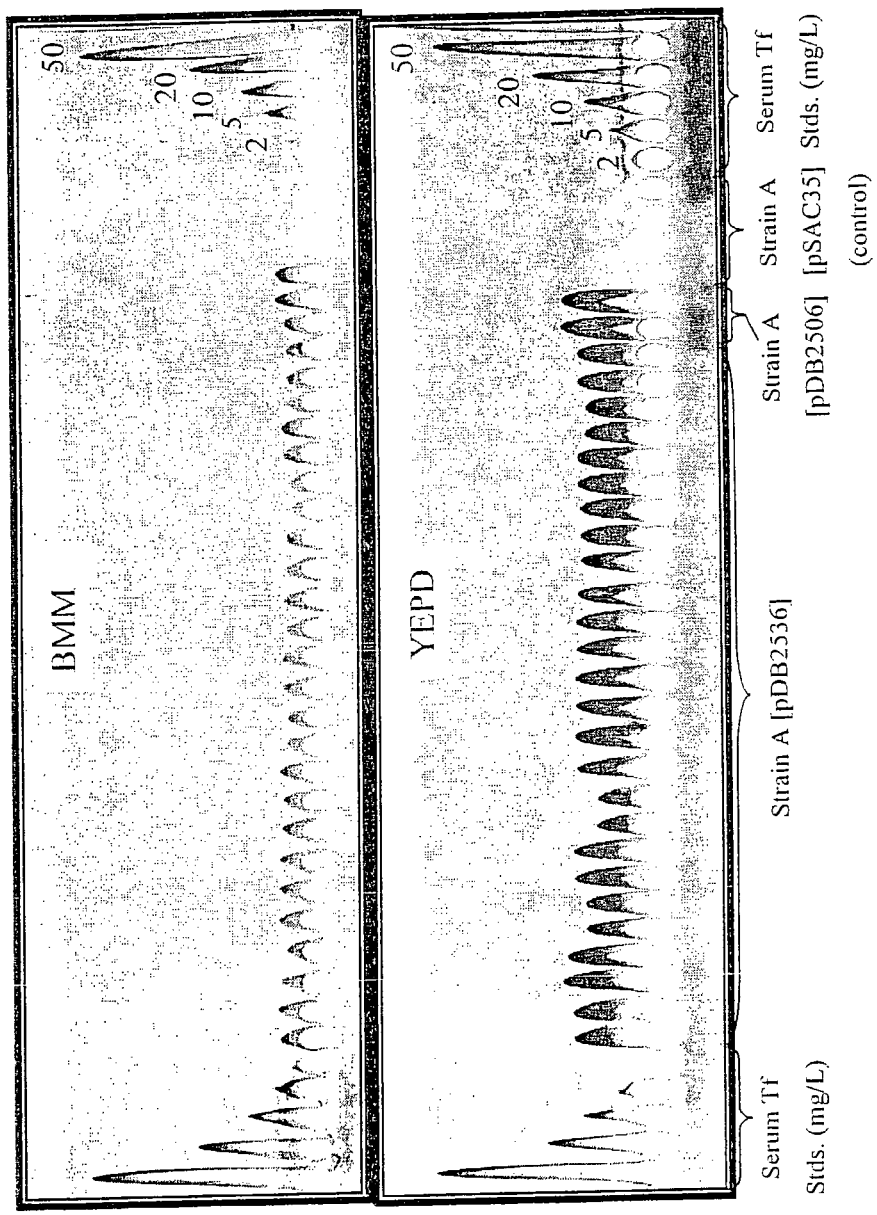
FIG. 6 shows RIE analysis of recombinant transferrin secretion from Strain A [pDB2536] and Strain A [pDB2506] grown in shake flask culture. 5-day BMMD or YEPD shake flask culture supernatants were loaded in duplicate at 5 mL per well.

The levels of transferrin secreted from Strain A [pDB2536] and Strain A [pDB2506] were compared by RIE for transformants grown in BMMD and YEPD (FIG. 6). Results indicated that a greater than 2-fold increase in titres of both non-glycosylated recombinant transferrin (N413Q, N611Q) and glycosylated recombinant transferrin was achieved by growth in YEPD (10-20 mg.L⁻¹ serum transferrin equivalent) compared to BMMD (2-5 mg.L⁻¹ serum transferrin equivalent). The increase in both glycosylated and non-glycosylated transferrin titre observed in YEPD suggested that both transferrin expression plasmids were sufficiently stable under non-selective growth conditions to allow the expected increased biomass which usually results from growth in YEPD to be translated into increased glycosylated and non-glycosylated transferrin productivity.

Figure 7:
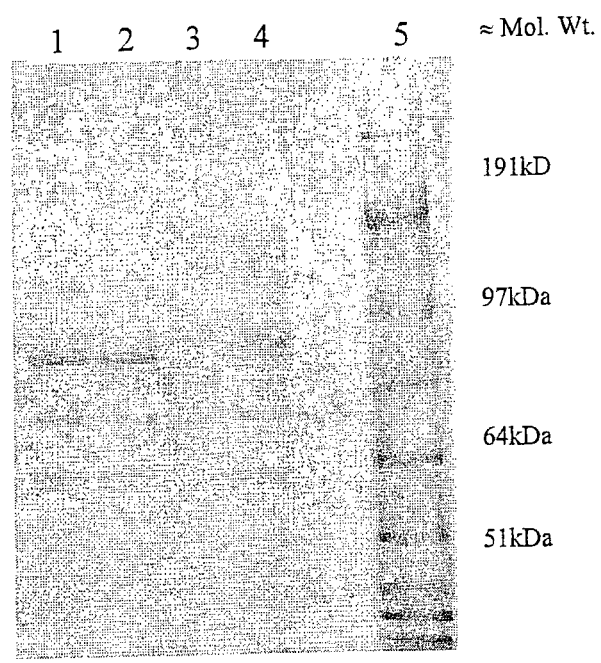
FIG. 7 shows SDS-PAGE analysis of recombinant transferrin secreted from Strain A [pDB2536] and Strain A [pDB2506] grown in shake flask culture. Cultures were grown for 5-days in BMMD and 30 mL supernatants analysed on SDS-PAGE (4-12% NuPAGE™, MOPS Buffer, InVitrogen) stained with GelCode, Blue Reagent (Pierce). 1) Strain A [pDB2536] transformant 1; 2) Strain A [pDB2536] transformant 2; 3) Strain A [pSAC35] control; 4) Strain A [pDB2506] transformant 1; 5) SeeBlue, Plus2 Protein Standards (approximate molecular weights only).

SDS-PAGE analysis of non-glycosylated transferrin (N413Q, N611Q) secreted from Strain A [pDB2536] and glycosylated transferrin from Strain A [pDB2506] grown in BMMD shake flask culture is shown in FIG. 7. Strain A [pDB2536] samples clearly showed an additional protein band compared to the Strain A [pSAC35] control. This extra band migrated at the expected position for the recombinant transferrin (N413Q, N611Q) secreted from control strain [pDB2536]. Strain A [pDB2506] culture supernatants appeared to contain a diffuse protein band at the position expected for transferrin. This suggested that the secreted recombinant transferrin was heterogeneous, possibly due to hyper-mannosylation at Asp413 and/or Asp611.

Example 4

Figure 22:
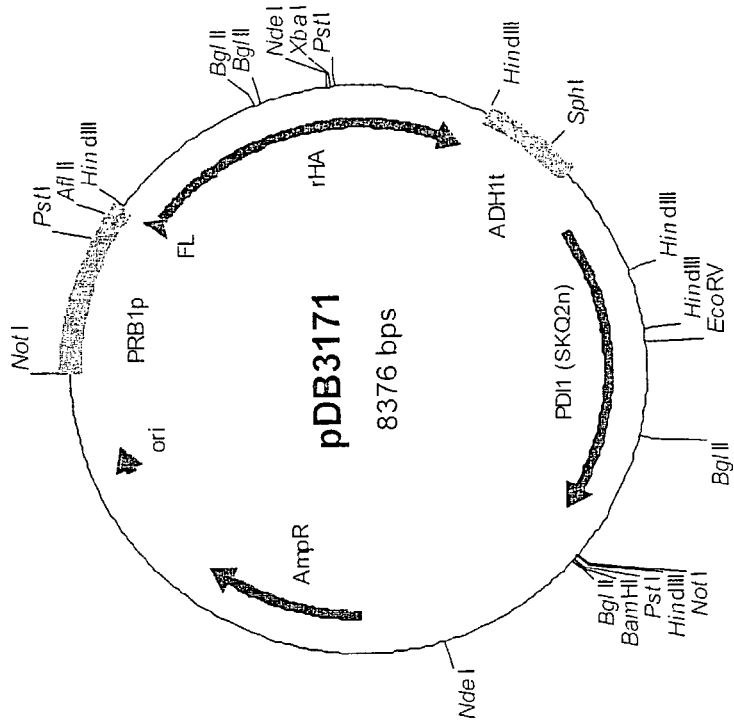
FIGS. 21 to 33 show various plasmid maps.

Comparing Transferrin Secretion from S. cerevisiae Control Strain Containing pDB2711 Within Transferrin Secretion from S. cerevisiae Strain A Plasmid pDB2711 is as described above. Plasmid pDB2712 (FIG. 22 of WO 2005/061718) was also produced with the NotI cassette in the opposite direction to pDB2711.

Control strain S. cerevisiae [cir⁰] was transformed to leucine prototrophy with pDB2711 and pDB2712. Transformants were selected on BMMD-agar and cryopreserved trehalose stocks of control strain [pDB2711] were prepared.

Figure 8:
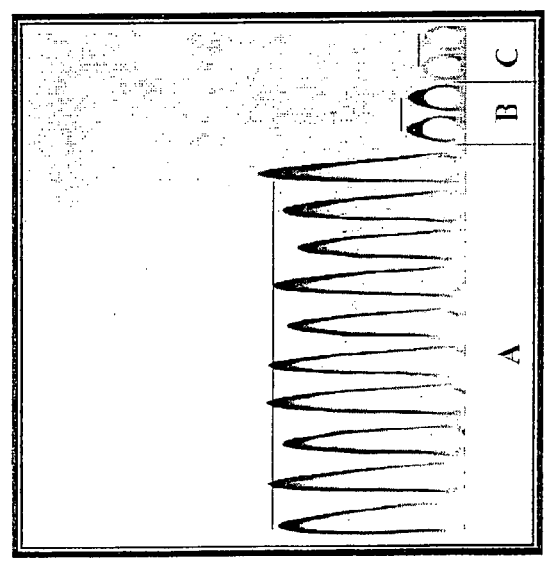
FIG. 8 shows RIE of recombinant transferrin secreted from S. cerevisiae strains with different PDI1 copy numbers. 3-day BMMD shake flask culture supernatants were loaded at 5 mL per well. Goat polyclonal anti-transferrin (human) antiserum (Calbiochem) was used at 30 mL per rocket immunoelectrophoresis gel (50 mL). (A) supernatant from S. cerevisiae control strain [pDB2711] or [pDB2712]; (B) supernatant from Strain A [pDB2536]; (C) supernatant from control strain [pDB2536].

Secretion of recombinant transferrin (N413Q, N611Q) by control strain [pDB2711], control strain [pDB2712], Strain A [pDB2536], control strain [pDB2536] and an alternative control strain [pDB2536] was compared in both BMMD and YEPD shake flask culture. RIE indicated that a significant increase in recombinant transferrin secretion had been achieved from control strain [pDB2711] with multiple episomal PDI1 copies, compared to Strain A [pDB2536] with two chromosomal copies of PDI1, and control strain [pDB2536] with a single chromosomal copy of PDI1 gene (FIG. 8). Control strain [pDB2711] and control strain [pDB2712] appeared to secrete similar levels of rTf (N413Q, N611Q) into the culture media. The levels of secretion were relatively consistent between control strain [pDB2711] and control strain [pDB2712] transformants in both BMMD and YEPD media, suggesting that plasmid stability was sufficient for high-level transferrin secretion even under non-selective conditions. This is in contrast to the previous published data in relation to recombinant PDGF-BB and HSA where introduction of PDI1 into multicopy 2 μm plasmids was shown to be detrimental to the host.

TABLE 2

Recombinant transferrin titres from high cell density fermentations

| | Supernatant (g · L⁻¹) | |
|---|---|---|
| Strain | GP-HPLC | SDS-PAGE |
| Control [pDB2536] | 0.5/0.4 | — |
| Alternative control [pDB2536] | 1.5/1.6 | 0.6 |
| | 0.9/0.9 | 0.4/0.4/0.5 |
| Strain A [pDB2536] | 0.7 | 0.6 |
| | 0.6 | — |
| Control [pDB2711] | 3.5 | 3.6 |
| | 3.4 | 2.7/3.1 |

Figure 9:
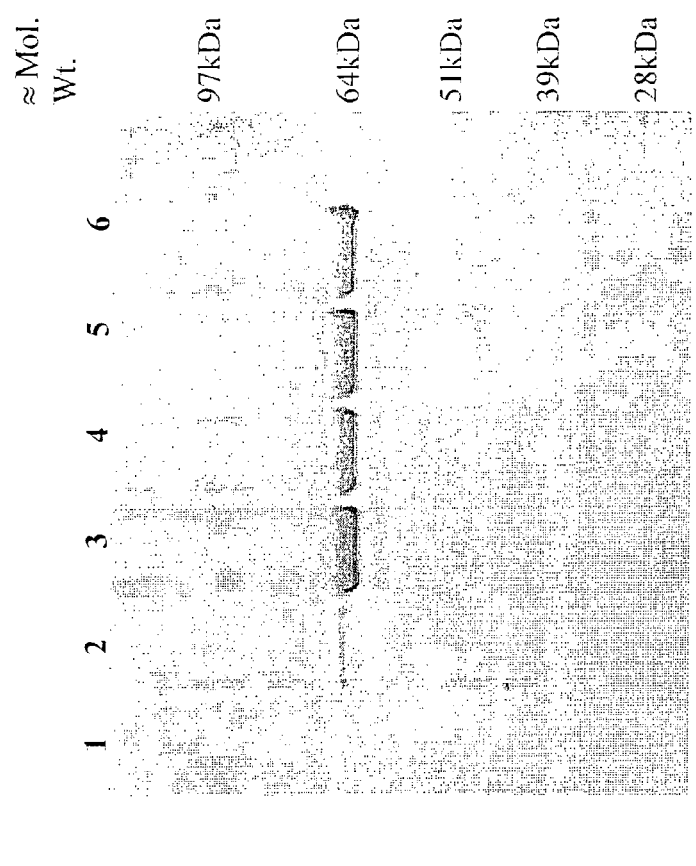
FIG. 9 shows SDS-PAGE analysis of recombinant transferrin secreted from S. cerevisiae strains with different PDI1 copy numbers. 4-12% NuPAGE reducing gel run with MOPS buffer (InVitrogen) after loading with 30 mL of 3-day BMMD shake flask culture supernatant per lane; (lane 1) supernatant from control strain [pDB2536]; (lane 2) supernatant from Strain A [pDB2536]; (lanes 3-6) supernatant from control strain [pDB2711] or [pDB2712]; (lane 7) molecular weight markers (SeeBlue Plus2, InVitrogen).

Reducing SDS-PAGE analysis of transferrin secreted from control strain [pDB2711], control strain [pDB2712], Strain A [pDB2536], control strain [pDB2536] and alternative control strain [pDB25361] in BMMD shake flask culture is shown in FIG. 9. This shows an abundant protein band in all samples from control strain [pDB2711] and control strain [pDB2712] at the position expected for transferrin (N413Q, N611Q). The relative stain intensity of the transferrin (N413Q, N611Q) band from the different strains suggested that Strain A [pDB2536] produced more than control strain [pDB2536] and alternative control strain [pDB2536], but that there was an even more dramatic increase in secretion from control strain [pDB2711] and control strain [pDB2712]. The increased recombinant transferrin secretion observed was concomitant with the increased PDI1 copy number in these strains. This suggested that Pdi1p levels were limiting transferrin secretion in control strain, Strain A and the alternative control strain, and that elevated PDI1 copy number was responsible for increased transferrin secretion. Elevated PDI1 copy number could increase the steady state expression level of PDI1 so increasing the amount of Pdi1p activity. There are a number of alternative methods by which this could be achieved without increasing the copy number of the PDI1 gene, for example the steady state PDI1 mRNA level could be increased by either increasing the transcription rate, say by use of a higher efficiency promoter, or by reducing the clearance rate of the PDI1 mRNA. Alternatively, protein engineering could be used to enhance the specific activity or turnover number of the Pdi1p protein.

In high cell density fermentations control strain [pDB2711] recombinant transferrin (N413Q, N611Q) production was measured at approximately 3 g.L$^{-1}$ by both GP-HPLC analysis and SDS-PAGE analysis (Table 2). This level of production is several fold-higher than control strain, the alternative control strain or Strain A containing pDB2536. Furthermore, for the production of proteins for therapeutic use in humans, expression systems such as control strain [pDB2711] have advantages over those using Strain A, as they do not contain bacterial DNA sequences.

CONCLUSIONS

Secretion of recombinant transferrin from a multicopy expression plasmid (pDB2536) was investigated in *S. cerevisiae* strains containing an additional copy of the PDI1 gene integrated into the yeast genome. Transferrin secretion was also investigated in *S. cerevisiae* transformed with a muiticopy expression plasmid, in which the PDI1 gene has been inserted into the multicopy episomal transferrin expression plasmid (pDB2711).

A *S. cerevisiae* strain with an additional copy of the PDI1 gene integrated into the genome at the endogenous PDI1 locus, secreted recombinant transferrin and non-glycosylated recombinant transferrin (N413Q, N611Q) at an elevated level compared to strains containing a single copy of PDI1. A further increase in PDI1 copy number was achieved by using pDB2711. In high cell density fermentation of the strain transformed with pDB2711, recombinant transferrin (N413Q, N611Q) was secreted at approximately 3 g.L$^{-1}$, as measured by SDS-PAGE and GP-HPLC analysis. Therefore, increased PDI1 gene copy number has produced a large increase in the quantity of recombinant transferrins secreted from *S. cerevisiae*.

The following conclusions are drawn—
1. In shake flask analysis of recombinant transferrin expression from pDB2536 (non-glycosylated transferrin (N413Q, N611Q) and pDB2506 (glycosylated transferrin) the *S. cerevisiae* strain Strain A secreted higher levels of both recombinant transferrins into the culture supernatant than control strains. This was attributed to the extra copy of PDI1 integrated at the PDI1 locus.
2. Control strain [pDB2711], which contained,the PDI1 gene on the multicopy expression plasmid, produced a several-fold increase in recombinant transferrin (N413Q, N611Q) secretion compared to Strain A [pDB2531] in both shake flask culture and high cell density fermentation.
3. Elevated PDI1 copy number in yeast such as *S. cerevisiae* will be advantageous during the production of desired proteins (such as a desired heterologous proteins), such as those from the transferrin family.
4. pSAC35-based plasmids containing additional copies of PDI1 gene have advantages for the production of proteins from the transferrin family, and their derivatives, such as fusions, mutants, domains and truncated forms.

Example 5

Insertion of a PDI1 Gene into a 2 μm-Like Plasmid Increased Secretion of Recombinant Transferrin from Various Different *S. cerevisiae* Strains The *S. cerevisiae* strain JRY188 cir$^+$ (National Collection of Yeast Cultures) and MT302/28B cir$^+$ (Finnis et al., 1993, *Eur. J. Biochem.*, 212, 201-210) was cured of the native 2 μm plasmid by galactose induced over-expression of FLP from Yep351-GAL-FLP1, as described by Rose and Broach (1990, *Meth. Enzymol.*, 185, 234-279) to create the *S. cerevisiae* strains JRY188 cir$^0$ and MT302/28B cir$^0$, respectively.

Figure 10:
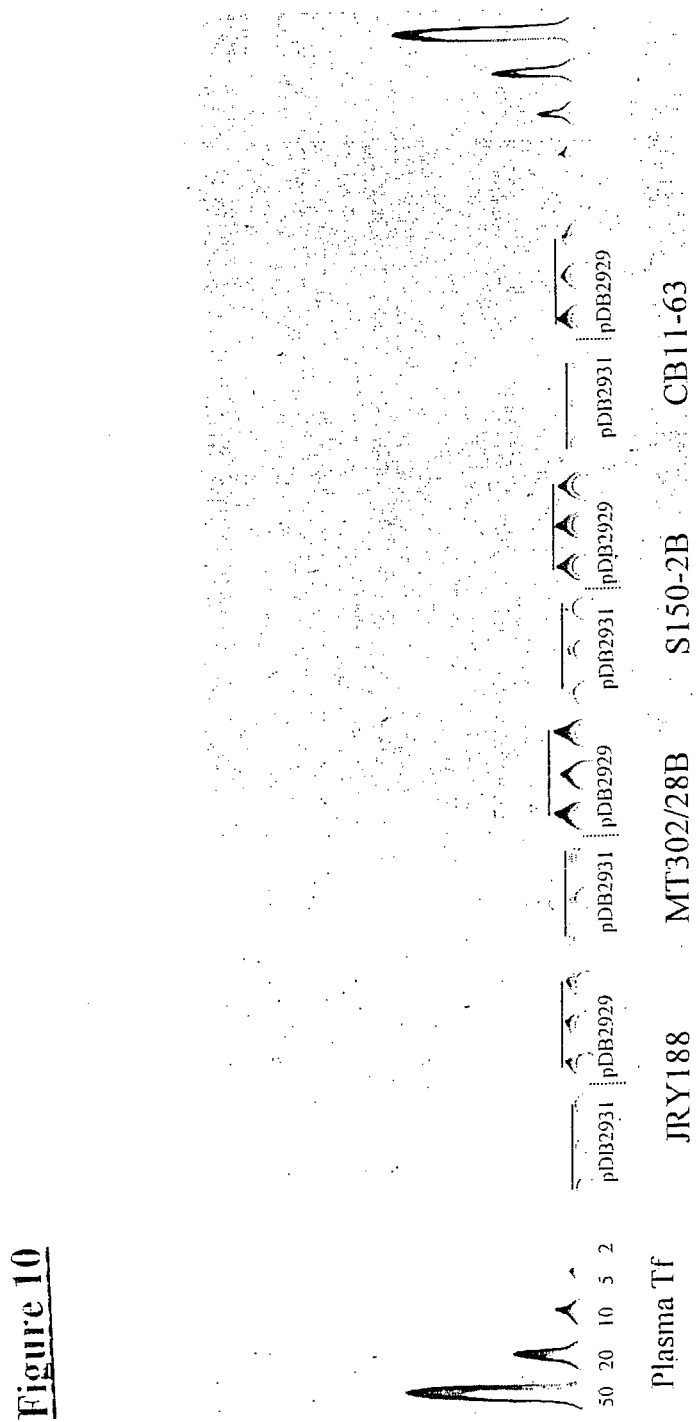
FIG. 10 shows RIE of recombinant transferrin secreted from different S. cerevisiae strains with and without additional PDI1 gene co-expression. 10 mL YEPD shake flasks were inoculated with yeast and incubated for 4-days at 30° C. 5 µL culture supernatant loaded per well of a rocket immunoelectrophoresis gel. Plasma of standards concentrations are in µg/mL. 20 µL goat anti-Tf/50 mL agragose. Precipin was stained with Coomassie blue.
Figure 12:
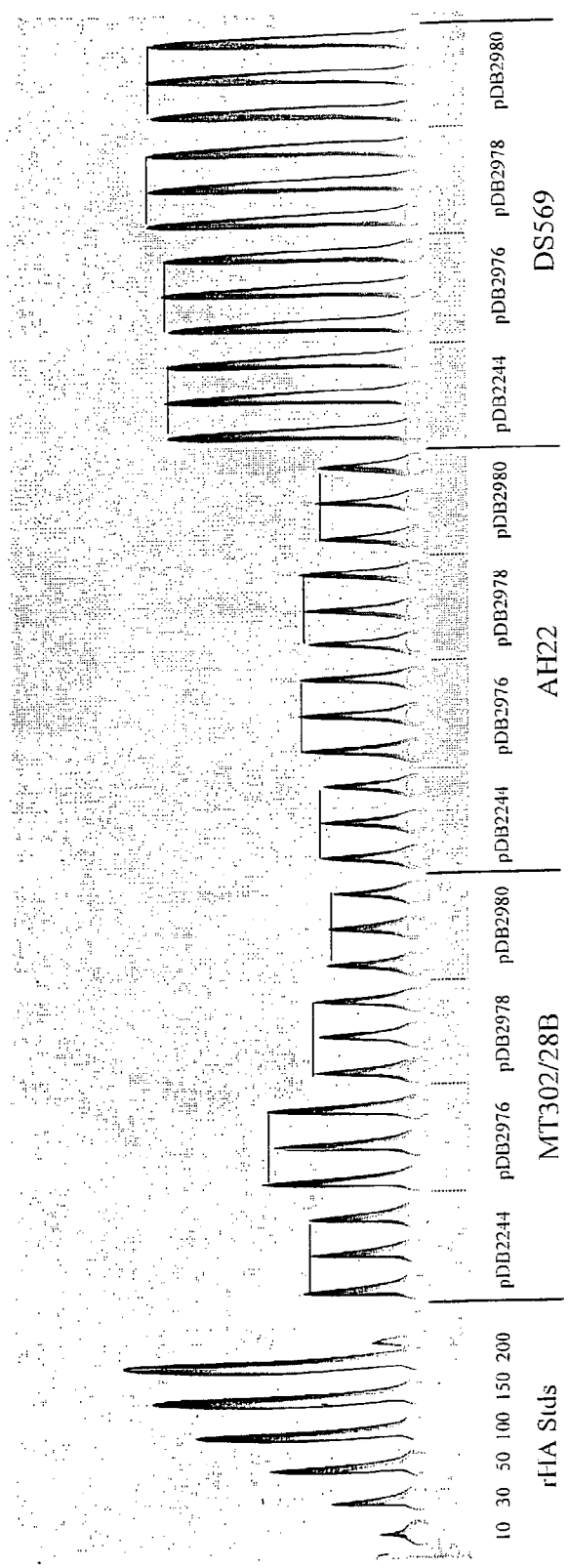
FIG. 12 shows RIE analysis of rHA expression in different S. cerevisiae strains when co-expressed with PDI1 genes having different length promoters. 10 mL YEPD shake flasks were inoculated with yeast and incubated for 4-days at 30° C. 4 µL culture supernatant loaded per well of a rocket immunoelectrophoresis gel. rHA standards concentrations are in µg/mL. 400 µL goat anti-HA (Sigma product A-1151 resuspended in 5 mL water)/50 mL agarose. Precipin was stained with Coomassie blue.

The *S. cerevisiae* strains JRY188 cir$^0$, MT302/28B cir$^0$, S150-2B cir$^0$ (Cashmore et al., 1986, *Mol. Gen. Genet.*, 203, 154-162), CB11-63 cir$^0$ (Zealey et al., 1988, *Mol. Gen. Genet.*, 211, 155-159) were all transformed to leucine prototrophy with pDB2931 (FIG. 14 of WO 2005/061718) and pDB2929 (FIG. 12 of WO 2005/061718). Transformants were selected on appropriately supplemented minimal media lacking leucine. Transformants of each strain were inoculated into 10 mL YEPD in 50 mL shake flasks and incubated in an orbital shaker at 30° C., 200 rpm for 4-days. Culture supernatants were harvested and the recombinant transferrin titres compared by rocket immunoelectrophoresis (FIG. 10). The results indicated that the transferrin titres in supernatants from all the yeast strains were higher when PDI1 was present in the 2 μm plasmid (pDB2929) than when it was not (pDB2931)

Example 6

Figure 27:
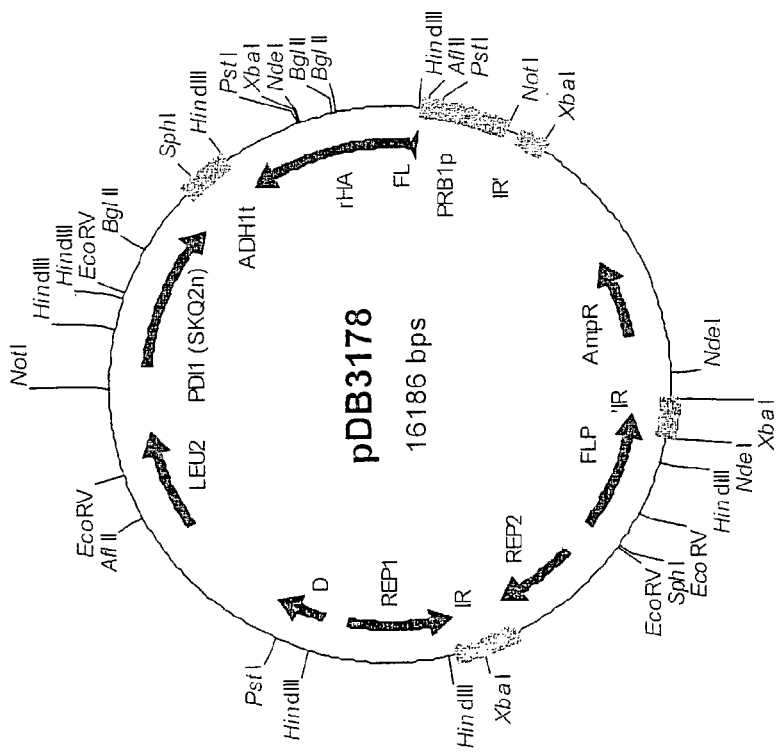

The Construction of Expression Vectors Containing Various PDI1 Genes and the Expression Cassettes for Various Heterologous Proteins on the Same 2 μm-Like Plasmid
PCR Amplification and Cloning of PDI1 Genes into YIplac211:

The PDI1 genes from *S. cerevisiae* S288c and *S. cerevisiae* SKQ2n were amplified by PCR to produce DNA fragments with different lengths of the 5'-untranslated region containing the promoter sequence. PCR primers were designed to permit cloning of the PCR products into the RcoRI and BamHI sites of YIplac211 (Gietz & Sugino, 1988, *Gene*, 74, 527-534). Additional restriction endonuclease sites were also incorporated into PCR primers to facilitate subsequent cloning. Table 3 describes the plasmids constructed and Table 4 gives the PCR primer sequences used to amplify the PDI1 genes. Differences in the PDI1 promoter length within these YIplac211-based plasmids are described in Table 3.

pDB2939 (FIG. 27 of WO 2005/061718) was produced by PCR amplification of the PDI1 gene from *S. cerevisiae* S288c genomic DNA with oligonucleotide primers DS248 and DS250 (Table 5), followed by digesting the PCR product with RcoRI and BamHI and cloning the approximately 1.98-kb fragment into YIplac211 (Gietz & Sugino, 1988, *Gene*, 74, 527-534), that had been cut with EcoRI and BamHI. DNA sequencing of pDB2939 identified a missing 'G' from within the DS248 sequence, which is marked in bold in Table 4. Oligonucleotide primers used for sequencing the PDI1 gene are listed in Table 5, and were designed from the published S288c PDI1 gene sequence (PDI1/YCL043C on chromosome III from coordinates 50221 to 48653 plus 1000 base pairs of upstream sequence and 1000 base pairs of doamstream sequence. (http://www.yeastgenome.org/Genebank Accession number NC001135).

TABLE 3

YIplac211-based Plasmids Containing PDI1 Genes

| Plasmid | Plasmid Base | PDI1 Gene Source | Promoter | Terminator | PCR Primers |
|---|---|---|---|---|---|
| pDB2939 | YIplac211 | S288c | Long (~210-bp) | → Bsu36I | DS248 + DS250 |
| pDB2941 | YIplac211 | S288c | Medium (~140-bp) | → Bsu36I | DS251 + DS250 |
| pDB2942 | YIplac211 | S288c | Short (~80-bp) | → Bsu36I | DS252 + DS250 |
| pDB2943 | YIplac211 | SKQ2n | Long (~210-bp) | → Bsu36I | DS248 + DS250 |
| pDB2963 | YIplac211 | SKQ2n | Medium (~140-bp) | → Bsu36I | DS267 + DS250 |
| pDB2945 | YIplac211 | SKQ2n | Short (~80-bp) | → Bsu36I | DS252 + DS250 |

TABLE 4

Oligonucleotide Primers for PCR Amplification of *S. cerevisiae* PDI1 Genes

| Primer | Sequence |
|---|---|
| DS248 | 5'-GTCAGAATTCGAGCTCTACGTATTAATTAAGGCCGGCCAGGCCCGGGCTAGTCTCTTTTTCCAATTTGCCACCGTGTAGCATTTTGTTGT-3' (SEQ ID NO: 3) |
| DS249 | 5'-GTCAGGATCCTACGTACCCGGGGATATCATTATCATCTTTGTCGTGCTCATCTTGTGTG-3' (SEQ ID NO: 4) |
| DS250 | 5'-GTCAGGATCCTACGTACCCGGGTAAGGCGTTCCTGCAGTGTGACGAATATAGCG-3' (SEQ ID NO: 5) |
| DS251 | 5'-GTCAGAATTCGAGCTCTACGTATTAATTAAGGCCGGCCAGGCCCGGGCCCGTATGGACATACATATATATATATATATATATATATATTTTGTTACGCG-3' (SEQ ID NO: 6) |
| DS252 | 5'-GTCAGAATTCGAGCTCTACGTATTAATTAAGGCCGGCCAGGCCCGGGCTTGTTGCAAGCAGCATGTCTAATTGGTAATTTTAAAGCTGCC-3' (SEQ ID NO: 7) |
| DS267 | 5'-GTCAGAATTCGAGCTCTACGTATTAATTAAGGCCGGCCAGGCCCGGGCCCGTATGGACATACATATATATATATATATATATATATATATTTTGTTACGCG-3' (SEQ ID NO: 8) |

TABLE 5

Oligonuclotide Primers for DNA Sequencing *S. cerevisiae* PDI1 Genes

| Primer | Sequence |
|---|---|
| DS253 | 5'-CCTCCCTGCTGCTCCCC-3' (SEQ ID NO: 9) |
| DS254 | 5'-CTGTAAGAACATGGCTCC-3' (SEQ ID NO: 10) |
| DS255 | 5'-CTCGATCGATTACGAGGG-3' (SEQ ID NO: 11) |
| DS256 | 5'-AAGAAAGCCGATATCGC-3' (SEQ ID NO: 12) |
| DS257 | 5'-CAACTCTCTGAAGACGCG-3' (SEQ ID NO: 13) |
| DS258 | 5'-CAACGCCACATCCGACG-3' (SEQ ID NO: 14) |
| DS259 | 5'-GTAATTCTGATCACTTTGG-3' (SEQ ID NO: 15) |
| DS260 | 5'-GCACTTATTATTACTACGTGG-3' (SEQ ID NO: 16) |
| DS261 | 5'-GTTTTCCTTGATGAAGTCG-3' (SEQ ID NO: 17) |
| DS262 | 5'-GTGACCACACCATGGGGC-3' (SEQ ID NO: 18) |
| DS263 | 5'-GTTGCCGGCGTGTCTGCC-3' (SEQ ID NO: 19) |

TABLE 5-continued

Oligonuclotide Primers for DNA Sequencing S. cerevisiae PDI1 Genes

| Primer | Sequence |
|---|---|
| DS264 | 5'-TTGAAATCATCCTCTGCG-3' (SEQ ID NO: 20) |
| DS265 | 5'-CGGCAGTTCTAGGTCCC-3' (SEQ ID NO: 21) |
| DS266 | 5'-CCACACCCTCTTGTTGGG-3' (SEQ ID NO: 22) |
| M13/pUC Primer (-40) | 5'-GTTTTCCCAGTCACGAC-3' (SEQ ID NO: 23) |

Figure 28:
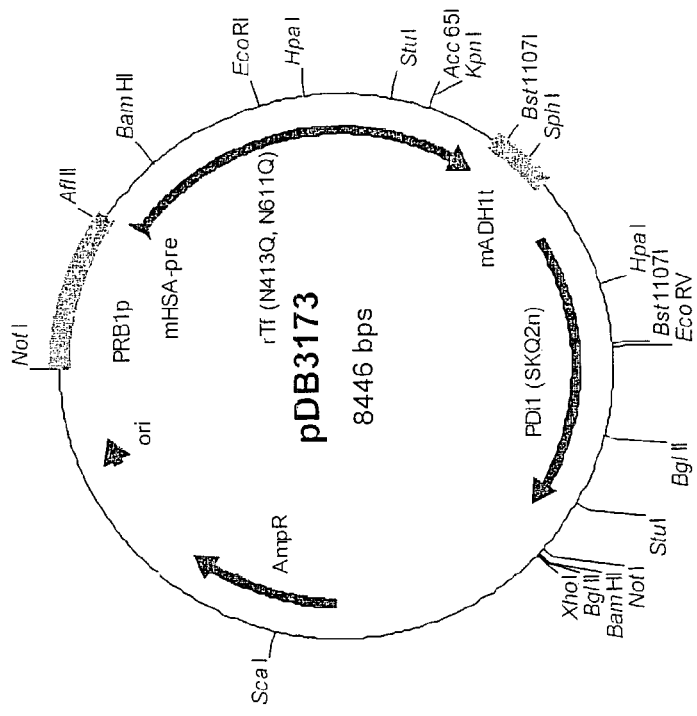
Figure 29:
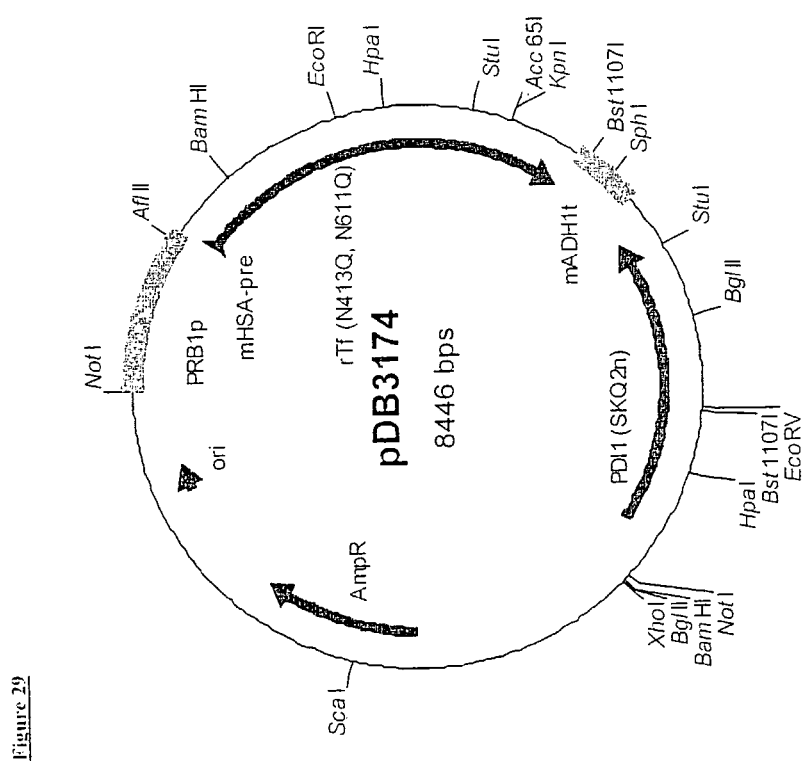

Plasmids pDB2941 (FIG. 28 of WO 2005/061718) and pDB2942 (FIG. 29 of WO 2005/061718) were constructed similarly using the PCR primers described in Tables 3 and 4, and by cloning the approximately 1.90-kb and 1.85-kb RcoRI-BamHI fragments, respectively, into YIplac211. The correct DNA sequences were confirmed for the PDI1 genes in pDB2941 and pDB2942.

Figure 30:
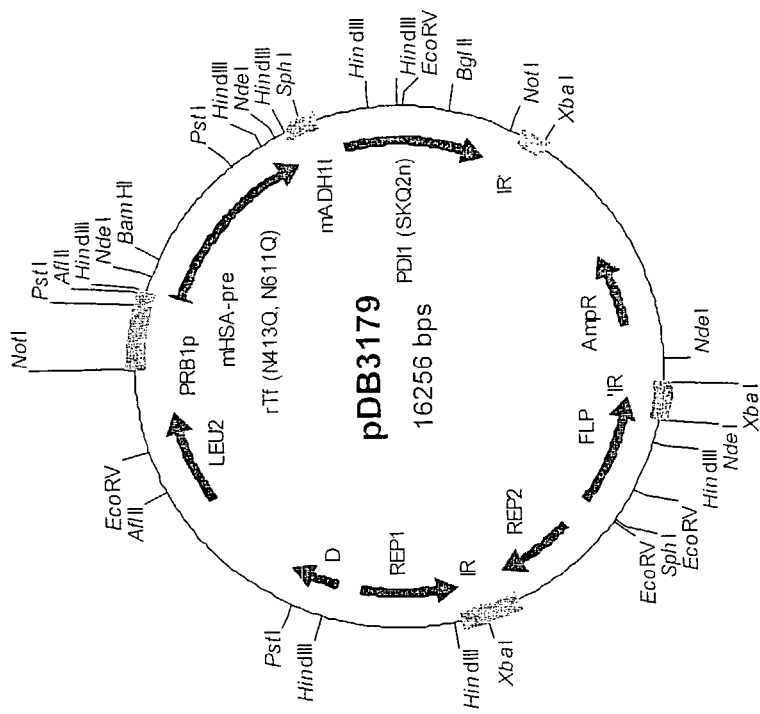

The S. cerevisiae SKQ2n PDI1 gene sequence was PCR amplified from plasmid DNA containing the PDI1 gene from pMA3a:C7 (U.S. Pat. No. 6,291,205), also known as Clone C7 (Crouzet & Tuite, 1987, supra; Farquhar et al, 1991, supra). The SKQ2n PDI1 gene was amplified using oligonucleotide primers DS248 and DS250 (Tables 3 and 4). The approximately 2.01-kb PCR product was digested with coRI and BamHI and ligated into YIplac211 (Gietz & Sugino, 1988, Gene, 74, 527-534) that has been cut with EcoRI and BamHI, to produce plasmid pDB2943 (FIG. 30 of WO 2005/061718). The 5' end of the SKQ2n PDI1 sequence is analogous to a blunt-ended SpeI-site extended to include the RcoRI, SacI, SnaBI, PacI, FseI, SfiI and SmaI sites, the 3' end extends up to a site analogous to a blunt-ended Bsu36I site, extended to include a SmaI, SnaBI and BamHI sites. The PDI1 promoter length is approximately 210 bp. The entire DNA sequence was determined for the PDI1 fragment using oligonucleotide primers given in Table 5. This confirmed the presence of a coding sequence for the PDI protein of S. cerevisiae strain SKQ2n (NCBI accession number CAA38402), but with a serine residue at position 114 (not an arginine residue as previously published). Similarly, in the same way as in the S. cerevisiae S288c sequence in pDB2939, pDB2943 also had a missing 'G' from within the DS248 sequence, which is marked in bold in Table 4.

Figure 32:
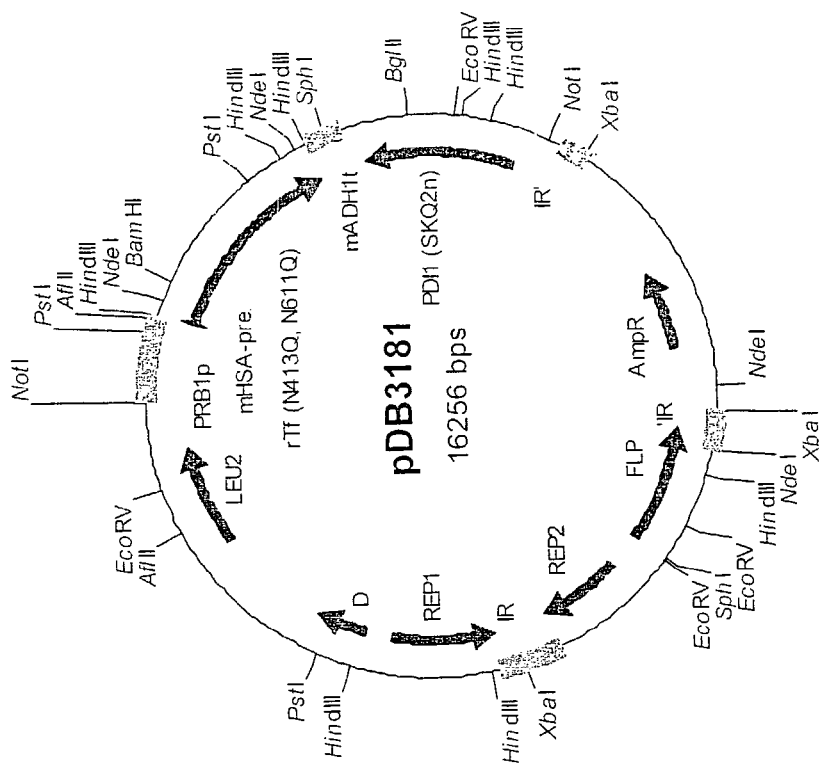
Figure 31:
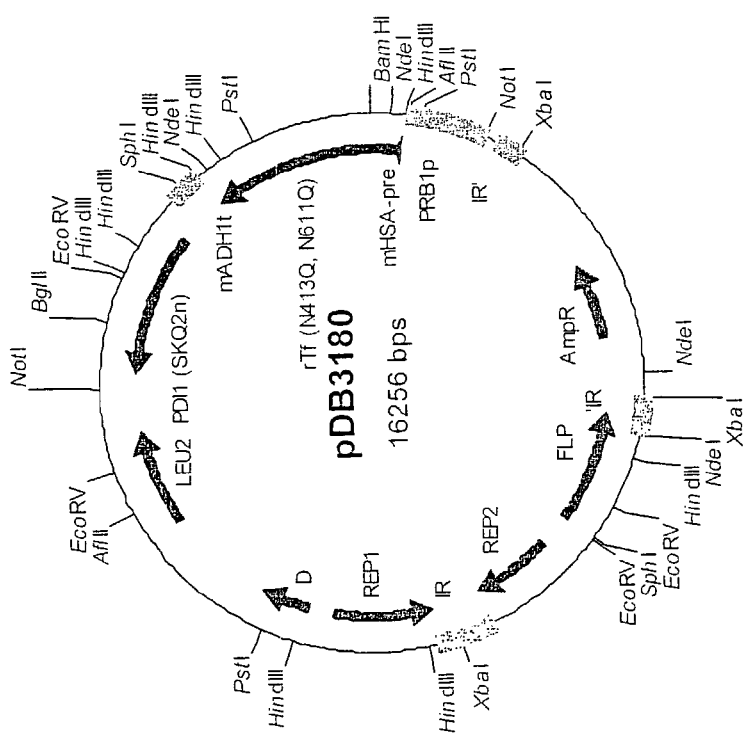

Plasmids pDB2963 (FIG. 31 of WO 2005/061718) and pDB2945 (FIG. 32 of WO 2005/061 718) were constructed similarly using the PCR primers described in Tables 3 and 4, and by cloning the approximately 1.94-kb and 1.87-kb RcoRI-BamHI fragments, respectively, into YIplac211. The expected DNA sequences were confirmed for the PDI1 genes in pDB2963 and pDB2945, with a serine codon at the position of amino acid 114.

The Construction of pSAC35-Based rHA Expression Plasmids with Different PDI1 Genes Inserted at the XcmI-Site after REP2:

pSAC35-based plasmids were constructed for the co-expression of rHA with different PDI1 genes (Table 6).

TABLE 6 pSAC35-based plasmids for co-expression of rHA with different PDI1 genes

| Plasmid | Plasmid Base | PDI1 Gene at XcmI-site after REP2 | | | | Heterologous Protein Expression Cassette (at NotI-site) |
|---|---|---|---|---|---|---|
| | | Source | Promoter | Terminator | Orientation | |
| pDB2982 | pSAC35 | SKQ2n | Long | → Bsu36I | A | rHA |
| pDB2983 | pSAC35 | SKQ2n | Long | → Bsu36I | B | rHA |
| pDB2984 | pSAC35 | SKQ2n | Medium | → Bsu36I | A | rHA |
| pDB2985 | pSAC35 | SKQ2n | Medium | → Bsu36I | B | rHA |
| pDB2986 | pSAC35 | SKQ2n | Short | → Bsu36I | A | rHA |
| pDB2987 | pSAC35 | SKQ2n | Short | → Bsu36I | B | rHA |
| pDB2976 | pSAC35 | S288c | Long | → Bsu36I | A | rHA |
| pDB2977 | pSAC35 | S288c | Long | → Bsu36I | B | rHA |
| pDB2978 | pSAC35 | S288c | Medium | → Bsu36I | A | rHA |
| pDB2979 | pSAC35 | S288c | Medium | → Bsu36I | B | rHA |
| pDB2980 | pSAC35 | S288c | Short | → Bsu36I | A | rHA |
| pDB2981 | pSAC35 | S288c | Short | → Bsu36I | B | rHA |

Figure 33:
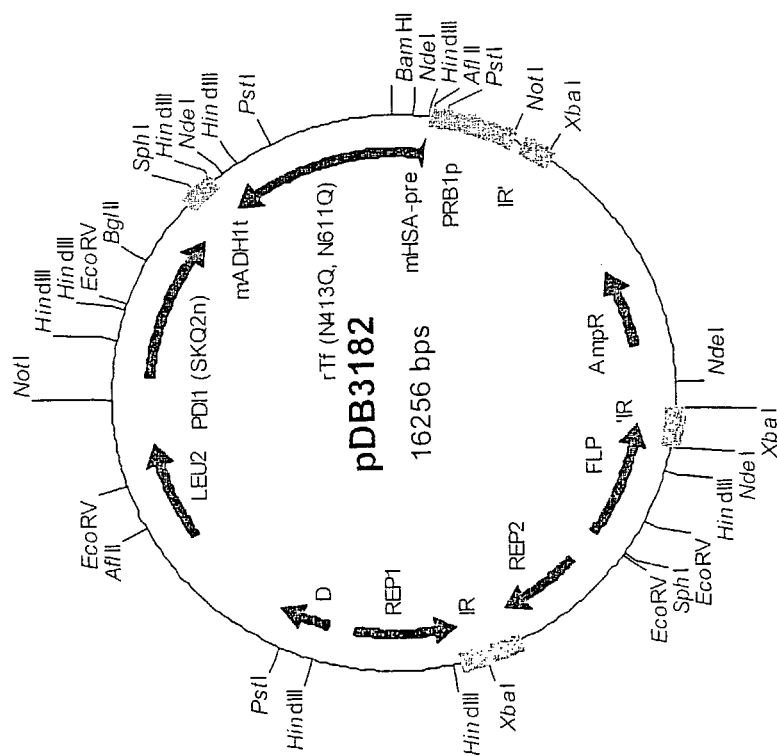

The rHA expression cassette from pDB2243 (FIG. 33 of WO 2005/061718, as also described in WO 00/44772) was first isolated on a 2,992-bp NotI fragment, which subsequently was cloned into the NotI-site of pDB2688 (FIG. 4 of WO 2005/061718) to produce pDB2693 (FIG. 34 of WO 2005/061718). pDB2693 was digested Amith SnaBI, treated with calf intestinal alkaline phosphatase, and ligated with SnaBI fragments containing the PDI1 genes from pDB2943, pDB2963, pDB2945, pDB2939, pDB2941 and pDB2942. This produced plasmids pDB2976 to pDB2987 (FIGS. 35 to 46 of WO 2005/061718). PDI1 transcribed in the same orientation as REP2 was designated "orientation A", whereas PDI1 transcribed in opposite orientation to REP2 was designated "orientation B" (Table 6).

The Construction of pSAC35-Based Transferrin Expression Plasmids with Different PDI1 Genes Inserted at the XcmI-Site after PEP2:

pSAC35-based plasmids were constructed for the co-expression of recombinant transferrin (N413Q, N611Q) with different PDI1 genes (Table 7).

TABLE 7 pSAC35-based plasmids for co-expression of transferrin with different PDI1 genes

| Plasmid | Plasmid Base | PDI1 Gene at XcmI-site after REP2 | | | | Heterologous Protein Expression Cassette (at NotI-site) |
|---|---|---|---|---|---|---|
| | | Source | Promoter | Terminator | Orientation | |
| pDB2929 | pSAC35 | SKQ2n | Long | → Bsu36I | A | rTf (N413Q, N611Q) |
| pDB3085 | pSAC35 | S288c | Long | → Bsu36I | A | rTf (N413Q, N611Q) |
| pDB3086 | pSAC35 | S288c | Medium | → Bsu36I | A | rTf (N413Q, N611Q) |
| pDB3087 | pSAC35 | S288c | Short | → Bsu36I | A | rTf (N413Q, N611Q) |

In order to achieve this, the NotI expression cassettes for rHA expression were first deleted from pDB2976, pDB2978, and pDB2980 by NotI digestion and circularisation of the vector backbone. This produced plasmids pDB3081 (FIG. 47 of WO 2005/061718), pDB3083 (FIG. 48 of WO 2005/061718) and pDB3084 (FIG. 49 of WO 2005/061718) as described in Table 8.

TABLE 8 pSAC35-based plasmids with different PDI1 genes

| Plasmid | Plasmid Base | PDI1 Gene at XcmI-site after REP2 | | | | Heterologous Protein Expression Cassette (at NotI-site) |
|---|---|---|---|---|---|---|
| | | Source | Promoter | Terminator | Orientation | |
| pDB2690 | pSAC35 | SKQ2n | Long | → Bsu36I | A | None |
| pDB3081 | pSAC35 | S288c | Long | → Bsu36I | A | None |
| pDB3083 | pSAC35 | S288c | Medium | → Bsu36I | A | None |
| pDB3084 | pSAC35 | S288c | Short | → Bsu36I | A | None |

The 3,256-bp NotI fragment from pDB2928 (FIG. 11 of WO 2005/061718) was cloned into the NotI-sites of pDB3081, pDB3083 and pDB3084, such that transcription from the transferrin gene was in the same direction as LEU2. This produced plasmids pDB3085 (FIG. 50 of WO 2005/061718), pDB3086 (FIG. 51 of WO 2005/061718) and pDB3087 (FIG. 52 of WO 2005/061718) as described in Table 7.

Example 7

Insertion and Optimisation of a PDI1 Gene in the 2 μm-Like Plasmid Increased the Secretion of Recombinant Human Serum Albumin by Various Different *S. cerevisiae* Strains The *S. cerevisiae* strains JRY188 cir°, MT302/28B cir°, S150-2B cir°, CB11-63 cir° (all described above), AH22 cir° (Mead et al., 1986, *Mol. Gen. Genet.*, 205, 417-421) and DS569 cir° (Sleep et al., 1991, *Bio/Technology)*, 9, 183-187) were transformed to leucine prototrophy with either pDB2244 (WO 00/44772), pDB2976 (FIG. 35 of WO 2005/061718), pDB2978 (FIG. 37 of WO 2005/061718) or pDB2980 (FIG. 39 of WO 2005/061718) using a modified lithium acetate method (Sigma yeast transformation kit, YEAST-1, protocol 2; (Ito et al, 1983, *J. Bacteriol.*, 153, 163; Elble, 1992, *Biotechniques,* 13, 18)). Transformants were selected on BMMD-agar plates with appropriate supplements, and were subsequently patched out on BMMD-agar plates with appropriate supplements.

Figure 11:
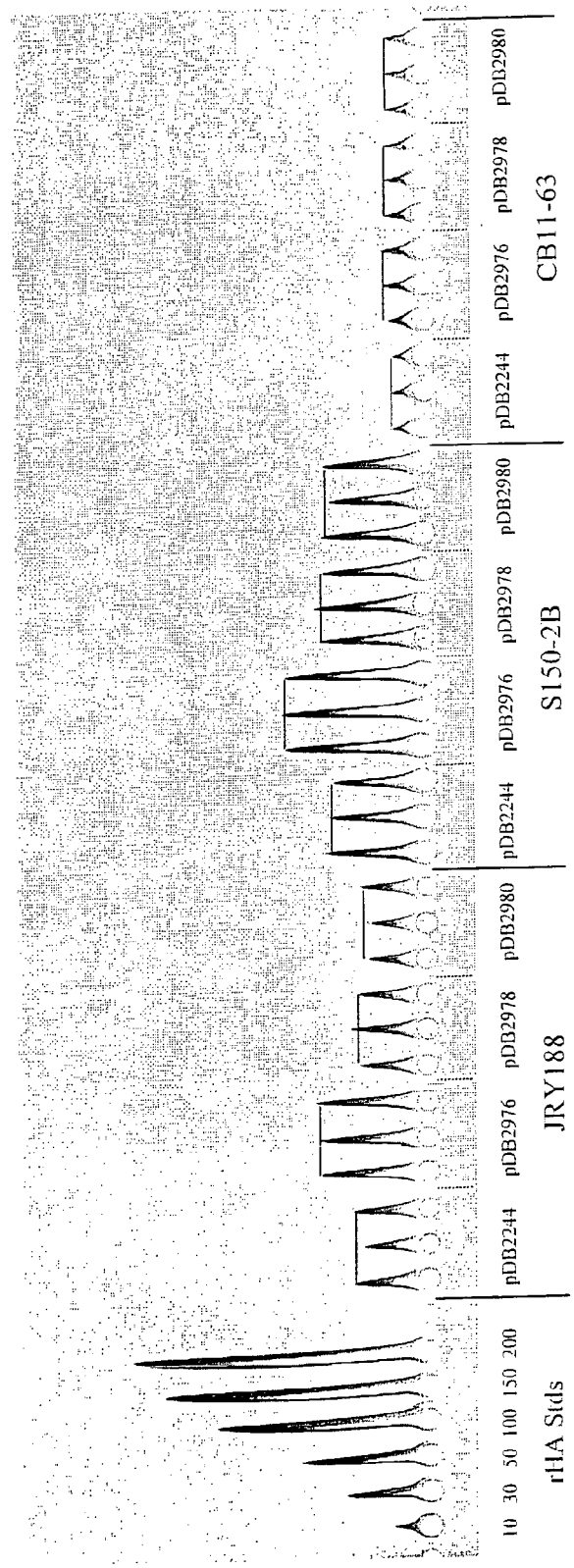
FIG. 11 shows RIE analysis of rHA expression in different S. cerevisiae strains when co-expressed with PDI1 genes having different length promoters. 10 mL YEPD shake flasks were inoculated with yeast and incubated for 4-days at 30° C. 4 µL culture supernatant loaded per well of a rocket immunoelectrophoresis gel. rHA standards concentrations are in µg/mL. 400 µL goat anti-HA (Sigma product A-1151 resuspended in 5 mL water)/50 mL agarose. Precipin was stained with Coomassie blue.

Transformants of each strain were inoculated into 10 mL YEPD in 50 mL shake flasks and incubated in an orbital shaker at 30° C., 200 rpm for 4-days. Culture supernatants were harvested and the recombinant albumin titres compared by rocket immunoelectrophoresis (FIGS. 11 and 12). The results indicated that the albumin titres in the culture supernatants from all the yeast strains were higher when PDI1 was present in the 2 μm plasmid than when it was not (pDB2244). The albumin titre in the culture supernatants in the absence of PDI1 on the plasmid was dependant upon which yeast strain was selected as the expression host, however, in most examples tested the largest increase in expression was observed when PDI1 with the long promoter (~210-bp) was present in the 2 μm plasmid (pDB2976). Modifying the PDI1 promoter by shortening, for example to delete regulation sites, had the affect of controlling the improvement. For one yeast strain, known to be a high rHA producing strain (DS569) a shorter promoter was preferred for optimal expression.

Example 8

PDI1 on the 2 μm-Based Plasmid Enhanced the Secretion of Recombinant Albumin Fusions.

The affect of co-expression of the *S. cerevisiae* SKQ2n PDI1 gene with the long promoter (~210-bp) upon the expression of recombinant albumin fusions was investigated.

The plasmids defined in Table 9 below were generated as described in Example 9 of WO 2005/061718, the contents of which are incorporated herein by reference.

TABLE 9

Summary of plasmids encoding albumin fusion proteins

| | Plasmid name | |
|---|---|---|
| Albumin fusion | With PDI1 | Without PDI1 |
| endostatin-albumin | pDB3100 | PDB3099 |
| angiostatin-albumin | pDB3107 | pDB2765 |
| Kringle5-(GGS)₄GG-albumin | pDB3104 | pDB2773 |
| DX-890-(GGS)₄GG-albumin | pDB3102 | pDB3101 |
| DPI-14-(GGS)₄GG-albumin | pDB3103 | pDB2679 |
| Axokine™-(GGS)₄GG-albumin | pDB3106 | pDB2618 |
| human IL10-(GGS)4-GG-albumin | pDB3105 | pDB2621 |

The same control yeast strain as used in previous examples was transformed to leucine prototrophy using a modified lithium acetate method (Sigma yeast transformation kit, YEAST-1, protocol 2; (Ito et al, 1983, *J. Bacteriol.*, 153, 163; Elble, 1992, *Biotechniques*, 13, 18)). Transformants were selected on BMMD-agar plates, and were subsequently patched out on BMMD-agar plates.

Cryopreserved trehalose stocks were prepared from 10 mL BMMD shake flask cultures (24 hrs, 30° C., 200 rpm).

Figure 13:
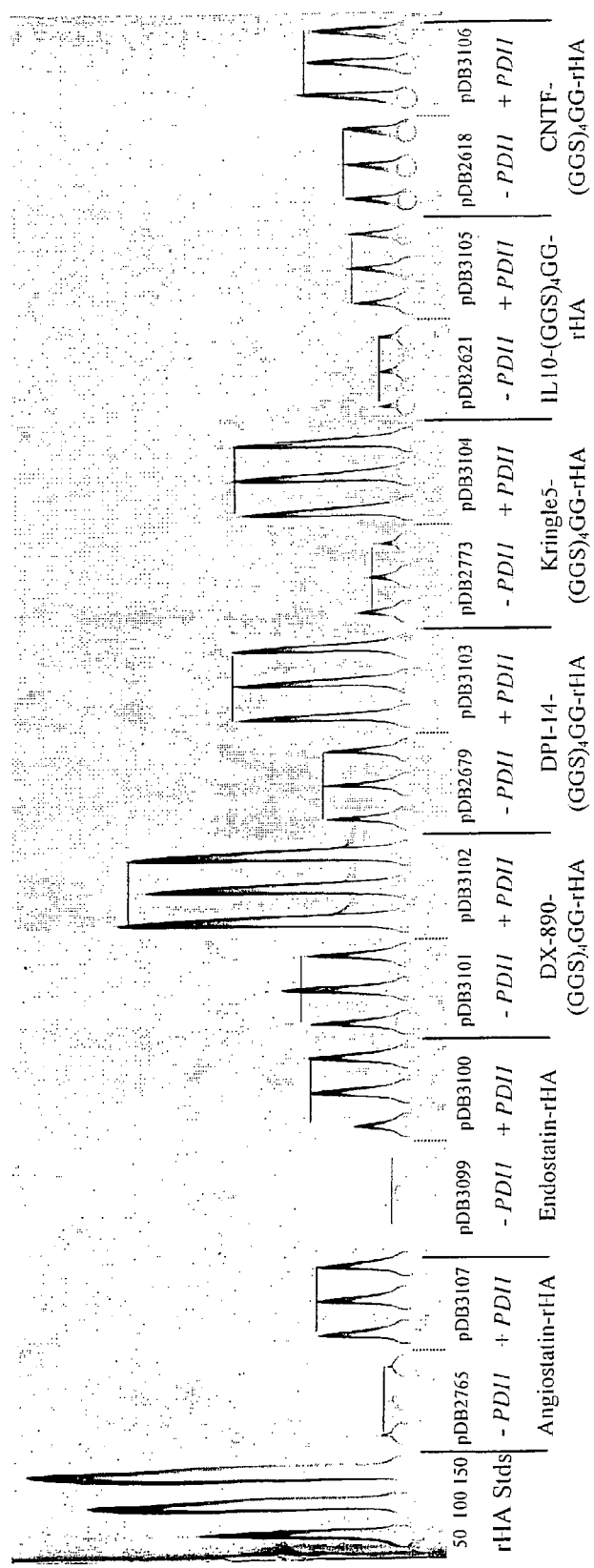
FIG. 13 shows RIE analysis of rHA fusion proteins with and without co-expressed recombinant PDI1. 10 mL BMMD shake flasks were inoculated with YBX7 transformed with albumin fusion expression plasmids and incubated for 4-days at 30° C. 4 µL culture supernatant loaded per well of a rocket immunoelectrophoresis gel. rHA standards concentrations are in µg/mL. 200 µL goat anti-HA (Sigma product A-1151 resuspended in 5 mL water)/50 mL agarose. Precipin was stained with Coomassie blue.

Transformants of each strain were inoculated into 10 mL BMMD in 50 mL shake flasks and incubated in an orbital shaker at 30° C., 200 rpm for 4-days. Culture supernatants were harvested and the recombinant albumin fusion titres compared by rocket immunoelectrophoresis (FIG. 13). The results indicated that the albumin fusion titre in the culture supernatants from yeast strain was higher when PDI1 was present in the 2 µm plasmid than when it was not.

Figure 14:
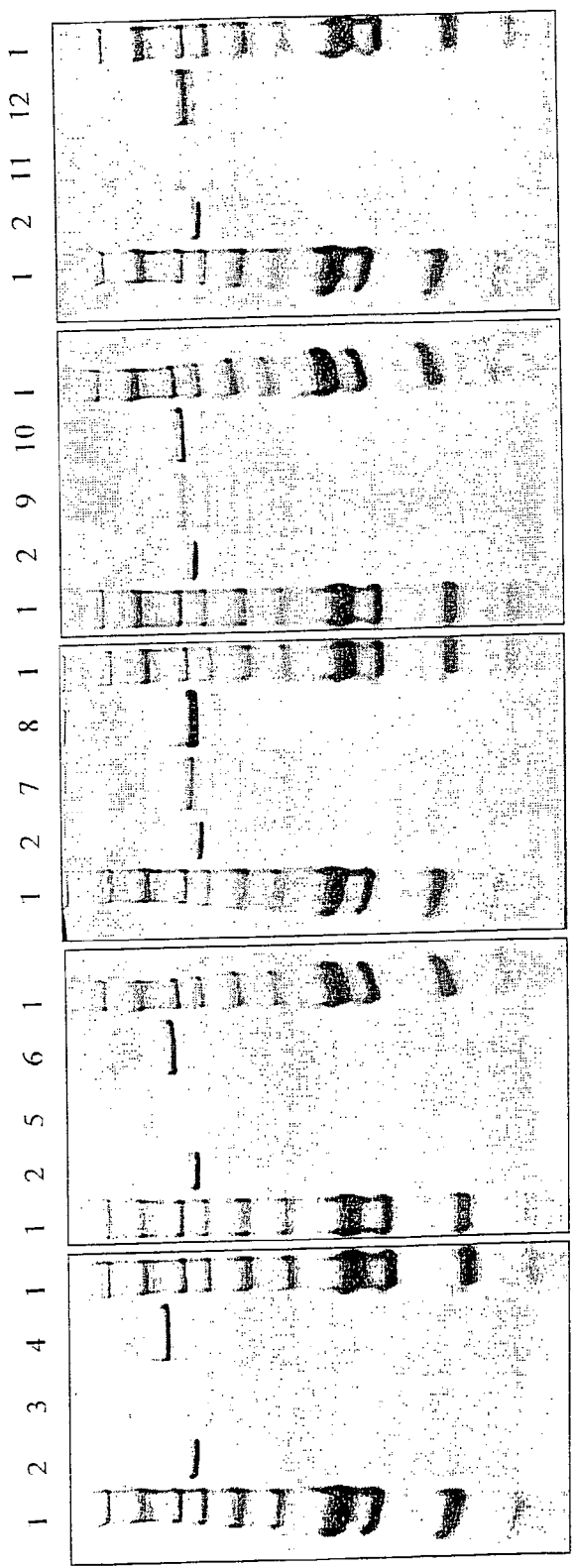
FIG. 14 shows SDS-PAGE analysis of recombinant albumin fusion secretion with and without PDI1 present on the expression plasmid. 10 mL BMMD shake flasks were inoculated with yeast and incubated for 4-days at 30° C. 200 rpm. 30 µL supernatant analysed on non-reducing SDS-PAGE (4-12% NuPAGE®, MES buffer, InVitrogen) with GelCode® Blue reagent (Pierce). 1=SeeBlue Plus2 Markers (InVitrogen); 2=1 µg rHA; 3=angiostatin-rHA; 4=angiostatin-rHA+PDI1; 5=endostatin-rHA; 6=endostatin-rHA+PDI1; 7=DX-890-(GGS)$_4$GG-rHA; 8 DX-890-(GGS)$_4$GG-rHA+PDI1; 9=DPI-14-(GGS)$_4$GG-rHA; 10=DPI-14-(GGS)$_4$GG-rHA+PDI1; 11=Axokine™ (CNTF$_{Ax15}$)-(GGS)$_4$GG-rHA (Lambert et al, 2001, Proc. Natl. Acad. Sci. USA, 98, 4652-4657); 12=Axokine™ (CNTF$_{Ax15}$)-(GGS)$_4$GG-rHA+PDI1.

The increase in expression of the albumin fusions detected by rocket immunoelectrophoresis was further studied by SDS-PAGE analysis. BMMD shake flask cultures of YBX7 expressing various albumin-fusions were grown for 4-days in an orbital shaker at 30° C., 200 rpm. A sample of the culture supernatant was analysed by SDS-PAGE (FIG. 14). A protein band of the expected size for the albumin fusion under study was observed increase in abundance.

Example 9

Co-expression of *S. cerevisiae* ORM2 and Recombinant Transferrin on a 2 µm-Based Plasmid The *S. cerevisiae* Control Strain and Strain A (as described in Example 3) were selected to investigate the effect on transferrin secretion when the transferrin and ORM2 genes were co-expressed from the 2 µm-based plasmids. The Control Strain and Strain A were transformed to leucine prototrophy by plasmids pDB3090, pDB3092 and pBD3093 (containing expression cassettes for rTf (N413Q, N611Q) and for ORM2), as well as a control plasmid pDB2931 (containing the rTf (N413Q, N611Q) expression cassette without ORM2). The construction of these plasmids is described in Example 10 of WO 2005/061718, the contents of which are incorporated herein by reference. Transformants were selected on BMMD agar and patched out on BMMD agar for subsequent analysis.

Figure 15:
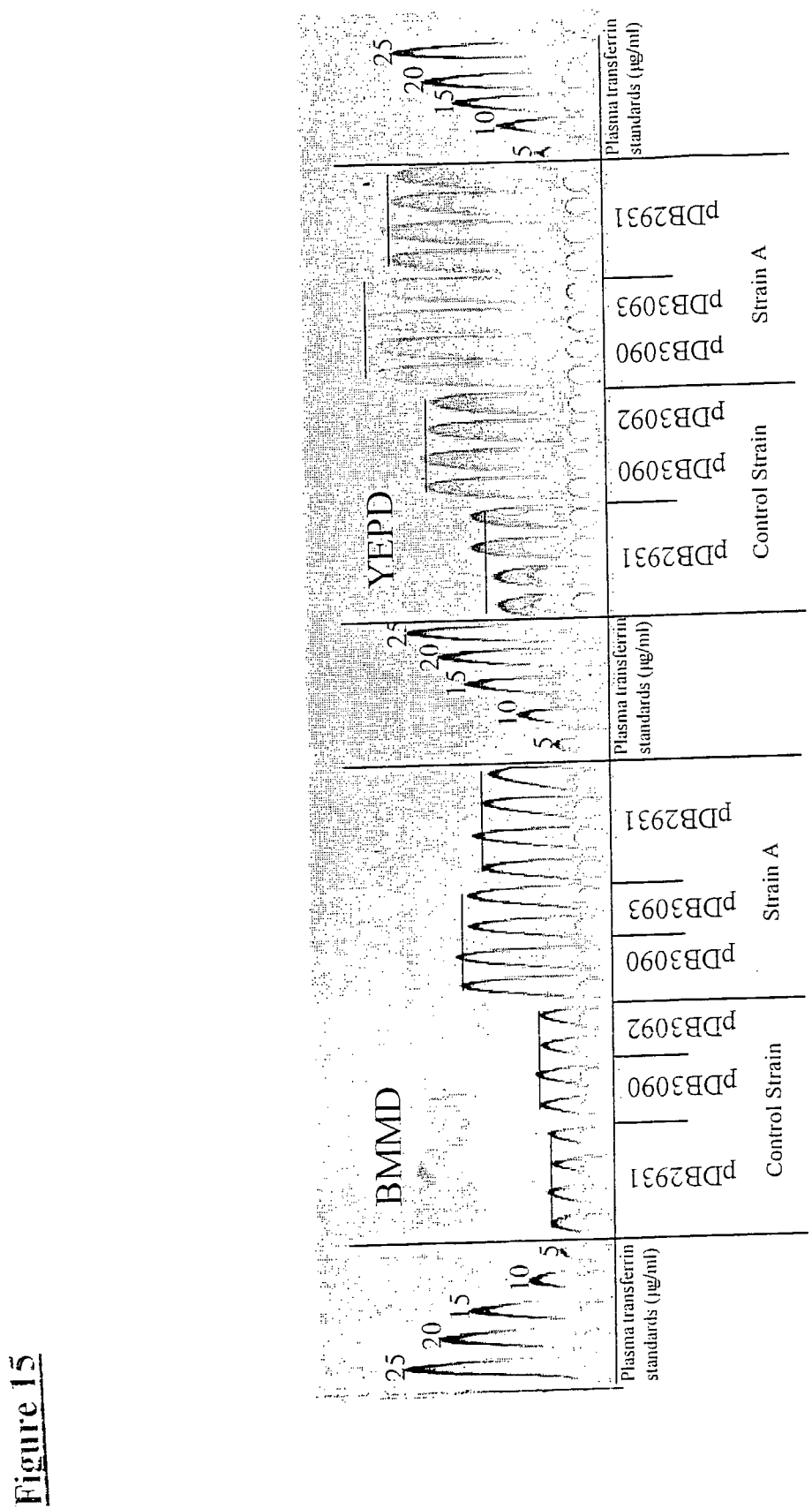
FIG. 15 shows RME analysis demonstrating increased transferrin secretion from S. cerevisiae with ORM2 co-expression from a 2 µm-based plasmid. Four day shake flask culture supernatants were loaded at 5 µl per well. Standards were human plasma holo-transferrin (Calbiochem), at 25, 20, 15. 10, 5 µg/ml, loaded 5 µl per well. Goat polygonal anti-transferrin (human) antiserum (Calbiochem) used at 20 µl per rocket immunoelectrophoresis gel (50 ml).

To investigate the effect of ORM2 co-expression on transferrin secretion, 10 mL selective (BMMD) and non-selective (YEPD) liquid media were inoculated with strains containing the ORM2/transferrin co-expression plasmids. The shake flask culture was then incubated at 30° C. with shaking (200 rpm) for 4 days. The relative level of transferrin secretion was determined by rocket gel inmmunoelectrophoresis (RIE) (FIG. 15).

Levels of transferrin secreted from Control Strain [pDB3090] and Control Strain [pDB3092] were greater than the levels from Control Strain [pDB2931] in both BMMD and YEPS media. Similarly, the levels of transferrin secreted from both Strain A [pDB3090] and Strain A [pDB3093] were greater than the levels from Strain A [pDB2931] in both BMMD and YEPS media. Transferrin secretion from all Strain A transformants was higher than the Control Strain transformants grown in the same media. Strain A contains an additional copy of PDI1 in the genome, which enhanced transferrin secretion. Therefore in Strain A, the increased expression of ORM2 and PDI1 had a cumulative effect on the secretion of transferrin.

Example 10

Co-Expression of *S. cerevisiae* PSE1 and Recombinant Transferrin on a 2 µm-Based Plasmid The *S. cerevisiae* Control Strain was transformed to leucine prototrophy by plasmids, pDB3097 and pBD3098 (containing expression cassettes for rTf (N413Q, N611Q) and for PSE1), as well as a control plasmid pDB2931 (containing the rTf (N413Q, N611Q) expression cassette without PSE1). The construction of these plasmids are described in Example 11 of WO 2005/061718, the contents of which are incorporated herein by reference. Transformants were selected on BMMD agar and patched out on BMMD agar for subsequent analysis.

Figure 16:
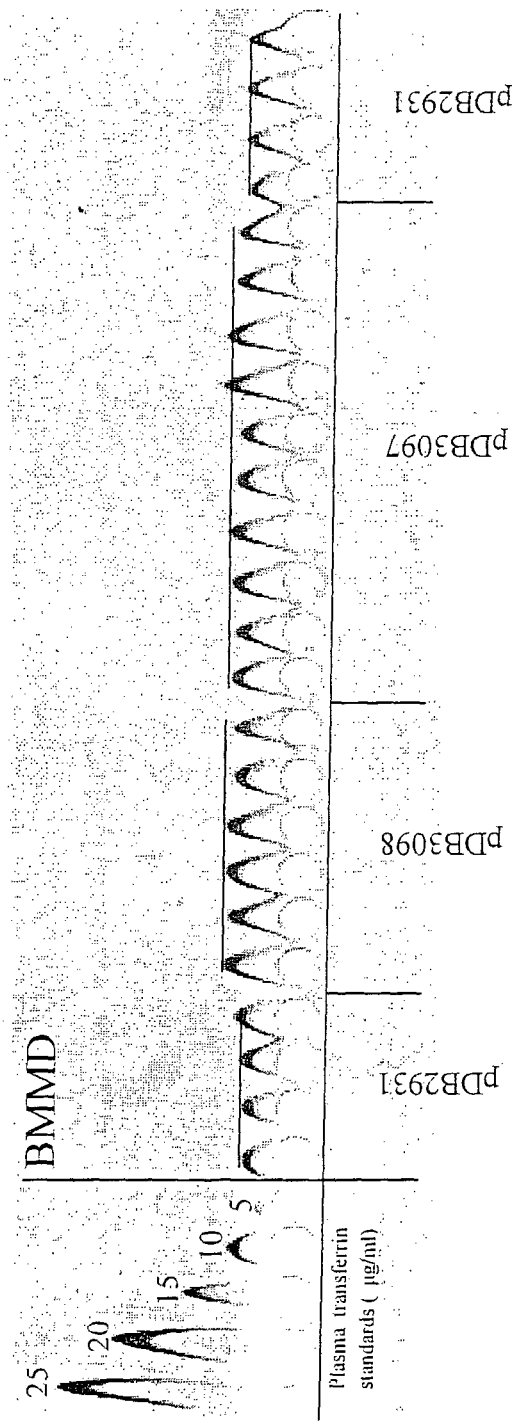
FIG. 16 shows RIE analysis demonstrating increased transferrin secretion from S. cerevisiae with PSE1 co-expression from a 2 µm-based plasmid. Four day shake flask culture supernatants were loaded at 5 µl per well. Standards were human plasma holo-transferrin (Calbiochem), at 25, 20, 15, 10, 5 µg/ml, loaded 5 µl per well. Goat polyclonal anti-transferrin (human) antiserum (Calbiochem) used at 20 µl per rocket immunoelectrophoresis gel (50 ml).

To investigate the effect of PSE1 expression on transferrin secretion, flasks containing 10 mL selective (BMMD) liquid media were inoculated with strains containing the PSE1/transferrin co-expression plasmids. The shake flask culture was then incubated at 30° C. with shaking (200 rpm) for 4 days. The relative level of transferrin secretion was determined by rocket gel immunoelectrophoresis (RIE) (FIG. 16).

Levels of transferrin secreted from Control Strain [pDB3097] and Control Strain [pDB3098] were greater than the levels from Control Strain [pDB2931] in BMMD media. Therefore, expression of PSE1 from the 2 µm-based plasmids had enhanced transferrin secretion from *S. cerevisiae*. Transferrin secretion was improved with the PSE1 gene transcribed in either direction relative to the REP2 gene in pDB3097 and pDB3098.

Example 11

Co-Expression of *S. cerevisiae* SSA1 and Recombinant Transferrin on a 2 µm-Based Plasmid The *S. cerevisiae* Control Strain was transformed to leucine prototrophy by plasmids, pDB3094 and pBD3095 (containing expression cassettes for rTf (N413Q, N611Q) and for SSA1), as well as a control plasmid pDB2931 (containing the rTf (N413Q, N611Q) expression cassette without SSA1). The construction of these plasmids are described in Example 12 of WO 2005/061718, the contents of which are incorporated herein by reference. Transformants were selected on BMMD agar and patched out on BMMD agar for subsequent analysis.

Figure 17:
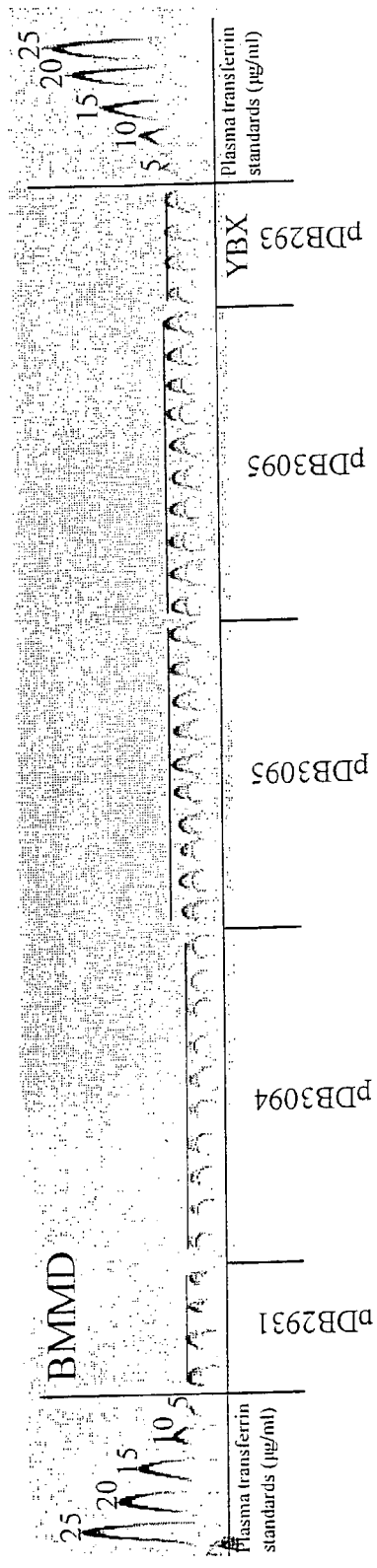
FIG. 17 shows RIE analysis demonstrating increased transferrin secretion from S. cerevisiae with SSA1 co-expression from a 2 µm-based plasmid. Four day shake flask culture supernatants were loaded at 5 µl per well. Standards were human plasma holo-transferrin (Calbiochem), at 25, 20, 15, 10, 5 µg/ml, loaded 5 µl per well. Goat polyclonal anti-transferrin (human) antiserum (Calbiochem) used at 20 µl per rocket immunoelectrophoresis gel (50 ml).

To investigate the effect of SSA1 expression on transferrin secretion., flasks containing 10 mL selective (BMMD) liquid media were inoculated with strains containing the SSA1/transferrin co-expression plasmids. The shake flask cultures were incubated at 30° C. with shaking (200 rpm) for 4 days. The relative level of transferrin secretion was determined by rocket gel immunoelectrophoresis (RIE) (FIG. 17).

Levels of transferrin secreted from Control Strain [pDB3095] were greater than the levels from Control Strain [pDB2931] and Control Strain [pDB3094] in BMMD media. Therefore, expression of SSA1 from the 2 µm-based plasmids had enhanced transferrin secretion from *S. cerevisiae*. Transferrin secretion was improved with the SSA1 gene transcribed in the opposite direction relative to the REP2 gene in pDB3094.

Example 12

PDI1 Gene Disruption, Combined with a PDI1 Gene on the 2 µm-Based Plasmid Enhanced the Secretion of Recombinant Albumin and Plasmid Stability.

Single stranded oligonucleotide DNA primers listed in Table 11 were designed to amplify a region upstream of the yeast PDI1 coding region and another a region downstream of the yeast PDI1 coding region.

TABLE 11

Oligonucleotide primers

| Primer | Description | Sequence |
|---|---|---|
| DS299 | 5' PDI1 primer, 38mer | 5'-CGTAGCGGCCGCCTGAAAGGGGTTGACCGTCCGT CGGC-3' (SEQ ID NO: 24) |
| DS300 | 5' PDI1 primer, 40mer | 5'-CGTAAAGCTTCGCCGCCCGACAGGGTAACATATTAT CAC-3' (SEQ ID NO: 25) |
| DS301 | 3' PI1 primer, 38mer | 5'-CGTAAAGCTTGACCACGTAGTAATAATAAGTGCAT GGC-3' (SEQ ID NO: 26) |
| DS302 | 3' PDI1 primer, 41mer | 5'-CGTACTGCAGATTGGATAGTGATTAGAGTGTATAGTCC CGG-3' (SEQ ID NO: 27) |
| DS303 | 18mer | 5'-GGAGCGACAAACCTTTCG-3' (SEQ ID NO: 28) |
| DS304 | 20mer | 5'-ACCGTAATAAAAGATGGCTG-3' (SEQ ID NO: 29) |
| DS305 | 24mer | 5'-CATCTTGTGTGTGAGTATGGTCGG-3' (SEQ ID NO: 30) |
| DS306 | 14mer | 5'-CCCAGGATAATTTTCAGG-3' (SEQ ID NO: 31) |

Primers DS299 and DS300 amplified the 5' region of PDI1 by PCR, while primers DS301 and DS302 amplified a region 3' of PDI1, using genomic DNA derived S288c as a template. The PCR conditions were as follows: 1 µL S288c template DNA (at 0.01 ng/µL, 0.1 ng/µL, 1 ng/µL, 10 ng/µL and 100 ng/µL), 5 µL 10×Buffer (Fast Start Taq+Mg, (Roche)), 1 µL 10 mM dNTP's, 5 µL each primer (2 µM), 0.4 µL Fast Start Taq, made up to 50 µL with H₂O. PCRs were performed using a Perkin-Elmer Thermal Cycler 9700. The conditions were: denature at 95° C. for 4 min [HOLD], then [CYCLE] denature at 95° C. for 30 seconds, anneal at 45° C. for 30 seconds, extend at 72° C. for 45 seconds for 20 cycles, then [HOLD] 72° C. for 10 min and then [HOLD] 4° C. The 0.22 kbp PDI1 5' PCR product was cut with NotI and HindIII, while the 0.34 kbp PDI1 3' PCR product was cut with HindIII and PstI.

Plasmid pMCS5 (Hoheisel, 1994, *Biotechniques* 17, 456-460) (FIG. 85 of WO 2005/061718) was digested to completion with HindIII, blunt ended with T4 DNA polymerase plus dNTPs and religated to create pDB2964 (FIG. 86 of WO 2005/061718).

Plasmid pDB2964 was HindIII digested, treated with calf intestinal phosphatase, and ligated with the 0.22 kbp PDI1 5' PCR product digested with NotI and HindIII and the 0.34 kbp PDI1 3' PCR product digested with HindIII and PstI to create pDB3069 (FIG. 87 of WO 2005/061718) which was sequenced with forward and reverse universal primers and the DNA sequencing primers DS303, DS304, DS305 and DS306 (Table 11).

Primers DS234 and DS235 (Table 12) were used to amplify the modified TRP1 marker gene from YIplac204 (Gietz & Sugino, 1988, *Gene*, 74, 527-534), incorporating HindIII restriction sites at either end of the PCR product. The PCR conditions were as follows: 1 µL template YIplac204 (at 0.01 ng/µL, 0.1 ng/µL, 1 ng/µL, 10 ng/µL and 100 ng/µL), 5 µL 10×Buffer (Fast Start Taq+Mg, (Roche)), 1 µL 10 mM dNTP's, 5 µL each primer (2 µM), 0.4 µL Fast Start Taq, made up to 50µL with H₂O. PCRs were performed using a Perkin-Elmer Thermal Cycler 9600. The conditions were: denature at 95° C. for 4 min [HOLD], then [CYCLE] denature at 95° C. for 30 seconds, anneal for 45 seconds at 45° C., extend at 72° C. for 90 sec for 20 cycles, then [HOLD] 72° C. for 10 min and then [HOLD] 4° C. The 0.86 kbp PCR product was digested with HindIII and cloned into the HindIII site of pMCS5 to create pDB2778 (FIG. 88 of WO 2005/061718). Restriction enzyme digestions and sequencing with universal forward and reverse primers as well as DS236, DS237, DS238 and DS239 (Table 12) confirmed that the sequence of the modified TPP1 gene was correct.

TABLE 12

Oligonucleotide primers

| Primer | Description | Sequence |
|---|---|---|
| DS230 | TRP1 5' UTR | 5'-TAGCGAATTC AATCAGTAAAAATCAACGG-3' (SEQ ID NO: 32) |
| DS231 | TRP1 5' UTR | 5'-GTCAAAGCTTCAAAAAAAGA AAAGCTCCGG-3' (SEQ ID NO: 33) |
| DS232 | TRP1 3' UTR | 5'-TAGCGGATCCGAATTCGGCGGTTGTTTGCAAGACC GAG-3' (SEQ ID NO: 34) |
| DS233 | TRP1 3' UTR | 5'-GTCAAAGCTTTAAAGATAATGCTAAATCATTTGG-3' (SEQ ID NO: 35) |

TABLE 12-continued

Oligonucleotide primers

| Primer | Description | Sequence |
|---|---|---|
| DS234 | TRP1 | 3'-TGACAAGCTTTCGGTCGAAAAAAGAAAAGG AG AGG-3' (SEQ ID NO: 36) |
| DS235 | TRP1 | 5'-TGACAAGCTTGATCTTTTATGCTTGCTTTTC-3' (SEQ ID NO: 37) |
| DS236 | TRP1 | 5'-AATAGTTCAGGCACTCCG-3' (SEQ ID NO: 38) |
| DS237 | TRP1 | 5'-TGGAAGGCAAGAGAGCC-3' (SEQ ID NO: 39) |
| DS238 | TRP1 | 5'-TAAAATGTAAGCTCTCGG-3' (SEQ ID NO: 40) |
| DS239 | TRP1 | 5'-CCAACCAAGTATTTCGG-3' (SEQ ID NO: 41) |
| CED005 | ΔTRP1 | 5'-GAGCTGACAGGGAAATGGTC-3' (SEQ ID NO: 42) |
| CED006 | ΔTRP1 | 5'-TACGAGGATACGGAGAGAGG-3' (SEQ ID NO: 43) |

The 0.86 kbp TRP1 gene was isolated from pDB2778 by digestion with HindIII and cloned into the HindIII site of pDB3069 to create pDB3078 (FIG. 89 of WO 2005/061718) and pDB3079 (FIG. 90 of WO 2005/061718). A 1.41 kb pdi1::TRP1 disrupting DNA fragment was isolated from pDB3078 or pDB3079 by digestion with NotI/PstI.

Yeast strains incorporating a TRP1 deletion (trp1Δ) were to be constructed in such a way that no homology to the TRP1 marker gene (pDB2778) should left in the genome once the trp1Δ had been created, so preventing homologous recombination between future TRP1 containing constructs and the TRP1 locus. In order to achieve the total removal of the native TRP1 sequence from the genome of the chosen host strains, oligonucleotides were designed to amplify areas of the 5' UTR and 3' UTR of the TRP1 gene outside of TRP1 marker gene present on integrating vector YIplac204 (Gietz & Sugino, 1988, Gene, 74, 527-534). The YIplac204 TRP1 marker gene differs from the native/chromosomal TRP1 gene in lo that internal HindIII, PstI and AbaI sites were removed by site directed mutagenesis (Gietz & Sugino, 1988, Gene, 74, 527-534). The YIplac204 modified TRP1 marker gene was constructed from a 1.453 kbp blunt-ended genomic fragment RcoRI fragment, which contained the TRP1 gene and only 102 bp of the TRP1 promoter (Gietz & Sugino, 1988, Gene, 74, 527-534). Although this was a relatively short promoter sequence it was clearly sufficient to complement tip1 auxotrophic mutations (Gietz & Sugino, 1988, Gene, 74, 527-534). Only DNA sequences upstream of the EcoRI site, positioned 102 bp 5' to the start of the TRP1 ORF were used to create the 5' TRP1 UTR. The selection of the 3' UTR was less critical as long as it was outside the 3' end of the functional modified TRP1 marker, which was chosen to be 85 bp downstream of the translation stop codon.

Single stranded oligonucleotide DNA primers were designed and constructed to amplify the 5' UTR and 3' UTR regions of the TRP1 gene so that during the PCR amplification restriction enzyme sites would be added to the ends of the PCR products to be used in later cloning steps. Primers DS230 and DS231 (Table 12) amplified the 5' region of TRP1 by PCR, while primers DS232 and DS233 (Table 12) amplified a region 3' of TRP1, using S288c cenomic DNA as a template. The PCR conditions were as follows: 1 μL template S288c genomic DNA (at 0.01 ng/μL, 0.1 ng/μL, 1 ng/μL, 10 ng/μL and 100 ng/μL), 5 μL 10×Buffer (Fast Start Taq+Mg, (Roche)), 1 μL 10 mM dNTP's, 5 μL each primer (2 μM), 0.4 μL Fast Start Taq, made up to 50 μL with $H_2O$. PCRs were performed using a Perkin-Elmer Thermal Cycler 9600. The conditions were: denature at 95° C. for 4 min [HOLD], then [CYCLE] denature at 95° C. for 30 seconds, anneal for 45 seconds at 45° C., extend at 72° C. for 90 sec for 20 cycles, then [HOLD] 72° C. for 10 min and then [HOLD] 4° C.

The 0.19 kbp TRP1 5' UTR PCR product was cut with EcoRI and HindIII, while the 0.2 kbp TRP1 3' UTR PCR product was cut with BamHI and HindIII and ligated into pAYE505 linearised with BamHI/EcoRI to create plasmid pDB2777 (FIG. 91 of WO 2005/061718). The construction of pAYE505 is described in WO 95/33833. DNA sequencing using forward and reverse primers, designed to prime from the plasmid backbone and sequence the cloned inserts, confirmed that in both cases the cloned 5' and 3' UTR sequences of the TRP1 gene had the expected DNA sequence. Plasmid pDB2777 contained a TRP1 disrupting fragment that comprised a fusion of sequences derived from the 5' and 3' UTRs of TRP1. This 0.383 kbp TRP1 disrupting fragment was excised from pDB2777 by complete digestion with RcoRI.

Yeast strain DXY1 (Kerry-Williams et al., 1998, Yeast, 14, 161-169) was transformed to leucine prototrophy with the albumin expression plasmid pDB2244 using a modified lithium acetate method (Sigma yeast transformation kit, YEAST-1, protocol 2; (Ito et al, 1983, J. Bacteriol., 153, 163; Elble, 1992, Biotechniques, 13, 18)) to create yeast strain DXY1 [pDB2244]. The construction of the albumin expression plasmid pDB2244 is described in WO 00/44772. Transformants were selected on BMMD-agar plates, and were subsequently patched out on BMMD-agar plates. Cryopreserved trehalose stocks were prepared from 10 mL BMMD shake flask cultures (24 hrs, 30° C., 200 rpm). DXY1 [pDB2244] was transformed to tryptophan autotrophy with the 0.383 kbp EcoRI TRP1 disrupting DNA fragment from pDB2777 using a nutrient agar incorporating the counter selective tryptophan analogue, 5-fluoroanthranilic acid (5-FAA), as described by Toyn et al., (2000 Yeast 16, 553-

560). Colonies resistant to the toxic effects of 5-FAA were picked and streaked onto a second round of 5-FAA plates to confirm that they really were resistant to 5-FAA and to select away from any background growth. Those colonies which grew were then were re-patched onto BMMD and BMMD plus tryptophan to identify which were tryptophan auxotrophs.

Subsequently colonies that had been shown to be tryptophan auxotrophs were selected for further analysis by transformation with YCplac22 (Gietz & Sugino, 1988, Gene, 74, 527-534) to ascertain which isolates were trp1.

PCR amplification across the TRP1 locus was used to confirm that the trp⁻ phenotype was due to a deletion in this region. Genomic DNA was prepared from isolates identified as resistant to 5-FAA and unable to grow on minimal media without the addition of tryptophan. PCR amplification of the genomic TRP1 locus with primers CED005 and CED006 (Table 12) was achieved as follows: 1 µL template genomic DNA, 5 µL 10×Buffer (Fast Start Taq+Mg, (Roche)), 1 µL 10 mM dNTP's, 5 µL each primer (2 µM), 0.4 µL Fast Start Taq, made up to 50 µL with $H_2O$. PCRs were performed using a Perkin-Elmer Thermal Cycler 9600. The conditions were: denature at 94° C. for 10 min [HOLD], then [CYCLE] denature at 94° C. for 30 seconds, anneal for 30 seconds at 55° C., extend at 72° C. for 120 sec for 40 cycles, then [HOLD] 72° C. for 10 min and then [HOLD] 4° C. PCR amplification of the wild type TRP1 locus resulted in a PCR product of 1.34 kbp in size, whereas amplification across the deleted TRP1 region resulted in a PCR product 0.84 kbp smaller at 0.50 kbp. PCR analysis identified a DXY1 derived trp⁻ strain (DXY1 trp1Δ [pDB2244]) as having the expected deletion event.

The yeast strain DXY1 trp1Δ [pDB2244] was cured of the expression plasmid pDB2244 as described by Sleep et al., (1991, Bio/Technology, 9, 183-187). DXY1 trp1Δ cir⁰ was re-transformed the leucine prototrophy with either pDB2244, pDB2976, pDB2977, pDB2978, pDB2979, pDB2980 or pDB2981 using a modified lithium acetate method (Sigma yeast transformation kit, YEAST-1, protocol 2; (Ito et al, 1983, J. Bacteriol., 153, 163; Elble, 1992, Biotechniques, 13, 18)). Transformants were selected on BMMD-agar plates supplemented with tryptophan, and were subsequently patched out on BMMD-agar plates supplemented with tryptophan. Cryopreserved trehalose stocks were prepared from 10 mL BMMD shake flask cultures supplemented with tryptophan (24 hrs, 30° C., 200 rpm).

The yeast strains DXY1 trp1Δ [pDB2976], DXY1 trp1Δ [pDB2977], DXY1 trp1Δ [pDB2978], DXY1 trp1Δ [pDB2979], DXY1 trp1Δ [pDB2980] or DXY1 trp1Δ [pDB2981] was transformed to tryptophan prototrophy using the modified lithium acetate method (Sigma yeast transformation kit, YEAST-1, protocol 2; (Ito et al, 1983, J. Bacteriol., 153, 163; Elble, 1992, Biotechniques, 13, 18)) with a 1.41 kb pdi1::TRP1 disrupting DNA fragment was isolated from pDB3078 by digestion with NotI/PstI. Transformants were selected on BMMD-agar plates and were subsequently patched out on BMMD-agar plates.

Six transformants of each strain were inoculated into 10 mL YEPD in 50 mL shake flasks and incubated in an orbital shaker at 30° C., 200 rpm for 4-days. Culture supernatants and cell biomass were harvested. Genomic DNA was prepared (Lee, 1992, Biotechniques, 12, 677) from the tryptophan prototrophs and DXY1 [pDB2244]. The genomic PDI1 locus amplified by PCR of with primers DS236 and DS303 (Table 11 and 12) was achieved as follows: 1 µL template genomic DNA, 5 µL 10×Buffer (Fast Start Taq+Mg, (Roche)), 1 µL 10 mM dNTP's, 5 µL each primer (2 µM), 0.4 µL Fast Start Taq, made up to 50 µL with $H_2O$. PCRs were performed using a Perkin-Elmer Thermal Cycler 9700. The conditions were: denature at 94° C. for 4 min [HOLD], then [CYCLE] denature at 94° C. for 30 seconds, anneal for 30 seconds at 50° C., extend at 72° C. for 60 sec for 30 cycles, then [HOLD] 72° C. for 10 min and then [HOLD] 4° C. PCR amplification of the wild type PDI1 locus resulted in no PCR product, whereas amplification across the deleted PDI1 region resulted in a PCR product 0.65 kbp. PCR analysis identified that all 36 potential pdi1::TRP1 strains tested had the expected pdi1::TRP1 deletion.

Figure 18:
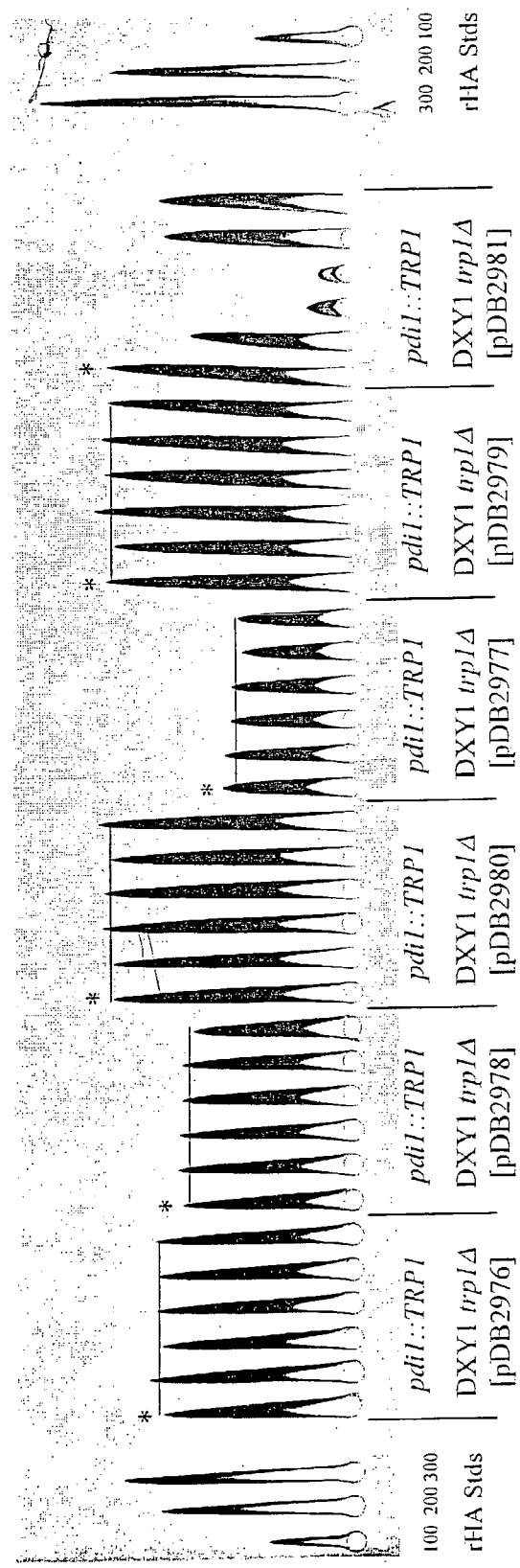
FIG. 18 shows the results of RIE. 10 mL YEPD shake flasks were inoculated with DXY1 trp1Δ [pDB2976], DXY1 trp1Δ [pDB2977], DXY1 trp1Δ [pDB2978], DXY1 trp1Δ [pDB2979], DXY1 trp1Δ [pDB2980] or DXY1 trp1Δ [pDB2981] transformed to tryptophan prototrophy with a 1.41 kb NotI/PstI pdi1::TRP1 disrupting DNA fragment was isolated from pDB3078. Transformants were grown for 4-days at 30° C., 200 rpm. 4 µL culture supernatant loaded per well of a rocket immunoelectrophoresis gel. rHA standards concentrations are in µg/mL. 700 µL goat anti-HA (Sigma product A-1151 resuspended in 5 mL water)/50 mL agarose. Precipin was stained with Coomassie blue. Isolates selected for further analysis are indicated (*).

The recombinant albumin titres were compared by rocket immunoelectrophoresis (FIG. 18). Within each group, all six pdi1::TRP1 disruptants of DXY1 trp1Δ [pDB2976], DXY1 trp1Δ [pDB2978], DXY1 trp1Δ [pDB2980], DXY1 trp1Δ [pDB2977] and DXY1 trp1Δ [pDB2979] had very similar rHA productivities. Only the six pdi1::TRP1 disruptants of DXY1 trp1Δ [pDB2981] showed variation in rHA expression titre. The six pdi1::TRP1 disruptants indicated in FIG. 18 were spread onto YEPD agar to isolate single colonies and then re-patched onto BMMD agar.

Figure 19:
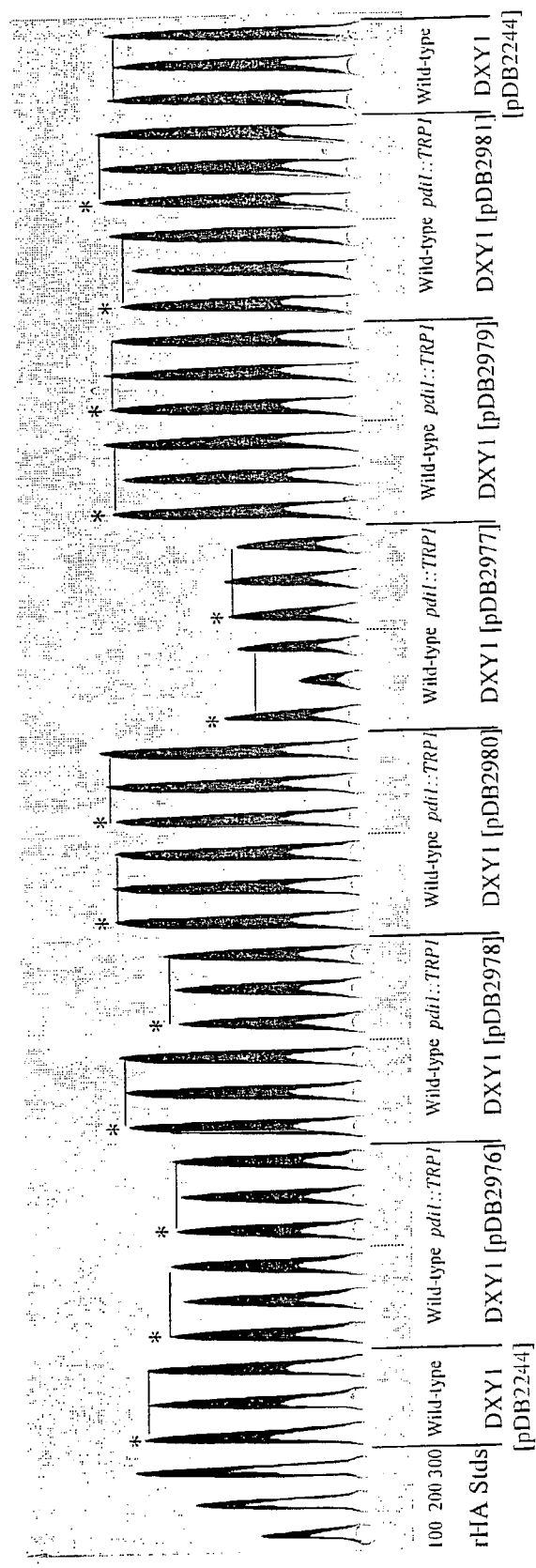
FIG. 19 shows the results of RIE. 10 mL YEPD shake flasks were inoculated with DXY1 [pDB2244], DXY1 [pDB2976], DXY1 trp1Δ pdi1::TRP1 [pDB2976], DXY1 [pDB2978], DXY1 trp1Δ pdi1::TRP1 [pDB2978], DXY1 [pDB2980], DXY1 trp1Δ pdi1::TRP1 [pDB2980], DXY1 [pDB2977], DXY1 trp1Δ pdi1::TRP1 [pDB2977], DXY1 [pDB2979] DXY1 trp1Δ pdi1::TRP1 [pDB2979], DXY1 [pDB2981] and DXY1 trp1Δ pdi1::TRP1 [pDB2981], and were grown for 4-days at 30° C., 200 rpm. 4 µL culture supernatant loaded per well of a rocket immunoelectrophoresis gel. rHA standards concentrations are in µg/mL. 800 µL goat anti-HA (Sigma product A-1151 resuspended in 5 mL water)/50 mL agarose. Precipin was stained with Coomassie blue. Isolates selected for further analysis are indicated (*)

Three single celled isolates of DXY1 trp1Δ pdi1::TRP1 [pDB2976], DXY1 trp1Δ pdi1::TRP1 [pDB2978], DXY1 trp1Δ pdi1::TRP1 [pDB2980], DXY1 trp1α pdi1::TRP1 [pDB2977], DXY1 trp1Δ pdi1::TRP1 [pDB2979] and DXY1 trp1Δ pdi1::TRP1 [pDB2981] along with DXY1 [pDB2244], DXY1 [pDB2976], DXY1 [pDB2978], DXY1 [pDB2980], DXY1 [pDB2977], DXY1 [pDB2979] and DXY1 [pDB2981] were inoculated into 10 mL YEPD in 50 mL shake flasks and incubated in an orbital shaker at 30° C., 200 rpm for 4-days. Culture supernatants were harvested and the recombinant albumin titres were compared by rocket immunoelectrophoresis (FIG. 19). The thirteen wild type PDI1 and pdi1::TRP1 disruptants indicated in FIG. 19 were spread onto YEPD agar to isolate single colonies. One hundred single celled colonies from each strain were then re-patched onto BMMD agar or YEPD agar containing a goat anti-HSA antibody to detect expression of recombinant albumin (Sleep et al., 1991, Bio/Technology, 9, 118-187) and the Leu+/rHA+, Leu+/rHA−, Leu−/rHA+ or Leu−/rHA− phenotype of each colony scored (Table 13).

TABLE 13

| | PDI1 | | | | pdi1::TRP1 | | | |
|---|---|---|---|---|---|---|---|---|
| | Leu+ rHA+ | Leu− rHA+ | Leu+ rHA− | Leu− rHA− | Leu+ rHA+ | Leu− rHA+ | Leu+ rHA− | Leu− rHA− |
| pDB2244 | 100 | 0 | 0 | 0 | | | | |
| pDB2976 | 7 | 0 | 47 | 46 | 97 | 0 | 3 | 0 |
| pDB2978 | 86 | 0 | 0 | 14 | 100 | 0 | 0 | 0 |
| pDB2980 | 98 | 0 | 0 | 2 | 100 | 0 | 0 | 0 |
| pDB2977 | 0 | 0 | 4 | 96 | 100 | 0 | 0 | 0 |
| pDB2979 | 69 | 0 | 6 | 25 | 100 | 0 | 0 | 0 |
| pDB2981 | 85 | 0 | 0 | 15 | 92 | 0 | 0 | 8 |

These data indicate plasmid retention is increased when the PDI1 gene is used as a selectable marker on a plasmid in a host strain having no chromosomally encoded PDI, even in a non-selective medium such as the exemplified rich medium.

Example 13

Construction of tie pSAC35-Based Expression Vectors pDB3175-pDB3182 for Co-expression of PDI1 with Recombinant Human Albumin or Transferrin (N413Q, N611Q) from the SnaBI/NotI-Site in the 2 µm UL-Region The NotI expression cassette from the pSAC35-based expression vector, pAYE316 (Sleep et al, 1991, Biotechnol-

*ogy* (N Y), 9, 183-187), designed for the secretion of recombinant human albumin, was cloned into the unique NotI-site of the *E. coli* cloning vector pBST(+) (Sleep et al, 2001, *Yeast*, 18, 403-421) to produce plasmid pQC262e. pQC262e was subsequently modified by site-directed mutagenesis (Kunkel et al, 1987, *Methods Enzymol.*, 154, 367-382) with oligonucleotide LRE49 (Table 14) to introduce a unique Asp718I-site immediately upstream of the NotI-site at the ADH1 terminator region of the expression cassette.

TABLE 14

Mutagenic Oligonucleotide

| Primer | Description | Sequence |
|---|---|---|
| LRE49 | Mutagenic 45mer ADH1 terminator region | 5'-GCTAGCGTCGACAAGCTTGCGG CGCGGTACCGTGTGGAAGAACG-3' (SEQ ID NO: 44) |

Figure 21:
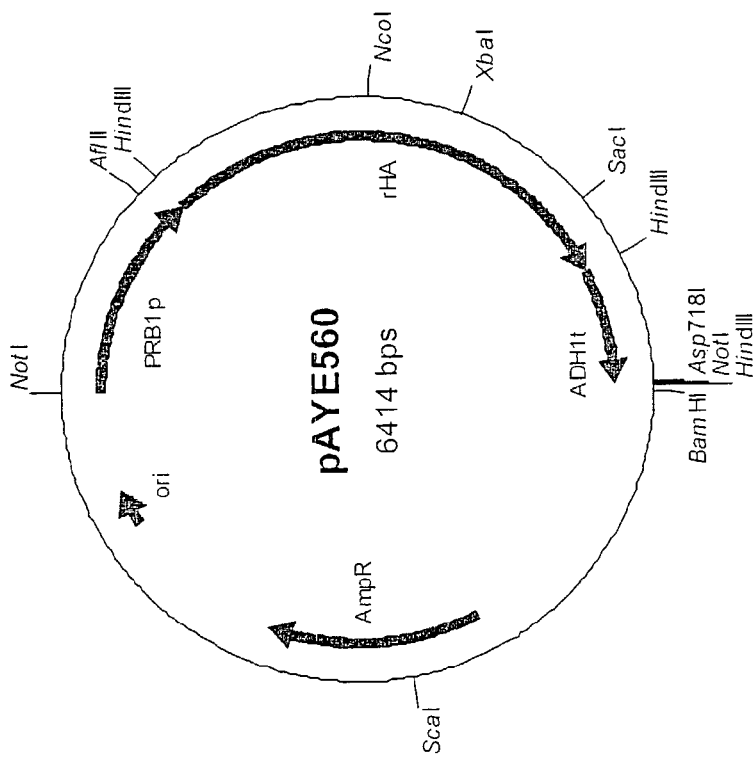
Figure 24:
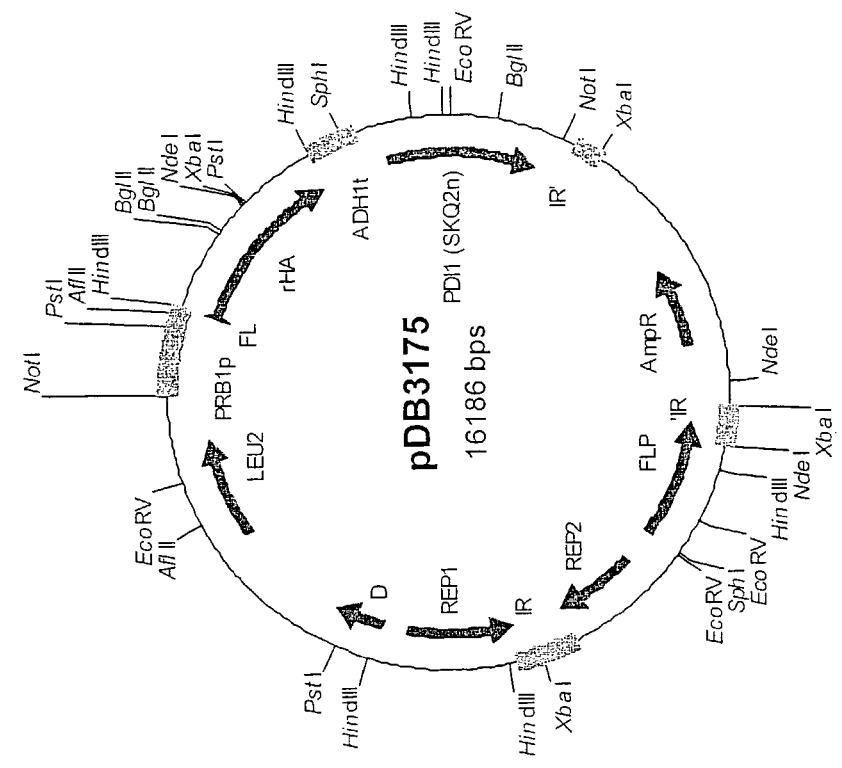
Figure 23:
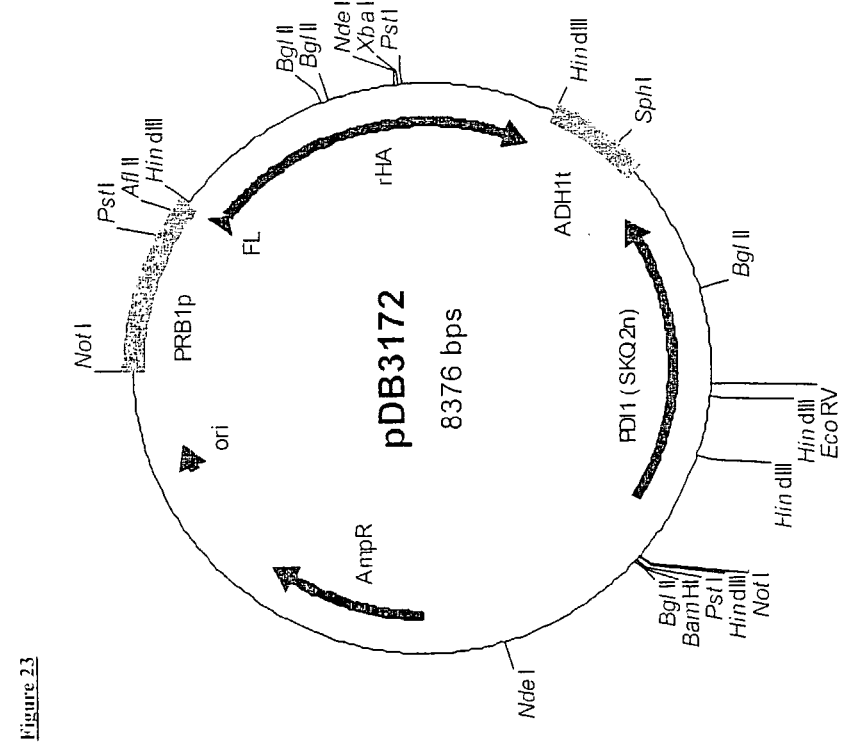
Figure 26:
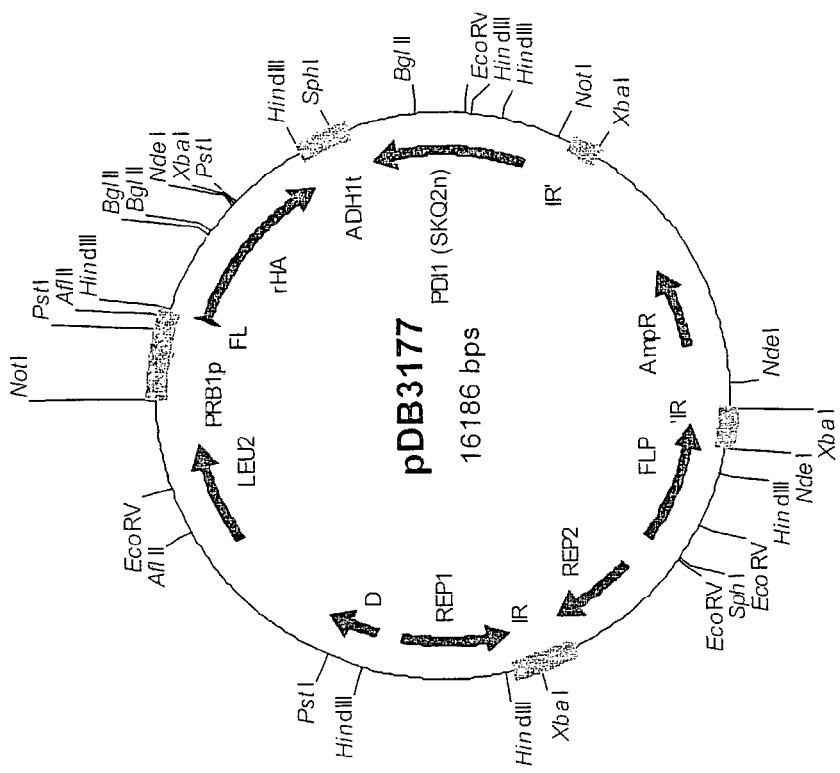
Figure 25:
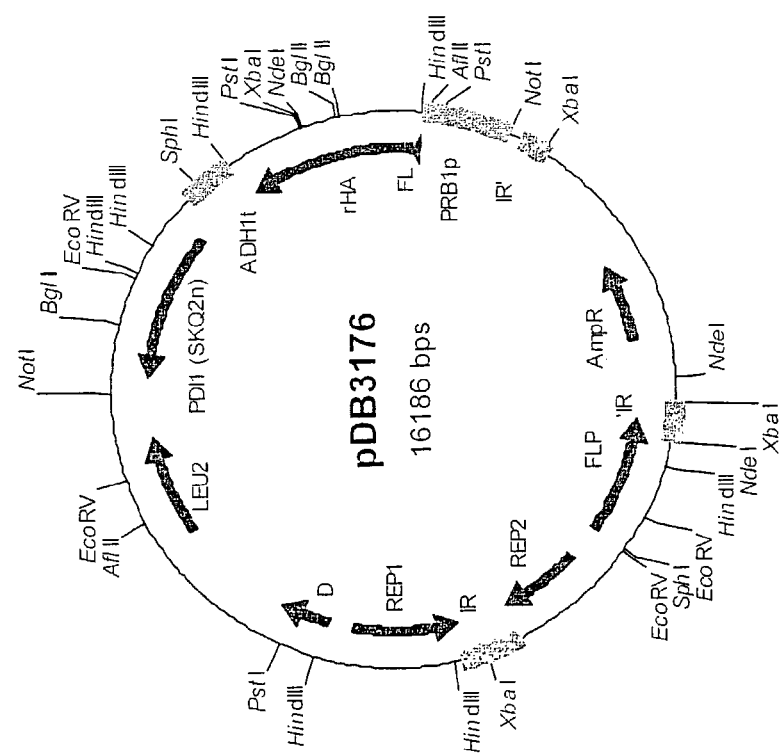

This produced plasmid pAYE560 (FIG. 21). The *S. cerevisiae* SKQ2n PDI1 gene with the long (~210-bp) promoter was isolated on 1.96-kb SmaI fragment from pDB2952 (FIG. 46 in WO 2005/061719, the contents of which are incorporated herein by reference). The pDB2952 PDI1 fragment was cloned into the unique Asp718I-site of pAYE560, following digestion with Asp718I, filling the 3'-recessed ends using T4 DNA polymerase, and calf intestinal alkaline phosphatase treatment of the blunt-ended product. This produced plasmids pDB3171 (FIG. 22) with the PDI1 gene transcribed in the same direction as rHA, and pDB3172 (FIG. 23) with converging transcription of the PDI1 and rHA genes.

pDB3175 and pDB3176 (FIGS. 24 and 25) were produced by cloning the ~5.1-kb rHA→PDI1→NotI expression cassette from pDB3171 into pSAC35, which had been digested with NotI and calf intestinal alkaline phosphatase. pDB3177 and pDB3178 (FIGS. 26 and 27) were produced similarly by cloning the ~5.1-kb NotI rHA→←PDI1 expression cassette from pDB3172 into pSAC35 digested with NotI and calf intestinal alkaline phosphatase.

To construct NotI expression cassettes for co-expression of recombinant unglycosylated human transferrin (N413Q, N611Q) and the *S. cerevisiae* SKQ2n PDI1 gene with the long (~210-bp) promoter, the ~6.1-kb AflI-SphI fragment from pDB3171 was ligated with the ~2.4-kb AflII-SphI fragment from pDB2928 (FIG. 11 of WO 2005/061718, the contents of which are incorporated herein by reference), thus replacing the rHA coding and adjacent sequences with those for transferrin (N413Q, N611Q) secretion. This produced plasmids pDB3173 (FIG. 28) with the PDI1 gene transcribed in the same direction as rTf (N413Q, N611Q), and pDB3174 (FIG. 29) with converging transcription of the PDI1 and rTf (N413Q, N611Q) genes.

pDB3179 and pDB3180 (FIGS. 30 and 31) were produced by cloning the ~5.2-kb rTf→PDI1→NotI expression cassette from pDB3173 into pSAC35, which had been digested with NotI and calf intestinal alkaline phosphatase. pDB3181 and pDB3182 (FIGS. 32 and 33) were produced by cloning the ~5.2-kb NotI rTf→←PDI1 expression cassette from pDB3174 into pSAC35 digested with NotI and calf intestinal alkaline phosphatase.

Example 14

*S. cerevisiae* PDI1 at the SnaBI/NotI-Site in the UL-Region of pSAC35-Based Expression Vectors as a Selectable Marker in *S. cerevisiae* Strain DXY1 Δtrp1 pdi1::TRP1

The yeast strains DXY1 (Kerry-Williams et al., 1998, *Yeast*, 14, 161-169) and DXY1 Δtrp1 (see Example 13 of WO 2005/061718, the contents of which are incorporated herein by reference) were transformed to leucine prototrophy with pSAC35-based plasmids pAYE316, pDB3175, pDB3176, pDB3177, pDB3178, pDB2931, pDB3179, pDB3180, pDB3181 and pDB3182 using a modified lithium acetate method (Sigma yeast transformation kit, YEAST-1, protocol 2; (Ito et al, 1983, *J. Bacteriol.*, 153, 163; Elble, 1992, *Bio/techniques*, 13, 18)). Transformants were selected on BMMD-agar plates with appropriate supplements, and were subsequently patched out on BMMD-agar plates with appropriate supplements.

DXY1 Δtrp1 [pDB3175], DXY1 Δtrp1 [pDB3176], DXY1 Δtrp1 [pDB3177], DXY1 Δtrp1 [pDB3178], DXY1 Δtrp1 [pDB3179], DXY1 Δtrp1 [pDB3180], DXY1 Δtrp1 [pDB3181], and DXY1 Δtrp1 [pDB3182] were transformed to tryptophan prototrophy using the modified lithium acetate method (Sigma yeast transformation kit, YEAST-1, protocol 2; (Ito et al, 1983, *J. Bacteriol.*, 153, 163; Elble, 1992, *Biotechniques*, 13, 18)) with a 1.41-kb pdi1::TRP1 disrupting DNA fragment isolated from pDB3078 by digestion with NotI/PstI. (see Example 13 of WO 2005/061718). Transformants were selected on BMMD-agar plates and were subsequently patched out on BMMD-agar plates.

Disruption of the PDI1 gene with the TRP1 marker was confirmed by diagnostic PCR amplification of an approximately 810-bp product using oligonucleotide primers CF247 and DS236 (Table 15). CF247 binds in the PDI1 promoter region upstream of the disruption site and DS236 binds within the TRP1 gene.

TABLE 15

Oligonucleotide Sequencing Primers

| Primer | Description | Sequence |
|---|---|---|
| CF247 | PDI1 promoter region, 20mer | 5'-GCGCGTTTTCATTAGTGCCC-3' (SEQ ID NO: 45) |
| DS236 | TRP1 coding region, 19mer | 5'-AAATAGTTCAGGCACTCCG-3' (SEQ ID NO: 38) |

DXY1 Δtrp1, DXY1 Δtrp1 containing pDB3175-pDB3182 and putative pdi1::TRP1 -disruptants were inoculated into 10 mL YEPD in 50 mL shake flasks, and incubated in an orbital shaker at 30° C., 200 rpm for 4-days. Genomic DNA was prepared (Lee, 1992, *Biotechniques*, 12, 677) from the biomass for subsequent use as template DNA in diagnostic PCR.

0.5 μL template genomic DNA. 2.5 μL 10×Buffer (Fast Start Taq+Mg, (Roche)), 0.5 μL 10 mM dNTP's, 2.5 μL each primer (2 μM), 0.2 μL Fast Start Taq were mixed and made up to 25 μL with H$_2$O. PCRs were performed using a Dyad™ DNA Engine Peltier thermal cycler (GRI) as follows; denaturation at 95° C. for 4 mins, then 25 cycles of 95° C. for 30s, 55° C. for 30s and 72° C. for 1 min followed by extension at 72° C. for 10 mins. A PCR product of ~810-bp was only amplified from DNA containing the TRP1 gene integrated at the pdi1 locus. DXY1 Δtrp1 pdi1::TRP1 containing pDB3175-pDB3182 were successfully identified. As expected, no PCR product was generated for the controls DXY1 Δtrp1 or DXY1 Δtrp1 containing pDB3175-pDB3182.

DXY1 containing pDB3175-pDB3182 were compared with DXY1 Δtrp1 pdi1::TRP1 containing pDB3175-pDB3182 for plasmid stability and secretion of recombinant human albumin or transferrin (N413Q, N611Q) in YEPD shake flask culture. 10 mL YEPD shake flasks were inoculated with the above strains and grown for 4-days at 30° C., 200 rpm. Samples were spread onto YEPD-agar plates and grown to single colonies. Fifty randomly selected colonies were patched out in replica onto BMMD and YEPD plates and incubated at 30° C. Plasmid stability was scored as the percentage of colonies able to grow on both media. The results shown in Tables 16 and 17 demonstrated that all of the plasmids pDB3175-pDB31182 were less than 100% stable in DXY1, regardless of the relative orientations of the PDI1 and rTf/rHA genes cloned at the SnaBI/NotI-site. However, 100% plasmid stability was determined in all cases in DXY1 Δtrp1 pdi1::TRP1 containing pDB31175-pDB3182. Hence, use of PDI1 as the sole selectable marker at the SnaBI/NotI-site of pSAC35-based vectors resulted in 100% plasmid stability in rich media.

TABLE 16

Plasmid stability of pSAC35-based vectors containing a recombinant albumin gene and the S. cerevisiae PDI1 gene at the SnaBI/NotI-site in the UL-region in strains DXY1 and DXY1 Δtrp1 pdi1::TRP1. 10 mL YEPD shake flasks were inoculated with DXY1 [pDB3175], DXY1 [pDB3176], DXY1 [pDB3177], DXY1 [pDB3178], DXY1 Δtrp1 pdi1::TRP1 [pDB3175], DXY1 Δtrp1 pdi1::TRP1 [pDB3176], DXY1 Δtrp1 pdi1::TRP1 [pDB3177], and DXY1 Δtrp1 pdi1::TRP1 [pDB3178] were grown for 4-days at 30° C., 200 rpm. Samples were spread onto YEPD-agar plates and grown to single colonies. Fifty randomly selected colonies were patched out in replica onto BMMD and YEPD plates and incubated at 30° C. Plasmid stability was scored as the percentage of colonies able to grow on both media.

| Plasmid | SnaBI/NotI Cassette* | | | Plasmid Stability (% Prototrophs) | | |
|---|---|---|---|---|---|---|
| | | | | DXY1 | DXY1 Δtrp1 | DXY1 Δtrp1 pdi1::TRP1 |
| pDB3175 | LEU2 → | rHA → | PDI1 → | 96 | 0 | 100 |
| pDB3176 | LEU2 → | PDI1 ← | rHA ← | 68 | 0 | 100 |
| pDB3177 | LEU2 → | rHA → | PDI1 ← | 86 | 0 | 100 |
| pDB3178 | LEU2 → | PDI1 → | rHA ← | 28 | 0 | 100 |

*Arrows indicate the direction of transcription relative to the LEU2 gene.

TABLE 17

Plasmid stability of pSAC35-based vectors containing a recombinant transferrin gene and the S. cerevisiae PDI1 gene at the SnaBI/NotI-site in the UL-region in strains DXY1 and DXY1 Δtrp1 pdi1::TRP1. 10 mL YEPD shake flasks were inoculated with DXY1 [pDB3179], DXY1 [pDB3180], DXY1 [pDB3181], DXY1 [pDB3182], DXY1 Δtrp1 pdi1::TRP1 [pDB3179], DXY1 Δtrp1 pdi1::TRP1 [pDB3180], DXY1 Δtrp1 pdi1::TRP1 [pDB3181], and DXY1 Δtrp1 pdi1::TRP1 [pDB3182] were grown for 4-days at 30° C., 200 rpm. Samples were spread onto YEPD-agar plates and grown to single colonies. Fifty randomly selected colonies were patched out in replica onto BMMD and YEPD plates and incubated at 30° C. Plasmid stability was scored as the percentage of colonies able to grow on both media.

| Plasmid | SnaBI/NotI Cassette | | | Plasmid Stability (% Prototrophs) | | |
|---|---|---|---|---|---|---|
| | | | | DXY1 | DXY1 Δtrp1 | DXY1 Δtrp1 pdi1::TRP1 |
| pDB3179 | LEU2 → | rTf → | PDI1 → | 56 | 0 | 100 |
| pDB3180 | LEU2 → | PDI1 ← | rTf ← | 36 | 0 | 100 |
| pDB3181 | LEU2 → | rTf → | PDI1 ← | 28 | 0 | 100 |
| pDB3182 | LEU2 → | PDI1 → | rTf ← | 15 | 0 | 100 |

*Arrows indicate the direction of transcription relative to the LEU2 gene.

Figure 34:
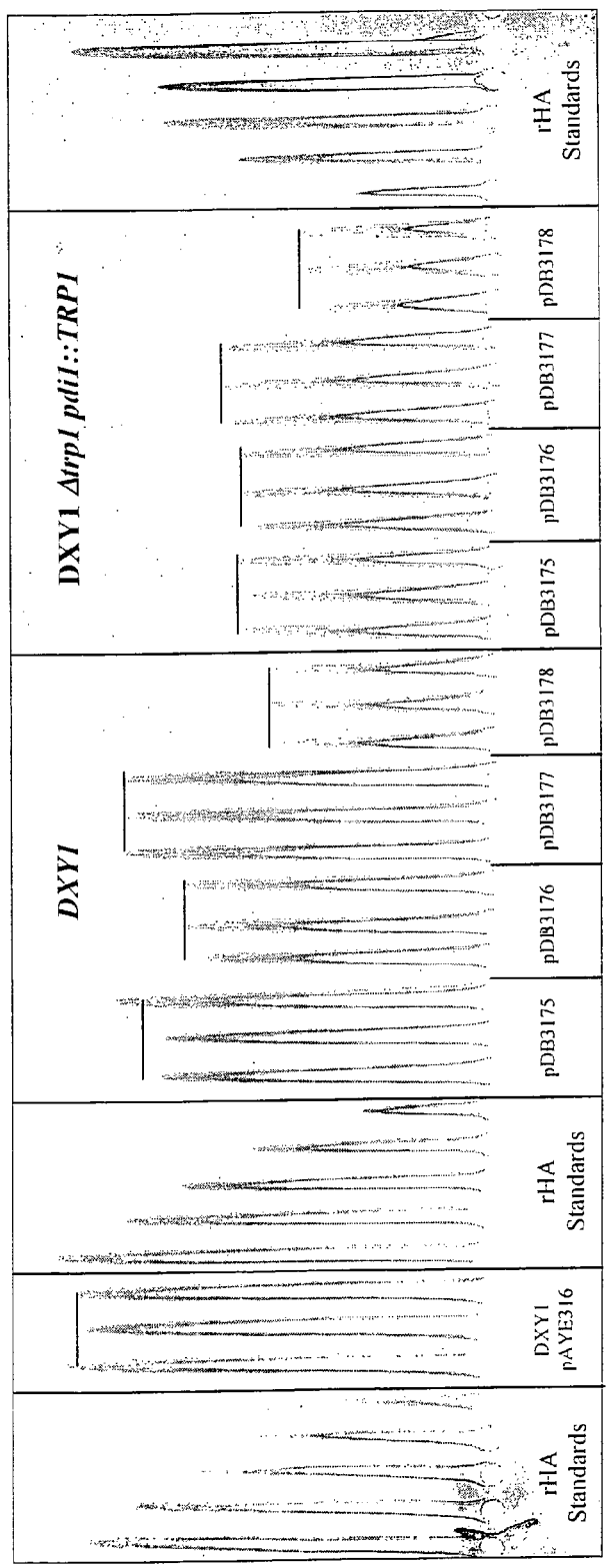
FIG. 34 shows Rocket Immunoelectrophoresis of YEPD shake flask culture supernatants from DXY1 and DXY1 Δtrp1 pdi1::TRP1 containing pDB3175 to pDB3178. 10 mL YEPD shake flasks were inoculated with DXY1 [pAYE316], DXY1 [pDB3175], DXY1 [pDB3176], DXY1 [pDB3177], DXY1 [pDB3178], DXY1 Δtrp1 pdi1::TRP1 [pDB3175], DXY1 Δtrp1 pdi1::TRP1 [pDB3176], DXY1 Δtrp1 pdi1:: TRP1 [pDB3177], and DXY1 Δtrp1 pdi1::TRP1 [pDB3178] were grown for 4-days at 30° C., 200 rpm. 5 µL culture supernatant was loaded per well of a 50 mL rocket immunoelectrophoresis gel in triplicate. rHA standard concentrations were 300, 200, 150, 100 and 50 µg/mL. 600 µL goat anti-HSA (Sigma product A-1151 resuspended in 5 mL water) per 50 mL agarose gel. Precipitin was stained with Coomassie blue.

DXY1 containing pDB3175-pDB3182 were compared with DXY1 Δtrp1 pdi1::TRP1 containing pDB3175-pDB3182 for the secretion of recombinant human albumin and transferrin (N413Q, N611Q). FIG. 34 shows that following disruption of the genomic PDI1 gene with TRP1 to increase plasmid stability to 100% (Table 16), there was a reduced recombinant human albumin titre for PDI1 inserted at the SnaBI-site. However, this is more than compensated for by the increased genetic stability following disruption of PDI1 in the genome, which increases the reproducibility and reliability of heterologous protein secretion, resulting in a more useful industrial organism for application in consistent protein production, especially in prolonged cultivation, such as fill and draw fermentation or continuous culture fermentation campaigns. Furthermore, when PDI1 was located at the XcmI-site after REP2 of pSAC35 (Example 12) there was no significant decrease in rHA titre following disruption of the genomic PDI1 gene with TRP1 to increase plasmid stability (Table 13). This suggests that the XcmI-site was preferred (but not essential) compared to the SnaBI-site for PDI1 on 2 μm-based plasmids expressing rHA. However, PDI1 expression can be modulated, for example by altering the length of the PDI1 promoter (Example 7) such that an increase in recombinant protein secretion is observed. In the above experiment the long PDI1 promoter was used, which was not the preferred promoter length for optimal rHA secretion in the closely related high rHA producing strain, DS569, where a short promoter resulted in increased rHA secretion. In the case of genomic PDI1 disruption in DXY1 [pDB2977] containing a long PDI1 promoter in PDI1 at the XcmI-site after REP2 of pSAC35 (FIG. 19), the analysis included three individual isolates (not triplicates of a single isolate as shown in FIG. 34), and demonstrated no decrease in rHA titre. Furthermore, the increased consistency and reproducibility is clearly demonstrated for these cultures following disruption of the genomic PDI1 gene.

Figure 35:
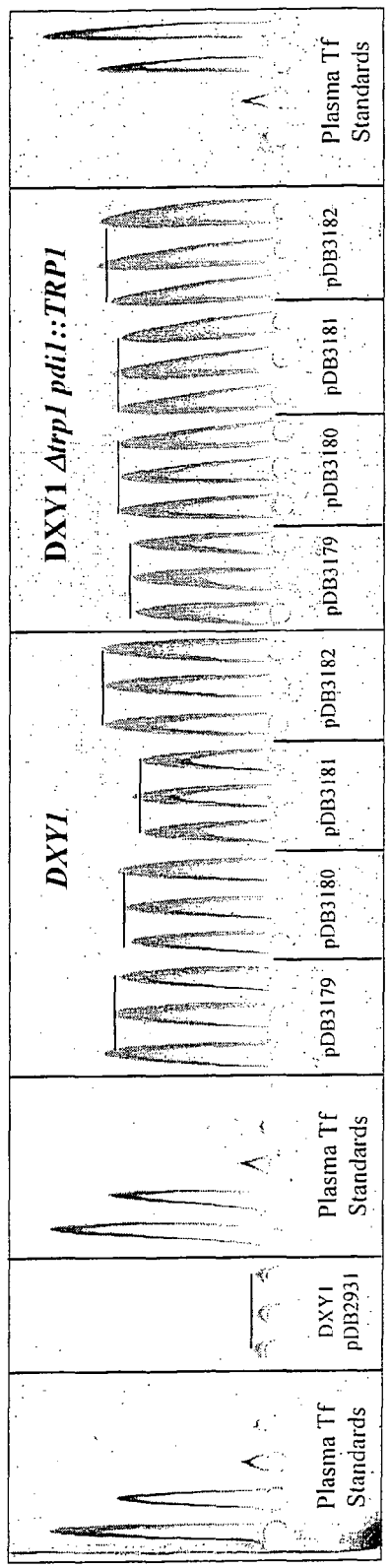
FIG. 35 shows Rocket Immnunoelectrophoresis of YEPD shake flask culture supernatants from DXY1 and DXY1 Δtrp1 pdi1::TRP1 containing pDB3179 to pDB3182. 10 mL YEPD shake flasks were inoculated with DXY1 [pDB2931], DXY1 [pDB3179], DXY1 [pDB3180], DXY1 [pDB3181], DXY1 [pDB3182], DXY1 Δtrp1 pdi1::TRP1 [pDB3179], DXY1 Δtrp1 pdi1::TRP1 [pDB3180], DXY1 Δtrp1 pdi1:: TRP1 [pDB3181], and DXY1 Δtrp1 pdi1::TRP1 [pDB3182] were grown for 4-days at 30° C., 200 rpm. 5 µL culture supernatant was loaded per well of a 50 mL rocket immunoelectrophoresis gel in triplicate. Plasma transferrin standard concentrations were 100, 50, 20, 10 and 5 µg/mL. 40 µL goat polyclonal anti human transferrin antiserum (Calbiochem) was used per 50 mL agarose gel. Precipitin was stained with Coomassie blue.

In FIG. 35 a large increase in recombinant transferrin secretion was observed between DXY1 [pDB2931] without PDI1 on the pSAC35-based vector (which itself was not 100% stable), and strains containing plasmids pDB3179-pDB3182, with PDI1 at the SnaBI/NotI-site. In DXY1 Δtrp1 pdi1::TRP1 containing plasmids pDB3179-pDB3182, PDI1 on the plasmid was acting as the sole selectable marker and resulted in improved genetic stability (see Table 17) where 100% plasmid stability was observed without any decrease in recombinant transferrin secretion. Hence, by placing PDI1 on the transferrin expression plasmid and disrupting PDI1 in the genome, the overall effect has been to increase secretion of the recombinant protein and also to improve the genetic stability of the production organism

The invention claimed is:

1. A plasmid comprising a gene encoding a heterologous protein, and as the sole yeast selectable marker, one or more genes encoding an essential chaperone that is essential to the viability of a yeast host cell when the one or more genes encoding the essential chaperone are deleted or inactivated in a yeast host cell and the host cell is inviable in culture and the deficiency cannot be complemented by additions or modifications to the culture medium, wherein the natural location of the one or more genes encoding the essential chaperone are modified to disrupt its function under normal growth conditions wherein the essential chaperone is a yeast chaperone comprising the sequence of a protein encoded by a gene selected from the group consisting of Protein Disulfide Isomerase (PDI) and Protein Disulfide Isomerase 1(PDI1).

2. The plasmid according to claim 1 wherein the essential chaperone is a yeast chaperone.

3. The plasmid in accordance with claim 1, which is a 2μm-family plasmid.

4. The plasmid in accordance with claim 1, which is not a 2μm-family plasmid.

5. The plasmid in accordance with claim 1, wherein the one or more genes encode a first essential chaperone and a second essential chaperone.

6. A plasmid in accordance with claim 5, wherein the second chaperone is selected from the group consisting of (i)-(iv):
   (i) has a sequence of a fungal chaperone, a yeast chaperone, a mammalian chaperone, or a human chaperone;
   (ii) comprises the sequence of a protein encoded by any one of Activator of Heat shock protein 90 ATPase 1 (AHA1), Chaperonin Containing TCP-1 1 (CCT2), Chaperonin Containing TCP-1 3 (CCT3), Chaperonin Containing TCP-1 4 (CCT4), Chaperonin Containing TCP-1 5 (CCT5), Chaperonin Containing TCP-1 6 (CCT6), Chaperonin Containing TCP-1 7 (CCT7), Chaperonin Containing TCP-1 8 (CCT8), CyclophiliN Seven suppressor (CNS1), Cyclosporin-sensitive Proline Rotamase 3 (CPRS), Cyclosporin-sensitive Proline Rotamase 6 (CPRE), EPS1, ER Oxidation or Endoplasmic Reticulum Oxidoreductin (ERO1), ER protein Unnecessary for Growth (EUG1), FMO1, High-Copy Hsp90 suppressor (HCH1), Heat Shock Protein 10 (HSP10), Heat Shock Protein 12 (HSP12), Heat Shock Protein 104 (HSP104), Heat Shock Protein 26 (HSP26), Heat Shock Protein 30 (HSP30), Heat Shock Protein 42 (HSP42), Heat Shock Protein 60 (HSP60), Heat Shock Protein 78 (HSP78), Heat Shock Protein 82 (HSP82), DnaJ-like protein of the ER Membrane (JEM1), Mitochondrial DnaJ 1 (MDJ1), Mitochondrial DnaJ 2 (MDJ2), MPD1, MPD2, Protein Disulfide Isomerase (PDI), Protein Disulfide Isomerase 1 (PDI1), PreFolDin (PFD1), COenzyme Q (ABC1), Anti-Prion DnaJ (APJ1), ATP synthase 11 (ATP11), ATP synthase 12 (ATP12), BTf Three (BTT1), Cell Division Cycle 37 (CDC37), Cyclosporin-sensitive Proline Rotamase 7 (CPR7), HSC82, KARyogamy 2 (KAR2), Lumenal Heat Shock Protein 70 (LHS1), Mitochondrial GrpE (MGE1), Translocase of the Inner Membrane 11 (MRS11), Nin1 (One) Binding (NOB1), ExtraCellular Mutant 10(ECM10), Stress-Seventy subfamily A 1 (SSA1), Stress-Seventy subfamily A 2(SSA2), Stress-Seventy subfamily A 2 (SSA3), Stress-Seventy subfamily A 4(SSA4), Stress-Seventy subfamily C 1 (SSC1), SSE2, Suppressor of the Ire1/Lhs1 double mutant (SIL1), Sigma Like Sequence (SLS1), Ubiquitin 4(UBI4), ORM1, ORM2, protein Processing in the ER (PER1), Phosphatase Two C (PTC2), Protein Secretion Enhancer (PSE1), Homologous to Atf/Creb1 (HAC1) or truncated intronless HAC1, Translocase of the Inner Mitochondrial membrane 9 (TIM9), Presequence translocase-Associated Motor 18 (PAM18) or Tailless Complex Polypeptide (TCP1) or a variant or fragment of any one of these;
   (iii) is protein disulphide isomerase; and
   (iv) is Orm2p or a variant or fragment thereof.

7. The plasmid in accordance with claim 5, wherein the plasmid comprises a third recombinant gene, which third recombinant gene encodes a desired heterologous protein.

8. The plasmid in accordance with claim 5, wherein the plasmid is a disintegration vector.

9. A host cell comprising the plasmid of claim 1, the plasmid further comprising a recombinant gene encoding a desired heterologous protein,
   wherein:
   (i) the essential chaperone is not HSP10; and
   (ii) the desired heterologous protein:
      (a) comprises a leader sequence; and/or
      (b) is not identical in sequence to a protein that is encoded by one or more other genes that occur naturally in the host cell; and/or
      (c) is a therapeutically active protein; and/or
      (d) is a diagnostically, industrially, domestically or nutritionally useful protein; and/or
      (e) is a protein selected from the group consisting of the sequence of albumin, a monoclonal antibody, an etoposide, a serum protein, antistasin, a tick anticoagulant peptide, transferrin, lactoferrin, endostatin, angiostatin, collagens, immunoglobulins, immunoglobulin-based molecules, a Kunitz domain protein, interferons, interleukins, IL10,IL11, IL2, interferon α species and subspecies, interferon β species and subspecies, interferon γ species and sub-species, leptin, CNTF, $CNTF_{Ax15}$, IL1-receptor antagonist, erythropoietin (EPO), EPO mimics, thrombopoietin, TPO mimics, prosaptide, cyanovirin-N, 5-helix, T20peptide, T1249 peptide, HIV gp41, HIV gp120, urokinase, prourokinase, tPA, hirudin, platelet derived growth factor, parathyroid hormone, proinsulin, insulin, glucagon, glucagon-like peptides, insulin-like growth factor, calcitonin, growth hormone, transforming growth factor β, tumor necrosis factor, G-CSF, GM-CSF, M-CSF, FGF, coagulation factors, plasminogen, fibrinogen, thrombin, pre-thrombin, pro-thrombin, von Willebrand's factor, $\alpha_1$-antitrypsin, plasminogen activators, Factor VII, Factor VIII, Factor IX, Factor X and Factor XIII, nerve growth factor, LACI, platelet-derived endothelial cell growth factor (PD-ECGF), glucose oxidase, serum cholinesterase, aprotinin, amyloid precursor protein, inter-alpha trypsin inhibitor, antithrombin III, apo-lipoprotein species, Protein C, Protein S, a metabolite, an antibiotic, a variant of any of the above, and functional fragment of any of the above.

10. The host cell in accordance with claim 9, wherein the essential chaperone is a yeast chaperone.

11. The host cell in accordance with claim 9, wherein, in the absence of the plasmid, the host cell is inviable.

12. The host cell according to claim 11 wherein, in the absence of the plasmid, the host cell is inviable and cannot be made viable by growing the host cell in a growth medium and making nutrient additions or modifications to that growth medium, and preferably cannot be made viable by growing the host cell in a growth medium and making any additions or modifications to that growth medium.

13. A host cell comprising the plasmid of claim 5.

14. The host cell according to claim 13 wherein, in the absence of the plasmid, the host cell does not produce the chaperone.

15. A method for producing a desired protein comprising:
(a) providing the host cell in accordance with claim 13 comprising a first recombinant gene encoding a protein comprising the sequence of a first chaperone protein, a second recombinant gene encoding a protein comprising the sequence of a second chaperone protein and a third gene, such a third recombinant gene, encoding a desired protein, wherein the first and second chaperones are different; and
(b) culturing the host cell in a culture medium to obtain expression of the first, second and third genes.

16. A method for producing a desired recombinant protein comprising the steps of: providing a host cell comprising the plasmid of claim 1, and a gene that encodes a desired protein; culturing the host cell in a culture medium under conditions that allow the expression of the essential chaperone and the desired protein.

17. The method according to claim 16, wherein the plasmid further comprises a recombinant gene encoding a desired heterologous protein wherein:
(i) the essential chaperone is not HSP10; and
(ii) the desired heterologous protein:
  (a) comprises a leader sequence; and/or
  (b) is not identical in sequence to a protein that is encoded by one or more other genes that occur naturally in the host cell; and/or
  (c) is a therapeutically active protein; and/or
  (d) is a diagnostically, industrially, domestically or nutritionally useful protein; and/or
  (e) is a protein comprising the sequence of albumin, a monoclonal antibody, an etoposide, a serum protein, antistasin, a tick anticoagulant peptide, transferrin, lactoferrin, endostatin, angiostatin, collagens, immunoglobulins, immunoglobulin-based molecules, a Kunitz domain protein, interferons, interleukins, IL10, IL11, IL2, interferon α species and sub-species, interferon β species and sub-species, interferon γ species and sub-species, leptin, CNTF, $CNTF_{Ax15}$, IL1-receptor antagonist, erythropoietin (EPO) and EPO mimics, thrombopoietin (TPO) and TPO mimics, prosaptide, cyanovirin-N, 5-helix, T20peptide, T1249 peptide, HIV gp41, HIV gp120, urokinase, prourokinase, tPA, hirudin, platelet derived growth factor, parathyroid hormone, proinsulin, insulin, glucagon, glucagon-like peptides, insulin-like growth factor, calcitonin, growth hormone, transforming growth factor β, tumor necrosis factor, G-CSF, GM-CSF, M-CSF, FGF, coagulation factors in both pre and active forms, plasminogen, fibrinogen, thrombin, pre-thrombin, pro-thrombin, von Willebrand's factor, $a_1$-antitrypsin, plasminogen activators, Factor VII, Factor VIII, Factor IX, Factor X and Factor XIII, nerve growth factor, LACI, platelet-derived endothelial cell growth factor (PD-ECGF), glucose oxidase, serum cholinesterase, aprotinin, amyloid precursor protein, inter-alpha trypsin inhibitor, antithrombin III, apo-lipoprotein species, Protein C, Protein S, a metabolite, an antibiotic, or a variant or functional fragment of any of the above.

18. A method for producing a desired protein comprising the steps of:
(a) providing the host cell in accordance with claim 9; and
(b) culturing the host cell in a culture medium under conditions that allow the expression of the essential chaperone and the desired protein.

19. The host cell in accordance with claim 9, wherein the host cell is a bacterial or yeast host cell.

20. The host cell in accordance with claim 9, wherein the host cell is a yeast cell selected from the group consisting of *Saccharomyces, Kluyveromyces, Arxula, Yarrowia, Candida, Schizosaccharomyces, Debaryomyces, Xanthophyllomyces, Geotrichum, Ashbya, Hortaea, Schwanniomyces, Trichosporon, Xanthophyllomyces, Saccharomyces cerevisiae, Kluyveromyces lactis, Pichia pastoris, Pichia membranaefaciens, Zygosaccharomyces rouxii, Zygosaccharomyces bailii, Zygosaccharomyces fermentati, Kluyveromyces drosphilarum, Pichia methanolica, Hansenula polymorpha, Pichia augusta, Arxula adeninivorans, Yarrowia lipolytica, Candida boidinii Candida utilis* and *Schizosaccharomyces pombe*.

21. The host cell in accordance with claim 20, wherein the plasmid is a 2μm-family plasmid and wherein:
(a) the plasmid is based on pSR1, pSB3 or pSB4 and the host cell is *Zygosaccharomyces rouxii*;
(b) the plasmid is based on pSB1 or pSB2 and the host cell is *Zygosaccharomyces bailli*;
(c) the plasmid is based on pSM1 and the host cell is *Zygosaccharomyces Fermentati*;
(d) the plasmid is based on pKD1 and the host cell is *Kluyveromyces Drosophilarum*;
(e) the plasmid is based on pPM1 and the host cell is *Pichia membranaefaciens*; or
(f) the plasmid is based on the 2μm plasmid and the host cell is *Saccharomyces cerevisiae* or *Saccharomyces carlsbergensis*.

22. The host cell in accordance with claim 19, in which the plasmid is based on the 2μm plasmid and the host cell is *Saccharomyces cerevisiae* or *Saccharomyces carlsbergensis*.

* * * * *

SEQUENCE LISTING

<160> NUMBER OF SEQ ID NOS: 45

<210> SEQ ID NO 1
<211> LENGTH: 24
<212> TYPE: PRT
<213> ORGANISM: Artificial sequence
<220> FEATURE:
<223> OTHER INFORMATION: Modified fusion leader

<400> SEQUENCE: 1

Met Lys Trp Val Phe Ile Val Ser Ile Leu Phe Leu Phe Ser Ser Ala
1               5                   10                  15

Tyr Ser Arg Ser Leu Asp Lys Arg
            20

<210> SEQ ID NO 2
<211> LENGTH: 18
<212> TYPE: PRT
<213> ORGANISM: Artificial sequence
<220> FEATURE:
<223> OTHER INFORMATION: Modified HSA(pre) leader sequence

<400> SEQUENCE: 2

Met Lys Trp Val Phe Ile Val Ser Ile Leu Phe Leu Phe Ser Ser Ala
1               5                   10                  15

Tyr Ser

<210> SEQ ID NO 3
<211> LENGTH: 90
<212> TYPE: DNA
<213> ORGANISM: Artificial sequence
<220> FEATURE:
<223> OTHER INFORMATION: Primer DS248

<400> SEQUENCE: 3
gtcagaattc gagctctacg tattaattaa ggccggccag gcccgggcta gtctcttttt      60
ccaatttgcc accgtgtagc attttgttgt                                       90

<210> SEQ ID NO 4
<211> LENGTH: 59
<212> TYPE: DNA
<213> ORGANISM: Artificial sequence
<220> FEATURE:
<223> OTHER INFORMATION: Primer DS249

<400> SEQUENCE: 4
gtcaggatcc tacgtacccg gggatatcat tatcatcttt gtcgtggtca tcttgtgtg       59

<210> SEQ ID NO 5
<211> LENGTH: 54
<212> TYPE: DNA
<213> ORGANISM: Artificial sequence
<220> FEATURE:
<223> OTHER INFORMATION: Primer DS250

<400> SEQUENCE: 5
gtcaggatcc tacgtacccg ggtaaggcgt tcgtgcagtg tgacgaatat agcg            54

<210> SEQ ID NO 6
<211> LENGTH: 99
<212> TYPE: DNA
<213> ORGANISM: Artificial sequence
<220> FEATURE:
<223> OTHER INFORMATION: Primer DS251

```
<400> SEQUENCE: 6
gtcagaattc gagctctacg tattaattaa ggccggccag gcccgggccc gtatggacat     60
acatatatat atatatatat atatatattt tgttacgcg                            99

<210> SEQ ID NO 7
<211> LENGTH: 90
<212> TYPE: DNA
<213> ORGANISM: Artificial sequence
<220> FEATURE:
<223> OTHER INFORMATION: Primer DS252

<400> SEQUENCE: 7
gtcagaattc gagctctacg tattaattaa ggccggccag gcccgggctt gttgcaagca     60
gcatgtctaa ttggtaattt taaagctgcc                                     90

<210> SEQ ID NO 8
<211> LENGTH: 103
<212> TYPE: DNA
<213> ORGANISM: Artificial sequence
<220> FEATURE:
<223> OTHER INFORMATION: Primer DS267

<400> SEQUENCE: 8
gtcagaattc gagctctacg tattaattaa ggccggccag gcccgggccc gtatggacat     60
acatatatat atatatatat atatatatat attttgttac gcg                      103

<210> SEQ ID NO 9
<211> LENGTH: 17
<212> TYPE: DNA
<213> ORGANISM: Artificial sequence
<220> FEATURE:
<223> OTHER INFORMATION: Primer DS253

<400> SEQUENCE: 9
cctccctgct gctcgcc                                                   17

<210> SEQ ID NO 10
<211> LENGTH: 18
<212> TYPE: DNA
<213> ORGANISM: Artificial sequence
<220> FEATURE:
<223> OTHER INFORMATION: Primer DS254

<400> SEQUENCE: 10
ctgtaagaac atggctcc                                                  18

<210> SEQ ID NO 11
<211> LENGTH: 18
<212> TYPE: DNA
<213> ORGANISM: Artificial sequence
<220> FEATURE:
<223> OTHER INFORMATION: Primer DS255

<400> SEQUENCE: 11
ctcgatcgat tacgaggg                                                  18

<210> SEQ ID NO 12
<211> LENGTH: 17
<212> TYPE: DNA
<213> ORGANISM: Artificial sequence
<220> FEATURE:
<223> OTHER INFORMATION: Primer DS256
```

<400> SEQUENCE: 12
aagaaagccg atatcgc                                                     17

<210> SEQ ID NO 13
<211> LENGTH: 18
<212> TYPE: DNA
<213> ORGANISM: Artificial sequence
<220> FEATURE:
<223> OTHER INFORMATION: Primer DS257

<400> SEQUENCE: 13
caactctctg aagaggcg                                                    18

<210> SEQ ID NO 14
<211> LENGTH: 17
<212> TYPE: DNA
<213> ORGANISM: Artificial sequence
<220> FEATURE:
<223> OTHER INFORMATION: Primer DS258

<400> SEQUENCE: 14
caacgccaca tccgacg                                                     17

<210> SEQ ID NO 15
<211> LENGTH: 19
<212> TYPE: DNA
<213> ORGANISM: Artificial sequence
<220> FEATURE:
<223> OTHER INFORMATION: Primer DS259

<400> SEQUENCE: 15
gtaattctga tcactttgg                                                   19

<210> SEQ ID NO 16
<211> LENGTH: 21
<212> TYPE: DNA
<213> ORGANISM: Artificial sequence
<220> FEATURE:
<223> OTHER INFORMATION: Primer DS260

<400> SEQUENCE: 16
gcacttatta ttactacgtg g                                                21

<210> SEQ ID NO 17
<211> LENGTH: 19
<212> TYPE: DNA
<213> ORGANISM: Artificial sequence
<220> FEATURE:
<223> OTHER INFORMATION: Primer DS261

<400> SEQUENCE: 17
gttttccttg atgaagtcg                                                   19

<210> SEQ ID NO 18
<211> LENGTH: 18
<212> TYPE: DNA
<213> ORGANISM: Artificial sequence
<220> FEATURE:
<223> OTHER INFORMATION: Primer DS262

<400> SEQUENCE: 18
gtgaccacac catggggc                                                    18

-continued

```
<210> SEQ ID NO 19
<211> LENGTH: 18
<212> TYPE: DNA
<213> ORGANISM: Artificial sequence
<220> FEATURE:
<223> OTHER INFORMATION: Primer DS263

<400> SEQUENCE: 19
gttgccggcg tgtctgcc                                                 18

<210> SEQ ID NO 20
<211> LENGTH: 18
<212> TYPE: DNA
<213> ORGANISM: Artificial sequence
<220> FEATURE:
<223> OTHER INFORMATION: Primer DS264

<400> SEQUENCE: 20
ttgaaatcat cgtctgcg                                                 18

<210> SEQ ID NO 21
<211> LENGTH: 17
<212> TYPE: DNA
<213> ORGANISM: Artificial sequence
<220> FEATURE:
<223> OTHER INFORMATION: Primer DS265

<400> SEQUENCE: 21
cggcagttct aggtccc                                                  17

<210> SEQ ID NO 22
<211> LENGTH: 18
<212> TYPE: DNA
<213> ORGANISM: Artificial sequence
<220> FEATURE:
<223> OTHER INFORMATION: Primer DS266

<400> SEQUENCE: 22
ccacagcctc ttgttggg                                                 18

<210> SEQ ID NO 23
<211> LENGTH: 17
<212> TYPE: DNA
<213> ORGANISM: Artificial sequence
<220> FEATURE:
<223> OTHER INFORMATION: Primer M13/pUC Primer (-40)

<400> SEQUENCE: 23
gttttcccag tcacgac                                                  17

<210> SEQ ID NO 24
<211> LENGTH: 38
<212> TYPE: DNA
<213> ORGANISM: Artificial sequence
<220> FEATURE:
<223> OTHER INFORMATION: Primer DS299

<400> SEQUENCE: 24
cgtagcggcc gcctgaaagg ggttgaccgt ccgtcggc                           38

<210> SEQ ID NO 25
<211> LENGTH: 39
<212> TYPE: DNA
<213> ORGANISM: Artificial sequence
<220> FEATURE:
<223> OTHER INFORMATION: Primer DS300
```

<400> SEQUENCE: 25
cgtaaagctt cgccgcccga cagggtaaca tattatcac        39

<210> SEQ ID NO 26
<211> LENGTH: 38
<212> TYPE: DNA
<213> ORGANISM: Artificial sequence
<220> FEATURE:
<223> OTHER INFORMATION: Primer DS301

<400> SEQUENCE: 26
cgtaaagctt gaccacgtag taataataag tgcatggc        38

<210> SEQ ID NO 27
<211> LENGTH: 41
<212> TYPE: DNA
<213> ORGANISM: Artificial sequence
<220> FEATURE:
<223> OTHER INFORMATION: Primer DS302

<400> SEQUENCE: 27
cgtactgcag attggatagt gattagagtg tatagtcccg g        41

<210> SEQ ID NO 28
<211> LENGTH: 18
<212> TYPE: DNA
<213> ORGANISM: Artificial sequence
<220> FEATURE:
<223> OTHER INFORMATION: Primer DS303

<400> SEQUENCE: 28
ggagcgacaa acctttcg        18

<210> SEQ ID NO 29
<211> LENGTH: 20
<212> TYPE: DNA
<213> ORGANISM: Artificial sequence
<220> FEATURE:
<223> OTHER INFORMATION: Primer DS304

<400> SEQUENCE: 29
accgtaataa aagatggctg        20

<210> SEQ ID NO 30
<211> LENGTH: 24
<212> TYPE: DNA
<213> ORGANISM: Artificial sequence
<220> FEATURE:
<223> OTHER INFORMATION: Primer DS305

<400> SEQUENCE: 30
catcttgtgt gtgagtatgg tcgg        24

<210> SEQ ID NO 31
<211> LENGTH: 18
<212> TYPE: DNA
<213> ORGANISM: Artificial sequence
<220> FEATURE:
<223> OTHER INFORMATION: Primer DS306

<400> SEQUENCE: 31
cccaggataa ttttcagg        18

```
<210> SEQ ID NO 32
<211> LENGTH: 29
<212> TYPE: DNA
<213> ORGANISM: Artificial sequence
<220> FEATURE:
<223> OTHER INFORMATION: Primer DS230

<400> SEQUENCE: 32
tagcgaattc aatcagtaaa aatcaacgg                              29

<210> SEQ ID NO 33
<211> LENGTH: 30
<212> TYPE: DNA
<213> ORGANISM: Artificial sequence
<220> FEATURE:
<223> OTHER INFORMATION: Primer DS231

<400> SEQUENCE: 33
gtcaaagctt caaaaaaga aaagctccgg                              30

<210> SEQ ID NO 34
<211> LENGTH: 38
<212> TYPE: DNA
<213> ORGANISM: Artificial sequence
<220> FEATURE:
<223> OTHER INFORMATION: Primer DS232

<400> SEQUENCE: 34
tagcggatcc gaattcggcg gttgtttgca agaccgag                    38

<210> SEQ ID NO 35
<211> LENGTH: 34
<212> TYPE: DNA
<213> ORGANISM: Artificial sequence
<220> FEATURE:
<223> OTHER INFORMATION: Primer DS233

<400> SEQUENCE: 35
gtcaaagctt taaagataat gctaaatcat ttgg                        34

<210> SEQ ID NO 36
<211> LENGTH: 35
<212> TYPE: DNA
<213> ORGANISM: Artificial sequence
<220> FEATURE:
<223> OTHER INFORMATION: Primer DS234

<400> SEQUENCE: 36
tgacaagctt tcggtcgaaa aagaaaagg agagg                        35

<210> SEQ ID NO 37
<211> LENGTH: 31
<212> TYPE: DNA
<213> ORGANISM: Artificial sequence
<220> FEATURE:
<223> OTHER INFORMATION: Primer DS235

<400> SEQUENCE: 37
tgacaagctt gatcttttat gcttgctttt c                           31

<210> SEQ ID NO 38
<211> LENGTH: 18
<212> TYPE: DNA
<213> ORGANISM: Artificial sequence
<220> FEATURE:
<223> OTHER INFORMATION: Primer DS236
```

```
<400> SEQUENCE: 38
aatagttcag gcactccg                                              18

<210> SEQ ID NO 39
<211> LENGTH: 17
<212> TYPE: DNA
<213> ORGANISM: Artificial sequence
<220> FEATURE:
<223> OTHER INFORMATION: Primer DS237

<400> SEQUENCE: 39
tggaaggcaa gagagcc                                               17

<210> SEQ ID NO 40
<211> LENGTH: 18
<212> TYPE: DNA
<213> ORGANISM: Artificial sequence
<220> FEATURE:
<223> OTHER INFORMATION: Primer DS238

<400> SEQUENCE: 40
taaaatgtaa gctctcgg                                              18

<210> SEQ ID NO 41
<211> LENGTH: 17
<212> TYPE: DNA
<213> ORGANISM: Artificial sequence
<220> FEATURE:
<223> OTHER INFORMATION: Primer DS239

<400> SEQUENCE: 41
ccaaccaagt atttcgg                                               17

<210> SEQ ID NO 42
<211> LENGTH: 20
<212> TYPE: DNA
<213> ORGANISM: Artificial sequence
<220> FEATURE:
<223> OTHER INFORMATION: Primer CED005

<400> SEQUENCE: 42
gagctgacag ggaaatggtc                                            20

<210> SEQ ID NO 43
<211> LENGTH: 20
<212> TYPE: DNA
<213> ORGANISM: Artificial sequence
<220> FEATURE:
<223> OTHER INFORMATION: Primer CED006

<400> SEQUENCE: 43
tacgaggata cggagagagg                                            20

<210> SEQ ID NO 44
<211> LENGTH: 44
<212> TYPE: DNA
<213> ORGANISM: Artificial sequence
<220> FEATURE:
<223> OTHER INFORMATION: Primer LRE49

<400> SEQUENCE: 44
gctagcgtcg acaagcttgc ggcgcggtac cgtgtggaag aacg                  44
```

```
<210> SEQ ID NO 45
<211> LENGTH: 20
<212> TYPE: DNA
<213> ORGANISM: Artificial sequence
<220> FEATURE:
<223> OTHER INFORMATION: Primer CF247

<400> SEQUENCE: 45
gcgcgttttc attagtgccc                                                 20
```